(12) United States Patent
Chen et al.

(10) Patent No.: US 12,049,485 B2
(45) Date of Patent: Jul. 30, 2024

(54) INTERLEUKIN-2 POLYPEPTIDE CONJUGATES AND THEIR USES

(71) Applicant: Ambrx, Inc., La Jolla, CA (US)

(72) Inventors: Sigeng Chen, La Jolla, CA (US); Yingchun Lu, La Jolla, CA (US); MD Harunur Rashid, La Jolla, CA (US); Nickolas Knudsen, La Jolla, CA (US); Feng Tian, La Jolla, CA (US)

(73) Assignee: Ambrx, Inc., La Jolla, CA (US)

( * ) Notice: Subject to any disclaimer, the term of this patent is extended or adjusted under 35 U.S.C. 154(b) by 0 days.

(21) Appl. No.: 17/275,662

(22) PCT Filed: Sep. 11, 2019

(86) PCT No.: PCT/US2019/050709
§ 371 (c)(1),
(2) Date: Mar. 11, 2021

(87) PCT Pub. No.: WO2020/056066
PCT Pub. Date: Mar. 19, 2020

(65) Prior Publication Data
US 2022/0056093 A1    Feb. 24, 2022

Related U.S. Application Data

(60) Provisional application No. 62/729,925, filed on Sep. 11, 2018, provisional application No. 62/815,964, filed on Mar. 8, 2019.

(51) Int. Cl.
| | | |
|---|---|---|
| *A61K 38/20* | (2006.01) | |
| *A61K 47/60* | (2017.01) | |
| *C07K 14/55* | (2006.01) | |
| *A61K 38/00* | (2006.01) | |

(52) U.S. Cl.
CPC .......... *C07K 14/55* (2013.01); *A61K 38/2013* (2013.01); *A61K 47/60* (2017.08); *A61K 38/00* (2013.01)

(58) Field of Classification Search
CPC ..... A61K 38/2013; A61K 47/60; C07K 14/55
See application file for complete search history.

(56) References Cited

U.S. PATENT DOCUMENTS

| | | |
|---|---|---|
| 4,289,872 A | 9/1981 | Denkewalter et al. |
| 4,412,989 A | 11/1983 | Iwashita et al. |
| 4,414,148 A | 11/1983 | Jansen |
| 4,485,045 A | 11/1984 | Regen |
| 4,511,502 A | 4/1985 | Builder et al. |
| 4,511,503 A | 4/1985 | Olson et al. |
| 4,512,922 A | 4/1985 | Jones et al. |
| 4,544,545 A | 10/1985 | Ryan et al. |
| 4,551,433 A | 11/1985 | Deboer |
| 4,569,789 A | 2/1986 | Blattler |
| 4,619,794 A | 10/1986 | Hauser |
| 4,659,839 A | 4/1987 | Nicolotti |
| 4,670,417 A | 6/1987 | Iwasaki et al. |
| 4,671,958 A | 6/1987 | Rodwell |
| 4,680,338 A | 7/1987 | Sundoro |
| 4,699,784 A | 11/1987 | Shih |
| 4,738,921 A | 4/1988 | Belagage et al. |
| 4,870,008 A | 9/1989 | Brake |
| 4,902,502 A | 2/1990 | Nitecki et al. |
| 4,931,373 A | 6/1990 | Kawasaki et al. |
| 5,021,234 A | 6/1991 | Ehrenfeld |
| 5,047,335 A | 9/1991 | Paulsen et al. |
| 5,122,614 A | 6/1992 | Zalipsky |
| 5,206,344 A | 4/1993 | Katre |
| 5,219,564 A | 6/1993 | Zalipsky et al. |
| 5,229,490 A | 7/1993 | Tam |
| 5,252,714 A | 10/1993 | Harris |
| 5,281,698 A | 1/1994 | Nitecki |
| 5,324,844 A | 6/1994 | Zalipsky |
| 5,382,657 A | 1/1995 | Karasiewicz et al. |
| 5,446,090 A | 8/1995 | Harris |
| 5,468,478 A | 11/1995 | Saifer et al. |
| 5,473,034 A | 12/1995 | Yasui et al. |
| 5,476,653 A | 12/1995 | Pitt et al. |
| 5,516,673 A | 5/1996 | Margel et al. |
| 5,559,213 A | 9/1996 | Hakimi et al. |
| 5,612,460 A | 3/1997 | Zalipsky |
| 5,629,384 A | 5/1997 | Veronese et al. |
| 5,643,575 A | 7/1997 | Martinez et al. |
| 5,650,234 A | 7/1997 | Dolence et al. |
| 5,672,662 A | 9/1997 | Harris et al. |
| 5,736,625 A | 4/1998 | Callstrom et al. |

(Continued)

FOREIGN PATENT DOCUMENTS

| | | |
|---|---|---|
| CN | 1799625 A | 7/2006 |
| CN | 101090980 A | 12/2007 |

(Continued)

OTHER PUBLICATIONS

Ogawa et al., J. Am. Chem. Soc., 122:8803-8804 (2000).
Tae, et al., J. Am. Chem. Soc., 123:7439-7440 (2001).
Meggers, et al., J. Am. Chem. Soc., 122:10714-10715 (2000).
Langer, et al., J. Biomed. Mater. Res., 15: 267-277 (1981).
Broadhead, J. et al., in Drug Dev. Ind. Pharm, 18 (11 & 12), 1169-1206 (1992).

(Continued)

*Primary Examiner* — Jeffrey E. Russel
(74) *Attorney, Agent, or Firm* — Barbara Potts; Sharon Beresford

(57) ABSTRACT

The present invention provides methods for targeting interleukin-2 receptor-expressing cells, and, in particular, inhibiting the growth of such cells by using an interleukin-2 (IL-2) variant conjugated to a biologically active molecule that will affect cells expressing the interleukin-2 receptor.

16 Claims, 21 Drawing Sheets

Specification includes a Sequence Listing.

(56) References Cited

U.S. PATENT DOCUMENTS

| | | | |
|---|---|---|---|
| 5,739,208 | A | 4/1998 | Harris |
| 5,747,646 | A | 5/1998 | Hakimi et al. |
| 5,808,096 | A | 9/1998 | Zalipsky |
| 5,824,778 | A | 10/1998 | Ishikawa et al. |
| 5,824,784 | A | 10/1998 | Kinstler et al. |
| 5,834,594 | A | 11/1998 | Hakimi et al. |
| 5,849,860 | A | 12/1998 | Hakimi et al. |
| 5,900,461 | A | 5/1999 | Harris |
| 5,932,462 | A | 8/1999 | Harris et al. |
| 5,980,948 | A | 11/1999 | Goedemoed et al. |
| 5,990,237 | A | 11/1999 | Bentley et al. |
| 6,004,573 | A | 12/1999 | Rath et al. |
| 6,129,912 | A | 10/2000 | Hortin et al. |
| 6,188,965 | B1 | 2/2001 | Mayo |
| 6,201,072 | B1 | 3/2001 | Rathi et al. |
| 6,214,966 | B1 | 4/2001 | Harris |
| 6,269,312 | B1 | 7/2001 | Mayo |
| 6,306,821 | B1 | 10/2001 | Mikos et al. |
| 6,403,312 | B1 | 6/2002 | Zach et al. |
| 6,420,339 | B1 | 7/2002 | Gegg et al. |
| 6,423,685 | B1 | 7/2002 | Drummond |
| 6,436,386 | B1 | 8/2002 | Roberts et al. |
| 6,451,346 | B1 | 9/2002 | Shah et al. |
| 6,461,603 | B2 | 10/2002 | Bentley et al. |
| 6,515,100 | B2 | 2/2003 | Harris |
| 6,521,427 | B1 | 2/2003 | Evans |
| 6,552,167 | B1 | 4/2003 | Rose |
| 6,608,183 | B1 | 8/2003 | Cox, III |
| 6,610,281 | B2 | 8/2003 | Harris |
| 6,646,110 | B2 | 11/2003 | Nissen et al. |
| 6,927,042 | B2 | 8/2005 | Schultz et al. |
| 7,045,337 | B2 | 5/2006 | Schultz |
| 7,083,970 | B2 | 8/2006 | Schultz |
| 9,266,938 | B2 * | 2/2016 | Ast .................. A61K 39/39558 |
| 10,610,571 | B2 | 4/2020 | Ptacin et al. |
| 2001/0021763 | A1 | 9/2001 | Therapeutics |
| 2001/0044526 | A1 | 11/2001 | Therapeutics |
| 2001/0056171 | A1 | 12/2001 | Therapeutics |
| 2002/0002250 | A1 | 1/2002 | Bentley et al. |
| 2002/0040076 | A1 | 4/2002 | Harris et al. |
| 2002/0052009 | A1 | 5/2002 | Hornauer et al. |
| 2002/0052430 | A1 | 5/2002 | Harris et al. |
| 2002/0072573 | A1 | 6/2002 | Bentley et al. |
| 2002/0082345 | A1 | 6/2002 | Kozlowski et al. |
| 2002/0086939 | A1 | 7/2002 | Kozlowski |
| 2002/0099133 | A1 | 7/2002 | Kozlowski |
| 2002/0156047 | A1 | 10/2002 | Zhao |
| 2003/0023023 | A1 | 1/2003 | Harris et al. |
| 2003/0105275 | A1 | 6/2003 | Bentley et al. |
| 2003/0114647 | A1 | 6/2003 | Harris et al. |
| 2003/0143596 | A1 | 7/2003 | Bentley et al. |
| 2003/0162949 | A1 | 8/2003 | Cox |
| 2003/0220447 | A1 | 11/2003 | Harris |
| 2003/0228274 | A1 | 12/2003 | Rose |
| 2003/0228593 | A1 | 12/2003 | Suga et al. |
| 2004/0001838 | A1 | 1/2004 | Zhao et al. |
| 2004/0013637 | A1 | 1/2004 | Bentley et al. |
| 2006/0194256 | A1 | 8/2006 | Miao et al. |
| 2006/0217289 | A1 | 9/2006 | Miao et al. |
| 2006/0217532 | A1 | 9/2006 | Miao et al. |
| 2014/0046026 | A1 | 2/2014 | Garcia |
| 2014/0221569 | A1 * | 8/2014 | Gaertner .............. A61K 47/595 525/54.1 |
| 2014/0328791 | A1 * | 11/2014 | Bossard .................. A61P 37/04 435/254.2 |
| 2017/0044229 | A1 * | 2/2017 | Garcia .................... A61P 17/06 |
| 2019/0351065 | A1 * | 11/2019 | Hickey ................ C07K 1/1077 |
| 2021/0024637 | A1 * | 1/2021 | Kley ...................... A61K 38/17 |

FOREIGN PATENT DOCUMENTS

| | | |
|---|---|---|
| CN | 103517718 | 1/2014 |
| CN | 103517718 A | 1/2014 |
| EP | 0036676 B1 | 9/1981 |
| EP | 0036776 B1 | 9/1981 |
| EP | 0052322 A2 | 5/1982 |
| EP | 0102324 A1 | 3/1984 |
| EP | 0102324 A2 | 3/1984 |
| EP | 0121775 A1 | 10/1984 |
| EP | 0052322 B1 | 3/1985 |
| EP | 0154316 A1 | 9/1985 |
| EP | 0143949 B1 | 12/1985 |
| EP | 0183503 A2 | 6/1986 |
| EP | 0188256 B1 | 7/1986 |
| EP | 0229108 B1 | 7/1987 |
| EP | 0400472 A2 | 12/1990 |
| EP | 0510356 A1 | 10/1992 |
| EP | 0605963 A2 | 7/1994 |
| EP | 0809996 A2 | 12/1997 |
| EP | 0921131 A1 | 6/1999 |
| JP | 2009515881 A | 4/2009 |
| JP | 2009528824 A | 8/2009 |
| TW | 201920241 | 6/2019 |
| TW | 201920241 A | 6/2019 |
| WO | WO 87/02670 A1 | 5/1987 |
| WO | 89/06546 A1 | 7/1989 |
| WO | 90/04606 A1 | 5/1990 |
| WO | WO 90/13540 A1 | 11/1990 |
| WO | WO 92/16555 A1 | 10/1992 |
| WO | WO 93/15189 A1 | 8/1993 |
| WO | WO 93/21259 A1 | 10/1993 |
| WO | WO 94/04193 A1 | 3/1994 |
| WO | WO 94/09027 A1 | 4/1994 |
| WO | WO 94/15625 A1 | 7/1994 |
| WO | WO 94/17039 A1 | 8/1994 |
| WO | WO 94/18247 A1 | 8/1994 |
| WO | WO 94/28024 A1 | 12/1994 |
| WO | WO 95/00162 A1 | 1/1995 |
| WO | 95/06058 A1 | 3/1995 |
| WO | 95/13312 A1 | 5/1995 |
| WO | WO 95/11924 A1 | 5/1995 |
| WO | WO95/13090 A1 | 5/1995 |
| WO | WO 95/33490 A1 | 12/1995 |
| WO | WO 96/00080 A1 | 1/1996 |
| WO | 96/07670 A1 | 3/1996 |
| WO | WO 96/21469 | 7/1996 |
| WO | 96/41813 A2 | 12/1996 |
| WO | WO 96/40791 A1 | 12/1996 |
| WO | 97/003106 A1 | 3/1997 |
| WO | WO 97/18832 A1 | 5/1997 |
| WO | WO 94/14758 A1 | 7/1997 |
| WO | WO 97/32607 A2 | 9/1997 |
| WO | 98/05363 A2 | 2/1998 |
| WO | WO 98/32466 A1 | 7/1998 |
| WO | WO 98/41562 A1 | 9/1998 |
| WO | WO 98/47089 A1 | 10/1998 |
| WO | WO 98/48837 A1 | 11/1998 |
| WO | WO 99/05297 A1 | 4/1999 |
| WO | WO 99/32134 A1 | 7/1999 |
| WO | WO 99/32139 A1 | 7/1999 |
| WO | WO 99/32140 A1 | 7/1999 |
| WO | WO 2002/085923 A2 | 10/2002 |
| WO | WO 03/101972 A1 | 12/2003 |
| WO | WO 2004/010957 A2 | 2/2004 |
| WO | 2005/007121 A2 | 1/2005 |
| WO | WO 2005/007121 A2 | 1/2005 |
| WO | WO 2005/007624 A2 | 1/2005 |
| WO | WO 2005/007870 A2 | 1/2005 |
| WO | WO 2005/019415 A2 | 3/2005 |
| WO | 2005/086751 A2 | 9/2005 |
| WO | WO 2005/086751 A2 | 9/2005 |
| WO | 2006069220 A2 | 6/2006 |
| WO | WO 2006/069246 A2 | 6/2006 |
| WO | 2007/079130 A2 | 2/2007 |
| WO | 2007056448 A2 | 5/2007 |
| WO | WO 2007/056448 A2 | 5/2007 |
| WO | WO 2007/070659 A2 | 6/2007 |
| WO | WO 2007/079130 A2 | 7/2007 |
| WO | 2007103307 A2 | 9/2007 |
| WO | 2008/077079 A1 | 6/2008 |
| WO | 2008/083346 A1 | 7/2008 |
| WO | 2012/065086 A1 | 5/2012 |
| WO | WO 2012/065086 A1 | 5/2012 |

(56) References Cited

FOREIGN PATENT DOCUMENTS

| WO | 2012/088446 A1 | 6/2012 |
|---|---|---|
| WO | WO 2012/088446 A1 | 6/2012 |
| WO | 2016/025385 A1 | 2/2016 |
| WO | WO 2016/025385 A1 | 2/2016 |
| WO | 2018/223108 A1 | 12/2018 |
| WO | WO 2019/028419 A1 | 2/2019 |
| WO | 2021/183832 A1 | 9/2021 |

OTHER PUBLICATIONS

Arakawa, et al. Pharm. Res. 8(3):285-291 (1991).
Pikal, M. Biopharm. 3(9)26-30 (1990).
Liu H., et al. J. Am. Chem. Soc. 125: 1702-1703 (2003).
Gaertner, et. al., Bioconjug. Chem. 3: 262-268 (1992).
Geoghegan, K. & Stroh, J., Bioconjug. Chem. 3:138-146 (1992).
Gaertner, et al., J. Biol. Chem. 269:7224-7230 (1994).
Jencks, W. P., J. Am. Chem. Soc. 81, 475-481 (1959).
Pepinsky R.B., et al., J. Pharmcol. & Exp. Ther. 297(3):1059-66 (2001).
Preneta, A.Z., Protein Purification Methods, a Practical Approach (Harris & Angal, Eds.) IRL Press 1989, 293-306.
Veronese, et al., App. Biochem. Biotech. 11: 141-52 (1985).
Shapiro and Recht (2001) New Engl. J. Med. 344:1997-2008.
Zalipsky, Bioconjugate Chem. 6: 150-165 (1995).
Mahal, L. K., et al., Science 276:1125-1128 (1997).
Eppstein, et al., Proc. Natl. Acad. Sci. U.S.A., 82: 3688-3692 (1985).
Delgado, et al., Critical Reviews in Therapeutic Drug Carrier Systems 9: 249-304 (1992).
Hwang, et al., Proc. Natl. Acad. Sci. U.S.A., 77: 4030-4034 (1980).
Wong, S.S and Wong, L.C., Enzyme Microb. Technol. 14: 866-874 (1992).
Scouten, Methods in Enzymology 135: 30-65 (1987).
Harris, Macromol. Chem. Phys. C25: 325-373 (1985).
Spencer, et al., J. Biol. Chem., 263:7862-7867 (1988).
Sawhney, et al., Macromolecules, 26:581-587 (1993).
Hang H. and Bertozzi C., Acc. Chem. Res. 34: 727-736 (2001).
Carrasco M. and Brown R., J. Org. Chem. 68: 8853-8858 (2003).
Rosenthal, G., Life Sci. 60: 1635-1641 (1997).
Woghiren, et al. Bioconj. Chem. 4:314-316 (1993).
Wang, Q., et al., J. Am. Chem. Soc. 125, 3192-3193 (2003).
Kogan, Synthetic Comm. 22:2417-2424 (1992).
Romani, et al., Chemistry of Peptides and Proteins 2:29-34 (1984).
Goodson R.J. and Katre N.V., Nature Biotechnology 8:343-346 (1990).
Knauf, M.J. et al., J. Biol. Chem., 263:15064-15070 (1988).
Kim, et. al., J Microbiol Biotechnol., 14(4), 810-815, (2004).
Pawelec, G. et al., Immunobiology 174: 67-75 (1987).
Harris, et al. J. Polym. Sci.: Polymer Chem. Ed. 22:341-352 (1984).
Robb, et al., Proc Natl Acad Sci USA 81:6486-6490 (1984).
Tian, et al., Proc Natl Acad Sci 111(5): pp. 1766-1771 (2014).
Arenas-Ramirez, N. et al., Trends in Immunology, 36:763-777 (2015).
Whittington, et al., Drugs, 46(3): pp. 446-514 (1993).
Mamot, C, et al., Cancer Res. 63: 3154-3161 (2003).
Nielsen, U.B., et al., Biochim. Biophys. Acta 1591:109-118 (2002).
Park, J.W., et al., Clin. Cancer Res. 8:1172-1181 (2002).
Klein, C. et al., Oncoimmunology V6(3):15 pages (http://dx.doi.org/10.1080/2162402X.2016.1277306) (2017).
Ferrara, P. et al., FEBS Letters, 226:47-52 (1987).
Park, J.W., et al., Proc. Natl. Acad. Sci. USA 92:1327-1331 (1995).
Stauber, D.J. et al., PNAS 103:2788-2793 (2006).
Charych, D. et al., PLOS One 12(7):1-24 https://doi.org/10.1371/journal.pone.0179431 (2017).
Ellman, J.A., et al., Science, 255:197-200 (1992).
Cech, T.R. Science, 236:1532-1539 (1987).
Illangakekare, et al., 1995 Science 267:643-647.
Lohse, P.A. and Szostak, J.W., 1996, Nature 381:442-444.
McCorkle, G.M. et al., Concepts Biochem. 64:221-226 (1987).
Hecht, S.M. Acc. Chem. Res. 1992, 25:545-552.
Heckler, T.G. et al., Biochemistry 1988, 27:7254-7262.
Hecht, S.M. et al., J. Biol. Chem. 1978, 253:4517-4520.
Cornish, V.W. et al., Angew. Chem. Int. Ed. Engl. 34:621-633 (1995).
Robertson, S.A. et al., J. Am. Chem. Soc. 113:2722-2729 (1991).
Joppich, M. and Luisi P.L. Makromol. Chem. 180:1381-1384 (1979).
Abuchowski, A. et al. Cancer Biochem. Biophys. 7:175-186 (1984).
Bain, J.D. et al. Nature 356:537-539 (1992).
Gallivan, J. P. et al., Chem. Biol. 4:739-749 (1997).
Turcatti, et al. J. Biol. Chem. 271:19991-19998 (1996).
Olson, K. et al. "Preparation and Characterization of Poly(ethylene glycol)ated Human Growth Hormone Antagonist" Chapter 12 in Poly(ethylene glycol) Chemistry & Biological Applications, pp. 170-181, Harris & Zalipsky Eds., American Chemical Society, Washington, D.C., 1997.
Saks, M.E. et al. J. Biol. Chem. 271:23169-23175 (1996).
Hohsaka, T. et al. J. Am. Chem. Soc. 121:34-40 (1999).
Andresz, H. et al. Makromol. Chem. 179:301-312 (1978).
Buckmann, A.F. and Morr, M. Makromol. Chem. 182:1379-1384 (1981).
Zalipsky, S. et al. Eur. Polym. J. 19:1177-1183 (1983).
Tornoe, et al., J. Org. Chem. 67:3057-3064 (2002).
Rostovtsev, et al., Angew. Chem. Int. Ed. 41:2596-2599 (2002).
Yang, J.C. et al., Cancer, 76:687-694 (1995).
Hortobagyi, New Engl. J. Med. 339:974-984 (1998).
Catalona, New Engl. J. Med. 331:996-1004 (1994).
Naylor and Hadden Int. Immunopharmacol. 3:1205-1215 (2003).
Le Chevalier et al. (The Int. Adjuvant Lung Cancer Trial Collaborative Group) New Engl. J. Med. 350:351-360 (2004).
Slamon, et al. New Engl. J. Med. 344:783-792 (2001).
Kudelka, et al. New Engl. J. Med. 338:991-992 (1998).
Van Netten, et al. New Engl. J. Med. 334:920-921 (1996).
Rao, et al. Leuk. Lymphoma 44:715-718 (2003).
Lane, et al. J. Cutan. Pathol. 29:608-612 (2002).
Ogawa, et al., J. Am. Chem. Soc., 122:3274-3287 (2000).
Batzer, et al., Nucleic Acid Res. 19:5081 (1991).
Ohtsuka, et al., J. Biol. Chem. 260:2605-2608 (1985).
Rossolini, et al., Mol. Cell. Probes 8:91-98 (1994).
Mcminn et al., J. Am. Chem. Soc., 121:11585-6 (1999).
Robb, R.J. et al. J. Exp. Med. 154:1455-1474 (1981).
Guckian and Kool, Angew. Chem. Int. Ed. Engl., 36, 2825-2828 (1997).
Ju, G. et al., J. Biol. Chem., 262:5723-5731 (1987).
Kool, Curr. Opin. Chem. Biol., 4:602-608 (2000).
Weir, M.P. et al., Biochemistry, 27:6883-6892 (1988).
Parisi, G. et al., Nature Communications,11:660 (https://doi.org/10.1038/s41467-019-12901-3) (2020).
Mehvar, R., J. Pharm. Pharmaceut. Sci., 3(1):125-136 (2000).
Piccirilli, et al., Nature, 343:33-37 (1990).
Switzer, et al., J. Am. Chem. Soc., 111:8322-8323 (1989).
Wu, Y., et al., J. Am. Chem. Soc. 124:14626-14630 (2002).
Gillam & Smith, Gene 8:81-97 (1979).
Roberts, et al., Nature, 328:731-734 (1987).
Schneider, E., et al., Protein Expr. Purif. 6:10-14 (1995).
Sharma, M. et al., Nature Communications, 11:661 (https://doi.org/10.1038/s41467-020-14471-1) (2020).
Moore, et al., J. Mol. Biol., 298:195-209 (2000).
Hirao, I. et al., Nature Biotechnology 20:177-182 (2002).
Hohsaka, et al., J. Am. Chem. Soc. 121, 12194-12195 (1999).
Magliery, et al., J. Mol. Biol. 307:755-769 (2001).
Ma, et al., Biochemistry, 32:7939-7945 (1993).
Anderson, et al., Chemistry and Biology, 9:237-244 (2002).
Chin, J. W., et al., Science 301:964-967 (2003).
Chin, J. W., et al., J. Am. Chem. Soc. 124:9026-9027 (2002).
Zhang, et al., Biochemistry, 42:6735-6746 (2003).
Kiick, et al., PNAS 99:19-24 (2002).
Wang, et al., Proc. Natl. Acad. Sci., 100:56-61 (2003).

(56) References Cited

OTHER PUBLICATIONS

Chin, et al., Proc. Natl. Acad. Sci., 99:11020-11024 (2002).
Wang, et al., Science 292:498-500 (2001).
Cornish, et al., J. Am. Chem. Soc., 118:8150-8151 (1996).
Dougherty, Current Opinion in Chemical Biology, 4:645-652 (2000).
Shao, J. and Tam, J, J. Am. Chem. Soc., 117 (14) 3893-3899 (1995).
Deiters, A., et al., J. Am. Chem. Soc. 125: 11782-11783 (2003).
Kayser, B., et al., Tetrahedron 53(7): 2475-2484 (1997).
Langer, Chemtech, 12: 98-105 (1982).
Liu, D. R., and Schultz, P. G. (1999) Proc. Natl. Acad. Sci. U.S.A. 96:4780-4785.
Pastrnak, M., et al., (2000) Helv. Chim. Acta 83:2277-2286.
Ohno, S., et al., (1998) J. Biochem. 124:1065-1068.
Kowal, A.K., et al., (2001) Proc. Natl. Acad. Sci. 98:2268-2273.
Edwards, H., and Schimmel, P. (1990) Mol. Cell. Biol. 10:1633-1641.
Sakamoto, K., et al., (2002) Nucleic Acids Res. 30:4692-4699.
Bowie, J.U. et al., Science 253:164-70, (1991).
Dahiyat and Mayo, Protein Sci 5: 895-903 (1996).
Desjarlais and Handel, Protein Science 4: 2006-2018 (1995).
Harbury et al., PNAS USA 92:8408-8412 (1995).
Kono, H. and Doi, J., Proteins: Structure, Function and Genetics 19:244-255 (1994).
Hellinga and Richards, PNAS USA 91:5803-5807 (1994).
Jones, Protein Science 3: 567-574 (1994).
Palva et al., Gene 22:229-235 (1983).
Mosbach et al., Nature 302:543-545 (1983).
Okkels, Ann. New York Acad. Sci. 202-207 (1996).
Cate, et al., Cell 45:685-698 (1986).
Coloma, M.J., et al. (1992) J. Immunol. Methods 152:89-104.
Hagenbuchle, O., et al., Nature 289:643-646 (1981).
Valls, L.A., et al., Cell 48:887-897 (1987).
Egel-Mitani, M. et al., Yeast 6:127-137 (1990).
Sartore, et al., Appl. Biochem. Biotech., 27:55-63 (1991).
Barany, F., Proc. Natl. Acad. Sci. 88:189-193 (1991).
Tondelli, et al. J. Controlled Release 1:251-257 (1985).
Raibaud, O. and Schwartz, M., Ann. Rev. Genet. (1984) 18:173-206.
Sauve, K. et al., Proc. Natl. Acad. Sci. USA 88:4636-4640 (1991).
Goeddel, et al., Nucleic Acids Research (1980) 8:4057-4073.
Yelverton, et al., Nucleic Acids Research (1981) 9:731-741.
Weissmann, C. "The cloning of interferon and other mistakes" in Gresser, I. (Ed.), Interferon, vol. 3, Academic Press, New York (1981), pp. 101-134.
Shimatake, H. and Rosenberg, M., Nature (1981) 292:128-132.
Amann, et al., Gene (1983) 25:167-178.
De Boer, et al., Proc. Natl. Acad. Sci. USA (1983) 80:21-25.
Studier, F.W. and Moffatt, B., J. Mol. Biol. (1986) 189:113-130.
Tabor, S. and Richardson, C.C., Proc Natl. Acad. Sci. USA (1985) 82:1074-1078.
Shine, J. and Dalgarno, L., Nature (1975) 254:34-38.
Steitz., J.A. "Genetic signals and nucleotide sequences in messenger RNA", Chapter 9, pp. 349-399 in Biological Regulation and Development: Gene Expression (Ed. R. F. Goldberger, 1979).
Beauchamp, et al., Anal. Biochem. 131:25-33 (1983).
Pitha, et al. Eur. J Biochem. 94:11-18 (1979).
Elling, L. and Kula, M., Biotech. Appl. Biochem. 13:354-362 (1991).
Debinski, et al. (1993) J. Biol. Chem. 268:14065-14070.
Kreitman and Pastan (1993) Bioconjug. Chem. 4:581-585.
Buchner, et al., (1992) Anal. Biochem. 205:263-270.
Noren, C.J., et al., Science 244:182-188 (1989).
Nowak, M.W., et al., Science 268:439-442 (1995).
Bain, J.D., et al., J. Am Chem Soc, 111:8013-8014 (1989).
Budisa, N., et al., FASEB J. 13:41-51 (1999).
Ellman, J., et al., Methods in Enz., 202:301-337 (1991).
Mendel, D., et al., Annu Rev Biophys. Biomol Struct. 24:435-62 (1995).
Sayers, J.R., et al., Nucleic Acids Res, 16:791-802 (1988).
Kobayashi, et al., (2003) Nature Structural Biology 10:425-432.
D. H. Charych et al: "NKTR-214, an Engineered Cytokine with Biased IL2 Receptor Binding, Increased Tumor Exposure, and Marked Efficacy in Mouse Tumor Models", Clinical Cancer Research,vol. 22, No. 3, Feb. 1, 2016, pp. 680-690.
Wang X. et al., Science, V310:1159-1163 (2005) and Supporting Online Material.
Joseph, I.B. et al., AACR Poster "THOR-707, a novel not-alpha IL-2, elicits durable pharmacodynamic responses in non-human primates and, efficacy as single agent and in combination with anti-PD1 in multiple syngeneic mouse models" presented at the American Association of Cancer Research (AACR) meeting, Mar. 27, 2019.
Joseph, I.B. et al., Cancer Res "Abstract 3258: THOR-707, a novel not-alpha IL-2, elicits durable pharmacodynamic responses in non-human primates and efficacy as single agent and in combination with anti PD-1 in multiple syngeneic mouse models" 79(13_Supplement): 3258 (2019).
Raeber M.E. et al., Sci. Transl. Med. "Interleukin-2-based therapies in cancer" 14, eabo5409, Nov. 9, 2022.
Lefevre, K., Biospace report, "Industry's IL-2 Struggles Continue as Sanofi Drops Program" Oct. 28, 2022 (https://www.biospace.com/article/sanofi-drops-program-releases-q3-report/).

* cited by examiner

FIGURE 5

SEQ ID NO: 24

FIGURE 6

βγ Activity Assay

αβγ Activity Assay

SEQUENCE LISTING

<160> NUMBER OF SEQ ID NOS: 26

<210> SEQ ID NO 1

```
<211> LENGTH: 153
<212> TYPE: PRT
<213> ORGANISM: Eukaryot

<400> SEQUENCE: 1
```

Met Tyr Arg Met Gln Leu Leu Ser Cys Ile Ala Leu Ser Leu Ala Leu
1               5                   10                  15

Val Thr Asn Ser Ala Pro Thr Ser Ser Thr Lys Lys Thr Gln Leu
            20                  25                  30

Gln Leu Glu His Leu Leu Leu Asp Leu Gln Met Ile Leu Asn Gly Ile
                35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
                100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
        130                 135                 140

Cys Gln Ser Ile Ile Ser Thr Leu Thr
145                 150

```
<210> SEQ ID NO 2
<211> LENGTH: 133
<212> TYPE: PRT
<213> ORGANISM: Eukaryot

<400> SEQUENCE: 2
```

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
                35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

```
<210> SEQ ID NO 3
<211> LENGTH: 133
<212> TYPE: PRT
<213> ORGANISM: E. Coli

<400> SEQUENCE: 3
```

-continued

```
Met Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
            115                 120                 125

Ile Ser Thr Leu Thr
        130
```

<210> SEQ ID NO 4
<211> LENGTH: 399
<212> TYPE: DNA
<213> ORGANISM: E. Coli

<400> SEQUENCE: 4

```
atgccgacca gcagtagcac caagaaaact cagctgcagc tggagcatct gctgctggat    60
ttacagatga ttctgaatgg cattaataat acaaaaatc cgaaactgac ccgcatgctg    120
accttcaagt tctacatgcc gaagaaggcc accgaactga agcatctgca gtgtttagaa    180
gaggaactga agccgctgga agaggtgctg aatttagccc agagcaaaaa cttccatctg    240
cgcccgcgcg atttaattag caatattaac gtgattgtgc tggaactgaa aggcagcgag    300
accaccttta tgtgcgagta cgcagatgag accgccacca tcgtggaatt tttaaaccgc    360
tggatcaccttcagccagag tatcattagc actttaacc                            399
```

<210> SEQ ID NO 5
<211> LENGTH: 134
<212> TYPE: PRT
<213> ORGANISM: E. Coli

<400> SEQUENCE: 5

```
Met Ala Pro Thr Ser Ser Ser Thr Lys Lys Thr Gln Leu Gln Leu Glu
1               5                   10                  15

His Leu Leu Leu Asp Leu Gln Met Ile Leu Asn Gly Ile Asn Asn Tyr
            20                  25                  30

Lys Asn Pro Lys Leu Thr Arg Met Leu Thr Phe Lys Phe Tyr Met Pro
        35                  40                  45

Lys Lys Ala Thr Glu Leu Lys His Leu Gln Cys Leu Glu Glu Glu Leu
    50                  55                  60

Lys Pro Leu Glu Glu Val Leu Asn Leu Ala Gln Ser Lys Asn Phe His
65                  70                  75                  80

Leu Arg Pro Arg Asp Leu Ile Ser Asn Ile Asn Val Ile Val Leu Glu
                85                  90                  95

Leu Lys Gly Ser Glu Thr Thr Phe Met Cys Glu Tyr Ala Asp Glu Thr
            100                 105                 110

Ala Thr Ile Val Glu Phe Leu Asn Arg Trp Ile Thr Phe Ser Gln Ser
```

```
                115                 120                 125
Ile Ile Ser Thr Leu Thr
            130

<210> SEQ ID NO 6
<211> LENGTH: 402
<212> TYPE: DNA
<213> ORGANISM: Human

<400> SEQUENCE: 6
atggcaccga ccagcagtag caccaagaaa actcagctgc agctggagca tctgctgctg      60
gatttacaga tgattctgaa tggcattaat aattacaaaa atccgaaact gacccgcatg     120
ctgaccttca gttctacat gccgaagaag ccaccgaac tgaagcatct gcagtgttta      180
gaagaggaac tgaagccgct ggaagaggtg ctgaatttag cccagagcaa aaacttccat     240
ctgcgcccgc gcgatttaat tagcaatatt aacgtgattg tgctggaact gaaaggcagc     300
gagaccacct ttatgtgcga gtacgcagat gagaccgcca ccatcgtgga atttttaaac     360
cgctggatca ccttcagcca gagtatcatt agcactttaa cc                        402

<210> SEQ ID NO 7
<211> LENGTH: 132
<212> TYPE: PRT
<213> ORGANISM: Human

<400> SEQUENCE: 7

Met Thr Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
        130

<210> SEQ ID NO 8
<211> LENGTH: 396
<212> TYPE: DNA
<213> ORGANISM: Human

<400> SEQUENCE: 8
atgaccagca gtagcaccaa gaaaactcag ctgcagctgg agcatctgct gctggattta      60
cagatgattc tgaatggcat taataattac aaaaatccga aactgacccg catgctgacc     120
ttcaagttct acatgccgaa gaaggccacc gaactgaagc atctgcagtg tttagaagag     180
gaactgaagc cgctggaaga ggtgctgaat ttagcccaga gcaaaaactt ccatctgcgc     240
ccgcgcgatt taattagcaa tattaacgtg attgtgctgg aactgaaagg cagcgagacc     300
```

```
accttatgt gcgagtacgc agatgagacc gccaccatcg tggaatttt aaaccgctgg      360 atcaccttca gccagagtat cattagcact ttaacc                              396
```

<210> SEQ ID NO 9
<211> LENGTH: 133
<212> TYPE: PRT
<213> ORGANISM: Human
<220> FEATURE:
<221> NAME/KEY: MISC_FEATURE
<222> LOCATION: (42)..(42)
<223> OTHER INFORMATION: Xaa = *U = Unnatural Amino Acid

<400> SEQUENCE: 9

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Xaa Lys Phe Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 10
<211> LENGTH: 133
<212> TYPE: PRT
<213> ORGANISM: Human
<220> FEATURE:
<221> NAME/KEY: misc_feature
<222> LOCATION: (44)..(44)
<223> OTHER INFORMATION: Xaa = *U = Unnatural Amino Acid

<400> SEQUENCE: 10

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Xaa Tyr Met Pro Lys
            35                  40                  45

Lys Ala Thr Glu Leu Lys His Leu Gln Cys Leu Glu Glu Glu Leu Lys
        50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130

<210> SEQ ID NO 11
<211> LENGTH: 133
<212> TYPE: PRT
<213> ORGANISM: Human
<220> FEATURE:
<221> NAME/KEY: misc_feature
<222> LOCATION: (45)..(45)
<223> OTHER INFORMATION: Xaa = *U = Unnatural Amino Acid

<400> SEQUENCE: 11

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Xaa Met Pro Lys
            35                  40                  45

Lys Ala Thr Glu Leu Lys His Leu Gln Cys Leu Glu Glu Glu Leu Lys
            50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
    130

<210> SEQ ID NO 12
<211> LENGTH: 133
<212> TYPE: PRT
<213> ORGANISM: Human
<220> FEATURE:
<221> NAME/KEY: misc_feature
<222> LOCATION: (65)..(65)
<223> OTHER INFORMATION: Xaa = *U = Unnatural Amino Acid

<400> SEQUENCE: 12

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
            50                  55                  60

Xaa Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

```
Ile Ser Thr Leu Thr
    130
```

<210> SEQ ID NO 13
<211> LENGTH: 133
<212> TYPE: PRT
<213> ORGANISM: Human
<220> FEATURE:
<221> NAME/KEY: misc_feature
<222> LOCATION: (72)..(72)
<223> OTHER INFORMATION: Xaa = *U = Unnatural Amino Acid

<400> SEQUENCE: 13

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Xaa Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130
```

<210> SEQ ID NO 14
<211> LENGTH: 133
<212> TYPE: PRT
<213> ORGANISM: Human
<220> FEATURE:
<221> NAME/KEY: misc_feature
<222> LOCATION: (61)..(61)
<223> OTHER INFORMATION: Xaa = *U = Unnatural Amino Acid

<400> SEQUENCE: 14

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Xaa Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
```

```
           130

<210> SEQ ID NO 15
<211> LENGTH: 133
<212> TYPE: PRT
<213> ORGANISM: Human
<220> FEATURE:
<221> NAME/KEY: misc_feature
<222> LOCATION: (62)..(62)
<223> OTHER INFORMATION: Xaa = *U = Unnatural Amino Acid
<220> FEATURE:
<221> NAME/KEY: misc_feature
<222> LOCATION: (68)..(68)
<223> OTHER INFORMATION: Xaa = *U = Unnatural Amino Acid

<400> SEQUENCE: 15

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Xaa Leu Lys
    50                  55                  60

Pro Leu Glu Xaa Val Leu Asn Leu Ala Gln Ser Lys Asn Phe His Leu
65              70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 16
<211> LENGTH: 133
<212> TYPE: PRT
<213> ORGANISM: Human
<220> FEATURE:
<221> NAME/KEY: misc_feature
<222> LOCATION: (35)..(35)
<223> OTHER INFORMATION: Xaa = *U = Unnatural Amino Acid

<400> SEQUENCE: 16

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Xaa Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65              70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
```

Ile Ser Thr Leu Thr
        130

<210> SEQ ID NO 17
<211> LENGTH: 133
<212> TYPE: PRT
<213> ORGANISM: Human
<220> FEATURE:
<221> NAME/KEY: misc_feature
<222> LOCATION: (38)..(38)
<223> OTHER INFORMATION: Xaa = *U = Unnatural Amino Acid

<400> SEQUENCE: 17

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Xaa Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 18
<211> LENGTH: 133
<212> TYPE: PRT
<213> ORGANISM: Human
<220> FEATURE:
<221> NAME/KEY: misc_feature
<222> LOCATION: (43)..(43)
<223> OTHER INFORMATION: Xaa = *U = Unnatural Amino Acid

<400> SEQUENCE: 18

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Xaa Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

```
Ile Ser Thr Leu Thr
    130

<210> SEQ ID NO 19
<211> LENGTH: 133
<212> TYPE: PRT
<213> ORGANISM: Human
<220> FEATURE:
<221> NAME/KEY: misc_feature
<222> LOCATION: (37)..(37)
<223> OTHER INFORMATION: Xaa = *U = Unnatural Amino Acid

<400> SEQUENCE: 19

Ala Pro Thr Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Xaa Arg Met Leu Thr Phe Lys Phe Tyr Met Pro Lys
            35                  40                  45

Lys Ala Thr Glu Leu Lys His Leu Gln Cys Leu Glu Glu Glu Leu Lys
            50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
    130

<210> SEQ ID NO 20
<211> LENGTH: 133
<212> TYPE: PRT
<213> ORGANISM: Human
<220> FEATURE:
<221> NAME/KEY: misc_feature
<222> LOCATION: (3)..(3)
<223> OTHER INFORMATION: Xaa = *U = Unnatural Amino Acid

<400> SEQUENCE: 20

Ala Pro Xaa Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
            50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125
```

```
Ile Ser Thr Leu Thr
    130
```

<210> SEQ ID NO 21
<211> LENGTH: 133
<212> TYPE: PRT
<213> ORGANISM: Human
<220> FEATURE:
<221> NAME/KEY: misc_feature
<222> LOCATION: (64)..(64)
<223> OTHER INFORMATION: Xaa = *U = Unnatural Amino Acid

<400> SEQUENCE: 21

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Xaa
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
    130
```

<210> SEQ ID NO 22
<211> LENGTH: 133
<212> TYPE: PRT
<213> ORGANISM: Human
<220> FEATURE:
<221> NAME/KEY: misc_feature
<222> LOCATION: (68)..(68)
<223> OTHER INFORMATION: Xaa = *U = Unnatural Amino Acid

<400> SEQUENCE: 22

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Xaa Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
```

<210> SEQ ID NO 23
<211> LENGTH: 133
<212> TYPE: PRT
<213> ORGANISM: Human
<220> FEATURE:
<221> NAME/KEY: misc_feature
<222> LOCATION: (107)..(107)
<223> OTHER INFORMATION: Xaa = *U = Unnatural Amino Acid

<400> SEQUENCE: 23

```
Ala Pro Thr Ser Ser Ser Thr Lys Lys Thr Gln Leu Gln Leu Glu His
1               5                   10                  15
Leu Leu Leu Asp Leu Gln Met Ile Leu Asn Gly Ile Asn Asn Tyr Lys
            20                  25                  30
Asn Pro Lys Leu Thr Arg Met Leu Thr Phe Lys Phe Tyr Met Pro Lys
        35                  40                  45
Lys Ala Thr Glu Leu Lys His Leu Gln Cys Leu Glu Glu Glu Leu Lys
    50                  55                  60
Pro Leu Glu Glu Val Leu Asn Leu Ala Gln Ser Lys Asn Phe His Leu
65                  70                  75                  80
Arg Pro Arg Asp Leu Ile Ser Asn Ile Asn Val Ile Val Leu Glu Leu
                85                  90                  95
Lys Gly Ser Glu Thr Thr Phe Met Cys Glu Xaa Ala Asp Glu Thr Ala
            100                 105                 110
Thr Ile Val Glu Phe Leu Asn Arg Trp Ile Thr Phe Cys Gln Ser Ile
        115                 120                 125
Ile Ser Thr Leu Thr
        130
```

<210> SEQ ID NO 24
<211> LENGTH: 891
<212> TYPE: DNA
<213> ORGANISM: Cricetulus griseus

<400> SEQUENCE: 24

```
cagagctgga agtggtgaaa agcagcgtgg ggtgttaact gccaatggtt tcctggtccc      60
agccacattg taaatcacct ggtgagggct aaatgcaagg aggtgacgct tcacaaggat     120
gggccactgg gcgagacggt gctggagtgc tacaactgcg gctgccgcaa cgtcttcctg     180
ctaggcttca tccctgccaa ggccgactcg gtggtggtgt tgctgtgcag tgagcttcct     240
gcagcagggt ggagtggggc ggggcaggga ctgttgggac ccaagagggc gcttctgtgt     300
gtactctggt caaattcaaa acgaagtctg gcttggtgta gtggtgccag cttttaatcc     360
cagcactggg gaggcagaga caggaggacc tgtgagttca aggccagcct ggtctacata     420
gagagtccag acagccaga gctacatagt gagcccctgt ctcttaaaaa aaaaaaaaa      480
aaaaaaggaa gcaagcaagt ctgctgtgag ctggggcctc ctgggcccag tcccaacctg     540
ttctcctgcc ccacacctgc acaggcagcc ctgtgccagc agagcagcc tgaaggacat      600
caactgggac agctcccagt ggcagcccct gatccaggac cggtgcttcc tgtcatggct     660
ggtcaagatt ccctcagagc aggaacagct acgggcacgg cagatcactg cccagcagat     720
caacaagctg gaggagcttt ggaaggtgag ccatccagag atgctttccc aagtctgcag     780
agacaaaagc acacagcctg cctggcatag acctttggga catggggagg aagggcatga     840
cctgagggag ctcttcggga actgagtggt ctttctgtac tagctgaagg g              891
```

```
<210> SEQ ID NO 25
<211> LENGTH: 86
<212> TYPE: DNA
<213> ORGANISM: Cricetulus griseus

<400> SEQUENCE: 25
ccagccatga caggaagcac cggtcctgga tcaggggctg ccactgggag ctcccactgg      60
gagctgtccc acttgatggg cccatg                                          86

<210> SEQ ID NO 26
<211> LENGTH: 52
<212> TYPE: DNA
<213> ORGANISM: Cricetulus griseus

<400> SEQUENCE: 26
ccagccatga cagggctgc cactgcgagc tgtcccactt gatgtccttc ct              52
```

INTERLEUKIN-2 POLYPEPTIDE CONJUGATES AND THEIR USES

REFERENCE TO RELATED APPLICATIONS

This application is a U.S. National Stage entry under 35 U.S.C. §371 of International Application No. PCT/US2019/050709, filed on Sep. 11, 2019, designating the United States of America and published in English on Mar. 19, 2020, which in turn claims priority to U.S. Provisional Application Nos. 62/729,925 and 62/815,964, filed on Sep. 11, 2018 and Mar. 8, 2019 respectively, each of which is hereby incorporated by reference in its entirety.

SEQUENCE LISTING

The instant application contains a Sequence Listing which has been submitted in ASCII format via EFS-Web and is hereby incorporated by reference in its entirety. The ASCII copy was created on Jul. 18, 2022, is named AMBX_0227_02US_ST25.txt and is 29,406 bytes in size.

FIELD OF THE INVENTION

The present invention provides methods for modulating the biological activities of interleukin-2, and, in particular, modulating specific receptor interactions by using an interleukin-2 (IL-2) variant conjugated to a polymer at positions in the amino acid sequence of the IL-2 protein that interact with the interleukin-2 receptor.

BACKGROUND OF THE INVENTION

Cancer is one of the most significant health conditions. In the United States, cancer is second only to heart disease in mortality accounting for one of four deaths. The incidence of cancer is widely expected to increase as the US population ages, further augmenting the impact of this condition. The current treatment regimens for cancer established in the 1970s and 1980s, have not changed dramatically. These treatments, which include chemotherapy, radiation and other modalities including newer targeted therapies, have shown limited overall survival benefit when utilized in most advanced stage common cancers since, among other things, these therapies primarily target tumor bulk.

More specifically, conventional cancer diagnosis and therapies to date have attempted to selectively detect and eradicate neoplastic cells that are largely fast-growing (i.e., cells that form the tumor bulk). Standard oncology regimens have often been largely designed to administer the highest dose of irradiation or a chemotherapeutic agent without undue toxicity, i.e., often referred to as the "maximum tolerated dose" (MTD) or "no observed adverse effect level" (NOAEL). Many conventional cancer chemotherapies (e.g., alkylating agents such as cyclophosphamide, antimetabolites such as 5-Fluorouracil, and plant alkaloids such as vincristine) and conventional irradiation therapies exert their toxic effects on cancer cells largely by interfering with cellular mechanisms involved in cell growth and DNA replication. Chemotherapy protocols also often involve administration of a combination of chemotherapeutic agents in an attempt to increase the efficacy of treatment. Despite the availability of a large variety of chemotherapeutic agents, these therapies have many drawbacks. For example, chemotherapeutic agents are notoriously toxic due to non-specific side effects on fast-growing cells whether normal or malignant; e.g. chemotherapeutic agents cause significant, and often dangerous, side effects, including bone marrow depression, immunosuppression, and gastrointestinal distress, etc.

Cancer Stem Cells

Cancer stem cells comprise a unique subpopulation (often 0.1-10% or so) of a tumor that, relative to the remaining 90% or so of the tumor (i.e., the tumor bulk), are more tumorigenic, relatively more slow-growing or quiescent, and often relatively more chemoresistant than the tumor bulk. Given that conventional therapies and regimens have, in large part, been designed to attack rapidly proliferating cells (i.e. those cancer cells that comprise the tumor bulk), cancer stem cells which are often slow-growing may be relatively more resistant than faster growing tumor bulk to conventional therapies and regimens. Cancer stem cells can express other features which make them relatively chemoresistant such as multi-drug resistance and anti-apoptotic pathways. The aforementioned would constitute a key reason for the failure of standard oncology treatment regimens to ensure long-term benefit in most patients with advanced stage cancers—i.e. the failure to adequately target and eradicate cancer stem cells. In some instances, a cancer stem cell(s) is the founder cell of a tumor (i.e., it is the progenitor of the cancer cells that comprise the tumor bulk).

IL-2 has been used in treating several cancers such as renal cell carcinoma and metastatic melanoma. The commercially available IL-2 Aldesleukin® is a recombinant protein that is nonglycosylated and has a removed alanine-1 and a replaced residue cysteine-125 by serine-125 (Whittington et al., 1993). Although IL-2 is the earliest FDA approved cytokine in cancer treatment, it has been shown that IL-2 exhibited severe side effects when used in high-dose. This greatly limited its application on potential patients. The underlying mechanism of the severe side effects has been attributed to the binding of IL-2 to one of its receptors, IL-2Rα. In general, IL-2 not only can form a heterotrimeric complex with its receptors including IL-2Rα (or CD25), IL-2Rβ (or CD122) and IL-2Rγ (or CD132) when all of three receptors are present in the tissue, but also can form heterodimeric complex with IL-2Rβ and IL-2Rγ. In clinical settings, when high dose of IL-2 is used, IL-2 starts to bind IL-2αβγ, which is a major receptor form in $T_{reg}$ cells. The suppressive effect of $T_{reg}$ cells causes undesired effects of IL-2 application in cancer immunotherapy. To mitigate the side effects of IL-2, many approaches have been employed previously. One form of IL-2 was made by Nektar that uses 6 PEGylated lysines to mask the IL2Rα binding region on the IL-2 surface (Charych et al., 2016). This form of PEGylated IL-2 has an extended half-life, comprises a mixture of single and multiple PEGylated forms, contains a very large amount of PEG, but also showed improved side effects. However, the results from activity studies showed that the effective form of PEGylated IL-2 in this heterogeneous 6-PEGylated IL-2 mixture is the single PEGylated form only. Therefore, a more effective PEGylated IL-2 with a homogeneous well-defined composition of the product that modulates side effects of IL-2 is needed.

The ability to incorporate non-genetically encoded amino acids into proteins permits the introduction of chemical functional groups that could provide valuable alternatives to the naturally-occurring functional groups, such as the epsilon —$NH_2$ of lysine, the sulfhydryl —SH of cysteine, the imino group of histidine, etc. Certain chemical functional groups are known to be inert to the functional groups found in the 20 common, genetically-encoded amino acids but react cleanly and efficiently to form stable linkages. Azide and acetylene groups, for example, are known in the art to undergo a Huisgen [3+2] cycloaddition reaction in aqueous conditions in the presence of a catalytic amount of copper. See, e.g., Tornoe, et al., (2002) J. Org. Chem. 67:3057-3064; and, Rostovtsev, et al., (2002) Angew. Chem. Int. Ed. 41:2596-2599. By introducing an azide moiety into a protein structure, for example, one is able to incorporate a functional group that is chemically inert to amines, sulfhydryls, carboxylic acids, hydroxyl groups found in proteins, but that also reacts smoothly and efficiently with an acetylene moiety to form a cycloaddition product. Importantly, in the absence of the acetylene moiety, the azide remains chemically inert and unreactive in the presence of other protein side chains and under physiological conditions.

The present invention addresses, among other things, problems associated with the activity and production of IL-2 polypeptide conjugates, and also addresses the production of IL-2 polypeptides with improved biological or pharmacological properties, such as enhanced activity against tumors and/or improved conjugation and/or improved therapeutic half-life. The IL-2 polypeptides of the present invention target both Treg cells known to express the trimeric IL-2 receptors, (alpha, beta, and gamma), and CD8 cells which primarily express beta and gamma dimers of IL-2 receptors. The IL-2 polypeptides of the present invention reduce binding to the alpha receptor of Treg cells and promote biased binding to the beta and gamma dimers of CD8 cells, thereby providing improved therapeutic application and improved prognosis for diseases or conditions in which IL-2 receptor alpha is highly expressed.

SUMMARY OF THE INVENTION

The present invention relates to Interleukin-2 (IL-2) polypeptides with one or more non-naturally encoded amino acids. The invention further relates to IL-2 polypeptide conjugates with one or more non-naturally encoded amino acids. The invention further relates to IL-2 polypeptide conjugates wherein a water-soluble polymer, such as PEG, is conjugated to an IL-2 variant through one or more non-naturally encoded amino acids within the IL-2 variant. The invention further relates to IL-2 polypeptide conjugates with one or more non-naturally encoded amino acids and one or more natural amino acid substitutions. The invention further relates to IL-2 polypeptide conjugates with one or more non-naturally encoded amino acids and one or more natural amino acid substitutions and one or more PEG molecules.

The present invention provides methods of modulating the receptor interactions of an IL-2 polypeptide of the present invention. The present invention provides methods of inhibiting or reducing the interaction of PEGylated-IL-2 with the IL2Rα subunit of the trimeric IL-2 receptor using a PEGylated IL-2 polypeptide of the present invention.

In one embodiment, the PEG-IL-2 is monopegylated. In one embodiment, the PEG-IL-2 is dipegylated. In one embodiment, the PEG-IL-2 has more than two (2) poly (ethylene) glycol molecules attached to it. Another embodiment of the present invention provides methods of using PEG-IL-2 polypeptides of the present invention to modulate the activity of cells of the immune system.

In this or any of the embodiments of the present invention, the PEG-IL-2 can comprise the full-length, mature (lacking the signal peptide), human interleukin-2 linked to a PEG polymer. In this or any of the embodiments of the present invention, the PEG-IL-2 can comprise the full-length, mature (lacking the signal peptide), human interleukin-2 linked to a PEG polymer or other biologically active molecule by a covalent bond. In some embodiments, the biologically active molecule is modified, as a non-limiting example the biologically active molecule may include one or more non-naturally encoded amino acids.

In PEG-IL2 conjugates, the PEG or other water-soluble polymer can be conjugated directly to the IL-2 protein or to the biologically active molecule or via a linker. Suitable linkers include, for example, cleavable and non-cleavable linkers.

The invention provides a method for treatment of cancer in mammals, e.g., mammals including but not limited to those with one or more of the following conditions: solid tumor, hematological tumor, colon cancer, ovarian cancer, breast cancer, melanoma, lung cancer, glioblastoma, and leukemia, by administering an effective amount of PEG-IL-2 polypeptides. In some embodiments the cancer is characterized by high levels of Treg cells. In some embodiments the cancer is characterized by high expression of IL-2 receptor alpha. In some embodiments, the invention provides a method for treating a cancer or condition or disease by administering to a subject an effective amount of a composition comprising an IL-2 polypeptide of the invention. In some embodiments the invention provides a method of treating an inherited disease by administering to a patient an effective amount of an IL-2 composition of the invention. In some embodiments the condition or disease is characterized by high expression of IL-2 receptor alpha. In some embodiments the condition or disease is characterized by high levels of Treg cells. In some embodiments, the cancer, condition or disease is treated by reducing, blocking or silencing IL-2 receptor alpha expression. In some embodiments, the cancer, condition or disease is treated by reducing binding of IL-2 receptor alpha on the surface of Treg cells resulting in the reduction of proliferation of Treg cells in the cancer, condition or disease to be treated.

As used herein, interleukin 2 or IL-2 is defined as a protein which (a) has an amino acid sequence substantially identical to a known sequence of IL-2, including IL-2 muteins, a mature IL-2 sequence (i.e., lacking a secretory leader sequence), and IL-2 as disclosed in SEQ ID NOs: 1, 2, 3, 5, or 7 of this application and (b) has at least one biological activity that is common to native or wild-type IL-2. For the purposes of this invention, both glycosylated (e.g., produced in eukaryotic cells such as yeast or CHO cells) and unglycosylated (e.g., chemically synthesized or produced in *E. coli*) IL-2 are equivalent and can be used interchangeably. Also included are other mutants and other analogs, including viral IL-2, which retain the biological activity of IL-2.

This invention provides IL-2 polypeptides conjugated to one or more water-soluble polymers wherein the PEGylated IL-2 polypeptide is also linked to another drug or biologically active molecule, and wherein the IL-2 polypeptide comprises one or more non-naturally encoded amino acids. The invention also provides monomers and dimers of IL-2 polypeptides. The invention also provides trimers of IL-2 polypeptides. The invention provides multimers of IL-2 polypeptides. The invention also provides IL-2 dimers comprising one or more non-naturally encoded amino acids. The invention provides IL-2 multimers comprising one or more non-naturally encoded amino acids. The invention provides homogenous IL-2 multimers comprising one or more non-naturally encoded amino acids, wherein each IL-2 polypeptide has the same amino acid sequence. The invention provides heterogenous IL-2 multimers, wherein at least one of the IL-2 polypeptides comprises at least one non-naturally encoded amino acid, wherein any or each of the IL-2 polypeptides in the multimer may have different amino acid sequences.

In some embodiments, the IL-2 polypeptides comprise one or more post-translational modifications. In some embodiments, the IL-2 polypeptide is linked to a linker, polymer, or biologically active molecule. In some embodiments the IL-2 monomers are homogenous. In some embodiments the IL-2 dimers are homogenous. In some embodiments the IL-2 multimers are conjugated to one water-soluble polymer. In some embodiments the IL-2 multimers are conjugated to two water-soluble polymers. In some embodiments the IL-2 multimers are conjugated to three water-soluble polymers. In some embodiments the IL-2 multimers are conjugated to more than three water-soluble polymers. In some embodiments, when the IL-2 polypeptide is linked to a linker long enough to permit formation of a dimer. In some embodiments, when the IL-2 polypeptide is linked to a linker long enough to permit formation of a trimer. In some embodiments, when the IL-2 polypeptide is linked to a linker long enough to permit formation of a multimer. In some embodiments, the IL-2 polypeptide is linked to a bifunctional polymer, bifunctional linker, or at least one additional IL-2 polypeptide. In some embodiments, the IL-2 polypeptides comprise one or more post-translational modifications. In some embodiments, the IL-2 polypeptide is linked to a linker, polymer, or biologically active molecule.

In some embodiments, the non-naturally encoded amino acid is linked to a water-soluble polymer. In some embodiments, the water-soluble polymer comprises a poly(ethylene glycol) (PEG) moiety. In some embodiments, the non-naturally encoded amino acid is linked to the water-soluble polymer with a linker or is bonded to the water-soluble polymer. In some embodiments, the poly(ethylene glycol) molecule is a bifunctional polymer. In some embodiments, the bifunctional polymer is linked to a second polypeptide. In some embodiments, the second polypeptide is IL-2. In some embodiments, the IL-2 or a variant thereof comprises at least two amino acids linked to a water-soluble polymer comprising a poly(ethylene glycol) moiety. In some embodiments, at least one amino acid is a non-naturally encoded amino acid.

In one embodiment, the IL-2 or PEG-IL-2 of the present invention is linked to a therapeutic agent, such as an immunomodulatory agent. The immunomodulatory agent may be any agent that exerts a therapeutic effect on immune cells that can be used as a therapeutic agent for conjugation to an IL-2, PEG-IL-2 or IL-2 variant.

In some embodiments, one non-naturally encoded amino acid is incorporated in one or more of the following positions in IL-2 or a variant thereof: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, or added to the carboxyl terminus of the protein, and any combination thereof (SEQ ID NO: 2 or the corresponding amino acid in SEQ ID NOs: 3, 5, or 7). In some embodiments, one or more biologically active molecules is directly conjugated to the IL-2 variant. In some embodiments, the one or more biologically active molecules are conjugated to the one or more non-naturally encoded amino acid(s) in the IL-2 polypeptide. In some embodiments, the IL-2 variant of the present invention is linked to a linker. In some embodiments, the IL-2 variant linked to a linker further comprises a biologically active molecule. In some embodiments of the present invention, the IL-2 the linker is linked to a non-naturally encoded amino acid.

In some embodiments, one or more non-naturally encoded amino acids are incorporated in one or more of the following positions in IL-2 or a variant thereof: position 3, 32, 35, 37, 38, 42, 43, 44, 45, 48, 49, 61, 62, 64, 65, 68, 72, 76, and 107, and any combination thereof (of SEQ ID NO: 2, or the corresponding amino acid position in SEQ ID NOs: 3, 5, or 7). In some embodiments, one or more non-naturally encoded amino acids are incorporated in one or more of the following positions in IL-2 or a variant thereof: before position 3, 35, 37, 38, 41, 42, 43, 44, 45, 61, 62, 64, 65, 68, 72, and 107, and any combination thereof (SEQ ID NO: 2, or the corresponding amino acid in SEQ ID NOs: 3, 5, or 7). In some embodiments one or more non-naturally encoded amino acids is incorporated in one or more of the following positions in IL-2 or a variant thereof: position 35, 37, 42, 45, 49, 61 or 65, and any combination thereof (of SEQ ID NO: 2, or the corresponding amino acid position in SEQ ID NOs: 3, 5, or 7). In some embodiments, one or more non-naturally encoded amino acids are incorporated in one or more of the following positions in IL-2 or a variant thereof: position 45, 61, and 65, and any combination thereof (of SEQ ID NO: 2, or the corresponding amino acid position in SEQ ID NOs: 3, 5, or 7). In some embodiments, one or more non-naturally encoded amino acids are incorporated in one or more of the following positions in IL-2 or a variant thereof: position 45, and 65, and any combination thereof (of SEQ ID NO: 2, or the corresponding amino acid position in SEQ ID NOs: 3, 5, or 7). In some embodiments one or more non-naturally encoded amino acids are incorporated at position 3 in IL-2 or a variant thereof of the invention. In some embodiments one or more non-naturally encoded amino acids are incorporated at position 32 in IL-2 or a variant thereof of the invention. In some embodiments one or more non-naturally encoded amino acids are incorporated at position 35 in IL-2 or a variant thereof of the invention. In some embodiments one or more non-naturally encoded amino acids are incorporated at position 37 in IL-2 or a variant thereof of the invention. In some embodiments one or more non-naturally encoded amino acids are incorporated at position 38 in IL-2 or a variant thereof of the invention. In some embodiments one or more non-naturally encoded amino acids are incorporated at position 41 in IL-2 or a variant thereof of the invention. In some embodiments one or more non-naturally encoded amino acids are incorporated at position 42 in IL-2 or a variant thereof of the invention. In some embodiments one or more non-naturally encoded amino acids are incorporated at position 43 in IL-2 or a variant thereof of the invention. In some embodiments one or more non-naturally encoded amino acids are incorporated at position 44 in IL-2 or a variant thereof of the invention. In some embodiments one or more non-naturally encoded amino acids are incorporated at position 45 in IL-2 or a variant thereof of the invention. In some embodiments one or more non-naturally encoded amino acids are incorporated at position 48 in IL-2 or a variant thereof of the invention. In some embodiments one or more non-naturally encoded amino acids are incorporated at position 49 in IL-2 or a variant thereof of the invention. In some embodiments one or more non-naturally encoded amino acids are incorporated at position 61 in IL-2 or a variant thereof of the invention. In some embodiments one or more non-naturally encoded amino acids are incorporated at position 62 in IL-2 or a variant thereof of the invention. In some embodiments one or more non-naturally encoded amino acids are incorporated at position 64 in IL-2 or a variant thereof of the invention. In some embodiments one or more non-naturally encoded amino acids are incorporated at position 65 in IL-2 or a variant thereof of the invention. In some embodiments one or more non-naturally encoded amino acids are incorporated at position 68 in IL-2 or a variant thereof of the invention. In some embodiments one or more non-naturally encoded amino acids are incorporated at position 72 in IL-2 or a variant thereof of the invention. In some embodiments one or more non-naturally encoded amino acids are incorporated at position 76 in IL-2 or a variant thereof of the invention. In some embodiments one or more non-naturally encoded amino acids are incorporated at position 107 in IL-2 or a variant thereof of the invention.

In some embodiments, one or more non-naturally encoded amino acids are incorporated at any position in one or more of the following regions corresponding to secondary structures or specific amino acids in IL-2 or a variant thereof as follows: at the sites of hydrophobic interactions; at or in proximity to the sites of interaction with IL-2 receptor subunits including IL2Rα; within amino acid positions 3 or 35 to 45; within the first 107 N-terminal amino acids; within amino acid positions 61-72; each of SEQ ID NO: 2, or the corresponding amino acid position in SEQ ID NOs: 3, 5, or 7. In some embodiments, one or more non-naturally encoded amino acids are incorporated at one or more of the following positions of IL-2 or a variant thereof: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43 and any combination thereof of SEQ ID NO: 2, or the corresponding amino acids in SEQ ID NOs: 3, 5, or 7. In some embodiments, one or more non-naturally encoded amino acids are incorporated at one or more of the following positions of IL-2 or a variant thereof: 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, or added to the carboxyl terminus of the protein, and any combination thereof of SEQ ID NO: 2, or the corresponding amino acids in SEQ ID NOs: 3, 5, or 7.

In some embodiments, the non-naturally occurring amino acid at one or more of these positions in IL-2 or a variant thereof is linked to a drug or other biologically active molecule, including but not limited to, positions: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, or added to the carboxyl terminus of the protein, and any combination thereof (SEQ ID NO: 2 or the corresponding amino acids in SEQ ID NOs: 3, 5, or 7). In some embodiments, the non-naturally occurring amino acid at one or more of these positions in IL-2 or a variant thereof is linked to a drug or other biologically active molecule, including but not limited to, at the sites of hydrophobic interactions; at or in proximity to the sites of interaction with IL-2 receptor subunits including IL2Rα; within amino acid positions 3 or 35 to 45; within the first 107 N-terminal amino acids; within amino acid positions 61-72; each of SEQ ID NO: 2, or the corresponding amino acid position in SEQ ID NOs: 3, 5, or 7. In some embodiments, the non-naturally occurring amino acid at one or more of these positions in IL-2 or a variant thereof is linked to a drug or other biologically active molecule, including but not limited to, positions: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43 and any combination thereof of SEQ ID NO: 2, or the corresponding amino acids in SEQ ID NOs: 3, 5, or 7. In some embodiments, the non-naturally occurring amino acid at one or more of these positions in IL-2 or a variant thereof is linked to a drug or other biologically active molecule, including but not limited to, positions of IL-2 or a variant thereof: 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, or added to the carboxyl terminus of the protein, and any combination thereof of SEQ ID NO: 2, or the corresponding amino acids in SEQ ID NOs: 3, 5, or 7. In some embodiments, one or more non-naturally encoded amino acids are incorporated in one or more of the following positions in IL-2 or a variant thereof and is linked to a drug or other biologically active molecule: position 3, 35, 37, 38, 41, 42, 43, 44, 45, 61, 62, 64, 65, 68, 72, and 107, and any combination thereof (SEQ ID NO: 2 or the corresponding amino acid in SEQ ID NOs: 3, 5, or 7).

In some embodiments, the non-naturally occurring amino acid at one or more of these positions in IL-2 or a variant thereof is linked to a linker, including but not limited to, positions: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, or added to the carboxyl terminus of the protein, and any combination thereof (SEQ ID NO: 2 or the corresponding amino acids in SEQ ID NOs: 3, 5, or 7). In some embodiments, one or more non-naturally encoded amino acids are incorporated in one or more of the following positions in IL-2 or a variant thereof and linked to a linker: position 3, 35, 37, 38, 41, 42, 43, 44, 45, 61, 62, 64, 65, 68, 72, and 107, and any combination thereof (SEQ ID NO: 2 or the corresponding amino acid in SEQ ID NOs: 3, 5, or 7).

In some embodiments, the non-naturally occurring amino acid at one or more of these positions in IL-2 or a variant thereof is linked to a linker that is further linked to a water-soluble polymer or a biologically active molecule, including but not limited to, positions: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, or added to the carboxyl terminus of the protein, and any combination thereof (SEQ ID NO: 2 or the corresponding amino acids in SEQ ID NOs: 3, 5, or 7). In some embodiments, one or more non-naturally encoded amino acids are incorporated in one or more of the following positions in IL-2 or a variant thereof and is linked to a linker that is further linked to a water-soluble polymer or a biologically active molecule, including but not limited to, positions: before position 3, 35, 37, 38, 41, 42, 43, 44, 45, 61, 62, 64, 65, 68, 72, and 107, and any combination thereof (SEQ ID NO: 2 or the corresponding amino acid in SEQ ID NOs: 3, 5, or 7).

In some embodiments, the non-naturally occurring amino acid at one or more of these positions in IL-2 or a variant thereof is linked to a water-soluble polymer, including but not limited to, positions: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, or added to the carboxyl terminus of the protein, and any combination thereof (SEQ ID NO: 2 or the corresponding amino acids in SEQ ID NOs: 3, 5, or 7). In some embodiments, one or more non-naturally encoded amino acids are incorporated in one or more of the following positions in IL-2 or a variant thereof and is linked to a linker that is further linked to a water-soluble polymer, including but not limited to, positions: 3, 35, 37, 38, 41, 42, 43, 44, 45, 61, 62, 64, 65, 68, 72, and 107, and any combination thereof (SEQ ID NO: 2 or the corresponding amino acid in SEQ ID NOs: 3, 5, or 7).

In some embodiments, the IL-2 or a variant thereof comprises a substitution, addition or deletion that modulates affinity of the IL-2 for an IL-2 receptor subunit or a variant thereof. In some embodiments, the IL-2 or a variant thereof comprises a substitution, addition or deletion that modulates affinity of the IL-2 or a variant thereof for an IL-2 receptor or binding partner, including but not limited to, a protein, polypeptide, lipid, fatty acid, small molecule, or nucleic acid. In some embodiments, the IL-2 or a variant thereof comprises a substitution, addition, or deletion that modulates the stability of the IL-2 when compared with the stability of the corresponding IL-2 without the substitution, addition, or deletion. Stability and/or solubility may be measured using a number of different assays known to those of ordinary skill in the art. Such assays include but are not limited to SE-HPLC and RP-HPLC. In some embodiments, the IL-2 comprises a substitution, addition, or deletion that modulates the immunogenicity of the IL-2 when compared with the immunogenicity of the corresponding IL-2 without the substitution, addition, or deletion. In some embodiments, the IL-2 comprises a substitution, addition, or deletion that modulates serum half-life or circulation time of the IL-2 when compared with the serum half-life or circulation time of the corresponding IL-2 without the substitution, addition, or deletion.

In some embodiments, the IL-2 or a variant thereof comprises a substitution, addition, or deletion that increases the aqueous solubility of the IL-2 when compared to aqueous solubility of the corresponding IL-2 or a variant thereof without the substitution, addition, or deletion. In some embodiments, the IL-2 or a variant thereof comprises a substitution, addition, or deletion that increases the solubility of the IL-2 or a variant thereof produced in a host cell when compared to the solubility of the corresponding IL-2 or a variant thereof without the substitution, addition, or deletion. In some embodiments, the IL-2 or a variant thereof comprises a substitution, addition, or deletion that increases the expression of the IL-2 in a host cell or increases synthesis in vitro when compared to the expression or synthesis of the corresponding IL-2 or a variant thereof without the substitution, addition, or deletion. The IL-2 or a variant thereof comprising this substitution retains agonist activity and retains or improves expression levels in a host cell. In some embodiments, the IL-2 or a variant thereof comprises a substitution, addition, or deletion that increases protease resistance of the IL-2 or a variant thereof when compared to the protease resistance of the corresponding IL-2 or a variant thereof without the substitution, addition, or deletion. In some embodiments, the IL-2 or a variant thereof comprises a substitution, addition, or deletion that modulates signal transduction activity of the IL-2 receptor when compared with the activity of the receptor upon interaction with the corresponding IL-2 or a variant thereof without the substitution, addition, or deletion. In some embodiments, the IL-2 or a variant thereof comprises a substitution, addition, or deletion that modulates its binding to another molecule such as a receptor when compared to the binding of the corresponding IL-2 without the substitution, addition, or deletion.

In some embodiments, the present invention provides methods for treating a proliferative condition, cancer, tumor, or precancerous condition such as a dysplasia, with PEG-IL-2 and at least one additional therapeutic or diagnostic agent. The additional therapeutic agent can be, e.g., a cytokine or cytokine antagonist, such as IL-12, interferon-alpha, or anti-epidermal growth factor receptor, doxorubicin, epirubicin, an anti-folate, e.g., methotrexate or fluorouracil, irinotecan, cyclophosphamide, radiotherapy, hormone or anti-hormone therapy, e.g., androgen, estrogen, anti-estrogen, flutamide, or diethylstilbestrol, surgery, tamoxifen, ifosfamide, mitolactol, an alkylating agent, e.g., melphalan or cis-platin, etoposide, vinorelbine, vinblastine, vindesine, a glucocorticoid, a histamine receptor antagonist, an angiogenesis inhibitor, radiation, a radiation sensitizer, anthracycline, *vinca* alkaloid, taxane, e.g., paclitaxel and docetaxel, a cell cycle inhibitor, e.g., a cyclin-dependent kinase inhibitor, a checkpoint inhibitor, an immunomodulatory drug, an immunostimulatory drug, a monoclonal antibody against another tumor antigen, a complex of monoclonal antibody and biologically active molecule, a T cell adjuvant, bone marrow transplant, or antigen presenting cells, e.g., dendritic cell therapy. Vaccines can be provided, e.g., as a soluble protein or as a nucleic acid encoding the protein (see, e.g., Le, et al., supra; Greco and Zellefsky (eds.) (2000) Radiotherapy of Prostate Cancer, Harwood Academic, Amsterdam; Shapiro and Recht (2001) New Engl. J. Med. 344: 1997-2008; Hortobagyi (1998) New Engl. J. Med. 339:974-984; Catalona (1994) New Engl. J. Med. 331:996-1004; Naylor and Hadden (2003) Int. Immunopharmacol. 3:1205-1215; The Int. Adjuvant Lung Cancer Trial Collaborative Group (2004) New Engl. J. Med. 350:351-360; Slamon, et al. (2001) New Engl. J. Med. 344:783-792; Kudelka, et al.

(1998) New Engl. J. Med. 338:991-992; van Netten, et al. (1996) New Engl. J. Med. 334:920-921).

Also provided are methods of treating extramedullary hematopoiesis (EMH) of cancer. EMH is described (see, e.g., Rao, et al. (2003) Leuk. Lymphoma 44:715-718; Lane, et al. (2002) J. Cutan. Pathol. 29:608-612).

In some embodiments, the PEG-IL-2 or a variant thereof comprises a substitution, addition, or deletion that modulates its receptor or receptor subunit binding compared to the receptor or receptor subunit binding activity of the corresponding IL-2 or a variant thereof without the substitution, addition, or deletion. In some embodiments, the IL-2 or a variant thereof comprises a substitution, addition, or deletion that inhibits its activity related to receptor or receptor subunit binding as compared to the receptor or receptor subunit binding activity of the corresponding IL-2 or a variant thereof without the substitution, addition, or deletion.

In some embodiments, the IL-2 or a variant thereof comprises a substitution, addition, or deletion that increases compatibility of the IL-2 or variant thereof with pharmaceutical preservatives (e.g., m-cresol, phenol, benzyl alcohol) when compared to compatibility of the corresponding wild type IL-2 without the substitution, addition, or deletion. This increased compatibility would enable the preparation of a preserved pharmaceutical formulation that maintains the physiochemical properties and biological activity of the protein during storage.

In some embodiments, one or more engineered bonds are created with one or more non-natural amino acids. The intramolecular bond may be created in many ways, including but not limited to, a reaction between two amino acids in the protein under suitable conditions (one or both amino acids may be a non-natural amino acid); a reaction with two amino acids, each of which may be naturally encoded or non-naturally encoded, with a linker, polymer, or other molecule under suitable conditions; etc.

In some embodiments, one or more amino acid substitutions in the IL-2 or a variant thereof may be with one or more naturally occurring or non-naturally occurring amino acids. In some embodiments the amino acid substitutions in the IL-2 or a variant thereof may be with naturally occurring or non-naturally occurring amino acids, provided that at least one substitution is with a non-naturally encoded amino acid. In some embodiments, one or more amino acid substitutions in the IL-2 or a variant thereof may be with one or more naturally occurring amino acids, and additionally at least one substitution is with a non-naturally encoded amino acid. In some embodiments the amino acid substitutions in IL-2 or a variant thereof may be with any naturally occurring amino acid and at least one substitution with a non-naturally encoded amino acid. In some embodiments, one or more natural amino acids can be substituted at one or more of the following positions of IL-2 or a variant thereof: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43 and any combination thereof (of SEQ ID NO: 2, or the corresponding amino acid positions in SEQ ID NOs: 3, 5, or 7). In some embodiments, one or more natural amino acid substitution can be at one or more of the following positions of IL-2 or a variant thereof: 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, or added to the carboxyl terminus of the protein, and any combination thereof (of SEQ ID NO: 2, or the corresponding amino acid positions in SEQ ID NOs: 3, 5, or 7). In some embodiments the amino acid substitutions in the IL-2 or a variant thereof may be with at least one naturally occurring amino acid and at least one substitution with a non-naturally encoded amino acid. In some embodiments the amino acid substitutions in the IL-2 or a variant thereof may be with at least two naturally occurring amino acids and at least one substitution with a non-naturally encoded amino acid. In some embodiments the one or more naturally occurring or encoded amino acids may be any of the 20 common amino acids including, but not limited to, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. In some embodiments the at least one naturally occurring amino acid substitution may be at the following positions of IL-2 or a variant thereof: position 38, 46 or 65. In some embodiments the naturally occurring amino acid substitution may be at position 38 of IL-2 or a variant thereof. In some embodiments the naturally occurring amino acid substitution at position 38 of IL-2 or a variant thereof may be selected from any of the 20 common natural amino acids including, but not limited to, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. In some embodiments the naturally occurring amino acid substitution at position 38 of IL-2 or a variant thereof may be an alanine substitution. In some embodiments the naturally occurring amino acid substitution may be at position 46 of IL-2 or a variant thereof. In some embodiments the naturally occurring amino acid substitution at position 46 of IL-2 or a variant thereof may be selected from any of the 20 common natural amino acids including, but not limited to, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. In some embodiments the naturally occurring amino acid substitution at position 46 of IL-2 or a variant thereof may be a leucine or an isoleucine substitution. In some embodiments the naturally occurring amino acid substitution may be at position 65 of IL-2 or a variant thereof. In some embodiments the naturally occurring amino acid substitution at position 65 of IL-2 or a variant thereof may be selected from any of the 20 common natural amino acids including, but not limited to, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. In some embodiments the naturally occurring amino acid substitution at position 65 of IL-2 or a variant thereof may be an arginine substitution. In some embodiments the amino acid substitutions in the IL-2 or a variant thereof may be a naturally occurring amino acid substitution at position 38, 46 or 65 and at least one substitution with a non-naturally encoded amino acid incorporated in one or more of the following positions in IL-2 or a variant thereof: position 3, 35, 37, 38, 41, 42, 43, 44, 45, 61, 62, 64, 65, 68, 72, and 107, and any combination thereof (of SEQ ID NO: 2, or the corresponding amino acid positions in SEQ ID NOs: 3, 5, or 7). In some embodiments the amino acid substitutions in the IL-2 or a variant thereof may be a naturally occurring amino acid substitution at position 38 and at least one substitution with a non-naturally encoded amino acid incorporated in one or more of the following positions in IL-2 or a variant thereof: position 3, 35, 37, 38, 41, 42, 43, 44, 45, 61, 62, 64, 65, 68, 72, and 107, and any combination thereof (of SEQ ID NO: 2, or the corresponding amino acid positions in SEQ ID NOs: 3, 5, or 7). In some embodiments the amino acid substitutions in the IL-2 or a variant thereof may be a naturally occurring amino acid substitution at position 46 and at least one substitution with a non-naturally encoded amino acid incorporated in one or more of the following positions in IL-2 or a variant thereof: position 3, 35, 37, 38, 41, 42, 43, 44, 45, 61, 62, 64, 65, 68, 72, and 107, and any combination thereof (of SEQ ID NO: 2, or the corresponding amino acid positions in SEQ ID NOs: 3, 5, or 7). In some embodiments the amino acid substitutions in the IL-2 or a variant thereof may be a naturally occurring amino acid substitution at position 65 and at least one substitution with a non-naturally encoded amino acid incorporated in one or more of the following positions in IL-2 or a variant thereof: position 3, 35, 37, 38, 41, 42, 43, 44, 45, 61, 62, 64, 65, 68, 72, and 107, and any combination thereof (of SEQ ID NO: 2, or the corresponding amino acid positions in SEQ ID NOs: 3, 5, or 7). In some embodiments the amino acid substitutions in the IL-2 or a variant thereof may be a naturally occurring amino acid substitution at position 38 and/or 46 and/or 65 and at least one substitution with a non-naturally encoded amino acid incorporated in one or more of the following positions in IL-2 or a variant thereof: position 3, 35, 37, 38, 41, 42, 43, 44, 45, 61, 62, 64, 65, 68, 72, and 107, and any combination thereof (of SEQ ID NO: 2, or the corresponding amino acid positions in SEQ ID NOs: 3, 5, or 7). In some embodiments the amino acid substitutions in the IL-2 or a variant thereof may be a naturally occurring amino acid substitution at position 38 and a non-naturally encoded amino acid incorporated in IL-2 or a variant thereof in position 42 (of SEQ ID NO: 2, or the corresponding amino acid position in SEQ ID NOs: 3, 5, or 7). In some embodiments the amino acid substitutions in the IL-2 or a variant thereof may be a naturally occurring amino acid substitution at positions 38 and 46 and a non-naturally encoded amino acid incorporated in IL-2 or a variant thereof in position 42 (of SEQ ID NO: 2, or the corresponding amino acid position in SEQ ID NOs: 3, 5, or 7). In some embodiments the amino acid substitutions in the IL-2 or a variant thereof may be a naturally occurring amino acid substitution at positions 38 and 65 and a non-naturally encoded amino acid incorporated in IL-2 or a variant thereof in position 42 (of SEQ ID NO: 2, or the corresponding amino acid position in SEQ ID NOs: 3, 5, or 7). In some embodiments the amino acid substitutions in the IL-2 or a variant thereof may be a naturally occurring amino acid substitution at positions 38, 46 and 65, and a non-naturally encoded amino acid incorporated in IL-2 or a variant thereof in position 42 (of SEQ ID NO: 2, or the corresponding amino acid position in SEQ ID NOs: 3, 5, or 7). In some embodiments the amino acid substitutions in the IL-2 or a variant thereof may be a naturally occurring amino acid substitution at position 38 and a non-naturally encoded amino acid incorporated in IL-2 or a variant thereof in position 45 (of SEQ ID NO: 2, or the corresponding amino acid position in SEQ ID NOs: 3, 5, or 7). In some embodiments the amino acid substitutions in the IL-2 or a variant thereof may be a naturally occurring amino acid substitution at positions 38 and 46 and a non-naturally encoded amino acid incorporated in IL-2 or a variant thereof in position 45 (of SEQ ID NO: 2, or the corresponding amino acid position in SEQ ID NOs: 3, 5, or 7). In some embodiments the amino acid substitutions in the IL-2 or a variant thereof may be a naturally occurring amino acid substitution at positions 38 and 65 and a non-naturally encoded amino acid incorporated in IL-2 or a variant thereof in position 45 (of SEQ ID NO: 2, or the corresponding amino acid position in SEQ ID NOs: 3, 5, or 7). In some embodiments the amino acid substitutions in the IL-2 or a variant thereof may be a naturally occurring amino acid substitution at positions 38, 46 and 65, and a non-naturally encoded amino acid incorporated in IL-2 or a variant thereof in position 45 (of SEQ ID NO: 2, or the corresponding amino acid position in SEQ ID NOs: 3, 5, or 7). In some embodiments the amino acid substitutions in the IL-2 or a variant thereof may be a naturally occurring amino acid substitution at position 38 and a non-naturally encoded amino acid incorporated in IL-2 or a variant thereof in position 65 (of SEQ ID NO: 2, or the corresponding amino acid position in SEQ ID NOs: 3, 5, or 7). In some embodiments the amino acid substitutions in the IL-2 or a variant thereof may be a naturally occurring amino acid substitution at positions 38 and 46 and a non-naturally encoded amino acid incorporated in IL-2 or a variant thereof in position 65 (of SEQ ID NO: 2, or the corresponding amino acid position in SEQ ID NOs: 3, 5, or 7).

In some embodiments, the non-naturally encoded amino acid comprises a carbonyl group, an acetyl group, an aminooxy group, a hydrazine group, a hydrazide group, a semicarbazide group, an azide group, or an alkyne group.

In some embodiments, the non-naturally encoded amino acid comprises a carbonyl group. In some embodiments, the non-naturally encoded amino acid has the structure:

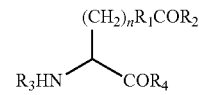

wherein n is 0-10; $R_1$ is an alkyl, aryl, substituted alkyl, or substituted aryl; $R_2$ is H, an alkyl, aryl, substituted alkyl, and substituted aryl; and $R_3$ is H, an amino acid, a polypeptide, or an amino terminus modification group, and $R_4$ is H, an amino acid, a polypeptide, or a carboxy terminus modification group.

In some embodiments, the non-naturally encoded amino acid comprises an aminooxy group. In some embodiments, the non-naturally encoded amino acid comprises a hydrazide group. In some embodiments, the non-naturally encoded amino acid comprises a hydrazine group. In some embodiments, the non-naturally encoded amino acid residue comprises a semicarbazide group.

In some embodiments, the non-naturally encoded amino acid residue comprises an azide group. In some embodiments, the non-naturally encoded amino acid has the structure:

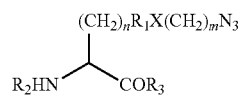

wherein n is 0-10; $R_1$ is an alkyl, aryl, substituted alkyl, substituted aryl or not present; X is O, N, S or not present; m is 0-10; $R_2$ is H, an amino acid, a polypeptide, or an amino terminus modification group, and $R_3$ is H, an amino acid, a polypeptide, or a carboxy terminus modification group.

In some embodiments, the non-naturally encoded amino acid comprises an alkyne group. In some embodiments, the non-naturally encoded amino acid has the structure:

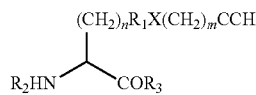

wherein n is 0-10; $R_1$ is an alkyl, aryl, substituted alkyl, or substituted aryl; X is O, N, S or not present; m is 0-10, $R_2$ is H, an amino acid, a polypeptide, or an amino terminus modification group, and $R_3$ is H, an amino acid, a polypeptide, or a carboxy terminus modification group.

In some embodiments, the polypeptide is an IL-2 agonist, partial agonist, antagonist, partial antagonist, or inverse agonist. In some embodiments, the IL-2 agonist, partial agonist, antagonist, partial antagonist, or inverse agonist comprises a non-naturally encoded amino acid linked to a water-soluble polymer. In some embodiments, the water-soluble polymer comprises a poly(ethylene glycol) moiety. In some embodiments, the IL-2 agonist, partial agonist, antagonist, partial antagonist, or inverse agonist comprises a non-naturally encoded amino acid and one or more post-translational modification, linker, polymer, or biologically active molecule.

The present invention also provides isolated nucleic acids comprising a polynucleotide that encode polypeptides of SEQ ID NOs: 1, 2, 3, 5, or 7 and the present invention provides isolated nucleic acids comprising a polynucleotide that hybridizes under stringent conditions to the polynucleotides encoding polypeptides of SEQ ID NOs: 1, 2, 3, 5, or 7. The present invention also provides isolated nucleic acids comprising a polynucleotide that encode polypeptides shown as SEQ ID NOs: 1, 2, 3, 5, or 7 wherein the polynucleotide comprises at least one selector codon. The present invention also provides isolated nucleic acids comprising a polynucleotide that encodes the polypeptides shown as SEQ ID NOs.: 1, 2, 3, 5, or 7 with one or more non-naturally encoded amino acids. It is readily apparent to those of ordinary skill in the art that a number of different polynucleotides can encode any polypeptide of the present invention.

In some embodiments, the selector codon is selected from the group consisting of an amber codon, ochre codon, opal codon, a unique codon, a rare codon, a five-base codon, and a four-base codon.

The present invention also provides methods of making an IL-2 or a variant thereof linked to a biologically active molecule. In some embodiments, the method comprises contacting an isolated IL-2 or a variant thereof comprising a non-naturally encoded amino acid with a biologically active molecule comprising a moiety that reacts with the non-naturally encoded amino acid. In some embodiments, the non-naturally encoded amino acid incorporated into the IL-2 or a variant thereof is reactive toward a biologically active molecule that is otherwise unreactive toward any of the 20 common amino acids. In some embodiments, the non-naturally encoded amino acid incorporated into the IL-2 is reactive toward a linker, polymer, or biologically active molecule that is otherwise unreactive toward any of the 20 common amino acids, that is linked to a biologically active molecule.

In some embodiments, the IL-2 or a variant thereof linked to the water-soluble polymer or biologically active molecule is made by reacting an IL-2 or a variant thereof comprising a carbonyl-containing amino acid with a water-soluble polymer or biologically active molecule comprising an aminooxy, hydrazine, hydrazide or semicarbazide group. In some embodiments, the aminooxy, hydrazine, hydrazide or semicarbazide group is linked to the biologically active molecule through an amide linkage. In some embodiments, the aminooxy, hydrazine, hydrazide or semicarbazide group is linked to the water-soluble polymer or biologically active molecule through a carbamate linkage.

The present invention also provides methods of making an IL-2 conjugate linked to a water-soluble polymer. In some embodiments, the method comprises contacting an isolated IL-2-biologically active molecule conjugate comprising a non-naturally encoded amino acid with a water-soluble polymer comprising a moiety that reacts with the non-naturally encoded amino acid. In some embodiments, the non-naturally encoded amino acid incorporated into the IL-2 conjugate is reactive toward a water-soluble polymer that is otherwise unreactive toward any of the 20 common amino acids. In some embodiments, the non-naturally encoded amino acid incorporated into the IL-2 conjugate is reactive toward a linker, polymer, or biologically active molecule that is otherwise unreactive toward any of the 20 common amino acids.

The present invention also provides methods of making an IL-2 or a variant thereof linked to a water-soluble polymer. In some embodiments, the method comprises contacting an isolated IL-2 or a variant thereof comprising a non-naturally encoded amino acid with a water-soluble polymer comprising a moiety that reacts with the non-naturally encoded amino acid. In some embodiments, the non-naturally encoded amino acid incorporated into the IL-2 or a variant thereof is reactive toward a water-soluble polymer that is otherwise unreactive toward any of the 20 common amino acids. In some embodiments, the non-naturally encoded amino acid incorporated into the IL-2 is reactive toward a linker, polymer, or biologically active molecule that is otherwise unreactive toward any of the 20 common amino acids.

In some embodiments, the IL-2 or a variant thereof linked to the water-soluble polymer is made by reacting an IL-2 or a variant thereof comprising a carbonyl-containing amino acid with a poly(ethylene glycol) molecule comprising an aminooxy, hydrazine, hydrazide or semicarbazide group. In some embodiments, the aminooxy, hydrazine, hydrazide or semicarbazide group is linked to the poly(ethylene glycol) molecule through an amide linkage. In some embodiments, the aminooxy, hydrazine, hydrazide or semicarbazide group is linked to the poly(ethylene glycol) molecule through a carbamate linkage.

In some embodiments, the IL-2 or a variant thereof linked to the water-soluble polymer is made by reacting a poly(ethylene glycol) molecule comprising a carbonyl group with a polypeptide comprising a non-naturally encoded amino acid that comprises an aminooxy, hydrazine, hydrazide or semicarbazide group.

In some embodiments, the IL-2 or a variant thereof linked to the water-soluble polymer is made by reacting an IL-2 comprising an alkyne-containing amino acid with a poly(ethylene glycol) molecule comprising an azide moiety. In some embodiments, the azide or alkyne group is linked to the poly(ethylene glycol) molecule through an amide linkage.

In some embodiments, the IL-2 or a variant thereof linked to the water-soluble polymer is made by reacting an IL-2 or a variant thereof comprising an azide-containing amino acid with a poly(ethylene glycol) molecule comprising an alkyne moiety. In some embodiments, the azide or alkyne group is linked to the poly(ethylene glycol) molecule through an amide linkage.

In some embodiments, the poly(ethylene glycol) molecule has a molecular weight of between about 0.1 kDa and about 100 kDa. In some embodiments, the poly(ethylene glycol) molecule has a molecular weight of between 0.1 kDa and 50 kDa. In some embodiments, the poly(ethylene glycol) has a molecular weight of between 1 kDa and 25 kDa, or between 2 and 22 kDa, or between 5 kDa and 20 kDa. For example, the molecular weight of the poly(ethylene glycol) polymer may be about 5 kDa, or about 10 kDa, or about 20 kDa. For example, the molecular weight of the poly(ethylene glycol) polymer may be 5 kDa or 10 kDa or 20 kDa. In some embodiments the poly(ethylene glycol) molecule is a 20K 2-branched PEG. In some embodiments the poly(ethylene glycol) molecule is a linear 5K PEG. In some embodiments the poly(ethylene glycol) molecule is a linear 10K PEG. In some embodiments the poly(ethylene glycol) molecule is a linear 20K PEG. In some embodiments, the molecular weight of the poly(ethylene glycol) polymer is an average molecular weight. In certain embodiments, the average molecular weight is the number average molecular weight (Mn). The average molecular weight may be determined or measured using GPC or SEC, SDS/PAGE analysis, RP-HPLC, mass spectrometry, or capillary electrophoresis. In some embodiments, one or more non-naturally encoded amino acids is incorporated in one or more of the following positions in IL-2 or a variant thereof: position 3, 35, 37, 38, 41, 42, 43, 44, 45, 61, 62, 64, 65, 68, 72, or 107, and any combination thereof (of SEQ ID NO: 2, or the corresponding amino acid position in SEQ ID NOs: 3, 5, or 7), and the IL-2 or variant thereof is linked to a linear 20K poly(ethylene glycol) molecule. In some embodiments, one or more non-naturally encoded amino acids is incorporated in one or more of the following positions in IL-2 or a variant thereof: position 35, 37, 42, 45, 49, 61, or 65, and any combination thereof (of SEQ ID NO: 2, or the corresponding amino acid position in SEQ ID NOs: 3, 5, or 7), and the IL-2 or variant thereof is linked to a linear 20K poly(ethylene glycol) molecule. In some embodiments, a non-naturally encoded amino acid is incorporated in position 65 in IL-2 or a variant thereof (of SEQ ID NO: 2, or the corresponding amino acid position in SEQ ID NOs: 3, 5, or 7), and the IL-2 or variant thereof is linked to a linear 20K poly(ethylene glycol) molecule. In some embodiments, a non-naturally encoded amino acid is incorporated in position 61 in IL-2 or a variant thereof (of SEQ ID NO: 2, or the corresponding amino acid position in SEQ ID NOs: 3, 5, or 7), and the IL-2 or variant thereof is linked to a linear 20K poly(ethylene glycol) molecule. In some embodiments, a non-naturally encoded amino acid is incorporated in position 49 in IL-2 or a variant thereof (of SEQ ID NO: 2, or the corresponding amino acid position in SEQ ID NOs: 3, 5, or 7), and the IL-2 or variant thereof is linked to a linear 20K poly(ethylene glycol) molecule. In some embodiments, a non-naturally encoded amino acid is incorporated in position 45 in IL-2 or a variant thereof (of SEQ ID NO: 2, or the corresponding amino acid position in SEQ ID NOs: 3, 5, or 7), and the IL-2 or variant thereof is linked to a linear 20K poly(ethylene glycol) molecule. In some embodiments, a non-naturally encoded amino acid is incorporated in position 42 in IL-2 or a variant thereof (of SEQ ID NO: 2, or the corresponding amino acid position in SEQ ID NOs: 3, 5, or 7), and the IL-2 or variant thereof is linked to a linear 20K poly(ethylene glycol) molecule. In some embodiments, a non-naturally encoded amino acid is incorporated in position 37 in IL-2 or a variant thereof (of SEQ ID NO: 2, or the corresponding amino acid position in SEQ ID NOs: 3, 5, or 7), and the IL-2 or variant thereof is linked to a linear 20K poly(ethylene glycol) molecule. In some embodiments, a non-naturally encoded amino acid is incorporated in position 35 in IL-2 or a variant thereof (of SEQ ID NO: 2, or the corresponding amino acid position in SEQ ID NOs: 3, 5, or 7), and the IL-2 or variant thereof is linked to a linear 20K poly(ethylene glycol) molecule.

In some embodiments, the poly(ethylene glycol) molecule is a branched polymer. In some embodiments, each branch of the poly(ethylene glycol) branched polymer has a molecular weight of between 1 kDa and 100 kDa, or between 1 kDa and 50 kDa. In some embodiments, each branch of the poly(ethylene glycol) branched polymer has a molecular weight of between 1 kDa and 25 kDa, or between 2 and 22 kDa, or between 5 kDa and 20 kDa. For example, the molecular weight of each branch of the poly(ethylyne glycol) branched polymer may be about 5 kDa, or about 10 kDa, or about 20 kDa. For example, the molecular weight of each branch of the poly(ethylene glycol) branched polymer may be 5 kDa or 10 kDa or 20 kDa. In some embodiments the poly(ethylene glycol) molecule is a 20K 2-branched PEG. In some embodiments the poly(ethylene glycol) molecule is a 20K 4-branched PEG. In some embodiments, the molecular weight of the poly(ethylene glycol) polymer is an average molecular weight. In certain embodiments, the average molecular weight is the number average molecular weight (Mn). The average molecular weight may be determined or measured using GPC or SEC, SDS/PAGE analysis, RP-HPLC, mass spectrometry, or capillary electrophoresis. In some embodiments, one or more non-naturally encoded amino acids is incorporated in one or more of the following positions in IL-2 or a variant thereof: position 3, 35, 37, 38, 41, 42, 43, 44, 45, 61, 62, 64, 65, 68, 72, or 107, and any combination thereof (of SEQ ID NO: 2, or the corresponding amino acid position in SEQ ID NOs: 3, 5, or 7), and the IL-2 or variant thereof is linked to a 20K 2-branched poly(ethylene glycol) molecule. In some embodiments, one or more non-naturally encoded amino acids is incorporated in one or more of the following positions in IL-2 or a variant thereof: position 35, 37, 42, 45, 49, 61 or 65, and any combination thereof (of SEQ ID NO: 2, or the corresponding amino acid position in SEQ ID NOs: 3, 5, or 7), and the IL-2 or variant thereof is linked to a 20K 2-branched poly (ethylene glycol) molecule. In some embodiments, a non-naturally encoded amino acid is incorporated in position 65 in IL-2 or a variant thereof (of SEQ ID NO: 2, or the corresponding amino acid position in SEQ ID NOs: 3, 5, or 7), and the IL-2 or variant thereof is linked to a 20K 2-branched poly(ethylene glycol) molecule. In some embodiments, a non-naturally encoded amino acid is incorporated in position 61 in IL-2 or a variant thereof (of SEQ ID NO: 2, or the corresponding amino acid position in SEQ ID NOs: 3, 5, or 7), and the IL-2 or variant thereof is linked to a 20K 2-branched poly(ethylene glycol) molecule. In some embodiments, a non-naturally encoded amino acid is incorporated in position 49 in IL-2 or a variant thereof (of SEQ ID NO: 2, or the corresponding amino acid position in SEQ ID NOs: 3, 5, or 7), and the IL-2 or variant thereof is linked to a 20K 2-branched poly(ethylene glycol) molecule. In some embodiments, a non-naturally encoded amino acid is incorporated in position 45 in IL-2 or a variant thereof (of SEQ ID NO: 2, or the corresponding amino acid position in SEQ ID NOs: 3, 5, or 7), and the IL-2 or variant thereof is linked to a 20K 2-branched poly(ethylene glycol) molecule. In some embodiments, a non-naturally encoded amino acid is incorporated in position 42 in IL-2 or a variant thereof (of SEQ ID NO: 2, or the corresponding amino acid position in SEQ ID NOs: 3, 5, or 7), and the IL-2 or variant thereof is linked to a 20K 2-branched poly(ethylene glycol) molecule. In some embodiments, a non-naturally encoded amino acid is incorporated in position 37 in IL-2 or a variant thereof (of SEQ ID NO: 2, or the corresponding amino acid position in SEQ ID NOs: 3, 5, or 7), and the IL-2 or variant thereof is linked to a 20K 2-branched poly(ethylene glycol) molecule. In some embodiments, a non-naturally encoded amino acid is incorporated in position 35 in IL-2 or a variant thereof (of SEQ ID NO: 2, or the corresponding amino acid position in SEQ ID NOs: 3, 5, or 7), and the IL-2 or variant thereof is linked to a 20K 2-branched poly(ethylene glycol) molecule. In some embodiments, one or more non-naturally encoded amino acids is incorporated in one or more of the following positions in IL-2 or a variant thereof: position 3, 35, 37, 38, 41, 42, 43, 44, 45, 61, 62, 64, 65, 68, 72, or 107, and any combination thereof (of SEQ ID NO: 2, or the corresponding amino acid position in SEQ ID NOs: 3, 5, or 7), and the IL-2 or variant thereof is linked to a 20K 4-branched poly(ethylene glycol) molecule. In some embodiments, one or more non-naturally encoded amino acids is incorporated in one or more of the following positions in IL-2 or a variant thereof: position 35, 37, 42, 45, 49, 61 or 65, and any combination thereof (of SEQ ID NO: 2, or the corresponding amino acid position in SEQ ID NOs: 3, 5, or 7), and the IL-2 or variant thereof is linked to a 20K 4-branched poly(ethylene glycol) molecule. In some embodiments, a non-naturally encoded amino acid is incorporated in position 65 in IL-2 or a variant thereof (of SEQ ID NO: 2, or the corresponding amino acid position in SEQ ID NOs: 3, 5, or 7), and the IL-2 or variant thereof is linked to a 20K 4-branched poly(ethylene glycol) molecule. In some embodiments, a non-naturally encoded amino acid is incorporated in position 61 in IL-2 or a variant thereof (of SEQ ID NO: 2, or the corresponding amino acid position in SEQ ID NOs: 3, 5, or 7), and the IL-2 or variant thereof is linked to a 20K 4-branched poly(ethylene glycol) molecule. In some embodiments, a non-naturally encoded amino acid is incorporated in position 49 in IL-2 or a variant thereof (of SEQ ID NO: 2, or the corresponding amino acid position in SEQ ID NOs: 3, 5, or 7), and the IL-2 or variant thereof is linked to a 20K 4-branched poly(ethylene glycol) molecule. In some embodiments, a non-naturally encoded amino acid is incorporated in position 45 in IL-2 or a variant thereof (of SEQ ID NO: 2, or the corresponding amino acid position in SEQ ID NOs: 3, 5, or 7), and the IL-2 or variant thereof is linked to a 20K 4-branched poly(ethylene glycol) molecule. In some embodiments, a non-naturally encoded amino acid is incorporated in position 42 in IL-2 or a variant thereof (of SEQ ID NO: 2, or the corresponding amino acid position in SEQ ID NOs: 3, 5, or 7), and the IL-2 or variant thereof is linked to a 20K 4-branched poly(ethylene glycol) molecule. In some embodiments, a non-naturally encoded amino acid is incorporated in position 37 in IL-2 or a variant thereof (of SEQ ID NO: 2, or the corresponding amino acid position in SEQ ID NOs: 3, 5, or 7), and the IL-2 or variant thereof is linked to a 20K 4-branched poly(ethylene glycol) molecule. In some embodiments, a non-naturally encoded amino acid is incorporated in position 35 in IL-2 or a variant thereof (of SEQ ID NO: 2, or the corresponding amino acid position in SEQ ID NOs: 3, 5, or 7), and the IL-2 or variant thereof is linked to a 20K 4-branched poly(ethylene glycol) molecule.

In some embodiments, the water-soluble polymer linked to the IL-2 or a variant thereof comprises a polyalkylene glycol moiety. In some embodiments, the non-naturally encoded amino acid residue incorporated into the IL-2 comprises a carbonyl group, an aminooxy group, a hydrazide group, a hydrazine, a semicarbazide group, an azide group, or an alkyne group. In some embodiments, the non-naturally encoded amino acid residue incorporated into the IL-2 or a variant thereof comprises a carbonyl moiety and the water-soluble polymer comprises an aminooxy, hydrazide, hydrazine, or semicarbazide moiety. In some embodiments, the non-naturally encoded amino acid residue incorporated into the IL-2 or a variant thereof comprises an alkyne moiety and the water-soluble polymer comprises an azide moiety. In some embodiments, the non-naturally encoded amino acid residue incorporated into the IL-2 or a variant thereof comprises an azide moiety and the water-soluble polymer comprises an alkyne moiety.

The present invention also provides compositions comprising an IL-2 or a variant thereof comprising a non-naturally encoded amino acid and a pharmaceutically acceptable carrier. In some embodiments, the non-naturally encoded amino acid is linked to a water-soluble polymer.

The present invention also provides cells comprising a polynucleotide encoding the IL-2 or IL-2 variant thereof comprising a selector codon. In some embodiments, the cells comprise an orthogonal RNA synthetase and/or an orthogonal tRNA for substituting a non-naturally encoded amino acid into the IL-2.

The present invention also provides cells comprising a polynucleotide encoding the IL-2 or variant thereof comprising a selector codon. In some embodiments, the cells comprise an orthogonal RNA synthetase and/or an orthogonal tRNA for substituting a non-naturally encoded amino acid into the IL-2 or variant thereof.

The present invention also provides methods of making a PEG-IL-2, an IL-2 or any variant thereof comprising a non-naturally encoded amino acid. In some embodiments, the methods comprise culturing cells comprising a polynucleotide or polynucleotides encoding an IL-2 an orthogonal RNA synthetase and/or an orthogonal tRNA under conditions to permit expression of the IL-2 or variant thereof; and purifying the IL-2 or variant thereof from the cells and/or culture medium.

The present invention also provides methods of increasing therapeutic half-life, serum half-life or circulation time of IL-2 or a variant thereof. The present invention also provides methods of modulating immunogenicity of IL-2 or a variant thereof. In some embodiments, the methods comprise substituting a non-naturally encoded amino acid for any one or more amino acids in naturally occurring IL-2 or a variant thereof and/or linking the IL-2 or a variant thereof to a linker, a polymer, a water-soluble polymer, or a biologically active molecule. In one embodiment of the present invention, the linker is long enough to permit flexibility and allow for dimer formation. In one embodiment of the invention, the linker is at least 3 amino acids, or 18 atoms, in length so as to permit for dimer formation.

The present invention also provides methods of treating a patient in need of such treatment with an effective amount of a PEG-IL-2 conjugate or variant thereof of the present invention. In some embodiments, the methods comprise administering to the patient a therapeutically-effective amount of a pharmaceutical composition comprising a PEG-IL-2 or variant thereof comprising a non-naturally-encoded amino acid and a pharmaceutically acceptable carrier. In some embodiments, the methods comprise administering to the patient a therapeutically-effective amount of a pharmaceutical composition comprising a PEG-IL-2 or variant thereof comprising a non-naturally-encoded amino acid and a natural amino acid substitution, and a pharmaceutically acceptable carrier. In some embodiments, the non-naturally encoded amino acid is linked to a water-soluble polymer. In some embodiments, the PEG-IL-2 or variant thereof is glycosylated. In some embodiments, the PEG-IL-2 or variant thereof is not glycosylated.

The present invention also provides methods of treating a patient in need of such treatment with an effective amount of an IL-2 or IL-2 variant molecule of the present invention. In some embodiments, the methods comprise administering to the patient a therapeutically-effective amount of a pharmaceutical composition comprising an IL-2 or IL-2 variant molecule comprising a non-naturally-encoded amino acid and a pharmaceutically acceptable carrier. In some embodiments, the methods comprise administering to the patient a therapeutically-effective amount of a pharmaceutical composition comprising an IL-2 or variant thereof comprising one or more non-naturally-encoded amino acids and one or more natural amino acid substitutions, and a pharmaceutically acceptable carrier. In some embodiments, the non-naturally encoded amino acid is linked to a water-soluble polymer. In some embodiments, the natural amino acid is linked to a water-soluble polymer. In some embodiments, the IL-2 is glycosylated. In some embodiments, the IL-2 is not glycosylated. In some embodiments the patient in need of treatment has a cancer, condition or disease, but not limited to such, characterized by high expression of IL-2 receptor alpha. In some embodiments, the invention provides a method for treating a cancer or condition or disease by administering to a subject a therapeutically-effective amount of an IL-2 composition of the invention. In some embodiments the invention provides a method of treating an inherited disease by administering to a patient a therapeutically-effective amount of an IL-2 composition of the invention. The IL-2 polypeptides of the invention are for use in treating a disease or condition in a cell having high IL-2 receptor alpha expression. In some embodiments, the cancer, condition or disease is treated by reducing, blocking or silencing IL-2 receptor alpha expression. The IL-2 polypeptides or variants of the invention are for use in the manufacture of a medicament for treating a cancer, disease or condition associated with high IL-2 receptor alpha expression. The IL-2 polypeptides or variants of the invention are for use in the manufacture of a medicament for treating a cancer. The IL-2 polypeptides or variants of the invention are for use in the manufacture of a medicament for treating an inherited disease.

The present invention also provides IL-2 comprising a sequence shown in SEQ ID NOs: 1, 2, 3, 5, or 7, or any other IL-2 sequence, except that at least one amino acid is substituted by a non-naturally encoded amino acid. In some embodiments, the non-naturally encoded amino acid is linked to a water-soluble polymer. In some embodiments, the water-soluble polymer comprises a poly(ethylene glycol) moiety. In some embodiments, the non-naturally encoded amino acid comprises a carbonyl group, an aminooxy group, a hydrazide group, a hydrazine group, a semicarbazide group, an azide group, or an alkyne group.

The present invention also provides pharmaceutical compositions comprising a pharmaceutically acceptable carrier and a PEG-IL-2 or natural variant thereof comprising the sequence shown in SEQ ID NOs: 1, 2, 3, 5, or 7, or any other IL-2 sequence, wherein at least one amino acid is substituted by a non-naturally encoded amino acid. The present invention also provides pharmaceutical compositions comprising a pharmaceutically acceptable carrier and an IL-2 or natural variant thereof comprising the sequence shown in SEQ ID NO: 1, 2, 3, 5, or 7. In some embodiments, the non-naturally encoded amino acid comprises a saccharide moiety. In some embodiments, the water-soluble polymer is linked to the IL-2 or natural variant thereof via a saccharide moiety. In some embodiments, a linker, polymer, or biologically active molecule is linked to the IL-2 or natural variant thereof via a saccharide moiety.

The present invention also provides an IL-2 or natural variant thereof comprising a water-soluble polymer linked by a covalent bond to the IL-2 at a single amino acid. In some embodiments, the water-soluble polymer comprises a poly(ethylene glycol) moiety. In some embodiments, the amino acid covalently linked to the water-soluble polymer is a non-naturally encoded amino acid present in the polypeptide.

The present invention provides an IL-2 or a variant thereof comprising at least one linker, polymer, or biologically active molecule, wherein said linker, polymer, or biologically active molecule is attached to the polypeptide through a functional group of a non-naturally encoded amino acid ribosomally incorporated into the polypeptide. In some embodiments, the IL-2 or variant thereof is monoPEGylated. The present invention also provides an IL-2 or variant thereof comprising a linker, polymer, or biologically active molecule that is attached to one or more non-naturally encoded amino acid wherein said non-naturally encoded amino acid is ribosomally incorporated into the polypeptide at pre-selected sites.

Included within the scope of this invention is the IL-2, or variant thereof leader, or signal sequence joined to an IL-2 coding region, as well as a heterologous signal sequence joined to an IL-2 coding region. The heterologous leader or signal sequence selected should be one that is recognized and processed, e.g. by host cell secretion system to secrete and possibly cleaved by a signal peptidase, by the host cell. A method of treating a condition or disorder with the IL-2 of the present invention is meant to imply treating with IL-2 or a variant thereof with or without a signal or leader peptide.

In another embodiment, conjugation of the IL-2 or a variant thereof comprising one or more non-naturally occurring amino acids to another molecule, including but not limited to PEG, provides substantially purified IL-2 due to the unique chemical reaction utilized for conjugation to the non-natural amino acid. Conjugation of IL-2, or variant thereof comprising one or more non-naturally encoded amino acids to another molecule, such as PEG, may be performed with other purification techniques performed prior to or following the conjugation step to provide substantially pure IL-2 or a variant thereof.

BRIEF DESCRIPTION OF THE DRAWINGS

FIG. 5 shows UPF1 genomic DNA sequence and design of CRISPR gRNA sites.

FIG. 6 shows sequence verification of UPF1 knockout cell lines.

DEFINITIONS

Figure 1:
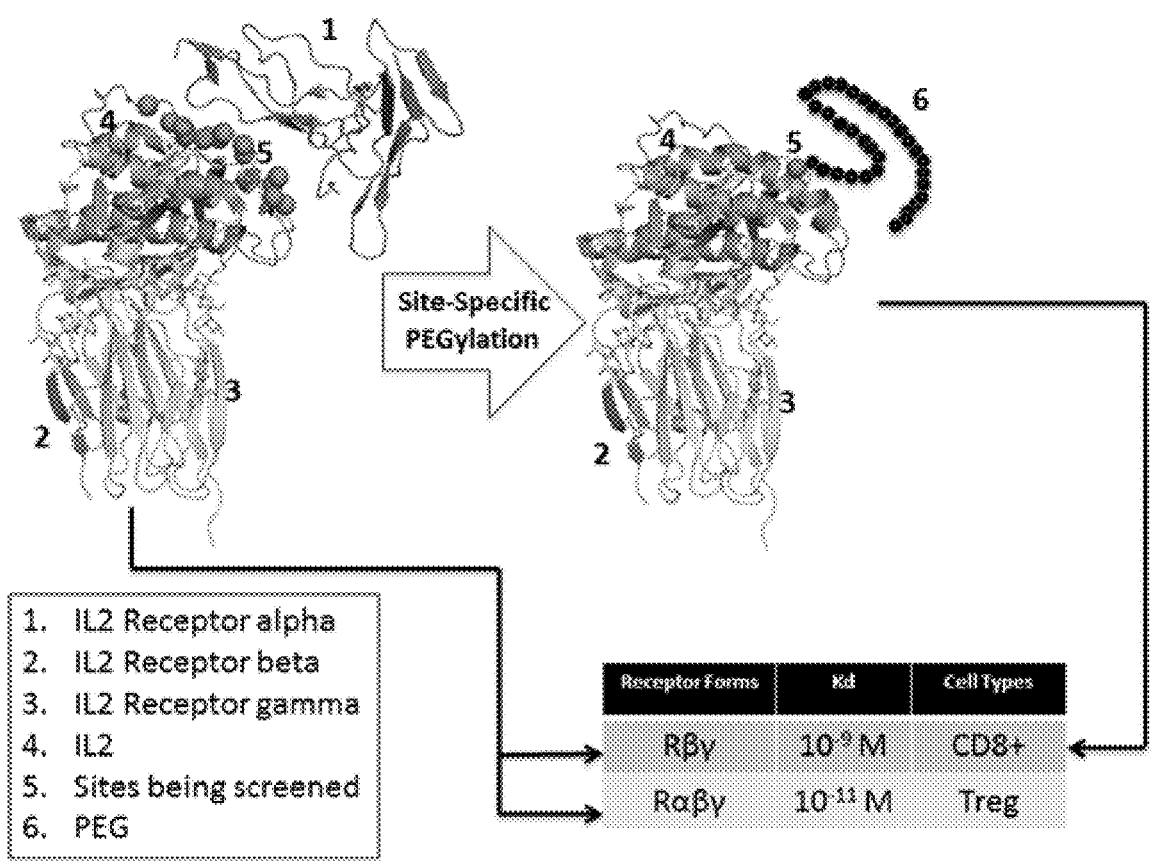
FIG. 1 shows a model showing a view of an IL-2 polypeptide with potential receptor interaction sites labeled with the structure of IL-2Rα and its interface with IL-2.

It is to be understood that this invention is not limited to the particular methodology, protocols, cell lines, constructs, and reagents described herein and as such may vary. It is also to be understood that the terminology used herein is for the purpose of describing particular embodiments only and is not intended to limit the scope of the present invention, which will be limited only by the appended claims.

As used herein and in the appended claims, the singular forms "a," "an," and "the" include plural reference unless the context clearly indicates otherwise. Thus, for example, reference to an "IL-2," "PEG-IL-2," "PEG-IL-2 conjugate," and various capitalized, hyphenated and unhyphenated forms is a reference to one or more such proteins and includes equivalents thereof known to those of ordinary skill in the art, and so forth.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

All publications and patents mentioned herein are incorporated herein by reference for the purpose of describing and disclosing, for example, the constructs and methodologies that are described in the publications, which might be used in connection with the presently described invention. The publications discussed herein are provided solely for their disclosure prior to the filing date of the present application. Nothing herein is to be construed as an admission that the inventors are not entitled to antedate such disclosure by virtue of prior invention or for any other reason.

The term "substantially purified" refers to an IL-2 or variant thereof that may be substantially or essentially free of components that normally accompany or interact with the protein as found in its naturally occurring environment, i.e. a native cell, or host cell in the case of recombinantly produced IL-2. IL-2 that may be substantially free of cellular material includes preparations of protein having less than about 30%, less than about 25%, less than about 20%, less than about 15%, less than about 10%, less than about 5%, less than about 4%, less than about 3%, less than about 2%, or less than about 1% (by dry weight) of contaminating protein. When the IL-2 or variant thereof is recombinantly produced by the host cells, the protein may be present at about 30%, about 25%, about 20%, about 15%, about 10%, about 5%, about 4%, about 3%, about 2%, or about 1% or less of the dry weight of the cells. When the IL-2 or variant thereof is recombinantly produced by the host cells, the protein may be present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. Thus, "substantially purified" IL-2 as produced by the methods of the present invention may have a purity level of at least about 30%, at least about 35%, at least about 40%, at least about 45%, at least about 50%, at least about 55%, at least about 60%, at least about 65%, at least about 70%, specifically, a purity level of at least about 75%, 80%, 85%, and more specifically, a purity level of at least about 90%, a purity level of at least about 95%, a purity level of at least about 99% or greater as determined by appropriate methods such as SDS/PAGE analysis, RP-HPLC, SEC, and capillary electrophoresis.

A "recombinant host cell" or "host cell" refers to a cell that includes an exogenous polynucleotide, regardless of the method used for insertion, for example, direct uptake, transduction, f-mating, or other methods known in the art to create recombinant host cells. The exogenous polynucleotide may be maintained as a nonintegrated vector, for example, a plasmid, or alternatively, may be integrated into the host genome.

As used herein, the term "medium" or "media" includes any culture medium, solution, solid, semi-solid, or rigid support that may support or contain any host cell, including bacterial host cells, yeast host cells, insect host cells, plant host cells, eukaryotic host cells, mammalian host cells, CHO cells, prokaryotic host cells, *E. coli*, or *Pseudomonas* host cells, and cell contents. Thus, the term may encompass medium in which the host cell has been grown, e.g., medium into which the IL-2 has been secreted, including medium either before or after a proliferation step. The term also may encompass buffers or reagents that contain host cell lysates, such as in the case where the IL-2 is produced intracellularly and the host cells are lysed or disrupted to release the IL-2.

"Reducing agent," as used herein with respect to protein refolding, is defined as any compound or material which maintains sulfhydryl groups in the reduced state and reduces intra- or intermolecular disulfide bonds. Suitable reducing agents include, but are not limited to, dithiothreitol (DTT), 2-mercaptoethanol, dithioerythritol, cysteine, cysteamine (2-aminoethanethiol), and reduced glutathione. It is readily apparent to those of ordinary skill in the art that a wide variety of reducing agents are suitable for use in the methods and compositions of the present invention.

"Oxidizing agent," as used herein with respect to protein refolding, is defined as any compound or material which is capable of removing an electron from a compound being oxidized. Suitable oxidizing agents include, but are not limited to, oxidized glutathione, cystine, cystamine, oxidized dithiothreitol, oxidized erythreitol, and oxygen. It is readily apparent to those of ordinary skill in the art that a wide variety of oxidizing agents are suitable for use in the methods of the present invention.

"Denaturing agent" or "denaturant," as used herein, is defined as any compound or material which will cause a reversible unfolding of a protein. The strength of a denaturing agent or denaturant will be determined both by the properties and the concentration of the particular denaturing agent or denaturant. Suitable denaturing agents or denaturants may be chaotropes, detergents, organic solvents, water miscible solvents, phospholipids, or a combination of two or more such agents. Suitable chaotropes include, but are not limited to, urea, guanidine, and sodium thiocyanate. Useful detergents may include, but are not limited to, strong detergents such as sodium dodecyl sulfate, or polyoxyethylene ethers (e.g. Tween or Triton detergents), Sarkosyl, mild non-ionic detergents (e.g., digitonin), mild cationic detergents such as N→2,3-(Dioleyoxy)-propyl-N,N,N-trimethylammonium, mild ionic detergents (e.g. sodium cholate or sodium deoxycholate) or zwitterionic detergents including, but not limited to, sulfobetaines (Zwittergent), 3-(3-chlolamidopropyl)dimethylammonio-1-propane sulfate (CHAPS), and 3-(3-chlolamidopropyl)dimethylammonio-2-hydroxy-1-propane sulfonate (CHAPSO). Organic, water miscible solvents such as acetonitrile, lower alkanols (especially $C_2$-$C_4$ alkanols such as ethanol or isopropanol), or lower alkandiols (especially $C_2$-$C_4$ alkandiols such as ethylene-glycol) may be used as denaturants. Phospholipids useful in the present invention may be naturally occurring phospholipids such as phosphatidylethanolamine, phosphatidylcholine, phosphatidylserine, and phosphatidylinositol or synthetic phospholipid derivatives or variants such as dihexanoylphosphatidylcholine or diheptanoylphosphatidylcholine.

"Refolding," as used herein describes any process, reaction or method which transforms disulfide bond containing polypeptides from an improperly folded or unfolded state to a native or properly folded conformation with respect to disulfide bonds.

"Cofolding," as used herein, refers specifically to refolding processes, reactions, or methods which employ at least two polypeptides which interact with each other and result in the transformation of unfolded or improperly folded polypeptides to native, properly folded polypeptides.

As used herein, "Interleukin-2", "IL-2" and hyphenated and unhyphenated forms thereof shall include those polypeptides and proteins that have at least one biological activity of an IL-2, as well as IL-2 analogs, IL-2 muteins, IL-2 variants, IL-2 isoforms, IL-2 mimetics, IL-2 fragments, hybrid IL-2 proteins, fusion proteins, oligomers and multimers, homologues, glycosylation pattern variants, variants, splice variants, and muteins, thereof, regardless of the biological activity of same, and further regardless of the method of synthesis or manufacture thereof including, but not limited to, recombinant (whether produced from cDNA, genomic DNA, synthetic DNA or other form of nucleic acid), in vitro, in vivo, by microinjection of nucleic acid molecules, synthetic, transgenic, and gene activated methods. The term "IL-2," "IL-2," "IL-2 variant", and "IL-2 polypeptide" encompass IL-2 comprising one or more amino acid substitutions, additions or deletions.

For sequences of IL-2 that lack a leader sequence and has no Methionine at the N-terminus see SEQ ID NO: 2 herein. For a sequence of IL-2 without a leader sequence, and with a Methionine at the N-terminus see SEQ ID NOs: 3, 5, or 7. In some embodiments, IL-2 or variants thereof of the invention are substantially identical to SEQ ID NOs: 2, 3, 5, or 7, or any other sequence of an IL-2. Nucleic acid molecules encoding IL-2 including mutant IL-2 and other variants as well as methods to express and purify these polypeptides are well known in the art.

The term "IL-2" also includes the pharmaceutically acceptable salts and prodrugs, and prodrugs of the salts, polymorphs, hydrates, solvates, biologically-active fragments, biologically active variants and stereoisomers of the naturally-occurring IL-2 as well as agonist, mimetic, and antagonist variants of the naturally-occurring IL-2 and polypeptide fusions thereof.

Various references disclose modification of polypeptides by polymer conjugation or glycosylation. The term "IL-2" includes polypeptides conjugated to a polymer such as PEG and may be comprised of one or more additional derivatizations of cysteine, lysine, or other residues. In addition, the IL-2 may comprise a linker or polymer, wherein the amino acid to which the linker or polymer is conjugated may be a non-natural amino acid according to the present invention or may be conjugated to a naturally encoded amino acid utilizing techniques known in the art such as coupling to lysine or cysteine.

The term "IL-2 polypeptide" also includes glycosylated IL-2, such as but not limited to, polypeptides glycosylated at any amino acid position, N-linked or O-linked glycosylated forms of the polypeptide. Variants containing single nucleotide changes are also considered as biologically active variants of IL-2 polypeptide. In addition, splice variants are also included.

The term "IL-2" also includes IL-2 heterodimers, homodimers, heteromultimers, or homomultimers of any one or more IL-2 or any other polypeptide, protein, carbohydrate, polymer, small molecule, linker, ligand, or other biologically active molecule of any type, linked by chemical means or expressed as a fusion protein, as well as polypeptide analogues containing, for example, specific deletions or other modifications yet maintain biological activity.

"Interleukin-2" or "IL-2", as used herein, whether conjugated to a biologically active molecule, conjugated to a polyethylene glycol, or in a non-conjugated form, is a protein comprising two subunits noncovalently joined to form a homodimer. As used herein, "Interleukin-2" and "IL-2" can refer to human or mouse IL-2 which are also referred to as "hIL-2" or "mIL-2".

The term "pegylated IL-2", "PEGylated IL-2" or "PEG-IL-2" is an IL-2 molecule having one or more polyethylene glycol molecules covalently attached to one or more than one amino acid residue of the IL-2 protein via a linker, such that the attachment is stable. The terms "monopegylated IL-2" and "mono-PEG-IL-2", mean that one polyethylene glycol molecule is covalently attached to a single amino acid residue on one subunit of the IL-2 dimer via a linker. The average molecular weight of the PEG moiety is preferably between about 5,000 and about 50,000 daltons. The method or site of PEG attachment to IL-2 is not critical, but preferably the pegylation does not alter, or only minimally alters, the activity of the biologically active molecule. Preferably, the increase in half-life is greater than any decrease in biological activity.

All references to amino acid positions in IL-2 described herein are based on the position in SEQ ID NO: 2, unless otherwise specified (i.e., when it is stated that the comparison is based on SEQ ID NO: 3, 5, or 7 or other IL-2). Those of skill in the art will appreciate that amino acid positions corresponding to positions in SEQ ID NO: 2 can be readily identified in any other IL-2 such as SEQ ID NOs: 3, 5, or 7. Those of skill in the art will appreciate that amino acid positions corresponding to positions in SEQ ID NOs: 2, 3, 5, or 7, or any other IL-2 sequence can be readily identified in any other IL-2 molecule such as IL-2 fusions, variants, fragments, etc. For example, sequence alignment programs such as BLAST can be used to align and identify a particular position in a protein that corresponds with a position in SEQ ID NOs: 2, 3, 5, or 7, or other IL-2 sequence. Substitutions, deletions or additions of amino acids described herein in reference to SEQ ID NOs: 2, 3, 5, or 7, or other IL-2 sequence are intended to also refer to substitutions, deletions or additions in corresponding positions in IL-2 fusions, variants, fragments, etc. described herein or known in the art and are expressly encompassed by the present invention.

IL-2 (IL3): Any form of IL-2 known in the art could be used in the compositions described herein. For experimental work, the mouse form of IL-2 is particularly useful. Those of skill in the art will recognize that some of the amino acid residues in IL2 may be changed without affecting its activity and that these modified forms of IL2 could also be joined to a carrier and used in the methods described herein.

The term "IL-2" or "IL-2" encompasses IL-2 comprising one or more amino acid substitutions, additions or deletions. IL-2 of the present invention may be comprised of modifications with one or more natural amino acids in conjunction with one or more non-natural amino acid modification. Exemplary substitutions in a wide variety of amino acid positions in naturally-occurring IL-2 polypeptides have been described, including but not limited to substitutions that modulate pharmaceutical stability, that modulate one or more of the biological activities of the IL-2 polypeptide, such as but not limited to, increase agonist activity, increase solubility of the polypeptide, decrease protease susceptibility, convert the polypeptide into an antagonist, etc. and are encompassed by the term "IL-2 polypeptide." In some embodiments, the IL-2 antagonist comprises a non-naturally encoded amino acid linked to a water-soluble polymer that is present in a receptor binding region of the IL-2 molecule.

In some embodiments, the IL-2 or variants thereof further comprise an addition, substitution or deletion that modulates biological activity of the IL-2 or variant polypeptide. In some embodiments, the IL-2 or variants further comprise an addition, substitution or deletion that modulates traits of IL-2 known and demonstrated through research such as treatment or alleviation in one or more symptoms of cancer. The additions, substitutions or deletions may modulate one or more properties or activities of IL-2 or variants. For example, the additions, substitutions or deletions may modulate affinity for the IL-2 receptor or one or more subunits of the receptor, modulate circulating half-life, modulate therapeutic half-life, modulate stability of the polypeptide, modulate cleavage by proteases, modulate dose, modulate release or bio-availability, facilitate purification, or improve or alter a particular route of administration. Similarly, IL-2 or variants may comprise protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification or other traits of the polypeptide.

The term "IL-2 polypeptide" also encompasses homodimers, heterodimers, homomultimers, and heteromultimers that are linked, including but not limited to those linked directly via non-naturally encoded amino acid side chains, either to the same or different non-naturally encoded amino acid side chains, to naturally-encoded amino acid side chains, or indirectly via a linker. Exemplary linkers including but are not limited to, small organic compounds, water-soluble polymers of a variety of lengths such as poly (ethylene glycol) or polydextran, or polypeptides of various lengths.

As used herein, the term "conjugate of the invention," "IL-2-biologically active molecule conjugate" or "PEG-IL-2" refers to interleukin-2 or a portion, analog or derivative thereof that binds to the interleukin-2 receptor or subunit thereof conjugated to a biologically active molecule, a portion thereof or an analog thereof. Unless otherwise indicated, the terms "compound of the invention" and "composition of the invention" are used as alternatives for the term "conjugate of the invention."

As used herein, the term "cytotoxic agent" may be any agent that exerts a therapeutic effect on cancer cells or activated immune cells that can be used as the therapeutic agent for use in conjunction with an IL-2, PEG-IL-2 or IL-2 variant (See, e.g., WO 2004/010957, "Drug Conjugates and Their Use for Treating Cancer, An Autoimmune Disease or an Infectious Disease"). Classes of cytotoxic or immunosuppressive agents for use with the present invention include, for example, antitubulin agents, auristatins, DNA minor groove binders, DNA replication inhibitors, alkylating agents (e.g., platinum complexes such as cis-platin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, *vinca* alkaloids, or the like.

Individual cytotoxic or immunosuppressive agents include, for example, an androgen, anthramycin (AMC), asparaginase, 5-azacytidine, azathioprine, bleomycin, busulfan, buthionine sulfoximine, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (formerly actinomycin), daunorubicin, decarbazine, docetaxel, doxorubicin, an estrogen, 5-fluordeoxyuridine, 5-fluorouracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbizine, streptozotocin, tenoposide, 6-thioguanine, thioTEPA, topotecan, vinblastine, vincristine, vinorelbine, VP-16 and VM-26.

In some typical embodiments, the therapeutic agent is a cytotoxic agent. Suitable cytotoxic agents include, for example, dolastatins (e.g., auristatin E, AFP, MMAF, MMAE), DNA minor groove binders (e.g., enediynes and lexitropsins), duocarmycins, taxanes (e.g., paclitaxel and docetaxel), puromycins, vinca alkaloids, CC-1065, SN-38, topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, discodermolide, eleutherobin, and mitoxantrone.

A "non-naturally encoded amino acid" refers to an amino acid that is not one of the 20 common amino acids or pyrrolysine or selenocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrrolysine and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O-phosphotyrosine.

An "amino terminus modification group" refers to any molecule that can be attached to the amino terminus of a polypeptide. Similarly, a "carboxy terminus modification group" refers to any molecule that can be attached to the carboxy terminus of a polypeptide. Terminus modification groups include, but are not limited to, various water-soluble polymers, peptides or proteins such as serum albumin, or other moieties that increase serum half-life of peptides.

The terms "functional group", "active moiety", "activating group", "leaving group", "reactive site", "chemically reactive group" and "chemically reactive moiety" are used in the art and herein to refer to distinct, definable portions or units of a molecule. The terms are somewhat synonymous in the chemical arts and are used herein to indicate the portions of molecules that perform some function or activity and are reactive with other molecules.

The term "linkage" or "linker" is used herein to refer to groups or bonds that normally are formed as the result of a chemical reaction and typically are covalent linkages. Hydrolytically stable linkages mean that the linkages are substantially stable in water and do not react with water at useful pH values, including but not limited to, under physiological conditions for an extended period of time, perhaps even indefinitely. Hydrolytically unstable or degradable linkages mean that the linkages are degradable in water or in aqueous solutions, including for example, blood. Enzymatically unstable or degradable linkages mean that the linkage can be degraded by one or more enzymes. As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent. Other hydrolytically degradable linkages include, but are not limited to, carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

The term "biologically active molecule", "biologically active moiety" or "biologically active agent" when used herein means any substance which can affect any physical or biochemical properties of a biological system, pathway, molecule, or interaction relating to an organism, including but not limited to, viruses, bacteria, bacteriophage, transposon, prion, insects, fungi, plants, animals, and humans. In particular, as used herein, biologically active molecules include, but are not limited to, any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs, vaccines, immunogens, hard drugs, soft drugs, carbohydrates, inorganic atoms or molecules, dyes, lipids, nucleosides, radionuclides, oligonucleotides, toxoids, biologically active molecules, prokaryotic and eukaryotic cells, viruses, polysaccharides, nucleic acids and portions thereof obtained or derived from viruses, bacteria, insects, animals or any other cell or cell type, liposomes, microparticles and micelles. Classes of biologically active agents that are suitable for use with the invention include, but are not limited to, drugs, prodrugs, radionuclides, imaging agents, polymers, antibiotics, fungicides, bile-acid resins, niacin, and/or statins, anti-inflammatory agents, anti-tumor agents, cardiovascular agents, anti-anxiety agents, hormones, growth factors, steroidal agents, microbially derived biologically active molecules, and the like. Biologically active agents also include amide compounds such as those described in Patent Application Publication Number 20080221112, Yamamori et al., which may be administered prior, post, and/or coadministered with IL-2 polypeptides of the present invention.

A "bifunctional polymer" refers to a polymer comprising two discrete functional groups that are capable of reacting specifically with other moieties (including but not limited to, amino acid side groups) to form covalent or non-covalent linkages. A bifunctional linker having one functional group reactive with a group on a particular biologically active component, and another group reactive with a group on a second biological component, may be used to form a conjugate that includes the first biologically active component, the bifunctional linker and the second biologically active component. Many procedures and linker molecules for attachment of various compounds to peptides are known. See, e.g., European Patent Application No. 188,256; U.S. Pat. Nos. 4,671,958, 4,659,839, 4,414,148, 4,699,784; 4,680,338; and 4,569,789 which are incorporated by reference herein. A "multi-functional polymer" refers to a polymer comprising two or more discrete functional groups that are capable of reacting specifically with other moieties (including but not limited to, amino acid side groups) to form covalent or non-covalent linkages. A bi-functional polymer or multi-functional polymer may be any desired length or molecular weight, and may be selected to provide a particular desired spacing or conformation between one or more molecules linked to the IL-2 and its receptor or IL-2.

Where substituent groups are specified by their conventional chemical formulas, written from left to right, they equally encompass the chemically identical substituents that would result from writing the structure from right to left, for example, the structure —$CH_2O$— is equivalent to the structure —$OCH_2$—.

The term "substituents" includes but is not limited to "non-interfering substituents". "Non-interfering substituents" are those groups that yield stable compounds. Suitable non-interfering substituents or radicals include, but are not limited to, halo, $C_1$-$C_{10}$ alkyl, $C_2$-$C_{10}$ alkenyl, $C_2$-$C_{10}$ alkynyl, $C_1$-$C_{10}$ alkoxy, $C_1$-$C_{12}$ aralkyl, $C_1$-$C_{12}$ alkaryl, $C_3$-$C_{12}$ cycloalkyl, $C_3$-$C_{12}$ cycloalkenyl, phenyl, substituted phenyl, toluoyl, xylenyl, biphenyl, $C_2$-$C_{12}$ alkoxyalkyl, $C_2$-$C_{12}$ alkoxyaryl, $C_7$-$C_{12}$ aryloxyalkyl, $C_7$-$C_{12}$ oxyaryl, $C_1$-$C_6$ alkylsulfinyl, $C_1$-$C_{10}$ alkylsulfonyl, —$(CH_2)_m$—O—($C_1$-$C_{10}$ alkyl) wherein m is from 1 to 8, aryl, substituted aryl, substituted alkoxy, fluoroalkyl, heterocyclic radical, substituted heterocyclic radical, nitroalkyl, —$NO_2$, —CN, —NRC(O)—($C_1$-$C_{10}$ alkyl), —C(O)—($C_1$-$C_{10}$ alkyl), $C_2$-$C_{10}$ alkyl thioalkyl, —C(O)O—($C_1$-$C_{10}$ alkyl), —OH, —$SO_2$, =S, —COOH, —$NR_2$, carbonyl, —C(O)—($C_1$-$C_{10}$ alkyl)-CF3, —C(O)—CF3, —C(O)NR2, —($C_1$-$C_{10}$ aryl)-S—($C_6$-$C_{10}$ aryl), —C(O)—($C_1$-$C_{10}$ aryl), —$(CH_2)_m$—O—(—$(CH_2)_m$—O—($C_1$-$C_{10}$ alkyl) wherein each m is from 1 to 8, —C(O)$NR_2$, —C(S)$NR_2$, — $SO_2NR_2$, —NRC(O) $NR_2$, —NRC(S) $NR_2$, salts thereof, and the like. Each R as used herein is H, alkyl or substituted alkyl, aryl or substituted aryl, aralkyl, or alkaryl.

The term "halogen" includes fluorine, chlorine, iodine, and bromine.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups which are limited to hydrocarbon groups are termed "homoalkyl".

The term "alkylene" by itself or as part of another substituent means a divalent radical derived from an alkane, as exemplified, but not limited, by the structures —$CH_2CH_2$— and —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being a particular embodiment of the methods and compositions described herein. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si and S, and wherein the nitrogen and sulfur atoms may optionally be oxidized and the nitrogen heteroatom may optionally be quaternized. The heteroatom(s) O, N, S and Si may be placed at any interior position of the heteroalkyl group or at the position at which the alkyl group is attached to the remainder of the molecule.

Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, the same or different heteroatoms can also occupy either or both of the chain termini (including but not limited to, alkyleneoxy, alkylenedioxy, alkyleneamino, alkylenediamino, aminooxyalkylene, and the like). Still further, for alkylene and heteroalkylene linking groups, no orientation of the linking group is implied by the direction in which the formula of the linking group is written. For example, the formula —C(O)$_2$R'— represents both —C(O)$_2$R'- and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Thus, a cycloalkyl or heterocycloalkyl include saturated, partially unsaturated and fully unsaturated ring linkages. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. Additionally, the term encompasses bicyclic and tricyclic ring structures. Similarly, the term "heterocycloalkylene" by itself or as part of another substituent means a divalent radical derived from heterocycloalkyl, and the term "cycloalkylene" by itself or as part of another substituent means a divalent radical derived from cycloalkyl.

As used herein, the term "water-soluble polymer" refers to any polymer that is soluble in aqueous solvents. Linkage of water-soluble polymers to IL-2 can result in changes including, but not limited to, increased or modulated serum half-life, or increased or modulated therapeutic half-life relative to the unmodified form, modulated immunogenicity, modulated physical association characteristics such as aggregation and multimer formation, altered receptor binding, altered binding to one or more binding partners, and altered receptor dimerization or multimerization. The water-soluble polymer may or may not have its own biological activity and may be utilized as a linker for attaching IL-2 to other substances, including but not limited to one or more IL-2, or one or more biologically active molecules. Suitable polymers include, but are not limited to, polyethylene glycol, polyethylene glycol propionaldehyde, mono C1-C10 alkoxy or aryloxy derivatives thereof (described in U.S. Pat. No. 5,252,714 which is incorporated by reference herein), monomethoxy-polyethylene glycol, polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polypropylene oxide/ethylene oxide copolymer, polyoxyethylated polyol, heparin, heparin fragments, polysaccharides, oligosaccharides, glycans, cellulose and cellulose derivatives, including but not limited to methylcellulose and carboxymethyl cellulose, starch and starch derivatives, polypeptides, polyalkylene glycol and derivatives thereof, copolymers of polyalkylene glycols and derivatives thereof, polyvinyl ethyl ethers, and alpha-beta-poly[(2-hydroxyethyl)-DL-aspartamide, and the like, or mixtures thereof. Examples of such water-soluble polymers include, but are not limited to, polyethylene glycol and serum albumin.

As used herein, the term "polyalkylene glycol" or "poly (alkene glycol)" refers to polyethylene glycol (poly(ethylene glycol)), polypropylene glycol, polybutylene glycol, and derivatives thereof. The term "polyalkylene glycol" encompasses both linear and branched polymers and average molecular weights of between 0.1 kDa and 100 kDa. Other exemplary embodiments are listed, for example, in commercial supplier catalogs, such as Shearwater Corporation's catalog "Polyethylene Glycol and Derivatives for Biomedical Applications" (2001).

The term "aryl" means, unless otherwise stated, a polyunsaturated, aromatic, hydrocarbon substituent which can be a single ring or multiple rings (including but not limited to, from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (including but not limited to, aryloxy, arylthioxy, arylalkyl) includes both aryl and heteroaryl rings as defined above. Thus, the term "arylalkyl" is meant to include those radicals in which an aryl group is attached to an alkyl group (including but not limited to, benzyl, phenethyl, pyridylmethyl and the like) including those alkyl groups in which a carbon atom (including but not limited to, a methylene group) has been replaced by, for example, an oxygen atom (including but not limited to, phenoxymethyl, 2-pyridyloxymethyl, 3-(1-naphthyloxy)propyl, and the like).

Each of the above terms (including but not limited to, "alkyl," "heteroalkyl," "aryl" and "heteroaryl") are meant to include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such a radical. R', R", R'" and R"" each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —CF$_3$ and —CH$_2$CF$_3$) and acyl (including but not limited to, —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, but are not limited to: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are independently selected from hydrogen, alkyl, heteroalkyl, aryl and heteroaryl. When a compound of the invention includes more than one R group, for example, each of the R groups is independently selected as are each R', R", R'" and R"" groups when more than one of these groups is present.

As used herein, the term "modulated serum half-life" means the positive or negative change in circulating half-life of a modified IL-2 relative to its non-modified form. Serum half-life is measured by taking blood samples at various time points after administration of IL-2 and determining the concentration of that molecule in each sample. Correlation of the serum concentration with time allows calculation of the serum half-life. Increased serum half-life desirably has at least about two-fold, but a smaller increase may be useful, for example where it enables a satisfactory dosing regimen or avoids a toxic effect. In some embodiments, the increase is at least about three-fold, at least about five-fold, or at least about ten-fold.

The term "modulated therapeutic half-life" as used herein means the positive or negative change in the half-life of the therapeutically effective amount of IL-2, relative to its non-modified form. Therapeutic half-life is measured by measuring pharmacokinetic and/or pharmacodynamic properties of the molecule at various time points after administration. Increased therapeutic half-life desirably enables a particular beneficial dosing regimen, a particular beneficial total dose, or avoids an undesired effect. In some embodiments, the increased therapeutic half-life results from increased potency, increased or decreased binding of the modified molecule to its target, increased or decreased breakdown of the molecule by enzymes such as proteases, or an increase or decrease in another parameter or mechanism of action of the non-modified molecule or an increase or decrease in receptor-mediated clearance of the molecule.

The term "isolated," when applied to a nucleic acid or protein, denotes that the nucleic acid or protein is free of at least some of the cellular components with which it is associated in the natural state, or that the nucleic acid or protein has been concentrated to a level greater than the concentration of its in vivo or in vitro production. It can be in a homogeneous state. Isolated substances can be in either a dry or semi-dry state, or in solution, including but not limited to, an aqueous solution. It can be a component of a pharmaceutical composition that comprises additional pharmaceutically acceptable carriers and/or excipients. Purity and homogeneity are typically determined using analytical chemistry techniques such as polyacrylamide gel electrophoresis or high-performance liquid chromatography. A protein which is the predominant species present in a preparation is substantially purified. In particular, an isolated gene is separated from open reading frames which flank the gene and encode a protein other than the gene of interest. The term "purified" denotes that a nucleic acid or protein gives rise to substantially one band in an electrophoretic gel. Particularly, it may mean that the nucleic acid or protein is at least 85% pure, at least 90% pure, at least 95% pure, at least 99% or greater pure.

The term "nucleic acid" refers to deoxyribonucleotides, deoxyribonucleosides, ribonucleosides, or ribonucleotides and polymers thereof in either single- or double-stranded form. Unless specifically limited, the term encompasses nucleic acids containing known analogues of natural nucleotides which have similar binding properties as the reference nucleic acid and are metabolized in a manner similar to naturally occurring nucleotides. Unless specifically limited otherwise, the term also refers to oligonucleotide analogs including PNA (peptidonucleic acid), analogs of DNA used in antisense technology (phosphorothioates, phosphoroamidates, and the like). Unless otherwise indicated, a particular nucleic acid sequence also implicitly encompasses conservatively modified variants thereof (including but not limited to, degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J Biol. Chem.* 260:2605-2608 (1985); Rossolini et al., *Mol. Cell. Probes* 8:91-98 (1994)).

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-naturally encoded amino acid. As used herein, the terms encompass amino acid chains of any length, including full length proteins, wherein the amino acid residues are linked by covalent peptide bonds.

The term "amino acid" refers to naturally occurring and non-naturally occurring amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrrolysine and selenocysteine. Amino acid analogs refer to compounds that have the same basic chemical structure as a naturally occurring amino acid, i.e., an α carbon that is bound to a hydrogen, a carboxyl group, an amino group, and an R group, such as, homoserine, norleucine, methionine sulfoxide, methionine methyl sulfonium. Such analogs have modified R groups (such as, norleucine) or modified peptide backbones, but retain the same basic chemical structure as a naturally occurring amino acid. Reference to an amino acid includes, for example, naturally occurring proteogenic L-amino acids; D-amino acids, chemically modified amino acids such as amino acid variants and derivatives; naturally occurring non-proteogenic amino acids such as β-alanine, ornithine, etc.; and chemically synthesized compounds having properties known in the art to be characteristic of amino acids. Examples of non-naturally occurring amino acids include, but are not limited to, α-methyl amino acids (e.g., α-methyl alanine), D-amino acids, histidine-like amino acids (e.g., 2-amino-histidine, β-hydroxy-histidine, homohistidine, α-fluoromethyl-histidine and α-methyl-histidine), amino acids having an extra methylene in the side chain ("homo" amino acids), and amino acids in which a carboxylic acid functional group in the side chain is replaced with a sulfonic acid group (e.g., cysteic acid). The incorporation of non-natural amino acids, including synthetic non-native amino acids, substituted amino acids, or one or more D-amino acids into the proteins of the present invention may be advantageous in a number of different ways. D-amino acid-containing peptides, etc., exhibit increased stability in vitro or in vivo compared to L-amino acid-containing counterparts. Thus, the construction of peptides, etc., incorporating D-amino acids can be particularly useful when greater intracellular stability is desired or required. More specifically, D-peptides, etc., are resistant to endogenous peptidases and proteases, thereby providing improved bioavailability of the molecule, and prolonged lifetimes in vivo when such properties are desirable. Additionally, D-peptides, etc., cannot be processed efficiently for major histocompatibility complex class II-restricted presentation to T helper cells, and are therefore, less likely to induce humoral immune responses in the whole organism.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, "conservatively modified variants" refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of ordinary skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of ordinary skill in the art will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the deletion of an amino acid, addition of an amino acid, or substitution of an amino acid with a chemically similar amino acid. Conservative substitution tables providing functionally similar amino acids are known to those of ordinary skill in the art. Such conservatively modified variants are in addition to and do not exclude polymorphic variants, interspecies homologs, and alleles of the invention.

Conservative substitution tables providing functionally similar amino acids are known to those of ordinary skill in the art. The following eight groups each contain amino acids that are conservative substitutions for one another:: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M); (see, e.g., Creighton, *Proteins: Structures and Molecular Properties* (W H Freeman & Co.; 2nd edition (December 1993).

The terms "identical" or percent "identity," in the context of two or more nucleic acids or polypeptide sequences, refer to two or more sequences or subsequences that are the same. Sequences are "substantially identical" if they have a percentage of amino acid residues or nucleotides that are the same (i.e., about 60% identity, about 65%, about 70%, about 75%, about 80%, about 85%, about 90%, or about 95% identity over a specified region), when compared and aligned for maximum correspondence over a comparison window, or designated region as measured using one of the following sequence comparison algorithms (or other algorithms available to persons of ordinary skill in the art) or by manual alignment and visual inspection. This definition also refers to the complement of a test sequence. The identity can exist over a region that is at least about 50 amino acids or nucleotides in length, or over a region that is 75-100 amino acids or nucleotides in length, or, where not specified, across the entire sequence of a polynucleotide or polypeptide. A polynucleotide encoding a polypeptide of the present invention, including homologs from species other than human, may be obtained by a process comprising the steps of screening a library under stringent hybridization conditions with a labeled probe having a polynucleotide sequence of the invention or a fragment thereof, and isolating full-length cDNA and genomic clones containing said polynucleotide sequence. Such hybridization techniques are well known to the skilled artisan.

The phrase "selectively (or specifically) hybridizes to" refers to the binding, duplexing, or hybridizing of a molecule only to a particular nucleotide sequence under stringent hybridization conditions when that sequence is present in a complex mixture (including but not limited to, total cellular or library DNA or RNA).

The phrase "stringent hybridization conditions" refers to hybridization of sequences of DNA, RNA, PNA, or other nucleic acid mimics, or combinations thereof under conditions of low ionic strength and high temperature as is known in the art. Typically, under stringent conditions a probe will hybridize to its target subsequence in a complex mixture of nucleic acid (including but not limited to, total cellular or library DNA or RNA) but does not hybridize to other sequences in the complex mixture. Stringent conditions are sequence-dependent and will be different in different circumstances. Longer sequences hybridize specifically at higher temperatures.

As used herein, the term "eukaryote" refers to organisms belonging to the phylogenetic domain *Eucarya* such as animals (including but not limited to, mammals, insects, reptiles, birds, etc.), ciliates, plants (including but not limited to, monocots, dicots, algae, etc.), fungi, yeasts, *flagellates*, microsporidia, protists, etc.

As used herein, the term "non-eukaryote" refers to non-eukaryotic organisms. For example, a non-eukaryotic organism can belong to the Eubacteria (including but not limited to, *Escherichia coli, Thermus thermophilus, Bacillus stearothermophilus, Pseudomonas fluorescens, Pseudomonas aeruginosa, Pseudomonas putida*, etc.) phylogenetic domain, or the *Archaea* (including but not limited to, *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix*, etc.) phylogenetic domain.

The term "subject" as used herein, refers to an animal, in some embodiments a mammal, and in other embodiments a human, who is the object of treatment, observation or experiment. An animal may be a companion animal (e.g., dogs, cats, and the like), farm animal (e.g., cows, sheep, pigs, horses, and the like) or a laboratory animal (e.g., rats, mice, guinea pigs, and the like).

The term "effective amount" as used herein refers to that amount of the modified non-natural amino acid polypeptide being administered which will relieve to some extent one or more of the symptoms of the disease, condition or disorder being treated. Compositions containing the modified non-natural amino acid polypeptide described herein can be administered for prophylactic, enhancing, and/or therapeutic treatments.

The terms "enhance" or "enhancing" means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system. When used in a patient, amounts effective for this use will depend on the severity and course of the disease, disorder or condition, previous therapy, the patient's health status and response to the drugs, and the judgment of the treating physician.

The term "modified," as used herein refers to any changes made to a given polypeptide, such as changes to the length of the polypeptide, the amino acid sequence, chemical structure, co-translational modification, or post-translational modification of a polypeptide. The form "(modified)" term means that the polypeptides being discussed are optionally modified, that is, the polypeptides under discussion can be modified or unmodified.

The term "post-translationally modified" refers to any modification of a natural or non-natural amino acid that occurs to such an amino acid after it has been incorporated into a polypeptide chain. The term encompasses, by way of example only, co-translational in vivo modifications, co-translational in vitro modifications (such as in a cell-free translation system), post-translational in vivo modifications, and post-translational in vitro modifications.

In prophylactic applications, compositions containing the IL-2 are administered to a patient susceptible to or otherwise at risk of a particular disease, disorder or condition. Such an amount is defined to be a "prophylactically effective amount." In this use, the precise amounts also depend on the patient's state of health, weight, and the like. It is considered well within the skill of the art for one to determine such prophylactically effective amounts by routine experimentation (e.g., a dose escalation clinical trial).

In therapeutic applications, compositions containing the modified non-natural amino acid polypeptide are administered to a patient already suffering from a disease, condition or disorder, in an amount sufficient to cure or at least partially arrest the symptoms of the disease, disorder or condition. Such an amount is defined to be a "therapeutically effective amount," and will depend on the severity and course of the disease, disorder or condition, previous therapy, the patient's health status and response to the drugs, and the judgment of the treating physician. It is considered well within the skill of the art for one to determine such therapeutically effective amounts by routine experimentation (e.g., a dose escalation clinical trial).

The term "treating" is used to refer to either prophylactic and/or therapeutic treatments.

Non-naturally encoded amino acid polypeptides presented herein may include isotopically-labelled compounds with one or more atoms replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as $^2H$, $^3H$, $^{13}C$, $^4C$, $^{15}N$, $^{18}O$, $^{17}O$, $^{35}S$, $^{18}F$, $^{36}Cl$, respectively. Certain isotopically-labelled compounds described herein, for example those into which radioactive isotopes such as $^3H$ and $^{14}C$ are incorporated, may be useful in drug and/or substrate tissue distribution assays. Further, substitution with isotopes such as deuterium, i.e., $^2H$, can afford certain therapeutic advantages resulting from greater metabolic stability, for example increased in vivo half-life or reduced dosage requirements.

All isomers including but not limited to diastereomers, enantiomers, and mixtures thereof are considered as part of the compositions described herein. In additional or further embodiments, the non-naturally encoded amino acid polypeptides are metabolized upon administration to an organism in need to produce a metabolite that is then used to produce a desired effect, including a desired therapeutic effect. In further or additional embodiments are active metabolites of non-naturally encoded amino acid polypeptides.

In some situations, non-naturally encoded amino acid polypeptides may exist as tautomers. In addition, the non-naturally encoded amino acid polypeptides described herein can exist in unsolvated as well as solvated forms with pharmaceutically acceptable solvents such as water, ethanol, and the like. The solvated forms are also considered to be disclosed herein. Those of ordinary skill in the art will recognize that some of the compounds herein can exist in several tautomeric forms. All such tautomeric forms are considered as part of the compositions described herein.

Unless otherwise indicated, conventional methods of mass spectroscopy, NMR, HPLC, protein chemistry, biochemistry, recombinant DNA techniques and pharmacology, within the skill of the art are employed.

DETAILED DESCRIPTION

I. Introduction

IL-2 molecules comprising at least one unnatural amino acid are provided in the invention. In certain embodiments of the invention, the IL-2 with at least one unnatural amino acid includes at least one post-translational modification. In one embodiment, the at least one post-translational modification comprises attachment of a molecule including but not limited to, a label, a dye, a polymer, a water-soluble polymer, a derivative of polyethylene glycol, a photocrosslinker, a radionuclide, a cytotoxic compound, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a saccharide, a water-soluble dendrimer, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, a quantum dot, a nanotransmitter, a radionucleotide, a radiotransmitter, a neutron-capture agent, or any combination of the above or any other desirable compound or substance, comprising a second reactive group to at least one unnatural amino acid comprising a first reactive group utilizing chemistry methodology that is known to one of ordinary skill in the art to be suitable for the particular reactive groups. For example, the first reactive group is an alkynyl moiety (including but not limited to, in the unnatural amino acid p-propargyloxyphenylalanine, where the propargyl group is also sometimes referred to as an acetylene moiety) and the second reactive group is an azido moiety, and [3+2] cycloaddition chemistry methodologies are utilized. In another example, the first reactive group is the azido moiety (including but not limited to, in the unnatural amino acid p-azido-L-phenylalanine or pAZ as it is sometimes referred to within this specification) and the second reactive group is the alkynyl moiety. In certain embodiments of the modified IL-2 of the present invention, at least one unnatural amino acid (including but not limited to, unnatural amino acid containing a keto functional group) comprising at least one post-translational modification, is used where the at least one post-translational modification comprises a saccharide moiety. In certain embodiments, the post-translational modification is made in vivo in a eukaryotic cell or in a non-eukaryotic cell. A linker, polymer, water-soluble polymer, or other molecule may attach the molecule to the polypeptide. In an additional embodiment the linker attached to the IL-2 is long enough to permit formation of a dimer. The molecule may also be linked directly to the polypeptide.

In certain embodiments, the IL-2 protein includes at least one post-translational modification that is made in vivo by one host cell, where the post-translational modification is not normally made by another host cell type. In certain embodiments, the protein includes at least one post-translational modification that is made in vivo by a eukaryotic cell, where the post-translational modification is not normally made by a non-eukaryotic cell. Examples of post-translational modifications include, but are not limited to, glycosylation, acetylation, acylation, lipid-modification, palmitoylation, palmitate addition, phosphorylation, glycolipid-linkage modification, and the like.

In some embodiments, the IL-2 comprise one or more non-naturally encoded amino acids for glycosylation, acetylation, acylation, lipid-modification, palmitoylation, palmitate addition, phosphorylation, or glycolipid-linkage modification of the polypeptide. In some embodiments, the IL-2 comprise one or more non-naturally encoded amino acids for glycosylation of the polypeptide. In some embodiments, the IL-2 comprise one or more naturally encoded amino acids for glycosylation, acetylation, acylation, lipid-modification, palmitoylation, palmitate addition, phosphorylation, or glycolipid-linkage modification of the polypeptide. In some embodiments, the IL-2, comprise one or more naturally encoded amino acids for glycosylation of the polypeptide.

In some embodiments, the IL-2 comprises one or more non-naturally encoded amino acid additions and/or substitutions that enhance glycosylation of the polypeptide. In some embodiments, the IL-2 comprises one or more deletions that enhance glycosylation of the polypeptide. In some embodiments, the IL-2 comprises one or more non-naturally encoded amino acid additions and/or substitutions that enhance glycosylation at a different amino acid in the polypeptide. In some embodiments, the IL-2 comprises one or more deletions that enhance glycosylation at a different amino acid in the polypeptide. In some embodiments, the IL-2 comprises one or more non-naturally encoded amino acid additions and/or substitutions that enhance glycosylation at a non-naturally encoded amino acid in the polypeptide. In some embodiments, the IL-2 comprises one or more non-naturally encoded amino acid additions and/or substitutions that enhance glycosylation at a naturally encoded amino acid in the polypeptide. In some embodiments, the IL-2 comprises one or more naturally encoded amino acid additions and/or substitutions that enhance glycosylation at a different amino acid in the polypeptide. In some embodiments, the IL-2 comprises one or more non-naturally encoded amino acid additions and/or substitutions that enhance glycosylation at a naturally encoded amino acid in the polypeptide. In some embodiments, the IL-2 comprises one or more non-naturally encoded amino acid additions and/or substitutions that enhance glycosylation at a non-naturally encoded amino acid in the polypeptide.

In one embodiment, the post-translational modification comprises attachment of an oligosaccharide to an asparagine by a GlcNAc-asparagine linkage (including but not limited to, where the oligosaccharide comprises (GlcNAc-Man)$_2$-Man-GlcNAc-GlcNAc, and the like). In another embodiment, the post-translational modification comprises attachment of an oligosaccharide (including but not limited to, Gal-GalNAc, Gal-GlcNAc, etc.) to a serine or threonine by a GalNAc-serine, a GalNAc-threonine, a GlcNAc-serine, or a GlcNAc-threonine linkage. In certain embodiments, a protein or polypeptide of the invention can comprise a secretion or localization sequence, an epitope tag, a FLAG tag, a polyhistidine tag, a GST fusion, and/or the like. Examples of secretion signal sequences include, but are not limited to, a prokaryotic secretion signal sequence, a eukaryotic secretion signal sequence, a eukaryotic secretion signal sequence 5'-optimized for bacterial expression, a novel secretion signal sequence, pectate lyase secretion signal sequence, Omp A secretion signal sequence, and a phage secretion signal sequence. Examples of secretion signal sequences include, but are not limited to, STII (prokaryotic), Fd GIII and M13 (phage), Bgl2 (yeast), and the signal sequence bla derived from a transposon. Any such sequence may be modified to provide a desired result with the polypeptide, including but not limited to, substituting one signal sequence with a different signal sequence, substituting a leader sequence with a different leader sequence, etc.

The protein or polypeptide of interest can contain at least one, at least two, at least three, at least four, at least five, at least six, at least seven, at least eight, at least nine, or ten or more unnatural amino acids. The unnatural amino acids can be the same or different, for example, there can be 1, 2, 3, 4, 5, 6, 7, 8, 9, 10 or more different sites in the protein that comprise 1, 2, 3, 4, 5, 6, 7, 8, 9, 10 or more different unnatural amino acids. In certain embodiments, at least one, but fewer than all, of a particular amino acid present in a naturally occurring version of the protein is substituted with an unnatural amino acid.

The present invention provides methods and compositions based on IL-2 comprising at least one non-naturally encoded amino acid. Introduction of at least one non-naturally encoded amino acid into IL-2 can allow for the application of conjugation chemistries that involve specific chemical reactions, including, but not limited to, with one or more non-naturally encoded amino acids while not reacting with the commonly occurring 20 amino acids. In some embodiments, IL-2 comprising the non-naturally encoded amino acid is linked to a water-soluble polymer, such as polyethylene glycol (PEG), via the side chain of the non-naturally encoded amino acid. This invention provides a highly efficient method for the selective modification of proteins with PEG derivatives, which involves the selective incorporation of non-genetically encoded amino acids, including but not limited to, those amino acids containing functional groups or substituents not found in the 20 naturally incorporated amino acids, including but not limited to a ketone, an azide or acetylene moiety, into proteins in response to a selector codon and the subsequent modification of those amino acids with a suitably reactive PEG derivative. Once incorporated, the amino acid side chains can then be modified by utilizing chemistry methodologies known to those of ordinary skill in the art to be suitable for the particular functional groups or substituents present in the non-naturally encoded amino acid. Known chemistry methodologies of a wide variety are suitable for use in the present invention to incorporate a water-soluble polymer into the protein. Such methodologies include but are not limited to a Huisgen [3+2] cycloaddition reaction (see, e.g., Padwa, A. in Comprehensive Organic Synthesis, Vol. 4, (1991) Ed. Trost, B. M., Pergamon, Oxford, p. 1069-1109; and, Huisgen, R. in 1,3-Dipolar Cycloaddition Chemistry, (1984) Ed. Padwa, A., Wiley, New York, p. 1-176) with, including but not limited to, acetylene or azide derivatives, respectively.

Because the Huisgen [3+2] cycloaddition method involves a cycloaddition rather than a nucleophilic substitution reaction, proteins can be modified with extremely high selectivity. The reaction can be carried out at room temperature in aqueous conditions with excellent regioselectivity (1,4>1,5) by the addition of catalytic amounts of Cu(I) salts to the reaction mixture. See, e.g., Tornoe, et al., (2002) J. Org. Chem. 67:3057-3064; and, Rostovtsev, et al., (2002) Angew. Chem. Int. Ed. 41:2596-2599; and WO 03/101972. A molecule that can be added to a protein of the invention through a [3+2] cycloaddition includes virtually any molecule with a suitable functional group or substituent including but not limited to an azido or acetylene derivative. These molecules can be added to an unnatural amino acid with an acetylene group, including but not limited to, p-propargyloxyphenylalanine, or azido group, including but not limited to p-azido-phenylalanine, respectively.

The five-membered ring that results from the Huisgen [3+2] cycloaddition is not generally reversible in reducing environments and is stable against hydrolysis for extended periods in aqueous environments. Consequently, the physical and chemical characteristics of a wide variety of substances can be modified under demanding aqueous conditions with the active PEG derivatives of the present invention. Even more importantly, because the azide and acetylene moieties are specific for one another (and do not, for example, react with any of the 20 common, genetically-encoded amino acids), proteins can be modified in one or more specific sites with extremely high selectivity.

The invention also provides water-soluble and hydrolytically stable derivatives of PEG derivatives and related hydrophilic polymers having one or more acetylene or azide moieties. The PEG polymer derivatives that contain acetylene moieties are highly selective for coupling with azide moieties that have been introduced selectively into proteins in response to a selector codon. Similarly, PEG polymer derivatives that contain azide moieties are highly selective for coupling with acetylene moieties that have been introduced selectively into proteins in response to a selector codon.

More specifically, the azide moieties comprise, but are not limited to, alkyl azides, aryl azides and derivatives of these azides. The derivatives of the alkyl and aryl azides can include other substituents so long as the acetylene-specific reactivity is maintained. The acetylene moieties comprise alkyl and aryl acetylenes and derivatives of each. The derivatives of the alkyl and aryl acetylenes can include other substituents so long as the azide-specific reactivity is maintained.

The present invention provides conjugates of substances having a wide variety of functional groups, substituents or moieties, with other substances including but not limited to a label; a dye; a polymer; a water-soluble polymer; a derivative of polyethylene glycol; a photocrosslinker; a radionuclide; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide; a water-soluble dendrimer; a cyclodextrin; an inhibitory ribonucleic acid; a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a photoisomerizable moiety; biotin; a derivative of biotin; a biotin analogue; a moiety incorporating a heavy atom; a chemically cleavable group; a photocleavable group; an elongated side chain; a carbon-linked sugar; a redox-active agent; an amino thio-acid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; a quantum dot; a nanotransmitter; a radionucleotide; a radiotransmitter; a neutron-capture agent; or any combination of the above, or any other desirable compound or substance. The present invention also includes conjugates of substances having azide or acetylene moieties with PEG polymer derivatives having the corresponding acetylene or azide moieties. For example, a PEG polymer containing an azide moiety can be coupled to a biologically active molecule at a position in the protein that contains a non-genetically encoded amino acid bearing an acetylene functionality. The linkage by which the PEG and the biologically active molecule are coupled includes but is not limited to the Huisgen [3+2]cycloaddition product.

It is well established in the art that PEG can be used to modify the surfaces of biomaterials (see, e.g., U.S. Pat. No. 6,610,281; Mehvar, R., J. Pharm Sci., 3(1):125-136 (2000) which are incorporated by reference herein). The invention also includes biomaterials comprising a surface having one or more reactive azide or acetylene sites and one or more of the azide- or acetylene-containing polymers of the invention coupled to the surface via the Huisgen [3+2] cycloaddition linkage. Biomaterials and other substances can also be coupled to the azide- or acetylene-activated polymer derivatives through a linkage other than the azide or acetylene linkage, such as through a linkage comprising a carboxylic acid, amine, alcohol or thiol moiety, to leave the azide or acetylene moiety available for subsequent reactions.

The invention includes a method of synthesizing the azide- and acetylene-containing polymers of the invention. In the case of the azide-containing PEG derivative, the azide can be bonded directly to a carbon atom of the polymer. Alternatively, the azide-containing PEG derivative can be prepared by attaching a linking agent that has the azide moiety at one terminus to a conventional activated polymer so that the resulting polymer has the azide moiety at its terminus. In the case of the acetylene-containing PEG derivative, the acetylene can be bonded directly to a carbon atom of the polymer. Alternatively, the acetylene-containing PEG derivative can be prepared by attaching a linking agent that has the acetylene moiety at one terminus to a conventional activated polymer so that the resulting polymer has the acetylene moiety at its terminus.

More specifically, in the case of the azide-containing PEG derivative, a water-soluble polymer having at least one active hydroxyl moiety undergoes a reaction to produce a substituted polymer having a more reactive moiety, such as a mesylate, tresylate, tosylate or halogen leaving group, thereon. The preparation and use of PEG derivatives containing sulfonyl acid halides, halogen atoms and other leaving groups are known to those of ordinary skill in the art. The resulting substituted polymer then undergoes a reaction to substitute for the more reactive moiety an azide moiety at the terminus of the polymer. Alternatively, a water-soluble polymer having at least one active nucleophilic or electrophilic moiety undergoes a reaction with a linking agent that has an azide at one terminus so that a covalent bond is formed between the PEG polymer and the linking agent and the azide moiety is positioned at the terminus of the polymer. Nucleophilic and electrophilic moieties, including amines, thiols, hydrazides, hydrazines, alcohols, carboxylates, aldehydes, ketones, thioesters and the like, are known to those of ordinary skill in the art.

More specifically, in the case of the acetylene-containing PEG derivative, a water-soluble polymer having at least one active hydroxyl moiety undergoes a reaction to displace a halogen or other activated leaving group from a precursor that contains an acetylene moiety. Alternatively, a water-soluble polymer having at least one active nucleophilic or electrophilic moiety undergoes a reaction with a linking agent that has an acetylene at one terminus so that a covalent bond is formed between the PEG polymer and the linking agent and the acetylene moiety is positioned at the terminus of the polymer. The use of halogen moieties, activated leaving group, nucleophilic and electrophilic moieties in the context of organic synthesis and the preparation and use of PEG derivatives is well established to practitioners in the art.

The invention also provides a method for the selective modification of proteins to add other substances to the modified protein, including but not limited to water-soluble polymers such as PEG and PEG derivatives containing an azide or acetylene moiety. The azide- and acetylene-containing PEG derivatives can be used to modify the properties of surfaces and molecules where biocompatibility, stability, solubility and lack of immunogenicity are important, while at the same time providing a more selective means of attaching the PEG derivatives to proteins than was previously known in the art.

II. General Recombinant Nucleic Acid Methods for Use with the Invention

In numerous embodiments of the present invention, nucleic acids encoding an IL-2 of interest will be isolated, cloned and often altered using recombinant methods. Such embodiments are used, including but not limited to, for protein expression or during the generation of variants, derivatives, expression cassettes, or other sequences derived from an IL-2. In some embodiments, the sequences encoding the polypeptides of the invention are operably linked to a heterologous promoter.

Amino acid sequence of mature human IL-2 protein is shown below in Table 1.

TABLE 1

| IL-2 Protein and DNA sequences | | |
|---|---|---|
| SEQ. ID. NO. | Description | Sequence |
| 1 | Amino acid sequence - wild type IL-2 with leader sequence, (eukaryotic expression) | MYRMQLLSCIALSLALVTNSAPTSSST KKTQLQLEHLLLDLQMILNGINNYKNP KLTRMLTFKFYMPKKATELKHLQCLE EELKPLEEVLNLAQSKNFHLRPRDLISN INVIVLELKGSETTFMCEYADETATIVE FLNRWITFCQSIISTLT |
| 2 | Amino acid sequence - mature human IL-2 protein (eukaryotic expression) | APTSSSTKKTQLQLEHLLLDLQMILNG INNYKNPKLTRMLTFKFYMPKKATEL KHLQCLEEELKPLEEVLNLAQSKNFH LRPRDLISNINVIVLELKGSETTFMCEY ADETATIVEFLNRWITFCQSIISTLT |
| 3 | Amino acid sequence - mature human IL-2 protein expressed in E. coli. | MPTSSSTKKTQLQLEHLLLDLQMILNGI NNYKNPKLTRMLTFKFYMPKKATELK HLQCLEEELKPLEEVLNLAQSKNFHLR PRDLISNINVIVLELKGSETTFMCEYAD ETATIVEFLNRWITFSQSIISTLT |
| 4 | DNA sequence - synthetic human IL-2 gene cloned into pKG0269 expression plasmid. (E. coli codon optimized). | ATGCCGACCAGCAGTAGCACCAAGA AAAACTCAGCTGCAGCTGGAGCATCT GCTGCTGGATTTACAGATGATTCTG AATGGCATTAATAATTACAAAAATC CGAAACTGACCCGCATGCTGACCTT CAAGTTCTACATGCCGAAGAAGGCC ACCGAACTGAAGCATCTGCAGTGTT TAGAAGAGGAACTGAAGCCGCTGG AAGAGGTGCTGAATTTAGCCCAGAG CAAAAACTTCCATCTGCGCCCGCGC GATTTAATTAGCAATATTAACGTGA TTGTGCTGGAACTGAAAGGCAGCGA GACCACCTTTATGTGCGAGTACGCA GATGAGACCGCCACCATCGTGGAAT TTTTAAACCGCTGGATCACCTTCAGC CAGAGTATCATTAGCACTTTAACC |
| 5 | Amino acid sequence - mature human IL-2 protein with N-terminal Alanine after start codon, ATG, expressed in E. coli. | MAPTSSSTKKTQLQLEHLLLDLQMIL NGINNYKNPKLTRMLTFKFYMPKKAT ELKHLQCLEEELKPLEEVLNLAQSKN FHLRPRDLISNINVIVLELKGSETTFMC EYADETATIVEFLNRWITFSQSIISTLT |
| 6 | DNA sequence - human IL-2 protein with N-terminal Alanine after start codon, ATG. | ATG GCA CCG ACC AGC AGT AGC ACC AAG AAA ACT CAG CTG CAG CTG GAG CAT CTG CTG CTG GAT TTA CAG ATG ATT CTG AAT GGC ATT AAT AAT TAC AAA AAT CCG AAA CTG ACC CGC ATG CTG ACC TTC AAG TTC TAC ATG CCG AAG AAG GCC ACC GAA CTG AAG CAT CTG CAG TGT TTA GAA GAG GAA CTG AAG CCG |

TABLE 1-continued

IL-2 Protein and DNA sequences

| SEQ. ID. NO. | Description | Sequence |
|---|---|---|
| | | CTG GAA GAG GTG CTG AAT TTA<br>GCC CAG AGC AAA AAC TTC CAT<br>CTG CGC CCG CGC GAT TTA ATT<br>AGC AAT ATT AAC GTG ATT GTG<br>CTG GAA CTG AAA GGC AGC GAG<br>ACC ACC TTT ATG TGC GAG TAC<br>GCA GAT GAG ACC GCC ACC ATC<br>GTG GAA TTT TTA AAC CGC TGG<br>ATC ACC TTC AGC CAG AGT ATC<br>ATT AGC ACT TTA ACC |
| 7 | Amino acid sequence - mature human IL-2 protein with N-terminal Proline deletion after start codon, ATG, expressed in E. coli. | MTSSSTKKTQLQLEHLLLDLQMILNGI<br>NNYKNPKLTRMLTFKFYMPKKATEL<br>KHLQCLEEELKPLEEVLNLAQSKNFH<br>LRPRDLISNINVIVLELKGSETTFMCEY<br>ADETATIVEFLNRWITFSQSIISTLT |
| 8 | DNA coding sequence - human IL-2 protein with N-terminal Proline deletion after start codon, ATG | ATG ACC AGC AGT AGC ACC AAG<br>AAA ACT CAG CTG CAG CTG GAG<br>CAT CTG CTG CTG GAT TTA CAG<br>ATG ATT CTG<br>AAT GGC ATT AAT AAT TAC AAA<br>AAT CCG AAA CTG ACC CGC ATG<br>CTG ACC TTC AAG TTC TAC ATG<br>CCG AAG AAG GCC ACC GAA CTG<br>AAG CAT CTG CAG TGT TTA GAA<br>GAG GAA CTG AAG CCG CTG GAA<br>GAG GTG CTG AAT TTA GCC CAG<br>AGC AAA AAC TTC CAT CTG CGC<br>CCG CGC GAT TTA ATT AGC AAT<br>ATT AAC GTG ATT GTG CTG GAA<br>CTG AAA GGC AGC GAG ACC ACC<br>TTT ATG TGC GAG TAC GCA GAT<br>GAG ACC GCC ACC ATC GTG GAA<br>TTT TTA AAC CGC TGG ATC ACC<br>TTC AGC CAG AGT ATC ATT AGC<br>ACT TTA ACC |

A nucleotide sequence encoding an IL-2 comprising a non-naturally encoded amino acid may be synthesized on the basis of the amino acid sequence of the parent polypeptide, including but not limited to, having the amino acid sequence shown in SEQ ID NO: 1, 2, 3, 5 or 7, and then changing the nucleotide sequence so as to effect introduction (i.e., incorporation or substitution) or removal (i.e., deletion or substitution) of the relevant amino acid residue(s). The nucleotide sequence may be conveniently modified by site-directed mutagenesis in accordance with conventional methods. Alternatively, the nucleotide sequence may be prepared by chemical synthesis, including but not limited to, by using an oligonucleotide synthesizer, wherein oligonucleotides are designed based on the amino acid sequence of the desired polypeptide, and preferably selecting those codons that are favored in the host cell in which the recombinant polypeptide will be produced. For example, several small oligonucleotides coding for portions of the desired polypeptide may be synthesized and assembled by PCR, ligation or ligation chain reaction. See, e.g., Barany, et al., Proc. Natl. Acad. Sci. 88: 189-193 (1991); U.S. Pat. No. 6,521,427 which are incorporated by reference herein.

A DNA sequence of synthetic human IL-2 gene that was cloned into pKG0269 expression plasmid is shown in Table 1, above, as SEQ ID NO: 4. This DNA sequence has been E. coli codon optimized.

This invention utilizes routine techniques in the field of recombinant genetics. Basic texts disclosing the general methods of use in this invention include Sambrook et al., Molecular Cloning, A Laboratory Manual (3rd ed. 2001); Kriegler, Gene Transfer and Expression: A Laboratory Manual (1990); and Current Protocols in Molecular Biology (Ausubel et al., eds., 1994)).

The invention also relates to eukaryotic host cells, non-eukaryotic host cells, and organisms for the in vivo incorporation of an unnatural amino acid via orthogonal tRNA/RS pairs. Host cells are genetically engineered (including but not limited to, transformed, transduced or transfected) with the polynucleotides of the invention or constructs which include a polynucleotide of the invention, including but not limited to, a vector of the invention, which can be, for example, a cloning vector or an expression vector.

Several well-known methods of introducing target nucleic acids into cells are available, any of which can be used in the invention. These include: fusion of the recipient cells with bacterial protoplasts containing the DNA, electroporation, projectile bombardment, and infection with viral vectors (discussed further, below), etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, kits are commercially available for the purification of plasmids from bacteria, (see, e.g., EasyPrep™, Flexi-iPrep™, both from Pharmacia Biotech; StrataClean™ from Stratagene; and, QIAprep™ from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (including but not limited to, shuttle vectors) and selection markers for both prokaryotic and eukaryotic systems. Vectors are suitable for replication and integration in prokaryotes, eukaryotes, or both. See, Gillam & Smith, Gene 8:81 (1979); Roberts, et al., Nature, 328:731 (1987); Schneider, E., et al., Protein Expr. Purif. 6(1):10-14 (1995); Ausubel, Sambrook, Berger (all supra). A catalogue of bacteria and bacteriophages useful for cloning is provided, e.g., by the ATCC, e.g., The ATCC Catalogue of Bacteria and Bacteriophage (1992) Ghema et al. (eds) published by the ATCC. Additional basic procedures for sequencing, cloning and other aspects of molecular biology and underlying theoretical considerations are also found in Watson et al. (1992) Recombinant DNA Second Edition Scientific American Books, NY. In addition, essentially any nucleic acid (and virtually any labeled nucleic acid, whether standard or non-standard) can be custom or standard ordered from any of a variety of commercial sources, such as the Midland Certified Reagent Company (Midland, TX available on the World Wide Web at mcrc.com), The Great American Gene Company (Ramona, CA available on the World Wide Web at genco.com), Express-Gen Inc. (Chicago, IL available on the World Wide Web at expressgen.com), Operon Technologies Inc. (Alameda, CA) and many others.

Selector Codons

Selector codons of the invention expand the genetic codon framework of protein biosynthetic machinery. For example, a selector codon includes, but is not limited to, a unique three base codon, a nonsense codon, such as a stop codon, including but not limited to, an amber codon (UAG), an ochre codon, or an opal codon (UGA), an unnatural codon, a four or more base codon, a rare codon, or the like. It is readily apparent to those of ordinary skill in the art that there is a wide range in the number of selector codons that can be introduced into a desired gene or polynucleotide, including but not limited to, one or more, two or more, three or more, 4, 5, 6, 7, 8, 9, 10 or more in a single polynucleotide encoding at least a portion of the IL-2.

In one embodiment, the methods involve the use of a selector codon that is a stop codon for the incorporation of one or more unnatural amino acids in vivo. For example, an O-tRNA is produced that recognizes the stop codon, including but not limited to, UAG, and is aminoacylated by an O—RS with a desired unnatural amino acid. This O-tRNA is not recognized by the naturally occurring host's aminoacyl-tRNA synthetases. Conventional site-directed mutagenesis can be used to introduce the stop codon, including but not limited to, TAG, at the site of interest in a polypeptide of interest. See, e.g., Sayers, J. R., et al. (1988), 5'-3' Exonucleases in phosphorothioate-based oligonucleotide-directed mutagenesis. Nucleic Acids Res, 16:791-802. When the O—RS, O-tRNA and the nucleic acid that encodes the polypeptide of interest are combined in vivo, the unnatural amino acid is incorporated in response to the UAG codon to give a polypeptide containing the unnatural amino acid at the specified position.

The incorporation of unnatural amino acids in vivo can be done without significant perturbation of the eukaryotic host cell. For example, because the suppression efficiency for the UAG codon depends upon the competition between the O-tRNA, including but not limited to, the amber suppressor tRNA, and a eukaryotic release factor (including but not limited to, eRF) (which binds to a stop codon and initiates release of the growing peptide from the ribosome), the suppression efficiency can be modulated by, including but not limited to, increasing the expression level of O-tRNA, and/or the suppressor tRNA.

Unnatural amino acids can also be encoded with rare codons. For example, when the arginine concentration in an in vitro protein synthesis reaction is reduced, the rare arginine codon, AGG, has proven to be efficient for insertion of Ala by a synthetic tRNA acylated with alanine. See, e.g., Ma et al., Biochemistry, 32:7939 (1993). In this case, the synthetic tRNA competes with the naturally occurring tRNAArg, which exists as a minor species in *Escherichia coli*. Some organisms do not use all triplet codons. An unassigned codon AGA in *Micrococcus luteus* has been utilized for insertion of amino acids in an in vitro transcription/translation extract. See, e.g., Kowal and Oliver, Nucl. Acid. Res., 25:4685 (1997). Components of the present invention can be generated to use these rare codons in vivo.

Selector codons also comprise extended codons, including but not limited to, four or more base codons, such as, four, five, six or more base codons. Examples of four base codons include, but are not limited to, AGGA, CUAG, UAGA, CCCU and the like. Examples of five base codons include, but are not limited to, AGGAC, CCCCU, CCCUC, CUAGA, CUACU, UAGGC and the like. A feature of the invention includes using extended codons based on frameshift suppression. Four or more base codons can insert, including but not limited to, one or multiple unnatural amino acids into the same protein. For example, in the presence of mutated O-tRNAs, including but not limited to, a special frameshift suppressor tRNAs, with anticodon loops, for example, with at least 8-10 nt anticodon loops, the four or more base codon is read as single amino acid. In other embodiments, the anticodon loops can decode, including but not limited to, at least a four-base codon, at least a five-base codon, or at least a six-base codon or more. Since there are 256 possible four-base codons, multiple unnatural amino acids can be encoded in the same cell using a four or more base codon. See, Anderson et al., Exploring the Limits of Codon and Anticodon Size, Chemistry and Biology, 9:237-244, (2002); Magliery, Expanding the Genetic Code: Selection of Efficient Suppressors of Four-base Codons and Identification of "Shifty" Four-base Codons with a Library Approach in *Escherichia coli*, J. Mol. Biol. 307: 755-769, (2001).

For example, four-base codons have been used to incorporate unnatural amino acids into proteins using in vitro biosynthetic methods. See, e.g., Ma et al., Biochemistry, 32:7939, (1993); and Hohsaka et al., J. Am. Chem. Soc., 121:34, (1999). CGGG and AGGU were used to simultaneously incorporate 2-naphthylalanine and an NBD derivative of lysine into streptavidin in vitro with two chemically acylated frameshift suppressor tRNAs. See, e.g., Hohsaka et al., J. Am. Chem. Soc., 121:12194, (1999). In an in vivo study, Moore et al. examined the ability of tRNALeu derivatives with NCUA anticodons to suppress UAGN codons (N can be U, A, G, or C), and found that the quadruplet UAGA can be decoded by a tRNALeu with a UCUA anticodon with an efficiency of 13 to 26% with little decoding in the 0 or −1 frame. See, Moore et al., J. Mol. Biol., 298:195, (2000). In one embodiment, extended codons based on rare codons or nonsense codons can be used in the present invention, which can reduce missense readthrough and frameshift suppression at other unwanted sites.

For a given system, a selector codon can also include one of the natural three base codons, where the endogenous system does not use (or rarely uses) the natural base codon. For example, this includes a system that is lacking a tRNA that recognizes the natural three base codon, and/or a system where the three base codon is a rare codon.

Selector codons optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs which can be adapted for methods and compositions include, e.g., Hirao, et al., An unnatural base pair for incorporating amino acid analogues into protein, Nature Biotechnology, 20:177-182, (2002). See, also, Wu, Y., et al., J. Am. Chem. Soc. 124:14626-14630, (2002). Other relevant publications are listed below.

For in vivo usage, the unnatural nucleoside is membrane permeable and is phosphorylated to form the corresponding triphosphate. In addition, the increased genetic information is stable and not destroyed by cellular enzymes. Previous efforts by Benner and others took advantage of hydrogen bonding patterns that are different from those in canonical Watson-Crick pairs, the most noteworthy example of which is the iso-C:iso-G pair. See, e.g., Switzer et al., J. Am. Chem. Soc., 111:8322, (1989); and Piccirilli et al., Nature, 343:33, (1990); Kool, Curr. Opin. Chem. Biol., 4:602, (2000). These bases in general mispair to some degree with natural bases and cannot be enzymatically replicated. Kool and co-workers demonstrated that hydrophobic packing interactions between bases can replace hydrogen bonding to drive the formation of base pair. See, Kool, Curr. Opin. Chem. Biol., 4:602, (2000); and Guckian and Kool, Angew. Chem. Int. Ed. Engl., 36, 2825, (1998). In an effort to develop an unnatural base pair satisfying all the above requirements, Schultz, Romesberg and co-workers have systematically synthesized and studied a series of unnatural hydrophobic bases. A PICS:PICS self-pair is found to be more stable than natural base pairs, and can be efficiently incorporated into DNA by Klenow fragment of *Escherichia coli* DNA polymerase I (KF). See, e.g., McMinn et al., J. Am. Chem. Soc., 121:11585-6, (1999); and Ogawa et al., J. Am. Chem. Soc., 122:3274, (2000). A 3MN:3MN self-pair can be synthesized by KF with efficiency and selectivity sufficient for biological function. See, e.g., Ogawa et al., J. Am. Chem. Soc., 122:8803, (2000). However, both bases act as a chain terminator for further replication. A mutant DNA polymerase has been recently evolved that can be used to replicate the PICS self pair. In addition, a 7AI self pair can be replicated. See, e.g., Tae et al., J. Am. Chem. Soc., 123:7439, (2001). A novel metallobase pair, Dipic:Py, has also been developed, which forms a stable pair upon binding Cu(II). See, Meggers et al., J. Am. Chem. Soc., 122:10714, (2000). Because extended codons and unnatural codons are intrinsically orthogonal to natural codons, the methods of the invention can take advantage of this property to generate orthogonal tRNAs for them.

A translational bypassing system can also be used to incorporate an unnatural amino acid in a desired polypeptide. In a translational bypassing system, a large sequence is incorporated into a gene but is not translated into protein. The sequence contains a structure that serves as a cue to induce the ribosome to hop over the sequence and resume translation downstream of the insertion.

In certain embodiments, the protein or polypeptide of interest (or portion thereof) in the methods and/or compositions of the invention is encoded by a nucleic acid. Typically, the nucleic acid comprises at least one selector codon, at least two selector codons, at least three selector codons, at least four selector codons, at least five selector codons, at least six selector codons, at least seven selector codons, at least eight selector codons, at least nine selector codons, ten or more selector codons.

Genes coding for proteins or polypeptides of interest can be mutagenized using methods known to one of ordinary skill in the art and described herein to include, for example, one or more selector codon for the incorporation of an unnatural amino acid. For example, a nucleic acid for a protein of interest is mutagenized to include one or more selector codon, providing for the incorporation of one or more unnatural amino acids. The invention includes any such variant, including but not limited to, mutant, versions of any protein, for example, including at least one unnatural amino acid. Similarly, the invention also includes corresponding nucleic acids, i.e., any nucleic acid with one or more selector codon that encodes one or more unnatural amino acid.

Nucleic acid molecules encoding a protein of interest such as an IL-2 may be readily mutated to introduce a cysteine at any desired position of the polypeptide. Cysteine is widely used to introduce reactive molecules, water-soluble polymers, proteins, or a wide variety of other molecules, onto a protein of interest. Methods suitable for the incorporation of cysteine into a desired position of a polypeptide are known to those of ordinary skill in the art, such as those described in U.S. Pat. No. 6,608,183, which is incorporated by reference herein, and standard mutagenesis techniques.

III. Non-Naturally Encoded Amino Acids

A very wide variety of non-naturally encoded amino acids are suitable for use in the present invention. Any number of non-naturally encoded amino acids can be introduced into a IL-2. In general, the introduced non-naturally encoded amino acids are substantially chemically inert toward the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). In some embodiments, the non-naturally encoded amino acids include side chain functional groups that react efficiently and selectively with functional groups not found in the 20 common amino acids (including but not limited to, azido, ketone, aldehyde and aminooxy groups) to form stable conjugates. For example, an IL-2 that includes a non-naturally encoded amino acid containing an azido functional group can be reacted with a polymer (including but not limited to, poly(ethylene glycol) or, alternatively, a second polypeptide containing an alkyne moiety) to form a stable conjugate resulting for the selective reaction of the azide and the alkyne functional groups to form a Huisgen [3+2] cycloaddition product.

The generic structure of an alpha-amino acid is illustrated as follows (Formula I).

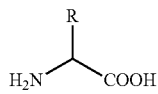

I

A non-naturally encoded amino acid is typically any structure having the above-listed formula wherein the R group is any substituent other than one used in the twenty natural amino acids, and may be suitable for use in the present invention. Because the non-naturally encoded amino acids of the invention typically differ from the natural amino acids only in the structure of the side chain, the non-naturally encoded amino acids form amide bonds with other amino acids, including but not limited to, natural or non-naturally encoded, in the same manner in which they are formed in naturally occurring polypeptides. However, the non-naturally encoded amino acids have side chain groups that distinguish them from the natural amino acids. For example, R optionally comprises an alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amino group, or the like or any combination thereof. Other non-naturally occurring amino acids of interest that may be suitable for use in the present invention include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, amino acids comprising polyethylene glycol or polyether, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

Exemplary non-naturally encoded amino acids that may be suitable for use in the present invention and that are useful for reactions with water-soluble polymers include, but are not limited to, those with carbonyl, aminooxy, hydrazine, hydrazide, semicarbazide, azide and alkyne reactive groups. In some embodiments, non-naturally encoded amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature—including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

Many of the non-naturally encoded amino acids provided herein are commercially available, e.g., from Sigma-Aldrich (St. Louis, MO, USA), Novabiochem (a division of EMD Biosciences, Darmstadt, Germany), or Peptech (Burlington, MA, USA). Those that are not commercially available are optionally synthesized as provided herein or using standard methods known to those of ordinary skill in the art. For organic synthesis techniques, see, e.g., Organic Chemistry by Fessendon and Fessendon, Second Edition, Willard Grant Press, Boston Mass, (1982); Advanced Organic Chemistry by March Third Edition, Wiley and Sons, New York, (1985); and Advanced Organic Chemistry by Carey and Sundberg, Third Edition, Parts A and B, Plenum Press, New York, (1990). See, also, U.S. Pat. Nos. 7,045,337 and 7,083,970, which are incorporated by reference herein. In addition to unnatural amino acids that contain novel side chains, unnatural amino acids that may be suitable for use in the present invention also optionally comprise modified backbone structures, including but not limited to, as illustrated by the structures of Formula II and III:

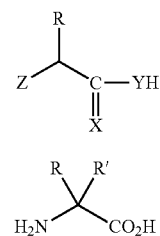

II

III wherein Z typically comprises OH, NH$_2$, SH, NH—R', or S—R'; X and Y, which can be the same or different, typically comprise S or O, and R and R', which are optionally the same or different, are typically selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids, α-aminothiocarboxylates, including but not limited to, with side chains corresponding to the common twenty natural amino acids or unnatural side chains. In addition, substitutions at the α-carbon optionally include, but are not limited to, L, D, or α-a-disubstituted amino acids such as D-glutamate, D-alanine, D-methyl-O-tyrosine, aminobutyric acid, and the like. Other structural alternatives include cyclic amino acids, such as proline analogues as well as 3, 4,6, 7, 8, and 9 membered ring proline analogues, β and γ amino acids such as substituted β-alanine and γ-amino butyric acid.

Many unnatural amino acids are based on natural amino acids, such as tyrosine, glutamine, phenylalanine, and the like, and are suitable for use in the present invention. Tyrosine analogs include, but are not limited to, para-substituted tyrosines, ortho-substituted tyrosines, and meta substituted tyrosines, where the substituted tyrosine comprises, including but not limited to, a keto group (including but not limited to, an acetyl group), a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, an alkynyl group or the like. In addition, multiply substituted aryl rings are also contemplated. Glutamine analogs that may be suitable for use in the present invention include, but are not limited to, α-hydroxy derivatives, γ-substituted derivatives, cyclic derivatives, and amide substituted glutamine derivatives. Example phenylalanine analogs that may be suitable for use in the present invention include, but are not limited to, para-substituted phenylalanines, ortho-substituted phenyalanines, and meta-substituted phenylalanines, where the substituent comprises, including but not limited to, a hydroxy group, a methoxy group, a methyl group, an allyl group, an aldehyde, an azido, an iodo, a bromo, a keto group (including but not limited to, an acetyl group), a benzoyl, an alkynyl group, or the like. Specific examples of unnatural amino acids that may be suitable for use in the present invention include, but are not limited to, a p-acetyl-L-phenylalanine, an O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcs-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, and a p-propargyloxy-phenylalanine, and the like. Examples of structures of a variety of unnatural amino acids that may be suitable for use in the present invention are provided in, for example, WO 2002/085923 entitled "In vivo incorporation of unnatural amino acids." See also Kiick et al., Incorporation of azides into recombinant proteins for chemoselective modification by the Staudinger ligation, PNAS 99:19-24, (2002), which is incorporated by reference herein, for additional methionine analogs. International Application No. PCT/US06/47822 entitled "Compositions Containing, Methods Involving, and Uses of Non-natural Amino Acids and Polypeptides," which is incorporated by reference herein, describes reductive alkylation of an aromatic amine moieties, including but not limited to, p-aminophenylalanine and reductive amination.

In another embodiment of the present invention, the IL-2 polypeptides with one or more non-naturally encoded amino acids are covalently modified. Selective chemical reactions that are orthogonal to the diverse functionality of biological systems are recognized as important tools in chemical biology. As relative newcomers to the repertoire of synthetic chemistry, these bioorthogonal reactions have inspired new strategies for compound library synthesis, protein engineering, functional proteomics, and chemical remodeling of cell surfaces. The azide has secured a prominent role as a unique chemical handle for bioconjugation. The Staudinger ligation has been used with phosphines to tag azidosugars metabolically introduced into cellular glycoconjugates. The Staudinger ligation can be performed in living animals without physiological harm; nevertheless, the Staudinger reaction is not without liabilities. The requisite phosphines are susceptible to air oxidation and their optimization for improved water solubility and increased reaction rate has proven to be synthetically challenging.

The azide group has an alternative mode of bioorthogonal reactivity: the [3+2]cycloaddition with alkynes described by Huisgen. In its classic form, this reaction has limited applicability in biological systems due to the requirement of elevated temperatures (or pressures) for reasonable reaction rates. Sharpless and coworkers surmounted this obstacle with the development of a copper(I)-catalyzed version, termed "click chemistry," that proceeds readily at physiological temperatures and in richly functionalized biological environs. This discovery has enabled the selective modification of virus particles, nucleic acids, and proteins from complex tissue lysates. Unfortunately, the mandatory copper catalyst is toxic to both bacterial and mammalian cells, thus precluding applications wherein the cells must remain viable. Catalyst-free Huisgen cycloadditions of alkynes activated by electron-withdrawing substituents have been reported to occur at ambient temperatures. However, these compounds undergo Michael reaction with biological nucleophiles.

In one embodiment, compositions of an IL-2 that include an unnatural amino acid (such asp-(propargyloxy)-phenylalanine) are provided. Various compositions comprising p-(propargyloxy)-phenylalanine and, including but not limited to, proteins and/or cells, are also provided. In one aspect, a composition that includes the p-(propargyloxy)-phenylalanine unnatural amino acid, further includes an orthogonal tRNA. The unnatural amino acid can be bonded (including but not limited to, covalently) to the orthogonal tRNA, including but not limited to, covalently bonded to the orthogonal tRNA though an amino-acyl bond, covalently bonded to a 3'OH or a 2'OH of a terminal ribose sugar of the orthogonal tRNA, etc.

The chemical moieties via unnatural amino acids that can be incorporated into proteins offer a variety of advantages and manipulations of the protein. For example, the unique reactivity of a keto functional group allows selective modification of proteins with any of a number of hydrazine- or hydroxylamine-containing reagents in vitro and in vivo. A heavy atom unnatural amino acid, for example, can be useful for phasing X-ray structure data. The site-specific introduction of heavy atoms using unnatural amino acids also provides selectivity and flexibility in choosing positions for heavy atoms. Photoreactive unnatural amino acids (including but not limited to, amino acids with benzophenone and arylazides (including but not limited to, phenylazide) side chains), for example, allow for efficient in vivo and in vitro photocrosslinking of protein. Examples of photoreactive unnatural amino acids include, but are not limited to, p-azido-phenylalanine and p-benzoyl-phenylalanine. The protein with the photoreactive unnatural amino acids can then be crosslinked at will by excitation of the photoreactive group-providing temporal control. In one example, the methyl group of an unnatural amino can be substituted with an isotopically labeled, including but not limited to, methyl group, as a probe of local structure and dynamics, including but not limited to, with the use of nuclear magnetic resonance and vibrational spectroscopy. Alkynyl or azido functional groups, for example, allow the selective modification of proteins with molecules through a [3+2] cycloaddition reaction.

A non-natural amino acid incorporated into a polypeptide at the amino terminus can be composed of an R group that is any substituent other than one used in the twenty natural amino acids and a $2^{nd}$ reactive group different from the $NH_2$ group normally present in α-amino acids (see Formula I). A similar non-natural amino acid can be incorporated at the carboxyl terminus with a $2^{nd}$ reactive group different from the COOH group normally present in α-amino acids (see Formula I).

The unnatural amino acids of the invention may be selected or designed to provide additional characteristics unavailable in the twenty natural amino acids. For example, unnatural amino acid may be optionally designed or selected to modify the biological properties of a protein, e.g., into which they are incorporated. For example, the following properties may be optionally modified by inclusion of an unnatural amino acid into a protein: toxicity, biodistribution, solubility, stability, e.g., thermal, hydrolytic, oxidative, resistance to enzymatic degradation, and the like, facility of purification and processing, structural properties, spectroscopic properties, chemical and/or photochemical properties, catalytic activity, redox potential, half-life, ability to react with other molecules, e.g., covalently or noncovalently, and the like.

In some embodiments the present invention provides IL-2 linked to a water-soluble polymer, e.g., a PEG, by an oxime bond. Many types of non-naturally encoded amino acids are suitable for formation of oxime bonds. These include, but are not limited to, non-naturally encoded amino acids containing a carbonyl, dicarbonyl, or hydroxylamine group. Such amino acids are described in U.S. Patent Publication Nos. 2006/0194256, 2006/0217532, and 2006/0217289 and WO 2006/069246 entitled "Compositions containing, methods involving, and uses of non-natural amino acids and polypeptides," which are incorporated herein by reference in their entirety. Non-naturally encoded amino acids are also described in U.S. Pat. Nos. 7,083,970 and 7,045,337, which are incorporated by reference herein in their entirety.

Some embodiments of the invention utilize IL-2 polypeptides that are substituted at one or more positions with a para-acetylphenylalanine amino acid. The synthesis of p-acetyl-(+/−)-phenylalanine and m-acetyl-(+/−)-phenylalanine are described in Zhang, Z., et al., Biochemistry 42: 6735-6746 (2003), incorporated by reference. Other carbonyl- or dicarbonyl-containing amino acids can be similarly prepared by one of ordinary skill in the art. Further, non-limiting exemplary syntheses of non-natural amino acid that are included herein are presented in FIGS. 4, 24-34 and 36-39 of U.S. Pat. No. 7,083,970, which is incorporated by reference herein in its entirety.

Amino acids with an electrophilic reactive group allow for a variety of reactions to link molecules via nucleophilic addition reactions among others. Such electrophilic reactive groups include a carbonyl group (including a keto group and a dicarbonyl group), a carbonyl-like group (which has reactivity similar to a carbonyl group (including a keto group and a dicarbonyl group) and is structurally similar to a carbonyl group), a masked carbonyl group (which can be readily converted into a carbonyl group (including a keto group and a dicarbonyl group)), or a protected carbonyl group (which has reactivity similar to a carbonyl group (including a keto group and a dicarbonyl group) upon deprotection). Such amino acids include amino acids having the structure of Formula (IV):

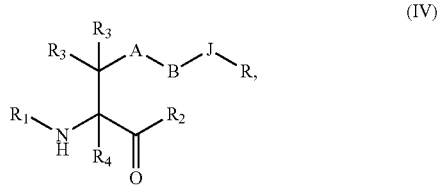

(IV)

wherein:
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl;

J is

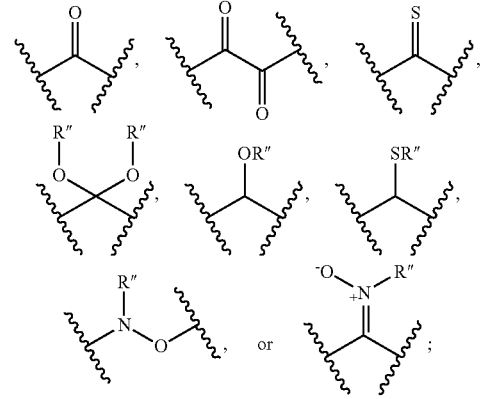

R is H, alkyl, substituted alkyl, cycloalkyl, or substituted cycloalkyl;
each R" is independently H, alkyl, substituted alkyl, or a protecting group, or when more than one R" group is present, two R" optionally form a heterocycloalkyl;
$R_1$ is optional, and when present, is H, an amino protecting group, resin, amino acid, polypeptide, or polynucleotide; and
$R_2$ is optional, and when present, is OH, an ester protecting group, resin, amino acid, polypeptide, or polynucleotide;
each of $R_3$ and $R_4$ is independently H, halogen, lower alkyl, or substituted lower alkyl, or $R_3$ and $R_4$ or two $R_3$ groups optionally form a cycloalkyl or a heterocycloalkyl;
or the -A-B-J-R groups together form a bicyclic or tricyclic cycloalkyl or heterocycloalkyl comprising at least one carbonyl group, including a dicarbonyl group, protected carbonyl group, including a protected dicarbonyl group, or masked carbonyl group, including a masked dicarbonyl group;
or the -J-R group together forms a monocyclic or bicyclic cycloalkyl or heterocycloalkyl comprising at least one carbonyl group, including a dicarbonyl group, protected carbonyl group, including a protected dicarbonyl group, or masked carbonyl group, including a masked dicarbonyl group;

with a proviso that when A is phenylene and each $R_3$ is H, B is present; and that when A is —$(CH_2)_4$— and each $R_3$ is H, B is not —NHC(O)($CH_2CH_2$)—; and that when A and B are absent and each $R_3$ is H, R is not methyl.

In addition, having the structure of Formula (V) are included:

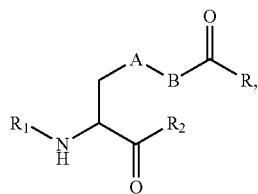

(V)

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

with a proviso that when A is phenylene, B is present; and that when A is —$(CH_2)_4$—, B is not —NHC(O)($CH_2CH_2$)—; and that when A and B are absent, R is not methyl.

In addition, amino acids having the structure of Formula (VI) are included:

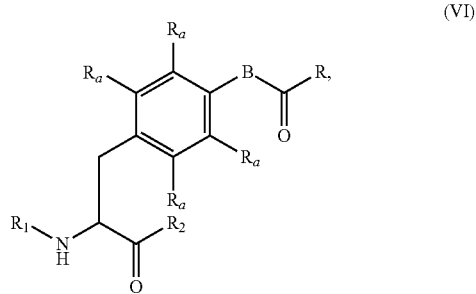

(VI)

wherein:

B is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

each $R_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl.

In addition, the following amino acids are included:

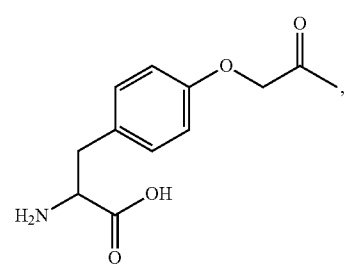

-continued

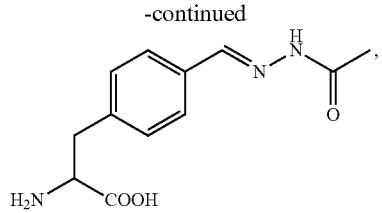

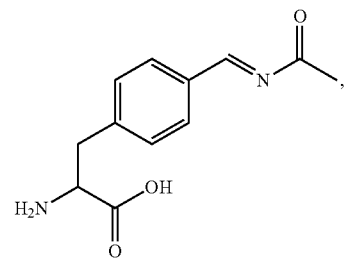 [SMILES: CC(=O)CCc1ccc(CC(N)C(=O)O)cc1]

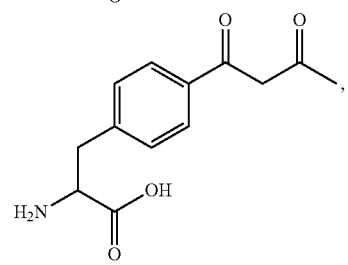

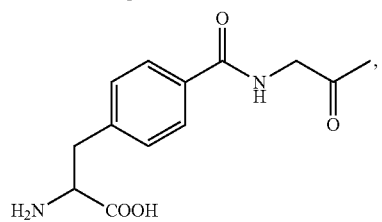

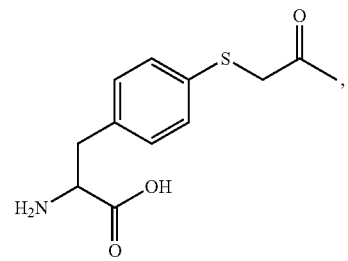

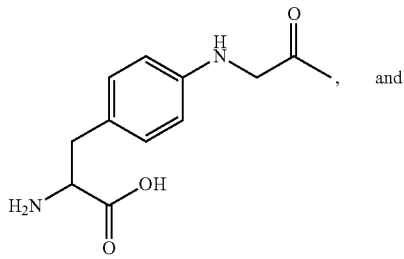

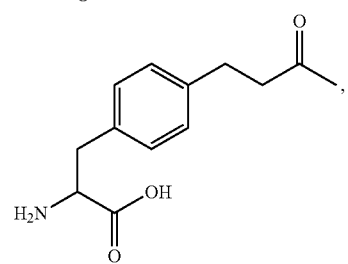

wherein such compounds are optionally amino protected group, carboxyl protected or a salt thereof. In addition, any of the following non-natural amino acids may be incorporated into a non-natural amino acid polypeptide.

In addition, the following amino acids having the structure of Formula (VII) are included:

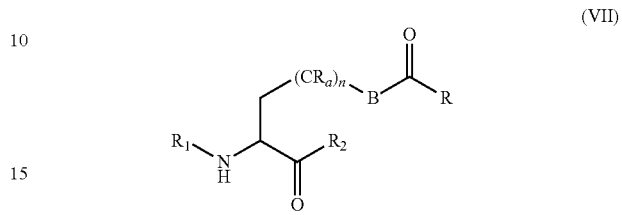

(VII)

wherein
B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl;
R is H, alkyl, substituted alkyl, cycloalkyl, or substituted cycloalkyl;
$R_1$ is optional, and when present, is H, an amino protecting group, resin, amino acid, polypeptide, or polynucleotide; and
$R_2$ is optional, and when present, is OH, an ester protecting group, resin, amino acid, polypeptide, or polynucleotide;
each $R_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl; and n is 0 to 8;
with a proviso that when A is —(CH$_2$)$_4$—, B is not —NHC(O)(CH$_2$CH$_2$)—.

In addition, the following amino acids are included:

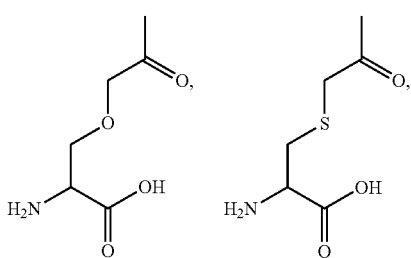

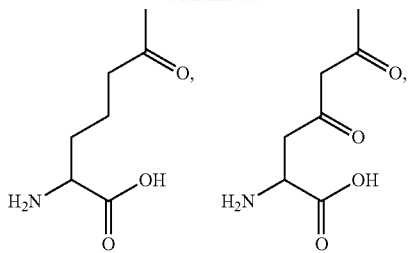
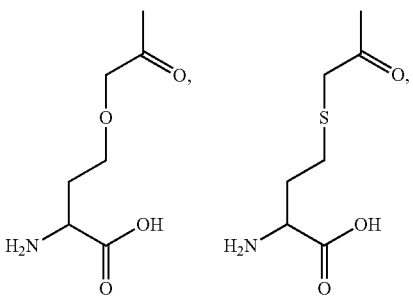
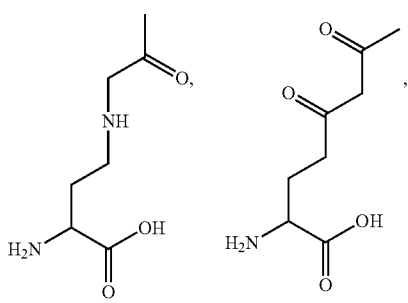
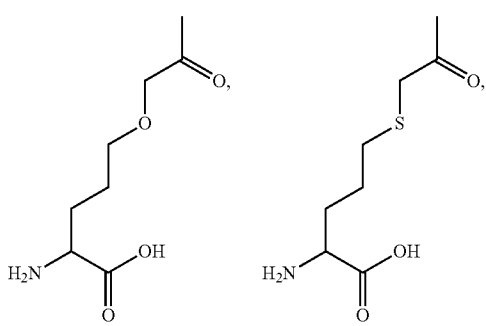
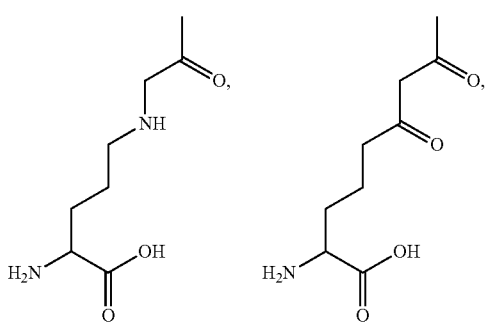
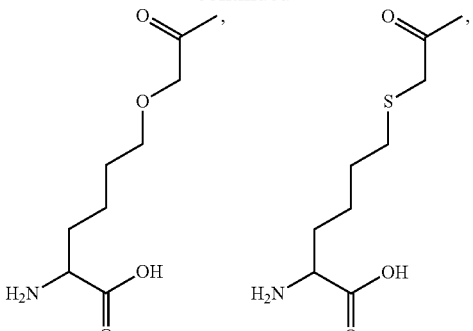
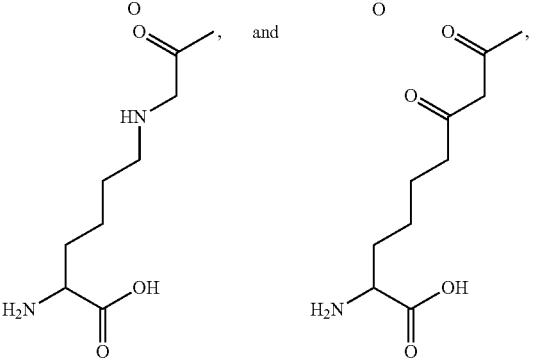

wherein such compounds are optionally amino protected, optionally carboxyl protected, optionally amino protected and carboxyl protected, or a salt thereof. In addition, these non-natural amino acids and any of the following non-natural amino acids may be incorporated into a non-natural amino acid polypeptide.

In addition, the following amino acids having the structure of Formula (VIII) are included:

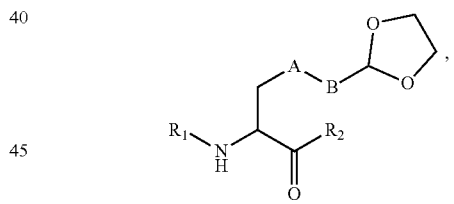

(VIII)

wherein A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$ (alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide.

In addition, the following amino acids having the structure of Formula (IX) are included:

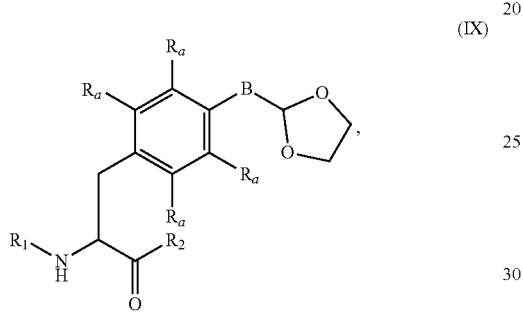

(IX)

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$-(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

wherein each $R_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl.

In addition, the following amino acids are included:

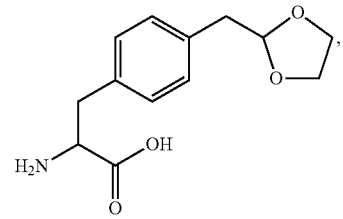

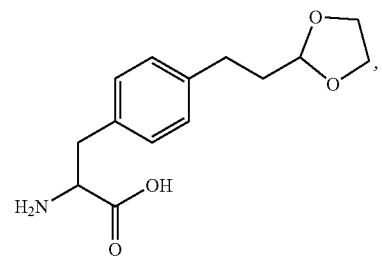

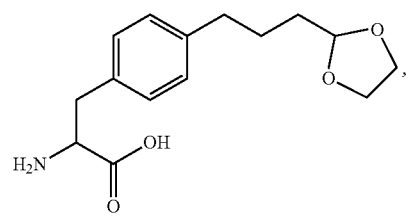

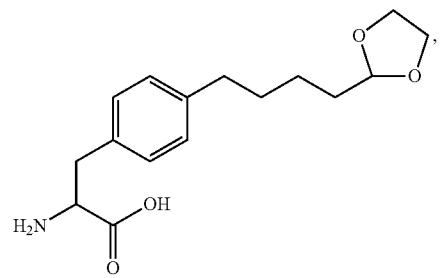

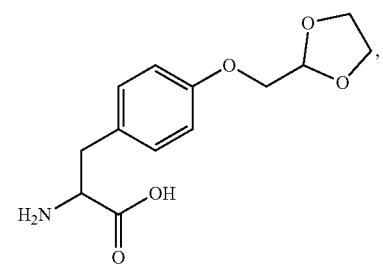

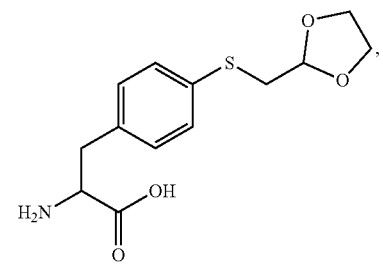

-continued

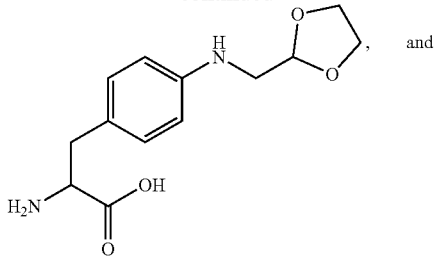
and

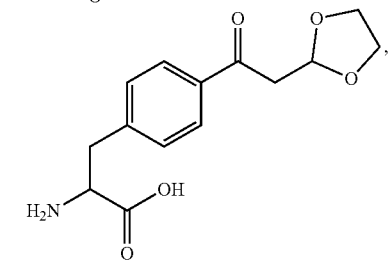

wherein such compounds are optionally amino protected, optionally carboxyl protected, optionally amino protected and carboxyl protected, or a salt thereof. In addition, these non-natural amino acids and any of the following non-natural amino acids may be incorporated into a non-natural amino acid polypeptide.

In addition, the following amino acids having the structure of Formula (X) are included:

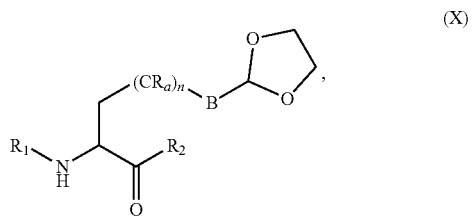
(X)

wherein B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl;

R is H, alkyl, substituted alkyl, cycloalkyl, or substituted cycloalkyl;

R$_1$ is optional, and when present, is H, an amino protecting group, resin, amino acid, polypeptide, or polynucleotide; and R$_2$ is optional, and when present, is OH, an ester protecting group, resin, amino acid, polypeptide, or polynucleotide;

each R$_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl; and n is 0 to 8.

In addition, the following amino acids are included:

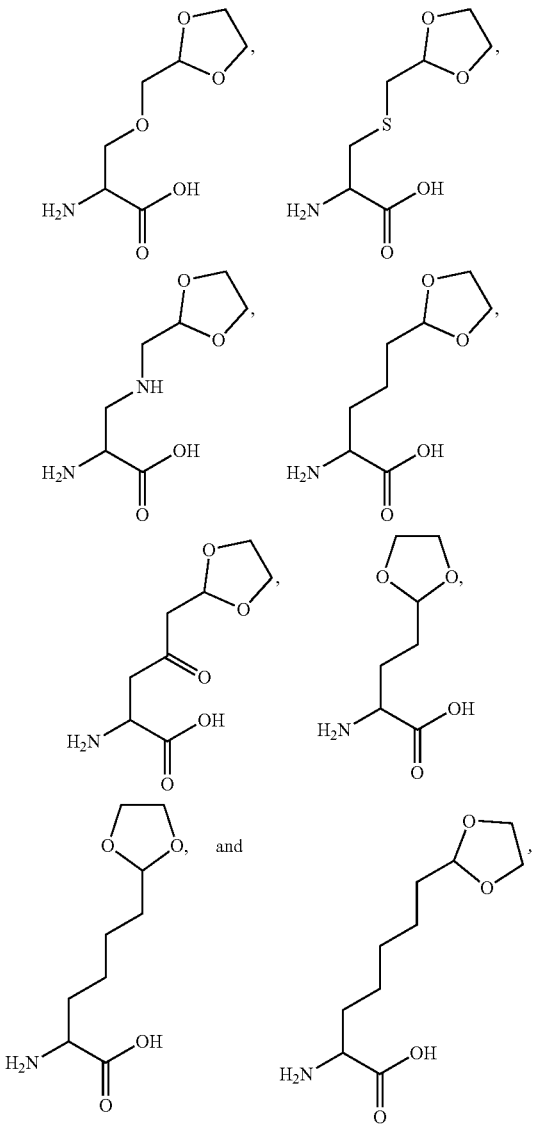

wherein such compounds are optionally amino protected, optionally carboxyl protected, optionally amino protected and carboxyl protected, or a salt thereof. In addition, these non-natural amino acids and any of the following non-natural amino acids may be incorporated into a non-natural amino acid polypeptide.

In addition to monocarbonyl structures, the non-natural amino acids described herein may include groups such as dicarbonyl, dicarbonyl like, masked dicarbonyl and protected dicarbonyl groups.

For example, the following amino acids having the structure of Formula (XI) are included:

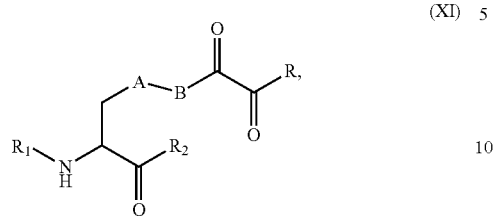

(XI)

wherein A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl;

R is H, alkyl, substituted alkyl, cycloalkyl, or substituted cycloalkyl;

R$_1$ is optional, and when present, is H, an amino protecting group, resin, amino acid, polypeptide, or polynucleotide; and R$_2$ is optional, and when present, is OH, an ester protecting group, resin, amino acid, polypeptide, or polynucleotide.

In addition, the following amino acids having the structure of Formula (XII) are included:

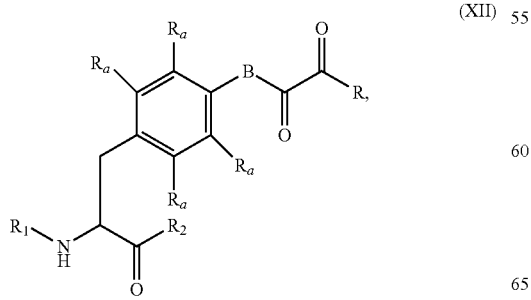

(XII)

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')═N—N═, —C(R')$_2$—N═N—, and —C(R')$_2$—N(R')—N(R')—, where each R' is independently H, alkyl, or substituted alkyl;

R is H, alkyl, substituted alkyl, cycloalkyl, or substituted cycloalkyl;

R$_1$ is optional, and when present, is H, an amino protecting group, resin, amino acid, polypeptide, or polynucleotide; and R$_2$ is optional, and when present, is OH, an ester protecting group, resin, amino acid, polypeptide, or polynucleotide;

wherein each R$_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl.

In addition, the following amino acids are included:

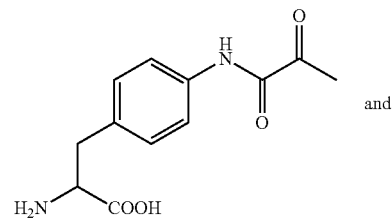

and

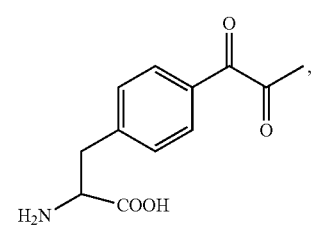

wherein such compounds are optionally amino protected, optionally carboxyl protected, optionally amino protected and carboxyl protected, or a salt thereof. In addition, these non-natural amino acids and any of the following non-natural amino acids may be incorporated into a non-natural amino acid polypeptide.

In addition, the following amino acids having the structure of Formula (XIII) are included:

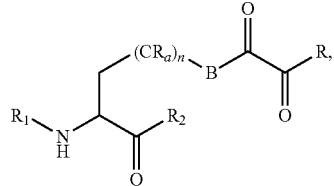
(XIII)

wherein B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N=, —C(R')=N—, —C(R')=N—N(R')—, —C(R')=N—N=, —C(R')$_2$—N=N—, and —C(R')$_2$—N(R')—N(R')—, where each R' is independently H, alkyl, or substituted alkyl;

R is H, alkyl, substituted alkyl, cycloalkyl, or substituted cycloalkyl; $R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide; each $R_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl; and n is 0 to 8.

In addition, the following amino acids are included:

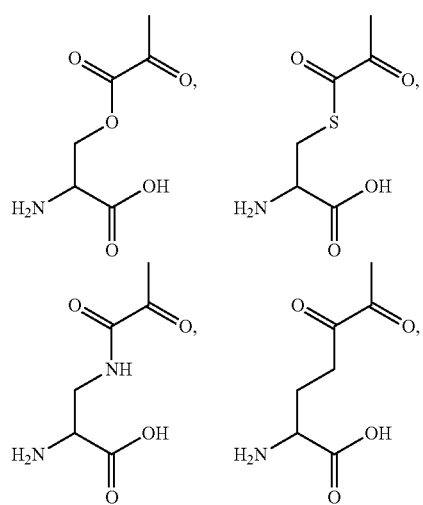

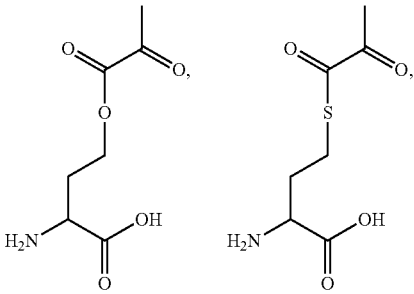

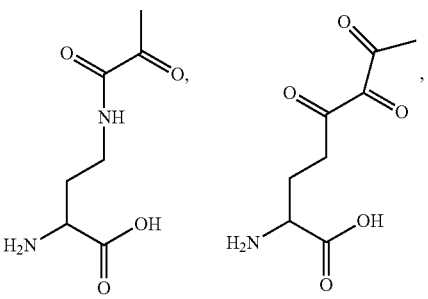

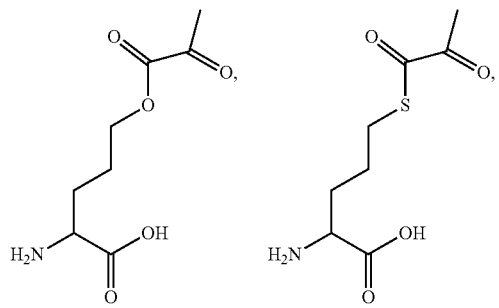

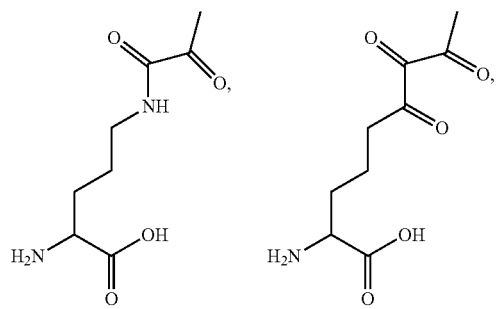

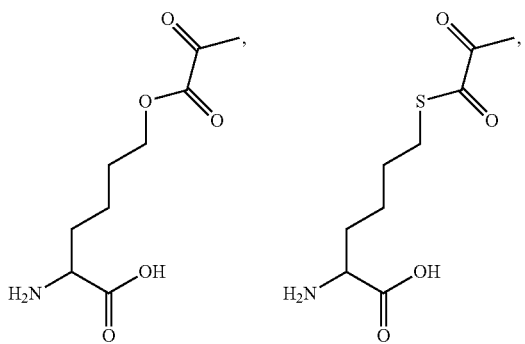

-continued

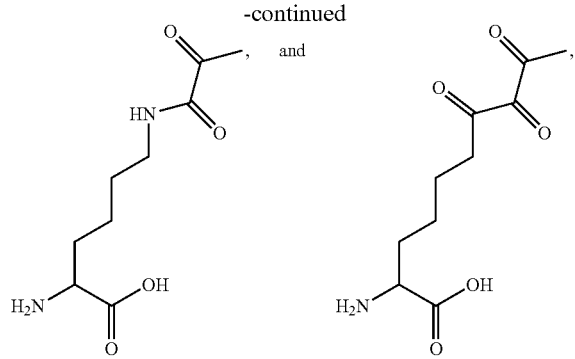

wherein such compounds are optionally amino protected, optionally carboxyl protected, optionally amino protected and carboxyl protected, or a salt thereof. In addition, these non-natural amino acids and any of the following non-natural amino acids may be incorporated into a non-natural amino acid polypeptide.

In addition, the following amino acids having the structure of Formula (XIV) are included:

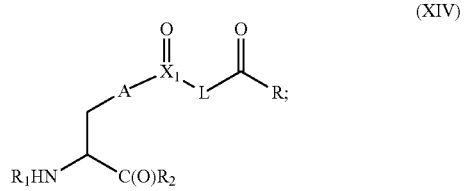

(XIV)

wherein:
- A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
- R is H, alkyl, substituted alkyl, cycloalkyl, or substituted cycloalkyl; $R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide; $X_1$ is C, S, or S(O); and L is alkylene, substituted alkylene, N(R')(alkylene) or N(R')(substituted alkylene), where R' is H, alkyl, substituted alkyl, cycloalkyl, or substituted cycloalkyl.

In addition, the following amino acids having the structure of Formula (XIV-A) are included:

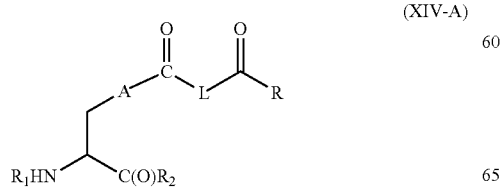

(XIV-A)

wherein:
- A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;
- R is H, alkyl, substituted alkyl, cycloalkyl, or substituted cycloalkyl; $R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;
- L is alkylene, substituted alkylene, N(R')(alkylene) or N(R')(substituted alkylene), where R' is H, alkyl, substituted alkyl, cycloalkyl, or substituted cycloalkyl.

In addition, the following amino acids having the structure of Formula (XIV-B) are included:

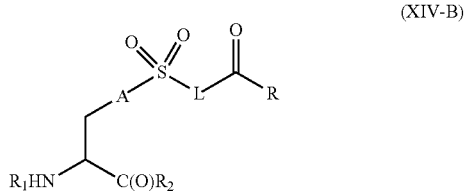

(XIV-B)

wherein:
- A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; R is H, alkyl, substituted alkyl, cycloalkyl, or substituted cycloalkyl;
- $R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide; L is alkylene, substituted alkylene, N(R')(alkylene) or N(R')(substituted alkylene), where R' is H, alkyl, substituted alkyl, cycloalkyl, or substituted cycloalkyl.

In addition, the following amino acids having the structure of Formula (XV) are included:

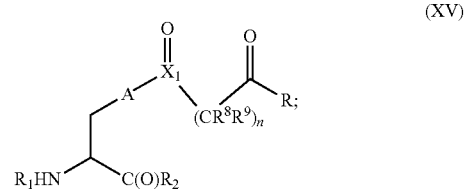

(XV)

wherein:
- A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; R is H, alkyl, substituted alkyl, cycloalkyl, or substituted cycloalkyl;

R$_1$ is optional, and when present, is H, an amino protecting group, resin, amino acid, polypeptide, or polynucleotide; and R$_2$ is optional, and when present, is OH, an ester protecting group, resin, amino acid, polypeptide, or polynucleotide; X$_1$ is C, S, or S(O); and n is 0, 1, 2, 3, 4, or 5; and each R$^8$ and R$^9$ on each CR$^8$R$^9$ group is independently selected from the group consisting of H, alkoxy, alkylamine, halogen, alkyl, aryl, or any R$^8$ and R$^9$ can together form =O or a cycloalkyl, or any to adjacent R$^8$ groups can together form a cycloalkyl.

In addition, the following amino acids having the structure of Formula (XV-A) are included:

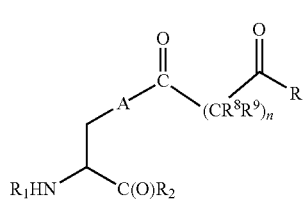

(XV-A)

wherein:
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl; R$_1$ is optional, and when present, is H, an amino protecting group, resin, amino acid, polypeptide, or polynucleotide; and R$_2$ is optional, and when present, is OH, an ester protecting group, resin, amino acid, polypeptide, or polynucleotide;

n is 0, 1, 2, 3, 4, or 5; and each R$^8$ and R$^9$ on each CR$^8$R$^9$ group is independently selected from the group consisting of H, alkoxy, alkylamine, halogen, alkyl, aryl, or any R$^8$ and R$^9$ can together form =O or a cycloalkyl, or any to adjacent R$^8$ groups can together form a cycloalkyl.

In addition, the following amino acids having the structure of Formula (XV-B) are included:

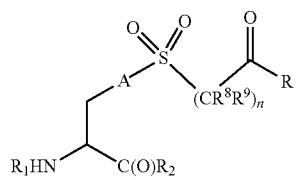

(XV-B)

wherein:
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl; R$_1$ is optional, and when present, is H, an amino protecting group, resin, amino acid, polypeptide, or polynucleotide; and R$_2$ is optional, and when present, is OH, an ester protecting group, resin, amino acid, polypeptide, or polynucleotide; n is 0, 1, 2, 3, 4, or 5; and each R$^8$ and R$^9$ on each CR$^8$R$_9$ group is independently selected from the group consisting of H, alkoxy, alkylamine, halogen, alkyl, aryl, or any R$^8$ and R$^9$ can together form =O or a cycloalkyl, or any to adjacent R$^8$ groups can together form a cycloalkyl.

In addition, the following amino acids having the structure of Formula (XVI) are included:

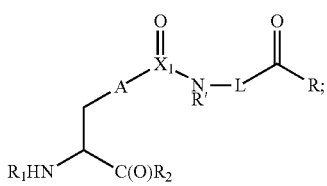

(XVI)

wherein:
A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; R is H, alkyl, substituted alkyl, cycloalkyl, or substituted cycloalkyl;

R$_1$ is optional, and when present, is H, an amino protecting group, resin, amino acid, polypeptide, or polynucleotide; and R$_2$ is optional, and when present, is OH, an ester protecting group, resin, amino acid, polypeptide, or polynucleotide; X$_1$ is C, S, or S(O); and L is alkylene, substituted alkylene, N(R')(alkylene) or N(R')(substituted alkylene), where R' is H, alkyl, substituted alkyl, cycloalkyl, or substituted cycloalkyl.

In addition, the following amino acids having the structure of Formula (XVI-A) are included:

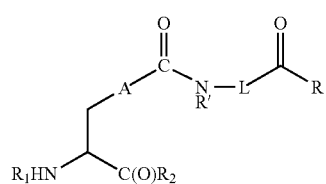

(XVI-A)

wherein:
- A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; R is H, alkyl, substituted alkyl, cycloalkyl, or substituted cycloalkyl;
- $R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide; L is alkylene, substituted alkylene, N(R')(alkylene) or N(R')(substituted alkylene), where R' is H, alkyl, substituted alkyl, cycloalkyl, or substituted cycloalkyl.

In addition, the following amino acids having the structure of Formula (XVI-B) are included:

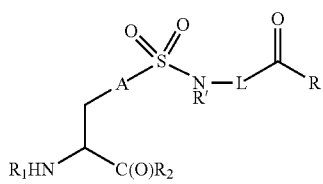

(XVI-B)

wherein:
- A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; R is H, alkyl, substituted alkyl, cycloalkyl, or substituted cycloalkyl;
- $R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide; L is alkylene, substituted alkylene, N(R')(alkylene) or N(R')(substituted alkylene), where R' is H, alkyl, substituted alkyl, cycloalkyl, or substituted cycloalkyl.

In addition, amino acids having the structure of Formula (XVII) are included:

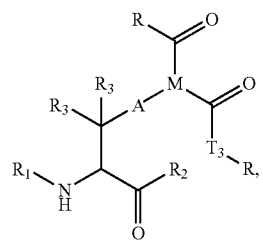

(XVII)

wherein:
- A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

M is

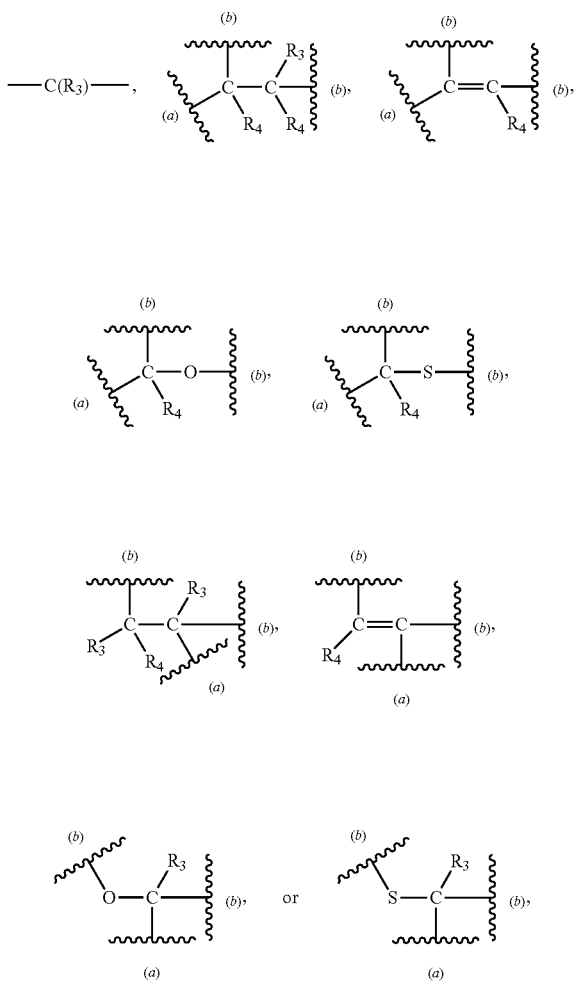

where (a) indicates bonding to the A group and (b) indicates bonding to respective carbonyl groups, $R_3$ and $R_4$ are independently chosen from H, halogen, alkyl, substituted alkyl, cycloalkyl, or substituted cycloalkyl, or $R_3$ and $R_4$ or two $R_3$ groups or two $R_4$ groups optionally form a cycloalkyl or a heterocycloalkyl; R is H, halogen, alkyl, substituted alkyl, cycloalkyl, or substituted cycloalkyl; T3 is a bond, C(R)(R), O, or S, and R is H, halogen, alkyl, substituted alkyl, cycloalkyl, or substituted cycloalkyl; $R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide.

In addition, amino acids having the structure of Formula (XVIII) are included:

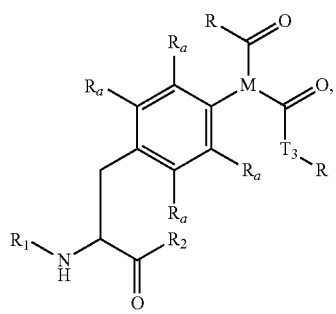
(XVIII)

wherein:

M is

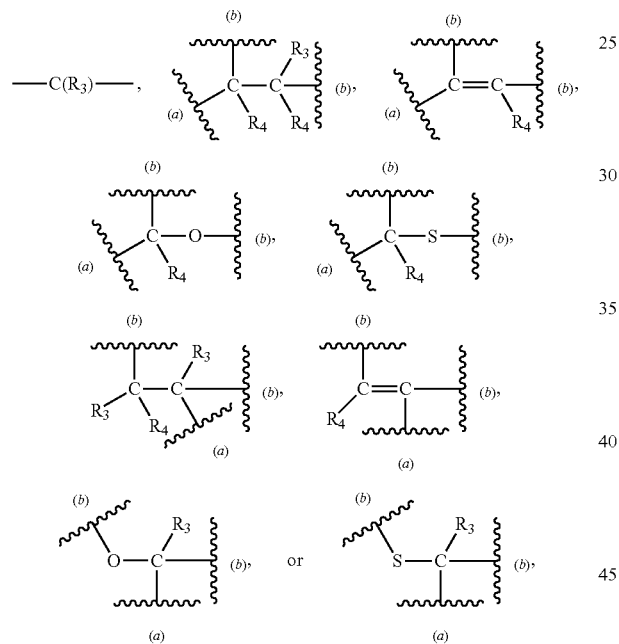

where (a) indicates bonding to the A group and (b) indicates bonding to respective carbonyl groups, $R_3$ and $R_4$ are independently chosen from H, halogen, alkyl, substituted alkyl, cycloalkyl, or substituted cycloalkyl, or $R_3$ and $R_4$ or two $R_3$ groups or two $R_4$ groups optionally form a cycloalkyl or a heterocycloalkyl; R is H, halogen, alkyl, substituted alkyl, cycloalkyl, or substituted cycloalkyl; T3 is a bond, C(R)(R), O, or S, and R is H, halogen, alkyl, substituted alkyl, cycloalkyl, or substituted cycloalkyl; $R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide; each $R_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl.

In addition, amino acids having the structure of Formula (XIX) are included:

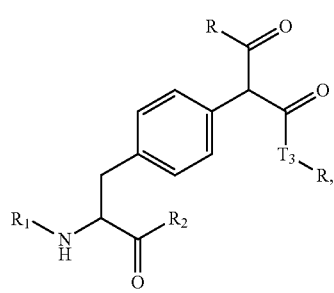
(XIX)

wherein:

R is H, halogen, alkyl, substituted alkyl, cycloalkyl, or substituted cycloalkyl; and $T_3$ is O, or S.

In addition, amino acids having the structure of Formula (XX) are included:

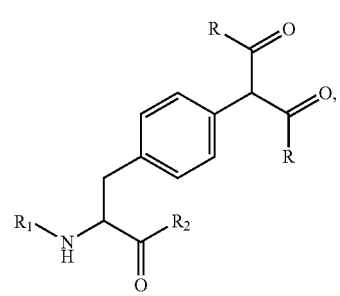
(XX)

wherein:

R is H, halogen, alkyl, substituted alkyl, cycloalkyl, or substituted cycloalkyl.

In addition, the following amino acids having structures of Formula (XXI) are included:

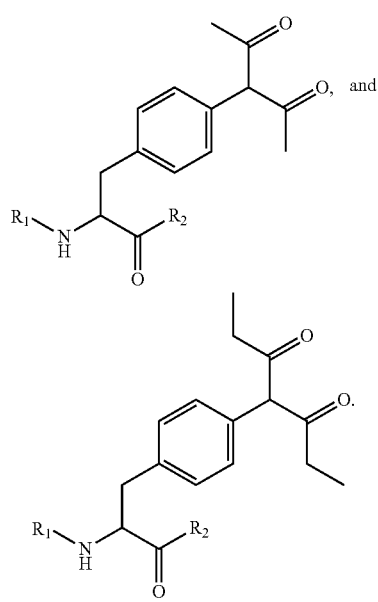

In some embodiments, a polypeptide comprising a non-natural amino acid is chemically modified to generate a reactive carbonyl or dicarbonyl functional group. For instance, an aldehyde functionality useful for conjugation reactions can be generated from a functionality having adjacent amino and hydroxyl groups. Where the biologically active molecule is a polypeptide, for example, an N-terminal serine or threonine (which may be normally present or may be exposed via chemical or enzymatic digestion) can be used to generate an aldehyde functionality under mild oxidative cleavage conditions using periodate. See, e.g., Gaertner, et. al., Bioconjug. Chem. 3: 262-268 (1992); Geoghegan, K. & Stroh, J., Bioconjug. Chem. 3:138-146 (1992); Gaertner et al., J. Biol. Chem. 269:7224-7230 (1994). However, methods known in the art are restricted to the amino acid at the N-terminus of the peptide or protein.

In the present invention, a non-natural amino acid bearing adjacent hydroxyl and amino groups can be incorporated into the polypeptide as a "masked" aldehyde functionality. For example, 5-hydroxylysine bears a hydroxyl group adjacent to the epsilon amine. Reaction conditions for generating the aldehyde typically involve addition of molar excess of sodium metaperiodate under mild conditions to avoid oxidation at other sites within the polypeptide. The pH of the oxidation reaction is typically about 7.0. A typical reaction involves the addition of about 1.5 molar excess of sodium meta periodate to a buffered solution of the polypeptide, followed by incubation for about 10 minutes in the dark. See, e.g. U.S. Pat. No. 6,423,685.

The carbonyl or dicarbonyl functionality can be reacted selectively with a hydroxylamine-containing reagent under mild conditions in aqueous solution to form the corresponding oxime linkage that is stable under physiological conditions. See, e.g., Jencks, W. P., J. Am. Chem. Soc. 81, 475-481 (1959); Shao, J. and Tam, J. P., J. Am. Chem. Soc. 117:3893-3899 (1995). Moreover, the unique reactivity of the carbonyl or dicarbonyl group allows for selective modification in the presence of the other amino acid side chains. See, e.g., Cornish, V. W., et al., J. Am. Chem. Soc. 118: 8150-8151 (1996); Geoghegan, K. F. & Stroh, J. G., Bioconjug. Chem. 3:138-146 (1992); Mahal, L. K., et al., Science 276:1125-1128 (1997).

A. Carbonyl Reactive Groups

Amino acids with a carbonyl reactive group allow for a variety of reactions to link molecules (including but not limited to, PEG or other water-soluble molecules) via nucleophilic addition or aldol condensation reactions among others.

Exemplary carbonyl-containing amino acids can be represented as follows:

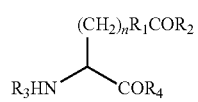

wherein n is 0-10; $R_1$ is an alkyl, aryl, substituted alkyl, or substituted aryl; $R_2$ is H, alkyl, aryl, substituted alkyl, and substituted aryl; and $R_3$ is H, an amino acid, a polypeptide, or an amino terminus modification group, and $R_4$ is H, an amino acid, a polypeptide, or a carboxy terminus modification group. In some embodiments, n is 1, $R_1$ is phenyl and $R_2$ is a simple alkyl (i.e., methyl, ethyl, or propyl) and the ketone moiety is positioned in the para position relative to the alkyl side chain. In some embodiments, n is 1, $R_1$ is phenyl and $R_2$ is a simple alkyl (i.e., methyl, ethyl, or propyl) and the ketone moiety is positioned in the meta position relative to the alkyl side chain.

The synthesis of p-acetyl-(+/−)-phenylalanine and m-acetyl-(+/−)-phenylalanine is described in Zhang, Z., et al., Biochemistry 42: 6735-6746 (2003), which is incorporated by reference herein. Other carbonyl-containing amino acids can be similarly prepared by one of ordinary skill in the art.

In some embodiments, a polypeptide comprising a non-naturally encoded amino acid is chemically modified to generate a reactive carbonyl functional group. For instance, an aldehyde functionality useful for conjugation reactions can be generated from a functionality having adjacent amino and hydroxyl groups. Where the biologically active molecule is a polypeptide, for example, an N-terminal serine or threonine (which may be normally present or may be exposed via chemical or enzymatic digestion) can be used to generate an aldehyde functionality under mild oxidative cleavage conditions using periodate. See, e.g., Gaertner, et al., Bioconjug. Chem. 3: 262-268 (1992); Geoghegan, K. & Stroh, J., Bioconjug. Chem. 3:138-146 (1992); Gaertner et al., J. Biol. Chem. 269:7224-7230 (1994). However, methods known in the art are restricted to the amino acid at the N-terminus of the peptide or protein.

In the present invention, a non-naturally encoded amino acid bearing adjacent hydroxyl and amino groups can be incorporated into the polypeptide as a "masked" aldehyde functionality. For example, 5-hydroxylysine bears a hydroxyl group adjacent to the epsilon amine. Reaction conditions for generating the aldehyde typically involve addition of molar excess of sodium metaperiodate under mild conditions to avoid oxidation at other sites within the polypeptide. The pH of the oxidation reaction is typically about 7.0. A typical reaction involves the addition of about 1.5 molar excess of sodium meta periodate to a buffered solution of the polypeptide, followed by incubation for about 10 minutes in the dark. See, e.g. U.S. Pat. No. 6,423,685, which is incorporated by reference herein.

The carbonyl functionality can be reacted selectively with a hydrazine-, hydrazide-, hydroxylamine-, or semicarbazide-containing reagent under mild conditions in aqueous solution to form the corresponding hydrazone, oxime, or semicarbazone linkages, respectively, that are stable under physiological conditions. See, e.g., Jencks, W. P., J. Am. Chem. Soc. 81, 475-481 (1959); Shao, J. and Tam, J. P., J. Am. Chem. Soc. 117:3893-3899 (1995). Moreover, the unique reactivity of the carbonyl group allows for selective modification in the presence of the other amino acid side chains. See, e.g., Cornish, V. W., et al., J. Am. Chem. Soc. 118:8150-8151 (1996); Geoghegan, K. F. & Stroh, J. G., Bioconjug. Chem. 3:138-146 (1992); Mahal, L. K., et al., Science 276:1125-1128 (1997).

B. Hydrazine, Hydrazide or Semicarbazide Reactive Groups

Non-naturally encoded amino acids containing a nucleophilic group, such as a hydrazine, hydrazide or semicarbazide, allow for reaction with a variety of electrophilic groups to form conjugates (including but not limited to, with PEG or other water-soluble polymers).

Exemplary hydrazine, hydrazide or semicarbazide-containing amino acids can be represented as follows:

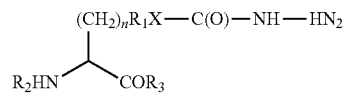

wherein n is 0-10; $R_1$ is an alkyl, aryl, substituted alkyl, or substituted aryl or not present; X, is O, N, or S or not present; $R_2$ is H, an amino acid, a polypeptide, or an amino terminus modification group, and $R_3$ is H, an amino acid, a polypeptide, or a carboxy terminus modification group.

In some embodiments, n is 4, $R_1$ is not present, and X is N. In some embodiments, n is 2, $R_1$ is not present, and X is not present. In some embodiments, n is 1, $R_1$ is phenyl, X is O, and the oxygen atom is positioned para to the aliphatic group on the aryl ring.

Hydrazide-, hydrazine-, and semicarbazide-containing amino acids are available from commercial sources. For instance, L-glutamate-γ-hydrazide is available from Sigma Chemical (St. Louis, MO). Other amino acids not available commercially can be prepared by one of ordinary skill in the art. See, e.g., U.S. Pat. No. 6,281,211, which is incorporated by reference herein.

Polypeptides containing non-naturally encoded amino acids that bear hydrazide, hydrazine or semicarbazide functionalities can be reacted efficiently and selectively with a variety of molecules that contain aldehydes or other functional groups with similar chemical reactivity. See, e.g., Shao, J. and Tam, J., J. Am. Chem. Soc. 117:3893-3899 (1995). The unique reactivity of hydrazide, hydrazine and semicarbazide functional groups makes them significantly more reactive toward aldehydes, ketones and other electrophilic groups as compared to the nucleophilic groups present on the 20 common amino acids (including but not limited to, the hydroxyl group of serine or threonine or the amino groups of lysine and the N-terminus).

C. Aminooxy-Containing Amino Acids

Non-naturally encoded amino acids containing an aminooxy (also called a hydroxylamine) group allow for reaction with a variety of electrophilic groups to form conjugates (including but not limited to, with PEG or other water-soluble polymers). Like hydrazines, hydrazides and semicarbazides, the enhanced nucleophilicity of the aminooxy group permits it to react efficiently and selectively with a variety of molecules that contain aldehydes or other functional groups with similar chemical reactivity. See, e.g., Shao, J. and Tam, J., J. Am. Chem. Soc. 117:3893-3899 (1995); H. Hang and C. Bertozzi, Acc. Chem. Res. 34: 727-736 (2001). Whereas the result of reaction with a hydrazine group is the corresponding hydrazone, however, an oxime results generally from the reaction of an aminooxy group with a carbonyl-containing group such as a ketone.

Exemplary amino acids containing aminooxy groups can be represented as follows:

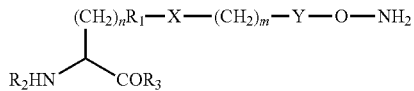

wherein n is 0-10; $R_1$ is an alkyl, aryl, substituted alkyl, or substituted aryl or not present; X is O, N, S or not present; m is 0-10; Y=C(O) or not present; $R_2$ is H, an amino acid, a polypeptide, or an amino terminus modification group, and $R_3$ is H, an amino acid, a polypeptide, or a carboxy terminus modification group. In some embodiments, n is 1, $R_1$ is phenyl, X is O, m is 1, and Y is present. In some embodiments, n is 2, $R_1$ and X are not present, m is 0, and Y is not present.

Aminooxy-containing amino acids can be prepared from readily available amino acid precursors (homoserine, serine and threonine). See, e.g., M. Carrasco and R. Brown, *J Org.* *Chem.* 68: 8853-8858 (2003). Certain aminooxy-containing amino acids, such as L-2-amino-4-(aminooxy)butyric acid), have been isolated from natural sources (Rosenthal, G., Life Sci. 60: 1635-1641 (1997). Other aminooxy-containing amino acids can be prepared by one of ordinary skill in the art.

D. Azide and Alkyne Reactive Groups

The unique reactivity of azide and alkyne functional groups makes them extremely useful for the selective modification of polypeptides and other biological molecules. Organic azides, particularly alphatic azides, and alkynes are generally stable toward common reactive chemical conditions. In particular, both the azide and the alkyne functional groups are inert toward the side chains (i.e., R groups) of the 20 common amino acids found in naturally-occurring polypeptides. When brought into close proximity, however, the "spring-loaded" nature of the azide and alkyne groups is revealed and they react selectively and efficiently via Huisgen [3+2] cycloaddition reaction to generate the corresponding triazole. See, e.g., Chin J., et al., Science 301:964-7 (2003); Wang, Q., et al., J. Am. Chem. Soc. 125, 3192-3193 (2003); Chin, J. W., et al., J. Am. Chem. Soc. 124:9026-9027 (2002).

Because the Huisgen cycloaddition reaction involves a selective cycloaddition reaction (see, e.g., Padwa, A., in Comprehensive Organic Synthesis, Vol. 4, ed. Trost, B. M., (1991), p. 1069-1109; Huisgen, R. in 1,3-Dipolar Cycloaddition Chemistry, ed. Padwa, A., (1984), p. 1-176) rather than a nucleophilic substitution, the incorporation of non-naturally encoded amino acids bearing azide and alkyne-containing side chains permits the resultant polypeptides to be modified selectively at the position of the non-naturally encoded amino acid. Cycloaddition reaction involving azide or alkyne-containing IL-2 can be carried out at room temperature under aqueous conditions by the addition of Cu(II) (including but not limited to, in the form of a catalytic amount of $CuSO_4$) in the presence of a reducing agent for reducing Cu(II) to Cu(I), in situ, in catalytic amount. See, e.g., Wang, Q., et al., J. Am. Chem. Soc. 125, 3192-3193 (2003); Tomoe, C. W., et al., J. Org. Chem. 67:3057-3064 (2002); Rostovtsev, et al., Angew. Chem. Int. Ed. 41:2596-2599 (2002). Exemplary reducing agents include, including but not limited to, ascorbate, metallic copper, quinine, hydroquinone, vitamin K, glutathione, cysteine, $Fe^{2+}$, $Co^{2+}$, and an applied electric potential.

In some cases, where a Huisgen [3+2] cycloaddition reaction between an azide and an alkyne is desired, the IL-2 comprises a non-naturally encoded amino acid comprising an alkyne moiety and the water-soluble polymer to be attached to the amino acid comprises an azide moiety. Alternatively, the converse reaction (i.e., with the azide moiety on the amino acid and the alkyne moiety present on the water-soluble polymer) can also be performed.

The azide functional group can also be reacted selectively with a water-soluble polymer containing an aryl ester and appropriately functionalized with an aryl phosphine moiety to generate an amide linkage. The aryl phosphine group reduces the azide in situ and the resulting amine then reacts efficiently with a proximal ester linkage to generate the corresponding amide. See, e.g., E. Saxon and C. Bertozzi, Science 287, 2007-2010 (2000). The azide-containing amino acid can be either an alkyl azide (including but not limited to, 2-amino-6-azido-1-hexanoic acid) or an aryl azide (p-azido-phenylalanine).

Exemplary water-soluble polymers containing an aryl ester and a phosphine moiety can be represented as follows:

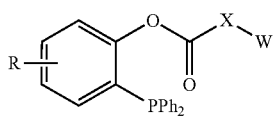

wherein X can be O, N, S or not present, Ph is phenyl, W is a water-soluble polymer and R can be H, alkyl, aryl, substituted alkyl and substituted aryl groups. Exemplary R groups include but are not limited to —CH$_2$, —C(CH$_3$)$_3$, —OR', —NR'R", —SR', -halogen, —C(O)R', —CONR'R", —S(O)$_2$R', —S(O)$_2$NR'R", —CN and —NO$_2$. R', R", R'" and R"" each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —CF$_3$ and —CH$_2$CF$_3$) and acyl (including but not limited to, —C(O)CH$_3$, —C(O)CF$_3$, —C(O)CH$_2$OCH$_3$, and the like).

The azide functional group can also be reacted selectively with a water-soluble polymer containing a thioester and appropriately functionalized with an aryl phosphine moiety to generate an amide linkage. The aryl phosphine group reduces the azide in situ and the resulting amine then reacts efficiently with the thioester linkage to generate the corresponding amide. Exemplary water-soluble polymers containing a thioester and a phosphine moiety can be represented as follows:

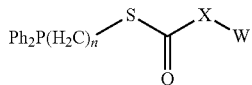

wherein n is 1-10; X can be O, N, S or not present, Ph is phenyl, and W is a water-soluble polymer.

Exemplary alkyne-containing amino acids can be represented as follows:

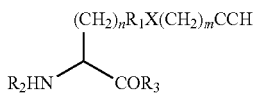

wherein n is 0-10; R$_1$ is an alkyl, aryl, substituted alkyl, or substituted aryl or not present; X is O, N, S or not present; m is 0-10, R$_2$ is H, an amino acid, a polypeptide, or an amino terminus modification group, and R$_3$ is H, an amino acid, a polypeptide, or a carboxy terminus modification group. In some embodiments, n is 1, R$_1$ is phenyl, X is not present, m is 0 and the acetylene moiety is positioned in the para position relative to the alkyl side chain. In some embodiments, n is 1, R$_1$ is phenyl, X is 0, m is 1 and the propargyloxy group is positioned in the para position relative to the alkyl side chain (i.e., 0-propargyl-tyrosine). In some embodiments, n is 1, R$_1$ and X are not present and m is 0 (i.e., proparylglycine).

Alkyne-containing amino acids are commercially available. For example, propargylglycine is commercially available from Peptech (Burlington, MA). Alternatively, alkyne-containing amino acids can be prepared according to standard methods. For instance, p-propargyloxyphenylalanine can be synthesized, for example, as described in Deiters, A., et al., J. Am. Chem. Soc. 125: 11782-11783 (2003), and 4-alkynyl-L-phenylalanine can be synthesized as described in Kayser, B., et al., Tetrahedron 53(7): 2475-2484 (1997). Other alkyne-containing amino acids can be prepared by one of ordinary skill in the art.

Exemplary azide-containing amino acids can be represented as follows:

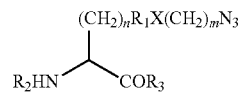

wherein n is 0-10; R$_1$ is an alkyl, aryl, substituted alkyl, substituted aryl or not present; X is O, N, S or not present; m is 0-10; R$_2$ is H, an amino acid, a polypeptide, or an amino terminus modification group, and R$_3$ is H, an amino acid, a polypeptide, or a carboxy terminus modification group. In some embodiments, n is 1, R$_1$ is phenyl, X is not present, m is 0 and the azide moiety is positioned para to the alkyl side chain. In some embodiments, n is 0-4 and R$_1$ and X are not present, and m=0. In some embodiments, n is 1, R$_1$ is phenyl, X is 0, m is 2 and the β-azidoethoxy moiety is positioned in the para position relative to the alkyl side chain.

Azide-containing amino acids are available from commercial sources. For instance, 4-azidophenylalanine can be obtained from Chem-Impex International, Inc. (Wood Dale, IL). For those azide-containing amino acids that are not commercially available, the azide group can be prepared relatively readily using standard methods known to those of ordinary skill in the art, including but not limited to, via displacement of a suitable leaving group (including but not limited to, halide, mesylate, tosylate) or via opening of a suitably protected lactone. See, e.g., Advanced Organic Chemistry by March (Third Edition, 1985, Wiley and Sons, New York).

E. Aminothiol Reactive Groups

The unique reactivity of beta-substituted aminothiol functional groups makes them extremely useful for the selective modification of polypeptides and other biological molecules that contain aldehyde groups via formation of the thiazolidine. See, e.g., J. Shao and J. Tam, J. Am. Chem. Soc., 117 (14) 3893-3899, (1995). In some embodiments, beta-substituted aminothiol amino acids can be incorporated into IL-2 polypeptides and then reacted with water-soluble polymers comprising an aldehyde functionality. In some embodiments, a water-soluble polymer, drug conjugate or other payload can be coupled to an IL-2 comprising a beta-substituted aminothiol amino acid via formation of the thiazolidine.

F. Additional Reactive Groups

Additional reactive groups and non-naturally encoded amino acids, including but not limited to para-amino-phenylalanine, that can be incorporated into IL-2 polypeptides of the invention are described in the following patent applications which are all incorporated by reference in their entirety herein: U.S. Patent Publication No. 2006/0194256, U.S. Patent Publication No. 2006/0217532, U.S. Patent Publication No. 2006/0217289, U.S. Provisional Patent No. 60/755,338; U.S. Provisional Patent No. 60/755,711; U.S. Provisional Patent No. 60/755,018; International Patent Application No. PCT/US06/49397; WO 2006/069246; U.S. Provisional Patent No. 60/743,041; U.S. Provisional Patent No. 60/743,040; International Patent Application No. PCT/US06/47822; U.S. Provisional Patent No. 60/882,819; U.S. Provisional Patent No. 60/882,500; and U.S. Provisional Patent No. 60/870,594. These applications also discuss reactive groups that may be present on PEG or other polymers, including but not limited to, hydroxylamine (aminooxy) groups for conjugation.

Polypeptides with Unnatural Amino Acids

The incorporation of an unnatural amino acid can be done for a variety of purposes, including but not limited to, modulating the interaction of a protein with its receptor or one or more subunits of its receptor, tailoring changes in protein structure and/or function, changing size, acidity, nucleophilicity, hydrogen bonding, hydrophobicity, accessibility of protease target sites, targeting to a moiety (including but not limited to, for a protein array), adding a biologically active molecule, attaching a polymer, attaching a radionuclide, modulating serum half-life, modulating tissue penetration (e.g. tumors), modulating active transport, modulating tissue, cell or organ specificity or distribution, modulating immunogenicity, modulating protease resistance, etc. Proteins that include an unnatural amino acid can have enhanced or even entirely new catalytic or biophysical properties. For example, the following properties are optionally modified by inclusion of an unnatural amino acid into a protein: receptor binding, toxicity, biodistribution, structural properties, spectroscopic properties, chemical and/or photochemical properties, catalytic ability, half-life (including but not limited to, serum half-life), ability to react with other molecules, including but not limited to, covalently or non-covalently, and the like. The compositions including proteins that include at least one unnatural amino acid are useful for, including but not limited to, novel therapeutics, diagnostics, catalytic enzymes, industrial enzymes, binding proteins (including but not limited to, antibodies), and including but not limited to, the study of protein structure and function. See, e.g., Dougherty, Unnatural Amino Acids as Probes of Protein Structure and Function, Current Opinion in Chemical Biology, 4:645-652, (2000).

In one aspect of the invention, a composition includes at least one protein with at least one, including but not limited to, at least two, at least three, at least four, at least five, at least six, at least seven, at least eight, at least nine, or at least ten or more unnatural amino acids. The unnatural amino acids can be the same or different, including but not limited to, there can be 1, 2, 3, 4, 5, 6, 7, 8, 9, or 10 or more different sites in the protein that comprise 1, 2, 3, 4, 5, 6, 7, 8, 9, or 10 or more different unnatural amino acids. In another aspect, a composition includes a protein with at least one, but fewer than all, of a particular amino acid present in the protein is substituted with the unnatural amino acid. For a given protein with more than one unnatural amino acids, the unnatural amino acids can be identical or different (including but not limited to, the protein can include two or more different types of unnatural amino acids, or can include two of the same unnatural amino acid). For a given protein with more than two unnatural amino acids, the unnatural amino acids can be the same, different or a combination of a multiple unnatural amino acid of the same kind with at least one different unnatural amino acid.

Proteins or polypeptides of interest with at least one unnatural amino acid are a feature of the invention. The invention also includes polypeptides or proteins with at least one unnatural amino acid produced using the compositions and methods of the invention. An excipient (including but not limited to, a pharmaceutically acceptable excipient) can also be present with the protein.

By producing proteins or polypeptides of interest with at least one unnatural amino acid in eukaryotic cells, proteins or polypeptides will typically include eukaryotic post-translational modifications. In certain embodiments, a protein includes at least one unnatural amino acid and at least one post-translational modification that is made in vivo by a eukaryotic cell, where the post-translational modification is not made by a prokaryotic cell. For example, the post-translation modification includes, including but not limited to, acetylation, acylation, lipid-modification, palmitoylation, palmitate addition, phosphorylation, glycolipid-linkage modification, glycosylation, and the like.

One advantage of an unnatural amino acid is that it presents additional chemical moieties that can be used to add additional molecules. These modifications can be made in vivo in a eukaryotic or non-eukaryotic cell, or in vitro. Thus, in certain embodiments, the post-translational modification is through the unnatural amino acid. For example, the post-translational modification can be through a nucleophilic-electrophilic reaction. Most reactions currently used for the selective modification of proteins involve covalent bond formation between nucleophilic and electrophilic reaction partners, including but not limited to the reaction of α-haloketones with histidine or cysteine side chains. Selectivity in these cases is determined by the number and accessibility of the nucleophilic residues in the protein. In proteins of the invention, other more selective reactions can be used such as the reaction of an unnatural keto-amino acid with hydrazides or aminooxy compounds, in vitro and in vivo. See, e.g., Cornish, et al., J. Am. Chem. Soc., 118:8150-8151, (1996); Mahal, et al., Science, 276:1125-1128, (1997); Wang, et al., Science 292:498-500, (2001); Chin, et al., J. Am. Chem. Soc. 124:9026-9027, (2002); Chin, et al., Proc. Natl. Acad. Sci., 99:11020-11024, (2002); Wang, et al., Proc. Natl. Acad. Sci., 100:56-61, (2003); Zhang, et al., Biochemistry, 42:6735-6746, (2003); and, Chin, et al., Science, 301:964-7, (2003), all of which are incorporated by reference herein. This allows selective labeling of virtually any protein with a host of reagents including fluorophores, crosslinking agents, saccharide derivatives and cytotoxic molecules. See U.S. Pat. No. 6,927,042 entitled "Glycoprotein synthesis," which is incorporated by reference herein. Post-translational modifications, including but not limited to, through an azido amino acid, can also made through the Staudinger ligation (including but not limited to, with triarylphosphine reagents). See, e.g., Kiick et al., Incorporation of azides into recombinant proteins for chemoselective modification by the Staudinger ligation, PNAS 99:19-24, (2002).

IV. In Vivo Generation of IL-2 Comprising Non-Naturally-Encoded Amino Acids

The IL-2 polypeptides of the invention can be generated in vivo using modified tRNA and tRNA synthetases to add to or substitute amino acids that are not encoded in naturally-occurring systems.

Methods for generating tRNAs and tRNA synthetases which use amino acids that are not encoded in naturally-occurring systems are described in, e.g., U.S. Pat. Nos. 7,045,337 and 7,083,970 which are incorporated by reference herein. These methods involve generating a translational machinery that functions independently of the synthetases and tRNAs endogenous to the translation system (and are therefore sometimes referred to as "orthogonal"). Typically, the translation system comprises an orthogonal tRNA (O-tRNA) and an orthogonal aminoacyl tRNA synthetase (O—RS). Typically, the O—RS preferentially aminoacylates the O-tRNA with at least one non-naturally occurring amino acid in the translation system and the O-tRNA recognizes at least one selector codon that is not recognized by other tRNAs in the system. The translation system thus inserts the non-naturally-encoded amino acid into a protein produced in the system, in response to an encoded selector codon, thereby "substituting" an amino acid into a position in the encoded polypeptide.

A wide variety of orthogonal tRNAs and aminoacyl tRNA synthetases have been described in the art for inserting particular synthetic amino acids into polypeptides and are generally suitable for use in the present invention. For example, keto-specific O-tRNA/aminoacyl-tRNA synthetases are described in Wang, L., et al., Proc. Natl. Acad. Sci. USA 100:56-61 (2003) and Zhang, Z. et al., Biochem. 42(22):6735-6746 (2003). Exemplary O—RS, or portions thereof, are encoded by polynucleotide sequences and include amino acid sequences disclosed in U.S. Pat. Nos. 7,045,337 and 7,083,970, each incorporated herein by reference. Corresponding O-tRNA molecules for use with the O-RSs are also described in U.S. Pat. Nos. 7,045,337 and 7,083,970 which are incorporated by reference herein. Additional examples of O-tRNA/aminoacyl-tRNA synthetase pairs are described in WO 2005/007870, WO 2005/007624; and WO 2005/019415.

An example of an azide-specific O-tRNA/aminoacyl-tRNA synthetase system is described in Chin, J. W., et al., J. Am. Chem. Soc. 124:9026-9027 (2002). Exemplary 0-RS sequences for p-azido-L-Phe include, but are not limited to, nucleotide sequences SEQ ID NOs: 14-16 and 29-32 and amino acid sequences SEQ ID NOs: 46-48 and 61-64 as disclosed in U.S. Pat. No. 7,083,970 which is incorporated by reference herein. Exemplary O-tRNA sequences suitable for use in the present invention include, but are not limited to, nucleotide sequences SEQ ID NOs: 1-3 as disclosed in U.S. Pat. No. 7,083,970, which is incorporated by reference herein. Other examples of O-tRNA/aminoacyl-tRNA synthetase pairs specific to particular non-naturally encoded amino acids are described in U.S. Pat. No. 7,045,337 which is incorporated by reference herein. O—RS and O-tRNA that incorporate both keto- and azide-containing amino acids in *S. cerevisiae* are described in Chin, J. W., et al., Science 301:964-967 (2003).

Several other orthogonal pairs have been reported. Glutaminyl (see, e.g., Liu, D. R., and Schultz, P. G. (1999) Proc. Natl. Acad. Sci. U.S.A. 96:4780-4785), aspartyl (see, e.g., Pastrnak, M., et al., (2000) Helv. Chim. Acta 83:2277-2286), and tyrosyl (see, e.g., Ohno, S., et al., (1998) J. Biochem. (Tokyo, Jpn.) 124:1065-1068; and, Kowal, A. K., et al., (2001) Proc. Natl. Acad. Sci. U.S.A. 98:2268-2273) systems derived from *S. cerevisiae* tRNA's and synthetases have been described for the potential incorporation of unnatural amino acids in *E. coli*. Systems derived from the *E. coli* glutaminyl (see, e.g., Kowal, A. K., et al., (2001) Proc. Natl. Acad. Sci. U.S.A. 98:2268-2273) and tyrosyl (see, e.g., Edwards, H., and Schimmel, P. (1990) Mol. Cell. Biol. 10:1633-1641) synthetases have been described for use in *S. cerevisiae*. The *E. coli* tyrosyl system has been used for the incorporation of 3-iodo-L-tyrosine in vivo, in mammalian cells. See, Sakamoto, K., et al., (2002) Nucleic Acids Res. 30:4692-4699.

Use of O-tRNA/aminoacyl-tRNA synthetases involves selection of a specific codon which encodes the non-naturally encoded amino acid (a selector codon). While any codon can be used, it is generally desirable to select a codon that is rarely or never used in the cell in which the O-tRNA/aminoacyl-tRNA synthetase is expressed. For example, exemplary codons include nonsense codon such as stop codons (amber, ochre, and opal), four or more base codons and other natural three-base codons that are rarely or unused.

Specific selector codon(s) can be introduced into appropriate positions in the IL-2 coding sequence using mutagenesis methods known in the art (including but not limited to, site-specific mutagenesis, cassette mutagenesis, restriction selection mutagenesis, etc.).

V. Location of Non-Naturally-Occurring Amino Acids in IL-2

The present invention contemplates incorporation of one or more non-naturally-occurring amino acids into IL-2. One or more non-naturally-occurring amino acids may be incorporated at a particular position which does not disrupt activity of the polypeptide. This can be achieved by making "conservative" substitutions, including but not limited to, substituting hydrophobic amino acids with hydrophobic amino acids, bulky amino acids for bulky amino acids, hydrophilic amino acids for hydrophilic amino acids and/or inserting the non-naturally-occurring amino acid in a location that is not required for activity.

A variety of biochemical and structural approaches can be employed to select the desired sites for substitution with a non-naturally encoded amino acid within the IL-2. It is readily apparent to those of ordinary skill in the art that any position of the polypeptide chain is suitable for selection to incorporate a non-naturally encoded amino acid, and selection may be based on rational design or by random selection for any or no particular desired purpose. Selection of desired sites may be for producing an IL-2 molecule having any desired property or activity, including but not limited to, modulating receptor binding or binding to one or more subunits of its receptor, agonists, super-agonists, inverse agonists, antagonists, receptor binding modulators, receptor activity modulators, dimer or multimer formation, no change to activity or property compared to the native molecule, or manipulating any physical or chemical property of the polypeptide such as solubility, aggregation, or stability. For example, locations in the polypeptide required for biological activity of IL-2 can be identified using point mutation analysis, alanine scanning, saturation mutagenesis and screening for biological activity, or homolog scanning methods known in the art. Other methods can be used to identify residues for modification of IL-2 include, but are not limited to, sequence profiling (Bowie and Eisenberg, Science 253 (5016): 164-70, (1991)), rotamer library selections (Dahiyat and Mayo, Protein Sci 5(5): 895-903 (1996); Dahiyat and Mayo, Science 278(5335): 82-7 (1997); Desjarlais and Handel, Protein Science 4: 2006-2018 (1995); Harbury et al, PNAS USA 92(18): 8408-8412 (1995); Kono et al., Proteins: Structure, Function and Genetics 19: 244-255 (1994); Hellinga and Richards, PNAS USA 91: 5803-5807 (1994)); and residue pair potentials (Jones, Protein Science 3: 567-574, (1994)), and rational design using Protein Design Automation® technology. (See U.S. Pat. Nos. 6,188,965; 6,269,312; 6,403,312; WO98/47089, which are incorporated by reference). Residues other than those identified as critical to biological activity by alanine or homolog scanning mutagenesis may be good candidates for substitution with a non-naturally encoded amino acid depending on the desired activity sought for the polypeptide. Alternatively, the sites identified as critical to biological activity may also be good candidates for substitution with a non-naturally encoded amino acid, again depending on the desired activity sought for the polypeptide. Another alternative would be to simply make serial substitutions in each position on the polypeptide chain with a non-naturally encoded amino acid and observe the effect on the activities of the polypeptide. It is readily apparent to those of ordinary skill in the art that any means, technique, or method for selecting a position for substitution with a non-natural amino acid into any polypeptide is suitable for use in the present invention.

The structure and activity of mutants of IL-2 polypeptides that contain deletions can also be examined to determine regions of the protein that are likely to be tolerant of substitution with a non-naturally encoded amino acid. In a similar manner, protease digestion and monoclonal antibodies can be used to identify regions of IL-2 that are responsible for binding the IL-2 receptor. Once residues that are likely to be intolerant to substitution with non-naturally encoded amino acids have been eliminated, the impact of proposed substitutions at each of the remaining positions can be examined. Thus, those of ordinary skill in the art can readily identify amino acid positions that can be substituted with non-naturally encoded amino acids.

One of ordinary skill in the art recognizes that such analysis of IL-2 enables the determination of which amino acid residues are surface exposed compared to amino acid residues that are buried within the tertiary structure of the protein. Therefore, it is an embodiment of the present invention to substitute a non-naturally encoded amino acid for an amino acid that is a surface exposed residue.

In some embodiments, one or more non-naturally encoded amino acids are incorporated in one or more of the following positions in IL-2: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, or added to the carboxyl terminus of the protein, and any combination thereof (SEQ ID NO: 2 or the corresponding amino acids in SEQ ID NOs: 3, 5, or 7).

In some embodiments, one or more non-naturally encoded amino acids are incorporated in one or more of the following positions in IL-2 or a variant thereof: before position 3, 35, 37, 38, 41, 42, 43, 44, 45, 61, 62, 64, 65, 68, 72, and 107, and any combination thereof (SEQ ID NO: 2 or the corresponding amino acid in SEQ ID NOs: 3, 5, or 7).

In some embodiments, one or more non-naturally encoded amino acids are incorporated at any position in one or more of the following regions corresponding to secondary structures or specific amino acids in IL-2 or a variant thereof as follows: at the sites of hydrophobic interactions; at or in proximity to the sites of interaction with IL-2 receptor subunits including IL2Rα; within amino acid positions 3, or 35 to 45; within the first 107 N-terminal amino acids; within amino acid positions 61-72; each of SEQ ID NO: 2, or the corresponding amino acid position in SEQ ID NOs: 3, 5, or 7. In some embodiments, one or more non-naturally encoded amino acids are incorporated at one or more of the following positions of IL-2 or a variant thereof: before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43 and any combination thereof of SEQ ID NO: 2, or the corresponding amino acids in SEQ ID NOs: 3, 5, or 7. In some embodiments, one or more non-naturally encoded amino acids are incorporated at one or more of the following positions of IL-2 or a variant thereof: 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, or added to the carboxyl terminus of the protein, and any combination thereof of SEQ ID NO: 2, or the corresponding amino acids in SEQ ID NOs: 3, 5, or 7.

In some embodiments, the IL-2 polypeptide is an agonist and the non-naturally occurring amino acid in one or more of these regions is linked to a water-soluble polymer, including but not limited to: 3, 35, 37, 38, 41, 42, 43, 44, 45, 61, 62, 64, 65, 68, 72, and 107. In some embodiments, the IL-2 polypeptide is an agonist and the non-naturally occurring amino acid in one or more of these regions is linked to a water-soluble polymer, including but not limited to: in proximity to 3, 35, 37, 38, 41, 42, 43, 44, 45, 61, 62, 64, 65, 68, 72, and 107.

A wide variety of non-naturally encoded amino acids can be substituted for, or incorporated into, a given position in IL-2. In general, a particular non-naturally encoded amino acid is selected for incorporation based on an examination of the three dimensional crystal structure of an IL-2 polypeptide or other IL-2 family member with its receptor, a preference for conservative substitutions (i.e., aryl-based non-naturally encoded amino acids, such as p-acetylphenylalanine or O-propargyltyrosine substituting for Phe, Tyr or Trp), and the specific conjugation chemistry that one desires to introduce into the IL-2 (e.g., the introduction of 4-azidophenylalanine if one wants to effect a Huisgen [3+2] cycloaddition with a water-soluble polymer bearing an alkyne moiety or a amide bond formation with a water-soluble polymer that bears an aryl ester that, in turn, incorporates a phosphine moiety).

In one embodiment, the method further includes incorporating into the protein the unnatural amino acid, where the unnatural amino acid comprises a first reactive group; and contacting the protein with a molecule (including but not limited to, a label, a dye, a polymer, a water-soluble polymer, a derivative of polyethylene glycol, a photocrosslinker, a radionuclide, a cytotoxic compound, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a saccharide, a water-soluble dendrimer, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, a quantum dot, a nanotransmitter, a radionucleotide, a radiotransmitter, a neutron-capture agent, or any combination of the above, or any other desirable compound or substance) that comprises a second reactive group. The first reactive group reacts with the second reactive group to attach the molecule to the unnatural amino acid through a [3+2] cycloaddition. In one embodiment, the first reactive group is an alkynyl or azido moiety and the second reactive group is an azido or alkynyl moiety. For example, the first reactive group is the alkynyl moiety (including but not limited to, in unnatural amino acid p-propargyloxyphenylalanine) and the second reactive group is the azido moiety. In another example, the first reactive group is the azido moiety (including but not limited to, in the unnatural amino acid p-azido-L-phenylalanine) and the second reactive group is the alkynyl moiety.

In some cases, the non-naturally encoded amino acid substitution(s) will be combined with other additions, substitutions or deletions within the IL-2 to affect other biological traits of the IL-2 polypeptide. In some cases, the other additions, substitutions or deletions may increase the stability (including but not limited to, resistance to proteolytic degradation) of the IL-2 or increase affinity of the IL-2 for its receptor. In some cases, the other additions, substitutions or deletions may increase the pharmaceutical stability of the IL-2. In some cases, the other additions, substitutions or deletions may enhance the activity of the IL-2 for tumor inhibition and/or tumor reduction. In some cases, the other additions, substitutions or deletions may increase the solubility (including but not limited to, when expressed in *E. coli* or other host cells) of the IL-2 or variants. In some embodiments additions, substitutions or deletions may increase the IL-2 solubility following expression in *E. coli* or other recombinant host cells. In some embodiments sites are selected for substitution with a naturally encoded or non-natural amino acid in addition to another site for incorporation of a non-natural amino acid that results in increasing the polypeptide solubility following expression in *E. coli* or other recombinant host cells. In some embodiments, the IL-2 polypeptides comprise another addition, substitution or deletion that modulates affinity for the IL-2 receptor, binding proteins, or associated ligand, modulates signal transduction after binding to the IL-2 receptor, modulates circulating half-life, modulates release or bio-availability, facilitates purification, or improves or alters a particular route of administration. In some embodiments, the IL-2 polypeptides comprise an addition, substitution or deletion that increases the affinity of the IL-2 variant for its receptor. In some embodiments, the IL-2 comprises an addition, substitution or deletion that increases the affinity of the IL-2 variant to IL-2-RT and/or IL-2-R2. Similarly, IL-2 polypeptides can comprise chemical or enzyme cleavage sequences, protease cleavage sequences, reactive groups, antibody-binding domains (including but not limited to, FLAG or poly-His) or other affinity based sequences (including, but not limited to, FLAG, poly-His, GST, etc.) or linked molecules (including, but not limited to, biotin) that improve detection (including, but not limited to, GFP), purification, transport through tissues or cell membranes, prodrug release or activation, IL-2 size reduction, or other traits of the polypeptide.

In some embodiments, the substitution of a non-naturally encoded amino acid generates an IL-2 antagonist. In some embodiments, a non-naturally encoded amino acid is substituted or added in a region involved with receptor binding. In some embodiments, IL-2 antagonists comprise at least one substitution that cause IL-2 to act as an antagonist. In some embodiments, the IL-2 antagonist comprises a non-naturally encoded amino acid linked to a water-soluble polymer that is present in a receptor binding region of the IL-2 molecule.

In some cases, 1, 2, 3, 4, 5, 6, 7, 8, 9, 10, or more amino acids are substituted with one or more non-naturally-encoded amino acids. In some cases, the IL-2 further includes 1, 2, 3, 4, 5, 6, 7, 8, 9, 10, or more substitutions of one or more non-naturally encoded amino acids for naturally-occurring amino acids. For example, in some embodiments, one or more residues in IL-2 are substituted with one or more non-naturally encoded amino acids. In some cases, the one or more non-naturally encoded residues are linked to one or more lower molecular weight linear or branched PEGs, thereby enhancing binding affinity and comparable serum half-life relative to the species attached to a single, higher molecular weight PEG.

VI. Expression in Non-Eukaryotes and Eukaryotes

To obtain high level expression of a cloned IL-2 polynucleotide, one typically subclones polynucleotides encoding an IL-2 polypeptide of the invention into an expression vector that contains a strong promoter to direct transcription, a transcription/translation terminator, and if for a nucleic acid encoding a protein, a ribosome binding site for translational initiation. Suitable bacterial promoters are known to those of ordinary skill in the art and described, e.g., in Sambrook et al. and Ausubel et al.

Bacterial expression systems for expressing IL-2 of the invention are available in, including but not limited to, *E. coli, Bacillus* sp., *Pseudomonas fluorescens, Pseudomonas aeruginosa, Pseudomonas putida*, and *Salmonella* (Palva et al., *Gene* 22:229-235 (1983); Mosbach et al., *Nature* 302: 543-545 (1983)). Kits for such expression systems are commercially available. Eukaryotic expression systems for mammalian cells, yeast, and insect cells are known to those of ordinary skill in the art and are also commercially available. In cases where orthogonal tRNAs and aminoacyl tRNA synthetases (described above) are used to express the IL-2 polypeptides of the invention, host cells for expression are selected based on their ability to use the orthogonal components. Exemplary host cells include Gram-positive bacteria (including but not limited to *B. brevis, B. subtilis*, or *Streptomyces*) and Gram-negative bacteria (*E. coli, Pseudomonas fluorescens, Pseudomonas aeruginosa, Pseudomonas putida*), as well as yeast and other eukaryotic cells. Cells comprising O-tRNA/O—RS pairs can be used as described herein.

A eukaryotic host cell or non-eukaryotic host cell of the present invention provides the ability to synthesize proteins that comprise unnatural amino acids in large useful quantities. In one aspect, the composition optionally includes, including but not limited to, at least 10 micrograms, at least 50 micrograms, at least 75 micrograms, at least 100 micrograms, at least 200 micrograms, at least 250 micrograms, at least 500 micrograms, at least 1 milligram, at least 10 milligrams, at least 100 milligrams, at least one gram, or more of the protein that comprises an unnatural amino acid, or an amount that can be achieved with in vivo protein production methods (details on recombinant protein production and purification are provided herein). In another aspect, the protein is optionally present in the composition at a concentration of, including but not limited to, at least 10 micrograms of protein per liter, at least 50 micrograms of protein per liter, at least 75 micrograms of protein per liter, at least 100 micrograms of protein per liter, at least 200 micrograms of protein per liter, at least 250 micrograms of protein per liter, at least 500 micrograms of protein per liter, at least 1 milligram of protein per liter, or at least 10 milligrams of protein per liter or more, in, including but not limited to, a cell lysate, a buffer, a pharmaceutical buffer, or other liquid suspension (including but not limited to, in a volume of, including but not limited to, anywhere from about 1 nl to about 100 L or more). The production of large quantities (including but not limited to, greater that that typically possible with other methods, including but not limited to, in vitro translation) of a protein in a eukaryotic cell including at least one unnatural amino acid is a feature of the invention.

A eukaryotic host cell or non-eukaryotic host cell of the present invention provides the ability to biosynthesize proteins that comprise unnatural amino acids in large useful quantities. For example, proteins comprising an unnatural amino acid can be produced at a concentration of, including but not limited to, at least 10 µg/liter, at least 50 µg/liter, at least 75 ag/liter, at least 100 µg/liter, at least 200 µg/liter, at least 250 µg/liter, or at least 500 µg/liter, at least 1 mg/liter, at least 2 mg/liter, at least 3 mg/liter, at least 4 mg/liter, at least 5 mg/liter, at least 6 mg/liter, at least 7 mg/liter, at least 8 mg/liter, at least 9 mg/liter, at least 10 mg/liter, at least 20, 30, 40, 50, 60, 70, 80, 90, 100, 200, 300, 400, 500, 600, 700, 800, 900 mg/liter, 1 g/liter, 5 g/liter, 10 g/liter or more of protein in a cell extract, cell lysate, culture medium, a buffer, and/or the like.

A number of vectors suitable for expression of IL-2 are commercially available. Useful expression vectors for eukaryotic hosts, include but are not limited to, vectors comprising expression control sequences from SV40, bovine papilloma virus, adenovirus and cytomegalovirus. Such vectors include pCDNA3.1(+)\Hyg (Invitrogen, Carlsbad, Calif, USA) and pCI-neo (Stratagene, La Jolla, Calif, USA). Bacterial plasmids, such as plasmids from E. coli, including pBR322, pET3a and pET12a, wider host range plasmids, such as RP4, phage DNAs, e.g., the numerous derivatives of phage lambda, e.g., NM989, and other DNA phages, such as M13 and filamentous single stranded DNA phages may be used. The 2 plasmid and derivatives thereof, the POT1 vector (U.S. Pat. No. 4,931,373 which is incorporated by reference), the pJSO37 vector described in (Okkels, Ann. New York Aced. Sci. 782, 202 207, 1996) and pPICZ A, B or C (Invitrogen) may be used with yeast host cells. For insect cells, the vectors include but are not limited to, pVL941, pBG311 (Cate et al., "Isolation of the Bovine and Human Genes for Mullerian Inhibiting Substance And Expression of the Human Gene In Animal Cells", Cell, 45, pp. 685 98 (1986), pBluebac 4.5 and pMelbac (Invitrogen, Carlsbad, CA).

The nucleotide sequence encoding an IL-2 or a variant thereofs thereof may or may not also include sequence that encodes a signal peptide. The signal peptide is present when the polypeptide is to be secreted from the cells in which it is expressed. Such signal peptide may be any sequence. The signal peptide may be prokaryotic or eukaryotic. Coloma, M (1992) J. Imm. Methods 152:89 104) describe a signal peptide for use in mammalian cells (murine Ig kappa light chain signal peptide). Other signal peptides include but are not limited to, the α-factor signal peptide from S. cerevisiae (U.S. Pat. No. 4,870,008 which is incorporated by reference herein), the signal peptide of mouse salivary amylase (O. Hagenbuchle et al., Nature 289, 1981, pp. 643-646), a modified carboxypeptidase signal peptide (L. A. Valls et al., Cell 48, 1987, pp. 887-897), the yeast BAR1 signal peptide (WO 87/02670, which is incorporated by reference herein), and the yeast aspartic protease 3 (YAP3) signal peptide (cf. M. Egel-Mitani et al., Yeast 6, 1990, pp. 127-137).

Examples of suitable mammalian host cells are known to those of ordinary skill in the art. Such host cells may be Chinese hamster ovary (CHO) cells, (e.g. CHO-KI; ATCC CCL-61), Green Monkey cells (COS) (e.g. COS 1 (ATCC CRL-1650), COS 7 (ATCC CRL-1651)); mouse cells (e.g. NS/O), Baby Hamster Kidney (BHK) cell lines (e.g. ATCC CRL-1632 or ATCC CCL-10), and human cells (e.g. HEK 293 (ATCC CRL-1573)), as well as plant cells in tissue culture. These cell lines and others are available from public depositories such as the American Type Culture Collection, Rockville, Md. In order to provide improved glycosylation of the IL-2 polypeptide, a mammalian host cell may be modified to express sialyltransferase, e.g. 1,6-sialyltransferase, e.g. as described in U.S. Pat. No. 5,047,335, which is incorporated by reference herein.

Methods for the introduction of exogenous DNA into mammalian host cells include but are not limited to, calcium phosphare-mediated transfection, electroporation, DEAE-dextran mediated transfection, liposome-mediated transfection, viral vectors and the transfection methods described by Life Technologies Ltd, Paisley, UK using Lipofectamin 2000 and Roche Diagnostics Corporation, Indianapolis, USA using FuGENE 6. These methods are well known in the art and are described by Ausbel et al. (eds.), 1996, Current Protocols in Molecular Biology, John Wiley & Sons, New York, USA. The cultivation of mammalian cells may be performed according to established methods, e.g. as disclosed in (Animal Cell Biotechnology, Methods and Protocols, Edited by Nigel Jenkins, 1999, Human Press Inc. Totowa, N.J., USA and Harrison Mass. and Rae I F, General Techniques of Cell Culture, Cambridge University Press 1997).

I. *E. Coli, Pseudomonas* species, and other Prokarvotes Bacterial expression techniques are known to those of ordinary skill in the art. A wide variety of vectors are available for use in bacterial hosts. The vectors may be single copy or low or high multicopy vectors. Vectors may serve for cloning and/or expression. In view of the ample literature concerning vectors, commercial availability of many vectors, and even manuals describing vectors and their restriction maps and characteristics, no extensive discussion is required here. As is well-known, the vectors normally involve markers allowing for selection, which markers may provide for cytotoxic agent resistance, prototrophy or immunity. Frequently, a plurality of markers is present, which provide for different characteristics.

A bacterial promoter is any DNA sequence capable of binding bacterial RNA polymerase and initiating the downstream (3') transcription of a coding sequence (e.g. structural gene) into mRNA. A promoter will have a transcription initiation region which is usually placed proximal to the 5' end of the coding sequence. This transcription initiation region typically includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*), (Raibaud et al., ANNU. REV. GENET. (1984) 18:173). Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac), (Chang et al., NATURE (1977) 198:1056), and maltose. Additional examples include promoter sequences derived from biosynthetic enzymes such as tryptophan (trp), (Goeddel et al., NUC. ACIDS RES. (1980) 8:4057; Yelverton et al., NUCL. ACIDS RES. (1981) 9:731; U.S. Pat. No. 4,738,921; EP Pub. Nos. 036 776 and 121 775, which are incorporated by reference herein). The β-galactosidase (bla) promoter system (Weissmann (1981) "The cloning of interferon and other mistakes." In Interferon 3 (Ed. I. Gresser)), bacteriophage lambda PL (Shimatake et al., NATURE (1981) 292:128) and T5 (U.S. Pat. No. 4,689,406, which are incorporated by reference herein) promoter systems also provide useful promoter sequences. Preferred methods of the present invention utilize strong promoters, such as the T7 promoter to induce IL-2 polypeptides at high levels. Examples of such vectors are known to those of ordinary skill in the art and include the pET29 series from Novagen, and the pPOP vectors described in WO99/05297, which is incorporated by reference herein. Such expression systems produce high levels of IL-2 polypeptides in the host without compromising host cell viability or growth parameters. pET19 (Novagen) is another vector known in the art.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter (U.S. Pat. No. 4,551,433, which is incorporated by reference herein). For example, the tac promoter is a hybrid trp-lac promoter comprised of both trp promoter and lac operon sequences that is regulated by the lac repressor (Amann et al., GENE (1983) 25:167; de Boer et al., PROC. NATL. ACAD. SCI. (1983) 80:21). Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system (Studier et al., J. MOL. BIOL. (1986) 189:113; Tabor et al., Proc Natl. Acad. Sci. (1985) 82:1074). In addition, a hybrid promoter can also be comprised of a bacteriophage promoter and an *E. coli* operator region (EP Pub. No. 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3-9 nucleotides in length located 3-11 nucleotides upstream of the initiation codon (Shine et al., NATURE (1975) 254:34). The SD sequence is thought to promote binding of mRNA to the ribosome by the pairing of bases between the SD sequence and the 3' and of *E. coli* 16S rRNA (Steitz et al. "Genetic signals and nucleotide sequences in messenger RNA", In Biological Regulation and Development: Gene Expression (Ed. R. F. Goldberger, 1979)). To express eukaryotic genes and prokaryotic genes with weak ribosome-binding site (Sambrook et al. "Expression of cloned genes in *Escherichia coli*", Molecular Cloning: A Laboratory Manual, 1989).

The term "bacterial host" or "bacterial host cell" refers to a bacteria that can be, or has been, used as a recipient for recombinant vectors or other transfer DNA. The term includes the progeny of the original bacterial host cell that has been transfected. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding a IL-2 polypeptide, are included in the progeny intended by this definition.

The selection of suitable host bacteria for expression of IL-2 polypeptides is known to those of ordinary skill in the art. In selecting bacterial hosts for expression, suitable hosts may include those shown to have, inter alia, good inclusion body formation capacity, low proteolytic activity, and overall robustness. Bacterial hosts are generally available from a variety of sources including, but not limited to, the Bacterial Genetic Stock Center, Department of Biophysics and Medical Physics, University of California (Berkeley, CA); and the American Type Culture Collection ("ATCC") (Manassas, VA). Industrial/pharmaceutical fermentation generally use bacterial derived from K strains (e.g. W3110) or from bacteria derived from B strains (e.g. BL21). These strains are particularly useful because their growth parameters are extremely well known and robust. In addition, these strains are non-pathogenic, which is commercially important for safety and environmental reasons. Other examples of suitable *E. coli* hosts include, but are not limited to, strains of BL21, DH10B, or derivatives thereof. In another embodiment of the methods of the present invention, the *E. coli* host is a protease minus strain including, but not limited to, OMP- and LON-. The host cell strain may be a species of *Pseudomonas*, including but not limited to, *Pseudomonas fluorescens*, *Pseudomonas aeruginosa*, and *Pseudomonas putida*. *Pseudomonas fluorescens* biovar 1, designated strain MB101, is known to be useful for recombinant production and is available for therapeutic protein production processes. Examples of a *Pseudomonas* expression system include the system available from The Dow Chemical Company as a host strain (Midland, MI available on the World Wide Web at dow.com).

Once a recombinant host cell strain has been established (i.e., the expression construct has been introduced into the host cell and host cells with the proper expression construct are isolated), the recombinant host cell strain is cultured under conditions appropriate for production of IL-2 polypeptides. As will be apparent to one of skill in the art, the method of culture of the recombinant host cell strain will be dependent on the nature of the expression construct utilized and the identity of the host cell. Recombinant host strains are normally cultured using methods that are known to those of ordinary skill in the art. Recombinant host cells are typically cultured in liquid medium containing assimilatable sources of carbon, nitrogen, and inorganic salts and, optionally, containing vitamins, amino acids, growth factors, and other proteinaceous culture supplements known to those of ordinary skill in the art. Liquid media for culture of host cells may optionally contain antibiotics or anti-fungals to prevent the growth of undesirable microorganisms and/or compounds including, but not limited to, antibiotics to select for host cells containing the expression vector.

Recombinant host cells may be cultured in batch or continuous formats, with either cell harvesting (in the case where the IL-2 polypeptide accumulates intracellularly) or harvesting of culture supernatant in either batch or continuous formats. For production in prokaryotic host cells, batch culture and cell harvest are preferred.

The IL-2 polypeptides of the present invention are normally purified after expression in recombinant systems. The IL-2 polypeptide may be purified from host cells or culture medium by a variety of methods known to the art. IL-2 polypeptides produced in bacterial host cells may be poorly soluble or insoluble (in the form of inclusion bodies). In one embodiment of the present invention, amino acid substitutions may readily be made in the IL-2 polypeptide that are selected for the purpose of increasing the solubility of the recombinantly produced protein utilizing the methods disclosed herein as well as those known in the art. In the case of insoluble protein, the protein may be collected from host cell lysates by centrifugation and may further be followed by homogenization of the cells. In the case of poorly soluble protein, compounds including, but not limited to, polyethylene imine (PEI) may be added to induce the precipitation of partially soluble protein. The precipitated protein may then be conveniently collected by centrifugation. Recombinant host cells may be disrupted or homogenized to release the inclusion bodies from within the cells using a variety of methods known to those of ordinary skill in the art. Host cell disruption or homogenization may be performed using well known techniques including, but not limited to, enzymatic cell disruption, sonication, dounce homogenization, or high pressure release disruption. In one embodiment of the method of the present invention, the high pressure release technique is used to disrupt the E. coli host cells to release the inclusion bodies of the IL-2 polypeptides. When handling inclusion bodies of IL-2 polypeptide, it may be advantageous to minimize the homogenization time on repetitions in order to maximize the yield of inclusion bodies without loss due to factors such as solubilization, mechanical shearing or proteolysis.

Insoluble or precipitated IL-2 polypeptide may then be solubilized using any of a number of suitable solubilization agents known to the art. The IL-2 polypeptide may be solubilized with urea or guanidine hydrochloride. The volume of the solubilized IL-2 polypeptide should be minimized so that large batches may be produced using conveniently manageable batch sizes. This factor may be significant in a large-scale commercial setting where the recombinant host may be grown in batches that are thousands of liters in volume. In addition, when manufacturing IL-2 polypeptide in a large-scale commercial setting, in particular for human pharmaceutical uses, the avoidance of harsh chemicals that can damage the machinery and container, or the protein product itself, should be avoided, if possible. It has been shown in the method of the present invention that the milder denaturing agent urea can be used to solubilize the IL-2 polypeptide inclusion bodies in place of the harsher denaturing agent guanidine hydrochloride. The use of urea significantly reduces the risk of damage to stainless steel equipment utilized in the manufacturing and purification process of IL-2 polypeptide while efficiently solubilizing the IL-2 polypeptide inclusion bodies.

In the case of soluble IL-2 protein, the IL-2 may be secreted into the periplasmic space or into the culture medium. In addition, soluble IL-2 may be present in the cytoplasm of the host cells. It may be desired to concentrate soluble IL-2 prior to performing purification steps. Standard techniques known to those of ordinary skill in the art may be used to concentrate soluble IL-2 from, for example, cell lysates or culture medium. In addition, standard techniques known to those of ordinary skill in the art may be used to disrupt host cells and release soluble IL-2 from the cytoplasm or periplasmic space of the host cells.

In general, it is occasionally desirable to denature and reduce expressed polypeptides and then to cause the polypeptides to re-fold into the preferred conformation. For example, guanidine, urea, DTT, DTE, and/or a chaperonin can be added to a translation product of interest. Methods of reducing, denaturing and renaturing proteins are known to those of ordinary skill in the art (see, the references above, and Debinski, et al. (1993) J. Biol. Chem., 268: 14065-14070; Kreitman and Pastan (1993) Bioconjug. Chem., 4: 581-585; and Buchner, et al., (1992) Anal. Biochem., 205: 263-270). Debinski, et al., for example, describe the denaturation and reduction of inclusion body proteins in guanidine-DTE. The proteins can be refolded in a redox buffer containing, including but not limited to, oxidized glutathione and L-arginine. Refolding reagents can be flowed or otherwise moved into contact with the one or more polypeptide or other expression product, or vice-versa.

In the case of prokaryotic production of IL-2 polypeptide, the IL-2 polypeptide thus produced may be misfolded and thus lacks or has reduced biological activity. The bioactivity of the protein may be restored by "refolding". In general, misfolded IL-2 polypeptide is refolded by solubilizing (where the IL-2 polypeptide is also insoluble), unfolding and reducing the polypeptide chain using, for example, one or more chaotropic agents (e.g. urea and/or guanidine) and a reducing agent capable of reducing disulfide bonds (e.g. dithiothreitol, DTT or 2-mercaptoethanol, 2-ME). At a moderate concentration of chaotrope, an oxidizing agent is then added (e.g., oxygen, cystine or cystamine), which allows the reformation of disulfide bonds. IL-2 polypeptide may be refolded using standard methods known in the art, such as those described in U.S. Pat. Nos. 4,511,502, 4,511,503, and 4,512,922, which are incorporated by reference herein. The IL-2 polypeptide may also be cofolded with other proteins to form heterodimers or heteromultimers.

After refolding, the IL-2 may be further purified. Purification of IL-2 may be accomplished using a variety of techniques known to those of ordinary skill in the art, including hydrophobic interaction chromatography, size exclusion chromatography, ion exchange chromatography, reverse-phase high performance liquid chromatography, affinity chromatography, and the like or any combination thereof. Additional purification may also include a step of drying or precipitation of the purified protein.

After purification, IL-2 may be exchanged into different buffers and/or concentrated by any of a variety of methods known to the art, including, but not limited to, diafiltration and dialysis. IL-2 that is provided as a single purified protein may be subject to aggregation and precipitation.

The purified IL-2 may be at least 90% pure (as measured by reverse phase high performance liquid chromatography, RP-HPLC, or sodium dodecyl sulfate-polyacrylamide gel electrophoresis, SDS-PAGE) or at least 95% pure, or at least 96% pure, or at least 97% pure, or at least 98% pure, or at least 99% or greater pure. Regardless of the exact numerical value of the purity of the IL-2, the IL-2 is sufficiently pure for use as a pharmaceutical product or for further processing, such as conjugation with a water-soluble polymer such as PEG.

Certain IL-2 molecules may be used as therapeutic agents in the absence of other active ingredients or proteins (other than excipients, carriers, and stabilizers, serum albumin and the like), or they may be complexed with another protein or a polymer.

Previously, it has been shown that unnatural amino acids can be site-specifically incorporated into proteins in vitro by the addition of chemically aminoacylated suppressor tRNAs to protein synthesis reactions programmed with a gene containing a desired amber nonsense mutation. Using these approaches, one can substitute a number of the common twenty amino acids with close structural homologues, e.g., fluorophenylalanine for phenylalanine, using strains auxotropic for a particular amino acid. See, e.g., Noren, C. J., Anthony-Cahill, Griffith, M. C., Schultz, P. G. *A general method for site-specific incorporation of unnatural amino acids into proteins*, Science, 244: 182-188 (1989); M. W. Nowak, et al., Science 268:439-42 (1995); Bain, J. D., Glabe, C. G., Dix, T. A., Chamberlin, A. R., Diala, E. S. *Biosynthetic site-specific Incorporation of a non-natural amino acid into a polypeptide*, J. Am Chem Soc, 111:8013-8014 (1989); N. Budisa et al., FASEB J. 13:41-51 (1999); Ellman, J. A., Mendel, D., Anthony-Cahill, S., Noren, C. J., Schultz, P. G. *Biosynthetic method for introducing unnatural amino acids site-specifically into proteins*, Methods in Enz., vol. 202, 301-336 (1992); and, Mendel, D., Cornish, V. W. & Schultz, P. G. Site-*Directed Mutagenesis with an Expanded Genetic Code*, Annu Rev Biophys. Biomol Struct. 24, 435-62 (1995).

For example, a suppressor tRNA was prepared that recognized the stop codon UAG and was chemically aminoacylated with an unnatural amino acid. Conventional site-directed mutagenesis was used to introduce the stop codon TAG, at the site of interest in the protein gene. See, e.g., Sayers, J. R., Schmidt, W. Eckstein, F. 5'-3' *Exonucleases in phosphorothioate-based olignoucleotide-directed mutagensis*, Nucleic Acids Res, 16(3):791-802 (1988). When the acylated suppressor tRNA and the mutant gene were combined in an in vitro transcription/translation system, the unnatural amino acid was incorporated in response to the UAG codon which gave a protein containing that amino acid at the specified position. Experiments using [$^3$H]-Phe and experiments with α-hydroxy acids demonstrated that only the desired amino acid is incorporated at the position specified by the UAG codon and that this amino acid is not incorporated at any other site in the protein. See, e.g., Noren, et al, supra; Kobayashi et al., (2003) Nature Structural Biology 10(6):425-432; and, Ellman, J. A., Mendel, D., Schultz, P. G. *Site-specific incorporation of novel backbone structures into proteins*, Science, 255(5041):197-200 (1992).

A tRNA may be aminoacylated with a desired amino acid by any method or technique, including but not limited to, chemical or enzymatic aminoacylation.

Aminoacylation may be accomplished by aminoacyl tRNA synthetases or by other enzymatic molecules, including but not limited to, ribozymes. The term "ribozyme" is interchangeable with "catalytic RNA." Cech and coworkers (Cech, 1987, Science, 236:1532-1539; McCorkle et al., 1987, Concepts Biochem. 64:221-226) demonstrated the presence of naturally occurring RNAs that can act as catalysts (ribozymes). However, although these natural RNA catalysts have only been shown to act on ribonucleic acid substrates for cleavage and splicing, the recent development of artificial evolution of ribozymes has expanded the repertoire of catalysis to various chemical reactions. Studies have identified RNA molecules that can catalyze aminoacyl-RNA bonds on their own (2')3'-termini (Illangakekare et al., 1995 Science 267:643-647), and an RNA molecule which can transfer an amino acid from one RNA molecule to another (Lohse et al., 1996, Nature 381:442-444).

U.S. Patent Application Publication 2003/0228593, which is incorporated by reference herein, describes methods to construct ribozymes and their use in aminoacylation of tRNAs with naturally encoded and non-naturally encoded amino acids. Substrate-immobilized forms of enzymatic molecules that can aminoacylate tRNAs, including but not limited to, ribozymes, may enable efficient affinity purification of the aminoacylated products. Examples of suitable substrates include agarose, sepharose, and magnetic beads. The production and use of a substrate-immobilized form of ribozyme for aminoacylation is described in Chemistry and Biology 2003, 10:1077-1084 and U.S. Patent Application Publication 2003/0228593, which are incorporated by reference herein.

Chemical aminoacylation methods include, but are not limited to, those introduced by Hecht and coworkers (Hecht, S. M. Acc. Chem. Res. 1992, 25, 545; Heckler, T. G.; Roesser, J. R.; Xu, C.; Chang, P.; Hecht, S. M. Biochemistry 1988, 27, 7254; Hecht, S. M.; Alford, B. L.; Kuroda, Y.; Kitano, S. J. Biol. Chem. 1978, 253, 4517) and by Schultz, Chamberlin, Dougherty and others (Comish, V. W.; Mendel, D.; Schultz, P. G. Angew. Chem. Int. Ed. Engl. 1995, 34, 621; Robertson, S. A.; Ellman, J. A.; Schultz, P. G. J. Am. Chem. Soc. 1991, 113, 2722; Noren, C. J.; Anthony-Cahill, S. J.; Griffith, M. C.; Schultz, P. G. Science 1989, 244, 182; Bain, J. D.; Glabe, C. G.; Dix, T. A.; Chamberlin, A. R. J. Am. Chem. Soc. 1989, 111, 8013; Bain, J. D. et al. Nature 1992, 356, 537; Gallivan, J. P.; Lester, H. A.; Dougherty, D. A. Chem. Biol. 1997, 4, 740; Turcatti, et al. J. Biol. Chem. 1996, 271, 19991; Nowak, M. W. et al. Science, 1995, 268, 439; Saks, M. E. et al. J. Biol. Chem. 1996, 271, 23169; Hohsaka, T. et al. J. Am. Chem. Soc. 1999, 121, 34), which are incorporated by reference herein, to avoid the use of synthetases in aminoacylation. Such methods or other chemical aminoacylation methods may be used to aminoacylate tRNA molecules.

Methods for generating catalytic RNA may involve generating separate pools of randomized ribozyme sequences, performing directed evolution on the pools, screening the pools for desirable aminoacylation activity, and selecting sequences of those ribozymes exhibiting desired aminoacylation activity.

Reconstituted translation systems may also be used. Mixtures of purified translation factors have also been used successfully to translate mRNA into protein as well as combinations of lysates or lysates supplemented with purified translation factors such as initiation factor-1 (IF-1), IF-2, IF-3 (α or β), elongation factor T (EF-Tu), or termination factors. Cell-free systems may also be coupled transcription/translation systems wherein DNA is introduced to the system, transcribed into mRNA and the mRNA translated as described in Current Protocols in Molecular Biology (F. M. Ausubel et al. editors, Wiley Interscience, 1993), which is hereby specifically incorporated by reference. RNA transcribed in eukaryotic transcription system may be in the form of heteronuclear RNA (hnRNA) or 5'-end caps (7-methyl guanosine) and 3'-end poly A tailed mature mRNA, which can be an advantage in certain translation systems. For example, capped mRNAs are translated with high efficiency in the reticulocyte lysate system.

IX. Macromolecular Polymers Coupled to IL-2 Polypeptides

Various modifications to the non-natural amino acid polypeptides described herein can be effected using the compositions, methods, techniques and strategies described herein. These modifications include the incorporation of further functionality onto the non-natural amino acid component of the polypeptide, including but not limited to, a label; a dye; a polymer; a water-soluble polymer; a derivative of polyethylene glycol; a photocrosslinker; a radionuclide; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide; a water-soluble dendrimer; a cyclodextrin; an inhibitory ribonucleic acid; a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a photoisomerizable moiety; biotin; a derivative of biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; a quantum dot; a nanotransmitter; a radionucleotide; a radiotransmitter; a neutron-capture agent; or any combination of the above, or any other desirable compound or substance. As an illustrative, non-limiting example of the compositions, methods, techniques and strategies described herein, the following description will focus on adding macromolecular polymers to the non-natural amino acid polypeptide with the understanding that the compositions, methods, techniques and strategies described thereto are also applicable (with appropriate modifications, if necessary and for which one of skill in the art could make with the disclosures herein) to adding other functionalities, including but not limited to those listed above.

A wide variety of macromolecular polymers and other molecules can be linked to IL-2 polypeptides of the present invention to modulate biological properties of the IL-2 polypeptide, and/or provide new biological properties to the IL-2 molecule. These macromolecular polymers can be linked to the IL-2 polypeptide via a naturally encoded amino acid, via a non-naturally encoded amino acid, or any functional substituent of a natural or non-natural amino acid, or any substituent or functional group added to a natural or non-natural amino acid. The molecular weight of the polymer may be of a wide range, including but not limited to, between about 100 Da and about 100,000 Da or more. The molecular weight of the polymer may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of the polymer is between about 100 Da and about 50,000 Da. In some embodiments, the molecular weight of the polymer is between about 100 Da and about 40,000 Da. In some embodiments, the molecular weight of the polymer is between about 1,000 Da and about 40,000 Da. In some embodiments, the molecular weight of the polymer is between about 5,000 Da and about 40,000 Da. In some embodiments, the molecular weight of the polymer is between about 10,000 Da and about 40,000 Da.

The present invention provides substantially homogenous preparations of polymer:protein conjugates. "Substantially homogenous" as used herein means that polymer:protein conjugate molecules are observed to be greater than half of the total protein. The polymer:protein conjugate has biological activity and the present "substantially homogenous" PEGylated IL-2 polypeptide preparations provided herein are those which are homogenous enough to display the advantages of a homogenous preparation, e.g., ease in clinical application in predictability of lot to lot pharmacokinetics.

One may also choose to prepare a mixture of polymer:protein conjugate molecules, and the advantage provided herein is that one may select the proportion of mono-polymer:protein conjugate to include in the mixture. Thus, if desired, one may prepare a mixture of various proteins with various numbers of polymer moieties attached (i.e., di-, tri-, tetra-, etc.) and combine said conjugates with the mono-polymer:protein conjugate prepared using the methods of the present invention, and have a mixture with a predetermined proportion of mono-polymer:protein conjugates.

The polymer selected may be water-soluble so that the protein to which it is attached does not precipitate in an aqueous environment, such as a physiological environment. The polymer may be branched or unbranched. For therapeutic use of the end-product preparation, the polymer will be pharmaceutically acceptable.

Examples of polymers include but are not limited to polyalkyl ethers and alkoxy-capped analogs thereof (e.g., polyoxyethylene glycol, polyoxyethylene/propylene glycol, and methoxy or ethoxy-capped analogs thereof, especially polyoxyethylene glycol, the latter is also known as polyethyleneglycol or PEG); polyvinylpyrrolidones; polyvinylalkyl ethers; polyoxazolines, polyalkyl oxazolines and polyhydroxyalkyl oxazolines; polyacrylamides, polyalkyl acrylamides, and polyhydroxyalkyl acrylamides (e.g., polyhydroxypropylmethacrylamide and derivatives thereof); polyhydroxyalkyl acrylates; polysialic acids and analogs thereof; hydrophilic peptide sequences; polysaccharides and their derivatives, including dextran and dextran derivatives, e.g., carboxymethyldextran, dextran sulfates, aminodextran; cellulose and its derivatives, e.g., carboxymethyl cellulose, hydroxyalkyl celluloses; chitin and its derivatives, e.g., chitosan, succinyl chitosan, carboxymethylchitin, carboxymethylchitosan; hyaluronic acid and its derivatives; starches; alginates; chondroitin sulfate; albumin; pullulan and carboxymethyl pullulan; polyaminoacids and derivatives thereof, e.g., polyglutamic acids, polylysines, polyaspartic acids, polyaspartamides; maleic anhydride copolymers such as: styrene maleic anhydride copolymer, divinylethyl ether maleic anhydride copolymer; polyvinyl alcohols; copolymers thereof; terpolymers thereof; mixtures thereof; and derivatives of the foregoing.

The proportion of polyethylene glycol molecules to protein molecules will vary, as will their concentrations in the reaction mixture. In general, the optimum ratio (in terms of efficiency of reaction in that there is minimal excess unreacted protein or polymer) may be determined by the molecular weight of the polyethylene glycol selected and on the number of available reactive groups available. As relates to molecular weight, typically the higher the molecular weight of the polymer, the fewer number of polymer molecules which may be attached to the protein. Similarly, branching of the polymer should be taken into account when optimizing these parameters. Generally, the higher the molecular weight (or the more branches) the higher the polymer:protein ratio.

As used herein, and when contemplating PEG: IL-2 polypeptide conjugates, the term "therapeutically effective amount" refers to an amount which gives the desired benefit to a patient. The amount will vary from one individual to another and will depend upon a number of factors, including the overall physical condition of the patient and the underlying cause of the condition to be treated. The amount of IL-2 polypeptide used for therapy gives an acceptable rate of change and maintains desired response at a beneficial level. A therapeutically effective amount of the present compositions may be readily ascertained by one of ordinary skill in the art using publicly available materials and procedures.

The water-soluble polymer may be any structural form including but not limited to linear, forked or branched. Typically, the water-soluble polymer is a poly(alkylene glycol), such as poly(ethylene glycol) (PEG), but other water-soluble polymers can also be employed. By way of example, PEG is used to describe certain embodiments of this invention.

PEG is a well-known, water-soluble polymer that is commercially available or can be prepared by ring-opening polymerization of ethylene glycol according to methods known to those of ordinary skill in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented as linked to the IL-2 polypeptide by the formula:

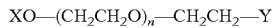

XO—(CH$_2$CH$_2$O)$_n$—CH$_2$CH$_2$—Y where n is 2 to 10,000 and X is H or a terminal modification, including but not limited to, a C$_{1-4}$ alkyl, a protecting group, or a terminal functional group.

In some cases, a PEG used in the invention terminates on one end with hydroxy or methoxy, i.e., X is H or CH$_3$ ("methoxy PEG"). Alternatively, the PEG can terminate with a reactive group, thereby forming a bifunctional polymer. Typical reactive groups can include those reactive groups that are commonly used to react with the functional groups found in the 20 common amino acids (including but not limited to, maleimide groups, activated carbonates (including but not limited to, p-nitrophenyl ester), activated esters (including but not limited to, N-hydroxysuccinimide, p-nitrophenyl ester) and aldehydes) as well as functional groups that are inert to the 20 common amino acids but that react specifically with complementary functional groups present in non-naturally encoded amino acids (including but not limited to, azide groups, alkyne groups). It is noted that the other end of the PEG, which is shown in the above formula by Y, will attach either directly or indirectly to a IL-2 polypeptide via a naturally-occurring or non-naturally encoded amino acid. For instance, Y may be an amide, carbamate or urea linkage to an amine group (including but not limited to, the epsilon amine of lysine or the N-terminus) of the polypeptide. Alternatively, Y may be a maleimide linkage to a thiol group (including but not limited to, the thiol group of cysteine). Alternatively, Y may be a linkage to a residue not commonly accessible via the 20 common amino acids. For example, an azide group on the PEG can be reacted with an alkyne group on the IL-2 polypeptide to form a Huisgen [3+2]cycloaddition product. Alternatively, an alkyne group on the PEG can be reacted with an azide group present in a non-naturally encoded amino acid to form a similar product. In some embodiments, a strong nucleophile (including but not limited to, hydrazine, hydrazide, hydroxylamine, semicarbazide) can be reacted with an aldehyde or ketone group present in a non-naturally encoded amino acid to form a hydrazone, oxime or semicarbazone, as applicable, which in some cases can be further reduced by treatment with an appropriate reducing agent. Alternatively, the strong nucleophile can be incorporated into the IL-2 polypeptide via a non-naturally encoded amino acid and used to react preferentially with a ketone or aldehyde group present in the water-soluble polymer.

Any molecular mass for a PEG can be used as practically desired, including but not limited to, from about 100 Daltons (Da) to 100,000 Da or more as desired (including but not limited to, sometimes 0.1-50 kDa or 10-40 kDa). The molecular weight of PEG may be of a wide range, including but not limited to, between about 100 Da and about 100,000 Da or more. PEG may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, PEG is between about 100 Da and about 50,000 Da. In some embodiments, PEG is between about 100 Da and about 40,000 Da. In some embodiments, PEG is between about 1,000 Da and about 40,000 Da. In some embodiments, PEG is between about 5,000 Da and about 40,000 Da. In some embodiments, PEG is between about 10,000 Da and about 40,000 Da. Branched chain PEGs, including but not limited to, PEG molecules with each chain having a MW ranging from 1-100 kDa (including but not limited to, 1-50 kDa or 5-20 kDa) can also be used. The molecular weight of each chain of the branched chain PEG may be, including but not limited to, between about 1,000 Da and about 100,000 Da or more. The molecular weight of each chain of the branched chain PEG may be between about 1,000 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of each chain of the branched chain PEG is between about 1,000 Da and about 50,000 Da. In some embodiments, the molecular weight of each chain of the branched chain PEG is between about 1,000 Da and about 40,000 Da. In some embodiments, the molecular weight of each chain of the branched chain PEG is between about 5,000 Da and about 40,000 Da. In some embodiments, the molecular weight of each chain of the branched chain PEG is between about 5,000 Da and about 20,000 Da. A wide range of PEG molecules are described in, including but not limited to, the Shearwater Polymers, Inc. catalog, Nektar Therapeutics catalog, incorporated herein by reference.

Generally, at least one terminus of the PEG molecule is available for reaction with the non-naturally-encoded amino acid. For example, PEG derivatives bearing alkyne and azide moieties for reaction with amino acid side chains can be used to attach PEG to non-naturally encoded amino acids as described herein. If the non-naturally encoded amino acid comprises an azide, then the PEG will typically contain either an alkyne moiety to effect formation of the [3+2] cycloaddition product or an activated PEG species (i.e., ester, carbonate) containing a phosphine group to effect formation of the amide linkage. Alternatively, if the non-naturally encoded amino acid comprises an alkyne, then the PEG will typically contain an azide moiety to effect formation of the [3+2] Huisgen cycloaddition product. If the non-naturally encoded amino acid comprises a carbonyl group, the PEG will typically comprise a potent nucleophile (including but not limited to, a hydrazide, hydrazine, hydroxylamine, or semicarbazide functionality) in order to effect formation of corresponding hydrazone, oxime, and semicarbazone linkages, respectively. In other alternatives, a reverse of the orientation of the reactive groups described above can be used, i.e., an azide moiety in the non-naturally encoded amino acid can be reacted with a PEG derivative containing an alkyne.

In some embodiments, the IL-2 polypeptide variant with a PEG derivative contains a chemical functionality that is reactive with the chemical functionality present on the side chain of the non-naturally encoded amino acid.

The invention provides in some embodiments azide- and acetylene-containing polymer derivatives comprising a water-soluble polymer backbone having an average molecular weight from about 800 Da to about 100,000 Da. The polymer backbone of the water-soluble polymer can be poly(ethylene glycol). However, it should be understood that a wide variety of water-soluble polymers including but not limited to poly(ethylene)glycol and other related polymers, including poly(dextran) and poly(propylene glycol), are also suitable for use in the practice of this invention and that the use of the term PEG or poly(ethylene glycol) is intended to encompass and include all such molecules. The term PEG includes, but is not limited to, poly(ethylene glycol) in any of its forms, including bifunctional PEG, multiarmed PEG, derivatized PEG, forked PEG, branched PEG, pendent PEG (i.e. PEG or related polymers having one or more functional groups pendent to the polymer backbone), or PEG with degradable linkages therein.

PEG is typically clear, colorless, odorless, soluble in water, stable to heat, inert to many chemical agents, does not hydrolyze or deteriorate, and is generally non-toxic. Poly (ethylene glycol) is considered to be biocompatible, which is to say that PEG is capable of coexistence with living tissues or organisms without causing harm. More specifically, PEG is substantially non-immunogenic, which is to say that PEG does not tend to produce an immune response in the body. When attached to a molecule having some desirable function in the body, such as a biologically active agent, the PEG tends to mask the agent and can reduce or eliminate any immune response so that an organism can tolerate the presence of the agent. PEG conjugates tend not to produce a substantial immune response or cause clotting or other undesirable effects. PEG having the formula —$CH_2CH_2O$—$(CH_2CH_2O)_n$—$CH_2CH_2$—, where n is from about 3 to about 4000, typically from about 20 to about 2000, is suitable for use in the present invention. PEG having a molecular weight of from about 800 Da to about 100,000 Da are in some embodiments of the present invention particularly useful as the polymer backbone. The molecular weight of PEG may be of a wide range, including but not limited to, between about 100 Da and about 100,000 Da or more. The molecular weight of PEG may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of PEG is between about 100 Da and about 50,000 Da. In some embodiments, the molecular weight of PEG is between about 100 Da and about 40,000 Da. In some embodiments, the molecular weight of PEG is between about 1,000 Da and about 40,000 Da. In some embodiments, the molecular weight of PEG is between about 5,000 Da and about 40,000 Da. In some embodiments, the molecular weight of PEG is between about 10,000 Da and about 40,000 Da.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, glycerol oligomers, pentaerythritol and sorbitol. The central branch moiety can also be derived from several amino acids, such as lysine. The branched poly(ethylene glycol) can be represented in general form as $R(-PEG-OH)_m$ in which R is derived from a core moiety, such as glycerol, glycerol oligomers, or pentaerythritol, and m represents the number of arms. Multi-armed PEG molecules, such as those described in U.S. Pat. Nos. 5,932,462; 5,643,575; 5,229,490; 4,289,872; U.S. Pat. Appl. 2003/0143596; WO 96/21469; and WO 93/21259, each of which is incorporated by reference herein in its entirety, can also be used as the polymer backbone.

Branched PEG can also be in the form of a forked PEG represented by $PEG(-YCHZ_2)_n$, where Y is a linking group and Z is an activated terminal group linked to CH by a chain of atoms of defined length.

Yet another branched form, the pendant PEG, has reactive groups, such as carboxyl, along the PEG backbone rather than at the end of PEG chains.

In addition to these forms of PEG, the polymer can also be prepared with weak or degradable linkages in the backbone. For example, PEG can be prepared with ester linkages in the polymer backbone that are subject to hydrolysis. As shown below, this hydrolysis results in cleavage of the polymer into fragments of lower molecular weight:

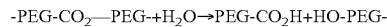

-PEG-$CO_2$—PEG-+$H_2O$→PEG-$CO_2$H+HO-PEG-

It is understood by those of ordinary skill in the art that the term poly(ethylene glycol) or PEG represents or includes all the forms known in the art including but not limited to those disclosed herein.

Many other polymers are also suitable for use in the present invention. In some embodiments, polymer backbones that are water-soluble, with from 2 to about 300 termini, are particularly useful in the invention. Examples of suitable polymers include, but are not limited to, other poly(alkylene glycols), such as poly(propylene glycol) ("PPG"), copolymers thereof (including but not limited to copolymers of ethylene glycol and propylene glycol), terpolymers thereof, mixtures thereof, and the like. Although the molecular weight of each chain of the polymer backbone can vary, it is typically in the range of from about 800 Da to about 100,000 Da, often from about 6,000 Da to about 80,000 Da. The molecular weight of each chain of the polymer backbone may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of each chain of the polymer backbone is between about 100 Da and about 50,000 Da. In some embodiments, the molecular weight of each chain of the polymer backbone is between about 100 Da and about 40,000 Da. In some embodiments, the molecular weight of each chain of the polymer backbone is between about 1,000 Da and about 40,000 Da. In some embodiments, the molecular weight of each chain of the polymer backbone is between about 5,000 Da and about 40,000 Da. In some embodiments, the molecular weight of each chain of the polymer backbone is between about 10,000 Da and about 40,000 Da.

Those of ordinary skill in the art will recognize that the foregoing list for substantially water-soluble backbones is by no means exhaustive and is merely illustrative, and that all polymeric materials having the qualities described above are contemplated as being suitable for use in the present invention.

In some embodiments of the present invention the polymer derivatives are "multi-functional", meaning that the polymer backbone has at least two termini, and possibly as many as about 300 termini, functionalized or activated with a functional group. Multifunctional polymer derivatives include, but are not limited to, linear polymers having two termini, each terminus being bonded to a functional group which may be the same or different.

In one embodiment, the polymer derivative has the structure:

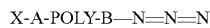

wherein:
N=N=N is an azide moiety;
B is a linking moiety, which may be present or absent;
POLY is a water-soluble non-antigenic polymer;
A is a linking moiety, which may be present or absent and which may be the same as B or different; and
X is a second functional group.

Examples of a linking moiety for A and B include, but are not limited to, a multiply-functionalized alkyl group containing up to 18, and may contain between 1-10 carbon atoms. A heteroatom such as nitrogen, oxygen or sulfur may be included with the alkyl chain. The alkyl chain may also be branched at a heteroatom. Other examples of a linking moiety for A and B include, but are not limited to, a multiply functionalized aryl group, containing up to 10 and may contain 5-6 carbon atoms. The aryl group may be substituted with one more carbon atoms, nitrogen, oxygen or sulfur atoms. Other examples of suitable linking groups include those linking groups described in U.S. Pat. Nos. 5,932,462; 5,643,575; and U.S. Pat. Appl. Publication 2003/0143596, each of which is incorporated by reference herein. Those of ordinary skill in the art will recognize that the foregoing list for linking moieties is by no means exhaustive and is merely illustrative, and that all linking moieties having the qualities described above are contemplated to be suitable for use in the present invention.

Examples of suitable functional groups for use as X include, but are not limited to, hydroxyl, protected hydroxyl, alkoxyl, active ester, such as N-hydroxysuccinimidyl esters and 1-benzotriazolyl esters, active carbonate, such as N-hydroxysuccinimidyl carbonates and 1-benzotriazolyl carbonates, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, tresylate, alkene, ketone, and azide. As is understood by those of ordinary skill in the art, the selected X moiety should be compatible with the azide group so that reaction with the azide group does not occur. The azide-containing polymer derivatives may be homobifunctional, meaning that the second functional group (i.e., X) is also an azide moiety, or heterobifunctional, meaning that the second functional group is a different functional group.

The term "protected" refers to the presence of a protecting group or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or tert-butyl. Other protecting groups known in the art may also be used in the present invention.

Specific examples of terminal functional groups in the literature include, but are not limited to, N-succinimidyl carbonate (see e.g., U.S. Pat. Nos. 5,281,698, 5,468,478), amine (see, e.g., Buckmann et al. Makromol. Chem. 182: 1379 (1981), Zalipsky et al. Eur. Polym. J. 19:1177 (1983)), hydrazide (See, e.g., Andresz et al. Makromol. Chem. 179: 301 (1978)), succinimidyl propionate and succinimidyl butanoate (see, e.g., Olson et al. in Poly(ethylene glycol) Chemistry & Biological Applications, pp 170-181, Harris & Zalipsky Eds., ACS, Washington, D.C., 1997; see also U.S. Pat. No. 5,672,662), succinimidyl succinate (See, e.g., Abuchowski et al. Cancer Biochem. Biophys. 7:175 (1984) and Joppich et al. Makromol. Chem. 180:1381 (1979), succinimidyl ester (see, e.g., U.S. Pat. No. 4,670,417), benzotriazole carbonate (see, e.g., U.S. Pat. No. 5,650,234), glycidyl ether (see, e.g., Pitha et al. Eur. J Biochem. 94:11 (1979), Elling et al., Biotech. Appl. Biochem. 13:354 (1991), oxycarbonylimidazole (see, e.g., Beauchamp, et al., Anal. Biochem. 131:25 (1983), Tondelli et al. J. Controlled Release 1:251 (1985)), p-nitrophenyl carbonate (see, e.g., Veronese, et al., Appl. Biochem. Biotech., 11: 141 (1985); and Sartore et al., Appl. Biochem. Biotech., 27:45 (1991)), aldehyde (see, e.g., Harris et al. J. Polym. Sci. Chem. Ed. 22:341 (1984), U.S. Pat. Nos. 5,824,784, 5,252,714), maleimide (see, e.g., Goodson et al. Biotechnology (NY) 8:343 (1990), Romani et al. in Chemistry of Peptides and Proteins 2:29 (1984)), and Kogan, Synthetic Comm. 22:2417 (1992)), orthopyridyl-disulfide (see, e.g., Woghiren, et al. Bioconj. Chem. 4:314(1993)), acrylol (see, e.g., Sawhney et al., Macromolecules, 26:581 (1993)), vinylsulfone (see, e.g., U.S. Pat. No. 5,900,461). All of the above references and patents are incorporated herein by reference.

In certain embodiments of the present invention, the polymer derivatives of the invention comprise a polymer backbone having the structure:

N=N=N wherein:
X is a functional group as described above; and
n is about 20 to about 4000.

In another embodiment, the polymer derivatives of the invention comprise a polymer backbone having the structure:

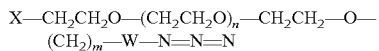
(CH$_2$)$_m$—W—N=N=N wherein:
W is an aliphatic or aromatic linker moiety comprising between 1-10 carbon atoms;
n is about 20 to about 4000; and
X is a functional group as described above. m is between 1 and 10.

The azide-containing PEG derivatives of the invention can be prepared by a variety of methods known in the art and/or disclosed herein. In one method, shown below, a water-soluble polymer backbone having an average molecular weight from about 800 Da to about 100,000 Da, the polymer backbone having a first terminus bonded to a first functional group and a second terminus bonded to a suitable leaving group, is reacted with an azide anion (which may be paired with any of a number of suitable counter-ions, including sodium, potassium, tert-butylammonium and so forth). The leaving group undergoes a nucleophilic displacement and is replaced by the azide moiety, affording the desired azide-containing PEG polymer.

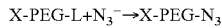

As shown, a suitable polymer backbone for use in the present invention has the formula X-PEG-L, wherein PEG is poly(ethylene glycol) and X is a functional group which does not react with azide groups and L is a suitable leaving group. Examples of suitable functional groups include, but are not limited to, hydroxyl, protected hydroxyl, acetal, alkenyl, amine, aminooxy, protected amine, protected hydrazide, protected thiol, carboxylic acid, protected carboxylic acid, maleimide, dithiopyridine, and vinylpyridine, and ketone. Examples of suitable leaving groups include, but are not limited to, chloride, bromide, iodide, mesylate, tresylate, and tosylate.

In another method for preparation of the azide-containing polymer derivatives of the present invention, a linking agent bearing an azide functionality is contacted with a water-soluble polymer backbone having an average molecular weight from about 800 Da to about 100,000 Da, wherein the linking agent bears a chemical functionality that will react selectively with a chemical functionality on the PEG polymer, to form an azide-containing polymer derivative product wherein the azide is separated from the polymer backbone by a linking group.

An exemplary reaction scheme is shown below:

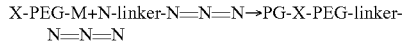

wherein:
PEG is poly(ethylene glycol) and X is a capping group such as alkoxy or a functional group as described above; and
M is a functional group that is not reactive with the azide functionality but that will react efficiently and selectively with the N functional group.

Examples of suitable functional groups include, but are not limited to, M being a carboxylic acid, carbonate or active ester if N is an amine; M being a ketone if N is a hydrazide or aminooxy moiety; M being a leaving group if N is a nucleophile.

Purification of the crude product may be accomplished by known methods including, but are not limited to, precipitation of the product followed by chromatography, if necessary.

A more specific example is shown below in the case of PEG diamine, in which one of the amines is protected by a protecting group moiety such as tert-butyl-Boc and the resulting mono-protected PEG diamine is reacted with a linking moiety that bears the azide functionality:

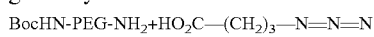

In this instance, the amine group can be coupled to the carboxylic acid group using a variety of activating agents such as thionyl chloride or carbodiimide reagents and N-hydroxysuccinimide or N-hydroxybenzotriazole to create an amide bond between the monoamine PEG derivative and the azide-bearing linker moiety. After successful formation of the amide bond, the resulting N-tert-butyl-Boc-protected azide-containing derivative can be used directly to modify bioactive molecules or it can be further elaborated to install other useful functional groups. For instance, the N-t-Boc group can be hydrolyzed by treatment with strong acid to generate an omega-amino-PEG-azide. The resulting amine can be used as a synthetic handle to install other useful functionality such as maleimide groups, activated disulfides, activated esters and so forth for the creation of valuable heterobifunctional reagents.

Heterobifunctional derivatives are particularly useful when it is desired to attach different molecules to each terminus of the polymer. For example, the omega-N-amino-N-azido PEG would allow the attachment of a molecule having an activated electrophilic group, such as an aldehyde, ketone, activated ester, activated carbonate and so forth, to one terminus of the PEG and a molecule having an acetylene group to the other terminus of the PEG.

In another embodiment of the invention, the polymer derivative has the structure:

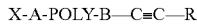

wherein:
R can be either H or an alkyl, alkene, alkyoxy, or aryl or substituted aryl group;
B is a linking moiety, which may be present or absent;
POLY is a water-soluble non-antigenic polymer;
A is a linking moiety, which may be present or absent and which may be the same as B or different; and
X is a second functional group.

Examples of a linking moiety for A and B include, but are not limited to, a multiply-functionalized alkyl group containing up to 18, and may contain between 1-10 carbon atoms. A heteroatom such as nitrogen, oxygen or sulfur may be included with the alkyl chain. The alkyl chain may also be branched at a heteroatom. Other examples of a linking moiety for A and B include, but are not limited to, a multiply functionalized aryl group, containing up to 10 and may contain 5-6 carbon atoms. The aryl group may be substituted with one more carbon atoms, nitrogen, oxygen, or sulfur atoms. Other examples of suitable linking groups include those linking groups described in U.S. Pat. Nos. 5,932,462 and 5,643,575 and U.S. Pat. Appl. Publication 2003/0143596, each of which is incorporated by reference herein. Those of ordinary skill in the art will recognize that the foregoing list for linking moieties is by no means exhaustive and is intended to be merely illustrative, and that a wide variety of linking moieties having the qualities described above are contemplated to be useful in the present invention.

Examples of suitable functional groups for use as X include hydroxyl, protected hydroxyl, alkoxyl, active ester, such as N-hydroxysuccinimidyl esters and 1-benzotriazolyl esters, active carbonate, such as N-hydroxysuccinimidyl carbonates and 1-benzotriazolyl carbonates, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate, alkene, ketone, and acetylene. As would be understood, the selected X moiety should be compatible with the acetylene group so that reaction with the acetylene group does not occur. The acetylene-containing polymer derivatives may be homobifunctional, meaning that the second functional group (i.e., X) is also an acetylene moiety, or heterobifunctional, meaning that the second functional group is a different functional group.

In another embodiment of the present invention, the polymer derivatives comprise a polymer backbone having the structure:

$$X\text{---}CH_2CH_2O\text{---}(CH_2CH_2O)_n\text{---}CH_2CH_2\text{---}O\text{---}(CH_2)_m\text{---}C\equiv CH$$

wherein:
 X is a functional group as described above;
 n is about 20 to about 4000; and
 m is between 1 and 10.
 Specific examples of each of the heterobifunctional PEG polymers are shown below.

The acetylene-containing PEG derivatives of the invention can be prepared using methods known to those of ordinary skill in the art and/or disclosed herein. In one method, a water-soluble polymer backbone having an average molecular weight from about 800 Da to about 100,000 Da, the polymer backbone having a first terminus bonded to a first functional group and a second terminus bonded to a suitable nucleophilic group, is reacted with a compound that bears both an acetylene functionality and a leaving group that is suitable for reaction with the nucleophilic group on the PEG. When the PEG polymer bearing the nucleophilic moiety and the molecule bearing the leaving group are combined, the leaving group undergoes a nucleophilic displacement and is replaced by the nucleophilic moiety, affording the desired acetylene-containing polymer.

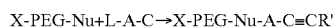

As shown, a preferred polymer backbone for use in the reaction has the formula X-PEG-Nu, wherein PEG is poly(ethylene glycol), Nu is a nucleophilic moiety and X is a functional group that does not react with Nu, L or the acetylene functionality.

Examples of Nu include, but are not limited to, amine, alkoxy, aryloxy, sulfhydryl, imino, carboxylate, hydrazide, aminoxy groups that would react primarily via a SN2-type mechanism. Additional examples of Nu groups include those functional groups that would react primarily via an nucleophilic addition reaction. Examples of L groups include chloride, bromide, iodide, mesylate, tresylate, and tosylate and other groups expected to undergo nucleophilic displacement as well as ketones, aldehydes, thioesters, olefins, alpha-beta unsaturated carbonyl groups, carbonates and other electrophilic groups expected to undergo addition by nucleophiles.

In another embodiment of the present invention, A is an aliphatic linker of between 1-10 carbon atoms or a substituted aryl ring of between 6-14 carbon atoms. X is a functional group which does not react with azide groups and L is a suitable leaving group In another method for preparation of the acetylene-containing polymer derivatives of the invention, a PEG polymer having an average molecular weight from about 800 Da to about 100,000 Da, bearing either a protected functional group or a capping agent at one terminus and a suitable leaving group at the other terminus is contacted by an acetylene anion.

An exemplary reaction scheme is shown below:

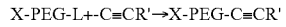

wherein:
 PEG is poly(ethylene glycol) and X is a capping group such as alkoxy or a functional group as described above; and
 R' is either H, an alkyl, alkoxy, aryl or aryloxy group or a substituted alkyl, alkoxyl, aryl or aryloxy group.

In the example above, the leaving group L should be sufficiently reactive to undergo SN2-type displacement when contacted with a sufficient concentration of the acetylene anion. The reaction conditions required to accomplish SN2 displacement of leaving groups by acetylene anions are known to those of ordinary skill in the art.

Purification of the crude product can usually be accomplished by methods known in the art including, but are not limited to, precipitation of the product followed by chromatography, if necessary.

Water-soluble polymers can be linked to the IL-2 polypeptides of the invention. The water-soluble polymers may be linked via a non-naturally encoded amino acid incorporated in the IL-2 polypeptide or any functional group or substituent of a non-naturally encoded or naturally encoded amino acid, or any functional group or substituent added to a non-naturally encoded or naturally encoded amino acid. Alternatively, the water-soluble polymers are linked to a IL-2 polypeptide incorporating a non-naturally encoded amino acid via a naturally-occurring amino acid (including but not limited to, cysteine, lysine or the amine group of the N-terminal residue). In some cases, the IL-2 polypeptides of the invention comprise 1, 2, 3, 4, 5, 6, 7, 8, 9, 10 non-natural amino acids, wherein one or more non-naturally-encoded amino acid(s) are linked to water-soluble polymer(s) (including but not limited to, PEG and/or oligosaccharides). In some cases, the IL-2 polypeptides of the invention further comprise 1, 2, 3, 4, 5, 6, 7, 8, 9, 10, or more naturally-encoded amino acid(s) linked to water-soluble polymers. In some cases, the IL-2 polypeptides of the invention comprise one or more non-naturally encoded amino acid(s) linked to water-soluble polymers and one or more naturally-occurring amino acids linked to water-soluble polymers. In some embodiments, the water-soluble polymers used in the present invention enhance the serum half-life of the IL-2 polypeptide relative to the unconjugated form.

The number of water-soluble polymers linked to an IL-2 polypeptide (i.e., the extent of PEGylation or glycosylation)

of the present invention can be adjusted to provide an altered (including but not limited to, increased or decreased) pharmacologic, pharmacokinetic or pharmacodynamic characteristic such as in vivo half-life. In some embodiments, the half-life of IL-2 is increased at least about 10, 20, 30, 40, 50, 60, 70, 80, 90 percent, 2-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 25-fold, 30-fold, 35-fold, 40-fold, 50-fold, or at least about 100-fold over an unmodified polypeptide.

PEG Derivatives Containing a Strong Nucleophilic Group (i.e., Hydrazide, Hydrazine, Hydroxylamine or Semicarbazide)

In one embodiment of the present invention, an IL-2 polypeptide comprising a carbonyl-containing non-naturally encoded amino acid is modified with a PEG derivative that contains a terminal hydrazine, hydroxylamine, hydrazide or semicarbazide moiety that is linked directly to the PEG backbone.

In some embodiments, the hydroxylamine-terminal PEG derivative will have the structure:

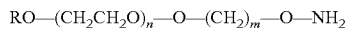
RO—(CH$_2$CH$_2$O)$_n$—O—(CH$_2$)$_m$—O—NH$_2$ where R is a simple alkyl (methyl, ethyl, propyl, etc.), m is 2-10 and n is 100-1,000 (i.e., average molecular weight is between 5-40 kDa).

In some embodiments, the hydrazine- or hydrazide-containing PEG derivative will have the structure:

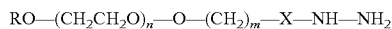
RO—(CH$_2$CH$_2$O)$_n$—O—(CH$_2$)$_m$—X—NH—NH$_2$ where R is a simple alkyl (methyl, ethyl, propyl, etc.), m is 2-10 and n is 100-1,000 and X is optionally a carbonyl group (C=O) that can be present or absent.

In some embodiments, the semicarbazide-containing PEG derivative will have the structure:

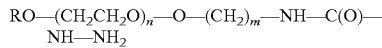
RO—(CH$_2$CH$_2$O)$_n$—O—(CH$_2$)$_m$—NH—C(O)—NH—NH$_2$ where R is a simple alkyl (methyl, ethyl, propyl, etc.), m is 2-10 and n is 100-1,000.

In another embodiment of the invention, an IL-2 polypeptide comprising a carbonyl-containing amino acid is modified with a PEG derivative that contains a terminal hydroxylamine, hydrazide, hydrazine, or semicarbazide moiety that is linked to the PEG backbone by means of an amide linkage.

In some embodiments, the hydroxylamine-terminal PEG derivatives have the structure:

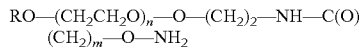
RO—(CH$_2$CH$_2$O)$_n$—O—(CH$_2$)$_2$—NH—C(O)(CH$_2$)$_m$—O—NH$_2$ where R is a simple alkyl (methyl, ethyl, propyl, etc.), m is 2-10 and n is 100-1,000 (i.e., average molecular weight is between 5-40 kDa).

In some embodiments, the hydrazine- or hydrazide-containing PEG derivatives have the structure:

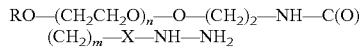
RO—(CH$_2$CH$_2$O)$_n$—O—(CH$_2$)$_2$—NH—C(O)(CH$_2$)$_m$—X—NH—NH$_2$ where R is a simple alkyl (methyl, ethyl, propyl, etc.), m is 2-10, n is 100-1,000 and X is optionally a carbonyl group (C=O) that can be present or absent.

In some embodiments, the semicarbazide-containing PEG derivatives have the structure:

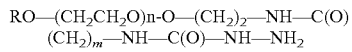
RO—(CH$_2$CH$_2$O)n-O—(CH$_2$)$_2$—NH—C(O)(CH$_2$)$_m$—NH—C(O)—NH—NH$_2$ where R is a simple alkyl (methyl, ethyl, propyl, etc.), m is 2-10 and n is 100-1,000.

In another embodiment of the invention, an IL-2 polypeptide comprising a carbonyl-containing amino acid is modified with a branched PEG derivative that contains a terminal hydrazine, hydroxylamine, hydrazide or semicarbazide moiety, with each chain of the branched PEG having a MW ranging from 10-40 kDa and, may be from 5-20 kDa.

In another embodiment of the invention, an IL-2 polypeptide comprising a non-naturally encoded amino acid is modified with a PEG derivative having a branched structure. For instance, in some embodiments, the hydrazine- or hydrazide-terminal PEG derivative will have the following structure:

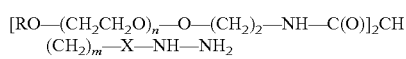
[RO—(CH$_2$CH$_2$O)$_n$—O—(CH$_2$)$_2$—NH—C(O)]$_2$CH(CH$_2$)$_m$—X—NH—NH$_2$ where R is a simple alkyl (methyl, ethyl, propyl, etc.), m is 2-10 and n is 100-1,000, and X is optionally a carbonyl group (C=O) that can be present or absent.

In some embodiments, the PEG derivatives containing a semicarbazide group will have the structure:

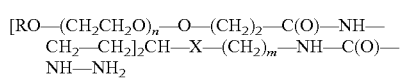
[RO—(CH$_2$CH$_2$O)$_n$—O—(CH$_2$)$_2$—C(O)—NH—CH$_2$—CH$_2$]$_2$CH—X—(CH$_2$)$_m$—NH—C(O)—NH—NH$_2$ where R is a simple alkyl (methyl, ethyl, propyl, etc.), X is optionally NH, O, S, C(O) or not present, m is 2-10 and n is 100-1,000.

In some embodiments, the PEG derivatives containing a hydroxylamine group will have the structure:

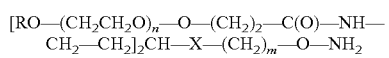
[RO—(CH$_2$CH$_2$O)$_n$—O—(CH$_2$)$_2$—C(O)—NH—CH$_2$—CH$_2$]$_2$CH—X—(CH$_2$)$_m$—O—NH$_2$ where R is a simple alkyl (methyl, ethyl, propyl, etc.), X is optionally NH, O, S, C(O) or not present, m is 2-10 and n is 100-1,000.

The degree and sites at which the water-soluble polymer(s) are linked to the IL-2 polypeptide can modulate the binding of the IL-2 polypeptide to the IL-2 receptor. In some embodiments, the linkages are arranged such that the IL-2 polypeptide binds the IL-2 receptor with a $K_d$ of about 400 nM or lower, with a $K_d$ of 150 nM or lower, and in some cases with a $K_d$ of 100 nM or lower, as measured by an equilibrium binding assay, such as that described in Spencer et al., *J Biol. Chem.*, 263:7862-7867 (1988).

Methods and chemistry for activation of polymers as well as for conjugation of peptides are described in the literature and are known in the art. Commonly used methods for activation of polymers include, but are not limited to, activation of functional groups with cyanogen bromide, periodate, glutaraldehyde, biepoxides, epichlorohydrin, divinylsulfone, carbodiimide, sulfonyl halides, trichlorotriazine, etc. (see, R. F. Taylor, (1991), PROTEIN IMMOBILISATION. FUNDAMENTAL AND APPLICATIONS, Marcel Dekker, N.Y.; S. S. Wong, (1992), CHEMISTRY OF PROTEIN CONJUGATION AND CROSS-LINKING, CRC Press, Boca Raton; G. T. Hermanson et al., (1993), IMMOBILIZED AFFINITY LIGAND TECHNIQUES, Academic Press, N.Y.; Dunn, R. L., et al., Eds. POLYMERIC DRUGS AND DRUG DELIVERY SYSTEMS, ACS Symposium Series Vol. 469, American Chemical Society, Washington, D.C. 1991).

Several reviews and monographs on the functionalization and conjugation of PEG are available. See, for example, Harris, *Macromol. Chem. Phys.* C25: 325-373 (1985); Scouten, *Methods in Enzymology* 135: 30-65 (1987); Wong et al., *Enzyme Microb. Technol.* 14: 866-874 (1992); Delgado et al., *Critical Reviews in Therapeutic Drug Carrier Systems* 9: 249-304 (1992); Zalipsky, *Bioconjugate Chem.* 6: 150-165 (1995).

Methods for activation of polymers can also be found in WO 94/17039, U.S. Pat. No. 5,324,844, WO 94/18247, WO 94/04193, U.S. Pat. Nos. 5,219,564, 5,122,614, WO 90/13540, U.S. Pat. No. 5,281,698, and WO 93/15189, and for conjugation between activated polymers and enzymes including but not limited to Coagulation Factor VIII (WO 94/15625), hemoglobin (WO 94/09027), oxygen carrying molecule (U.S. Pat. No. 4,412,989), ribonuclease and superoxide dismutase (Veronese at al., *App. Biochem. Biotech.* 11: 141-52 (1985)). All references and patents cited are incorporated by reference herein.

PEGylation (i.e., addition of any water-soluble polymer) of IL-2 polypeptides containing a non-naturally encoded amino acid, such as p-azido-L-phenylalanine, is carried out by any convenient method. For example, IL-2 polypeptide is PEGylated with an alkyne-terminated mPEG derivative. Briefly, an excess of solid mPEG(5000)-O—CH$_2$—C≡CH is added, with stirring, to an aqueous solution of p-azido-L-Phe-containing IL-2 polypeptide at room temperature. Typically, the aqueous solution is buffered with a buffer having a pKa near the pH at which the reaction is to be carried out (generally about pH 4-10). Examples of suitable buffers for PEGylation at pH 7.5, for instance, include, but are not limited to, HEPES, phosphate, borate, TRIS-HCl, EPPS, and TES. The pH is continuously monitored and adjusted if necessary. The reaction is typically allowed to continue for between about 1-48 hours.

The reaction products are subsequently subjected to hydrophobic interaction chromatography to separate the PEGylated IL-2 polypeptide variants from free mPEG (5000)-O—CH$_2$—C≡CH and any high-molecular weight complexes of the pegylated IL-2 polypeptide which may form when unblocked PEG is activated at both ends of the molecule, thereby crosslinking IL-2 polypeptide variant molecules. The conditions during hydrophobic interaction chromatography are such that free mPEG(5000)-O—CH$_2$—C≡CH flows through the column, while any crosslinked PEGylated IL-2 polypeptide variant complexes elute after the desired forms, which contain one IL-2 polypeptide variant molecule conjugated to one or more PEG groups. Suitable conditions vary depending on the relative sizes of the cross-linked complexes versus the desired conjugates and are readily determined by those of ordinary skill in the art. The eluent containing the desired conjugates is concentrated by ultrafiltration and desalted by diafiltration.

Substantially purified PEG-IL-2 can be produced using the elution methods outlined above where the PEG-IL-2 produced has a purity level of at least about 30%, at least about 35%, at least about 40%, at least about 45%, at least about 50%, at least about 55%, at least about 60%, at least about 65%, at least about 70%, specifically, a purity level of at least about 75%, 80%, 85%, and more specifically, a purity level of at least about 90%, a purity level of at least about 95%, a purity level of at least about 99% or greater as determined by appropriate methods such as SDS/PAGE analysis, RP-HPLC, SEC, and capillary electrophoresis. If necessary, the PEGylated IL-2 polypeptide obtained from the hydrophobic chromatography can be purified further by one or more procedures known to those of ordinary skill in the art including, but are not limited to, affinity chromatography; anion- or cation-exchange chromatography (using, including but not limited to, DEAE SEPHAROSE); chromatography on silica; reverse phase HPLC; gel filtration (using, including but not limited to, SEPHADEX G-75); hydrophobic interaction chromatography; size-exclusion chromatography, metal-chelate chromatography; ultrafiltration/diafiltration; ethanol precipitation; ammonium sulfate precipitation; chromatofocusing; displacement chromatography; electrophoretic procedures (including but not limited to preparative isoelectric focusing), differential solubility (including but not limited to ammonium sulfate precipitation), or extraction. Apparent molecular weight may be estimated by GPC by comparison to globular protein standards (Preneta, AZ in PROTEIN PURIFICATION METHODS, A PRACTICAL APPROACH (Harris & Angal, Eds.) IRL Press 1989, 293-306). The purity of the IL-2-PEG conjugate can be assessed by proteolytic degradation (including but not limited to, trypsin cleavage) followed by mass spectrometry analysis. Pepinsky R B., et al., *J. Pharmcol. & Exp. Ther.* 297(3):1059-66 (2001).

A water-soluble polymer linked to an amino acid of an IL-2 polypeptide of the invention can be further derivatized or substituted without limitation.

Azide-Containing PEG Derivatives

In another embodiment of the invention, an IL-2 polypeptide is modified with a PEG derivative that contains an azide moiety that will react with an alkyne moiety present on the side chain of the non-naturally encoded amino acid. In general, the PEG derivatives will have an average molecular weight ranging from 1-100 kDa and, in some embodiments, from 10-40 kDa.

In some embodiments, the azide-terminal PEG derivative will have the structure:

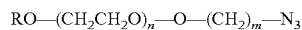

RO—(CH$_2$CH$_2$O)$_n$—O—(CH$_2$)$_m$—N$_3$ where R is a simple alkyl (methyl, ethyl, propyl, etc.), m is 2-10 and n is 100-1,000 (i.e., average molecular weight is between 5-40 kDa).

In another embodiment, the azide-terminal PEG derivative will have the structure:

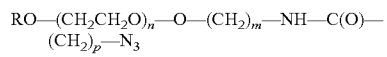

RO—(CH$_2$CH$_2$O)$_n$—O—(CH$_2$)$_m$—NH—C(O)—(CH$_2$)$_p$—N$_3$ where R is a simple alkyl (methyl, ethyl, propyl, etc.), m is 2-10, p is 2-10 and n is 100-1,000 (i.e., average molecular weight is between 5-40 kDa).

In another embodiment of the invention, an IL-2 polypeptide comprising a alkyne-containing amino acid is modified with a branched PEG derivative that contains a terminal azide moiety, with each chain of the branched PEG having a MW ranging from 10-40 kDa and may be from 5-20 kDa. For instance, in some embodiments, the azide-terminal PEG derivative will have the following structure:

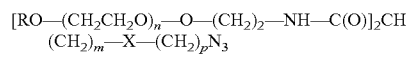

[RO—(CH$_2$CH$_2$O)$_n$—O—(CH$_2$)$_2$—NH—C(O)]$_2$CH(CH$_2$)$_m$—X—(CH$_2$)$_p$N$_3$ where R is a simple alkyl (methyl, ethyl, propyl, etc.), m is 2-10, p is 2-10, and n is 100-1,000, and X is optionally an O, N, S or carbonyl group (C=O), in each case that can be present or absent.

Alkyne-Containing PEG Derivatives

In another embodiment of the invention, an IL-2 polypeptide is modified with a PEG derivative that contains an alkyne moiety that will react with an azide moiety present on the side chain of the non-naturally encoded amino acid.

In some embodiments, the alkyne-terminal PEG derivative will have the following structure:

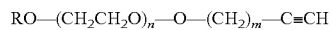

RO—(CH$_2$CH$_2$O)$_n$—O—(CH$_2$)$_m$—C≡CH where R is a simple alkyl (methyl, ethyl, propyl, etc.), m is 2-10 and n is 100-1,000 (i.e., average molecular weight is between 5-40 kDa).

In another embodiment of the invention, an IL-2 polypeptide comprising an alkyne-containing non-naturally encoded amino acid is modified with a PEG derivative that contains a terminal azide or terminal alkyne moiety that is linked to the PEG backbone by means of an amide linkage.

In some embodiments, the alkyne-terminal PEG derivative will have the following structure:

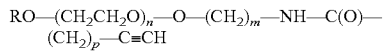
RO—(CH$_2$CH$_2$O)$_n$—O—(CH$_2$)$_m$—NH—C(O)—(CH$_2$)$_p$—C≡CH where R is a simple alkyl (methyl, ethyl, propyl, etc.), m is 2-10, p is 2-10 and n is 100-1,000.

In another embodiment of the invention, an IL-2 polypeptide comprising an azide-containing amino acid is modified with a branched PEG derivative that contains a terminal alkyne moiety, with each chain of the branched PEG having a MW ranging from 10-40 kDa and may be from 5-20 kDa. For instance, in some embodiments, the alkyne-terminal PEG derivative will have the following structure:

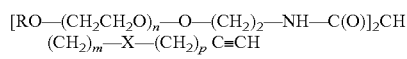
[RO—(CH$_2$CH$_2$O)$_n$—O—(CH$_2$)$_2$—NH—C(O)]$_2$CH (CH$_2$)$_m$—X—(CH$_2$)$_p$ C≡CH where R is a simple alkyl (methyl, ethyl, propyl, etc.), m is 2-10, p is 2-10, and n is 100-1,000, and X is optionally an O, N, S or carbonyl group (C═O), or not present.

Phosphine-Containing PEG Derivatives

In another embodiment of the invention, an IL-2 polypeptide is modified with a PEG derivative that contains an activated functional group (including but not limited to, ester, carbonate) further comprising an aryl phosphine group that will react with an azide moiety present on the side chain of the non-naturally encoded amino acid. In general, the PEG derivatives will have an average molecular weight ranging from 1-100 kDa and, in some embodiments, from 10-40 kDa.

In some embodiments, the PEG derivative will have the structure:

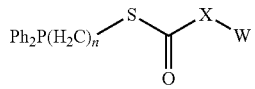

wherein n is 1-10; X can be O, N, S or not present, Ph is phenyl, and W is a water-soluble polymer.

In some embodiments, the PEG derivative will have the structure:

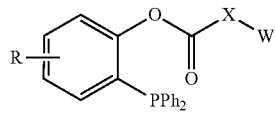

wherein X can be O, N, S or not present, Ph is phenyl, W is a water-soluble polymer and R can be H, alkyl, aryl, substituted alkyl and substituted aryl groups. Exemplary R groups include but are not limited to —CH$_2$, —C(CH$_3$)$_3$, —OR', —NR'R", —SR', -halogen, —C(O)R', —CONR'R", —S(O)$_2$R', —S(O)$_2$NR'R", —CN and —NO$_2$. R', R", R'" and R"" each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —CF$_3$ and —CH$_2$CF$_3$) and acyl (including but not limited to, —C(O)CH$_3$, —C(O)CF$_3$, —C(O)CH$_2$OCH$_3$, and the like).

Other PEG Derivatives and General PEGylation Techniques

Other exemplary PEG molecules that may be linked to IL-2 polypeptides, as well as PEGylation methods include, but are not limited to, those described in, e.g., U.S. Patent Publication No. 2004/0001838; 2002/0052009; 2003/0162949; 2004/0013637; 2003/0228274; 2003/0220447; 2003/0158333; 2003/0143596; 2003/0114647; 2003/0105275; 2003/0105224; 2003/0023023; 2002/0156047; 2002/0099133; 2002/0086939; 2002/0082345; 2002/0072573; 2002/0052430; 2002/0040076; 2002/0037949; 2002/0002250; 2001/0056171; 2001/0044526; 2001/0021763; U.S. Pat. Nos. 6,646,110; 5,824,778; 5,476,653; 5,219,564; 5,629,384; 5,736,625; 4,902,502; 5,281,698; 5,122,614; 5,473,034; 5,516,673; 5,382,657; 6,552,167; 6,610,281; 6,515,100; 6,461,603; 6,436,386; 6,214,966; 5,990,237; 5,900,461; 5,739,208; 5,672,662; 5,446,090; 5,808,096; 5,612,460; 5,324,844; 5,252,714; 6,420,339; 6,201,072; 6,451,346; 6,306,821; 5,559,213; 5,747,646; 5,834,594; 5,849,860; 5,980,948; 6,004,573; 6,129,912; WO 97/32607, EP 229,108, EP 402,378, WO 92/16555, WO 94/04193, WO 94/14758, WO 94/17039, WO 94/18247, WO 94/28024, WO 95/00162, WO 95/11924, WO95/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439 508, WO 97/03106, WO 96/21469, WO 95/13312, EP 921 131, WO 98/05363, EP 809 996, WO 96/41813, WO 96/07670, EP 605 963, EP 510 356, EP 400 472, EP 183 503 and EP 154 316, which are incorporated by reference herein. Any of the PEG molecules described herein may be used in any form, including but not limited to, single chain, branched chain, multiarm chain, single functional, bi-functional, multi-functional, or any combination thereof.

Additional polymer and PEG derivatives including but not limited to, hydroxylamine (aminooxy) PEG derivatives, are described in the following patent applications which are all incorporated by reference in their entirety herein: U.S. Patent Publication No. 2006/0194256, U.S. Patent Publication No. 2006/0217532, U.S. Patent Publication No. 2006/0217289, U.S. Provisional Patent No. 60/755,338; U.S. Provisional Patent No. 60/755,711; U.S. Provisional Patent No. 60/755,018; International Patent Application No. PCT/US06/49397; WO 2006/069246; U.S. Provisional Patent No. 60/743,041; U.S. Provisional Patent No. 60/743,040; International Patent Application No. PCT/US06/47822; U.S. Provisional Patent No. 60/882,819; U.S. Provisional Patent No. 60/882,500; and U.S. Provisional Patent No. 60/870,594.

X. Glycosylation of IL-2 Polypeptides

The invention includes IL-2 polypeptides incorporating one or more non-naturally encoded amino acids bearing saccharide residues. The saccharide residues may be either natural (including but not limited to, N-acetylglucosamine) or non-natural (including but not limited to, 3-fluorogalactose). The saccharides may be linked to the non-naturally encoded amino acids either by an N- or O-linked glycosidic linkage (including but not limited to, N-acetylgalactose-L-serine) or a non-natural linkage (including but not limited to, an oxime or the corresponding C- or S-linked glycoside).

The saccharide (including but not limited to, glycosyl) moieties can be added to IL-2 polypeptides either in vivo or in vitro. In some embodiments of the invention, an IL-2 polypeptide comprising a carbonyl-containing non-naturally encoded amino acid is modified with a saccharide derivatized with an aminooxy group to generate the corresponding glycosylated polypeptide linked via an oxime linkage. Once attached to the non-naturally encoded amino acid, the saccharide may be further elaborated by treatment with glycosyltransferases and other enzymes to generate an oligosaccharide bound to the IL-2 polypeptide. See, e.g., H. Liu, et al. *J. Am. Chem. Soc.* 125: 1702-1703 (2003).

In some embodiments of the invention, an IL-2 polypeptide comprising a carbonyl-containing non-naturally encoded amino acid is modified directly with a glycan with defined structure prepared as an aminooxy derivative. One of ordinary skill in the art will recognize that other functionalities, including azide, alkyne, hydrazide, hydrazine, and semicarbazide, can be used to link the saccharide to the non-naturally encoded amino acid. In some embodiments of the invention, an IL-2 polypeptide comprising an azide or alkynyl-containing non-naturally encoded amino acid can then be modified by, including but not limited to, a Huisgen [3+2] cycloaddition reaction with, including but not limited to, alkynyl or azide derivatives, respectively. This method allows for proteins to be modified with extremely high selectivity.

X. IL-2 Dimers and Multimers

The present invention also provides for IL-2 and IL-2 analog combinations such as homodimers, heterodimers, homomultimers, or heteromultimers (i.e., trimers, tetramers, etc.) where IL-2 containing one or more non-naturally encoded amino acids is bound to another IL-2 variant thereof or any other polypeptide that is not IL-2 variant thereof, either directly to the polypeptide backbone or via a linker. Due to its increased molecular weight compared to monomers, the IL-2 dimer or multimer conjugates may exhibit new or desirable properties, including but not limited to different pharmacological, pharmacokinetic, pharmacodynamic, modulated therapeutic half-life, or modulated plasma half-life relative to the monomeric IL-2. In some embodiments, IL-2 dimers of the invention will modulate signal transduction of the IL-2 receptor. In other embodiments, the IL-2 dimers or multimers of the present invention will act as a IL-2 receptor antagonist, agonist, or modulator.

In some embodiments, one or more of the IL-2 molecules present in an IL-2 containing dimer or multimer comprises a non-naturally encoded amino acid linked to a water-soluble polymer. In some embodiments, the IL-2 polypeptides are linked directly, including but not limited to, via an Asn-Lys amide linkage or Cys-Cys disulfide linkage. In some embodiments, the IL-2 polypeptides, and/or the linked non-IL-2 molecule, will comprise different non-naturally encoded amino acids to facilitate dimerization, including but not limited to, an alkyne in one non-naturally encoded amino acid of a first IL-2 polypeptide and an azide in a second non-naturally encoded amino acid of a second molecule will be conjugated via a Huisgen [3+2] cycloaddition. Alternatively, IL-2, and/or the linked non-IL-2 molecule comprising a ketone-containing non-naturally encoded amino acid can be conjugated to a second polypeptide comprising a hydroxylamine-containing non-naturally encoded amino acid and the polypeptides are reacted via formation of the corresponding oxime.

Alternatively, the two IL-2 polypeptides, and/or the linked non-IL-2 molecule, are linked via a linker. Any hetero- or homo-bifunctional linker can be used to link the two molecules, and/or the linked non-IL-2 molecules, which can have the same or different primary sequence. In some cases, the linker used to tether the IL-2, and/or the linked non-IL-2 molecules together can be a bifunctional PEG reagent. The linker may have a wide range of molecular weight or molecular length. Larger or smaller molecular weight linkers may be used to provide a desired spatial relationship or conformation between IL-2 and the linked entity or between IL-2 and its receptor, or between the linked entity and its binding partner, if any. Linkers having longer or shorter molecular length may also be used to provide a desired space or flexibility between IL-2 and the linked entity, or between the linked entity and its binding partner, if any.

In some embodiments, the invention provides water-soluble bifunctional linkers that have a dumbbell structure that includes: a) an azide, an alkyne, a hydrazine, a hydrazide, a hydroxylamine, or a carbonyl-containing moiety on at least a first end of a polymer backbone; and b) at least a second functional group on a second end of the polymer backbone. The second functional group can be the same or different as the first functional group. The second functional group, in some embodiments, is not reactive with the first functional group. The invention provides, in some embodiments, water-soluble compounds that comprise at least one arm of a branched molecular structure. For example, the branched molecular structure can be dendritic.

In some embodiments, the invention provides multimers comprising one or more IL-2 polypeptide, formed by reactions with water-soluble activated polymers that have the structure:

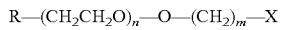

wherein n is from about 5 to 3,000, m is 2-10, X can be an azide, an alkyne, a hydrazine, a hydrazide, an aminooxy group, a hydroxylamine, an acetyl, or carbonyl-containing moiety, and R is a capping group, a functional group, or a leaving group that can be the same or different as X. R can be, for example, a functional group selected from the group consisting of hydroxyl, protected hydroxyl, alkoxyl, N-hydroxysuccinimidyl ester, 1-benzotriazolyl ester, N-hydroxysuccinimidyl carbonate, 1-benzotriazolyl carbonate, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate, alkene, and ketone.

XII. Measurement of IL-2 Polypeptide Activity and Affinity of IL-2 Polypeptide for the IL-2 Receptor IL-2 polypeptide activity can be determined using standard or known in vitro or in vivo assays. PEG-IL-2 may be analyzed for biological activity by suitable methods known in the art. Such assays include, but are not limited to, activation of IL-2-responsive genes, receptor binding assays, anti-viral activity assays, cytopathic effect inhibition assays, anti-proliferative assays, immunomodulatory assays and assays that monitor the induction of MHC molecules.

PEG-IL-2 polypeptides may be analyzed for their ability to activate IL-2-sensitive signal transduction pathways. One example is the interferon-stimulated response element (ISRE) assay. Cells which constitutively express the IL-2 receptor are transiently transfected with an ISRE-luciferase vector (pISRE-luc, Clontech). After transfection, the cells are treated with an IL-2 polypeptide. A number of protein concentrations, for example from 0.0001-10 ng/mL, are tested to generate a dose-response curve. If the IL-2 polypeptide binds and activates the IL-2 receptor, the resulting signal transduction cascade induces luciferase expression. Luminescence can be measured in a number of ways, for example by using a TopCount™ or Fusion™ microplate reader and Steady-Glo® Luciferase Assay System (Promega).

IL-2 polypeptides may be analyzed for their ability to bind to the IL-2 receptor. For a non-PEGylated or PEGylated IL-2 polypeptide comprising a non-natural amino acid, the affinity of IL-2 for its receptor can be measured by using a BIAcore™ biosensor (Pharmacia). Suitable binding assays include, but are not limited to, BIAcore assays (Pearce et al., Biochemistry 38:81-89 (1999)) and AlphaScreen™ assays (PerkinElmer).

Regardless of which methods are used to create the IL-2 polypeptides, the IL-2 polypeptides are subject to assays for biological activity. In general, the test for biological activity should provide analysis for the desired result, such as increase or decrease in biological activity (as compared to modified IL-2), different biological activity (as compared to modified IL-2), receptor or binding partner affinity analysis, conformational or structural changes of the IL-2 itself or its receptor (as compared to the modified IL-2), or serum half-life analysis.

XII. Measurement of Potency, Functional In Vivo Half-Life, and Pharmacokinetic Parameters An important aspect of the invention is the prolonged biological half-life that is obtained by construction of the IL-2 polypeptide with or without conjugation of the polypeptide to a water-soluble polymer moiety. The rapid post administration decrease of IL-2 polypeptide serum concentrations has made it important to evaluate biological responses to treatment with conjugated and non-conjugated IL-2 polypeptide and variants thereof. The conjugated and non-conjugated IL-2 polypeptide and variants thereof of the present invention may have prolonged serum half-lives also after administration via, e.g. subcutaneous or i.v. administration, making it possible to measure by, e.g. ELISA method or by a primary screening assay. ELISA or RIA kits from commercial sources may be used such as Invitrogen (Carlsbad, CA). Measurement of in vivo biological half-life is carried out as described herein.

The potency and functional in vivo half-life of an IL-2 polypeptide comprising a non-naturally encoded amino acid can be determined according to protocols known to those of ordinary skill in the art.

Pharmacokinetic parameters for a IL-2 polypeptide comprising a non-naturally encoded amino acid can be evaluated in normal Sprague-Dawley male rats (N=5 animals per treatment group). Animals will receive either a single dose of 25 ug/rat iv or 50 ug/rat sc, and approximately 5-7 blood samples will be taken according to a pre-defined time course, generally covering about 6 hours for a IL-2 polypeptide comprising a non-naturally encoded amino acid not conjugated to a water-soluble polymer and about 4 days for a IL-2 polypeptide comprising a non-naturally encoded amino acid and conjugated to a water-soluble polymer. Pharmacokinetic data for IL-2 without a non-naturally encoded amino acid can be compared directly to the data obtained for IL-2 polypeptides comprising a non-naturally encoded amino acid.

XIV. Administration and Pharmaceutical Compositions

The polypeptides or proteins of the invention (including but not limited to, IL-2, synthetases, proteins comprising one or more unnatural amino acid, etc.) are optionally employed for therapeutic uses, including but not limited to, in combination with a suitable pharmaceutical carrier. Such compositions, for example, comprise a therapeutically effective amount of the compound, and a pharmaceutically acceptable carrier or excipient. Such a carrier or excipient includes, but is not limited to, saline, buffered saline, dextrose, water, glycerol, ethanol, and/or combinations thereof. The formulation is made to suit the mode of administration. In general, methods of administering proteins are known to those of ordinary skill in the art and can be applied to administration of the polypeptides of the invention. Compositions may be in a water-soluble form, such as being present as pharmaceutically acceptable salts, which is meant to include both acid and base addition salts.

Therapeutic compositions comprising one or more polypeptide of the invention are optionally tested in one or more appropriate in vitro and/or in vivo animal models of disease, to confirm efficacy, tissue metabolism, and to estimate dosages, according to methods known to those of ordinary skill in the art. In particular, dosages can be initially determined by activity, stability or other suitable measures of unnatural herein to natural amino acid homologues (including but not limited to, comparison of an IL-2 polypeptide modified to include one or more unnatural amino acids to a natural amino acid IL-2 polypeptide and comparison of an IL-2 polypeptide modified to include one or more unnatural amino acids to a currently available IL-2 treatment), i.e., in a relevant assay.

Administration is by any of the routes normally used for introducing a molecule into ultimate contact with blood or tissue cells. The unnatural amino acid polypeptides of the invention are administered in any suitable manner, optionally with one or more pharmaceutically acceptable carriers. Suitable methods of administering such polypeptides in the context of the present invention to a patient are available, and, although more than one route can be used to administer a particular composition, a particular route can often provide a more immediate and more effective action or reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

IL-2 polypeptides of the invention may be administered by any conventional route suitable for proteins or peptides, including, but not limited to, parenterally, e.g. injections including, but not limited to, subcutaneously or intravenously or any other form of injections or infusions. Polypeptide compositions can be administered by a number of routes including, but not limited to, oral, intravenous, intraperitoneal, intramuscular, transdermal, subcutaneous, topical, sublingual, or rectal means. Compositions comprising non-natural amino acid polypeptides, modified or unmodified, can also be administered via liposomes. Such administration routes and appropriate formulations are generally known to those of skill in the art. The IL-2 polypeptide, may be used alone or in combination with other suitable components such as a pharmaceutical carrier. The IL-2 polypeptide may be used in combination with other agents or therapeutics.

The IL-2 polypeptide comprising a non-natural amino acid, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of IL-2 can be presented in unit-dose or multi-dose sealed containers, such as ampules and vials.

Parenteral administration and intravenous administration are preferred methods of administration. In particular, the routes of administration already in use for natural amino acid homologue therapeutics (including but not limited to, those typically used for EPO, GH, G-CSF, GM-CSF, IFNs e.g. IL-2, interleukins, antibodies, FGFs, and/or any other pharmaceutically delivered protein), along with formulations in current use, provide preferred routes of administration and formulation for the polypeptides of the invention.

The dose administered to a patient, in the context of the present invention, is sufficient to have a beneficial therapeutic response in the patient over time, or other appropriate activity, depending on the application. The dose is determined by the efficacy of the particular vector, or formulation, and the activity, stability or serum half-life of the unnatural amino acid polypeptide employed and the condition of the patient, as well as the body weight or surface area of the patient to be treated. The size of the dose is also determined by the existence, nature, and extent of any adverse side-effects that accompany the administration of a particular vector, formulation, or the like in a particular patient.

In determining the effective amount of the vector or formulation to be administered in the treatment or prophylaxis of disease (including but not limited to, neutropenia, aplastic anemia, cyclic neutropenia, idiopathic neutropenia, Chdiak-Higashi syndrome, systemic lupus erythematosus (SLE), leukemia, myelodysplastic syndrome and myelofibrosis, or the like), the physician evaluates circulating plasma levels, formulation toxicities, progression of the disease, and/or where relevant, the production of anti-unnatural amino acid polypeptide antibodies.

The dose administered, for example, to a 70 kilogram patient, is typically in the range equivalent to dosages of currently-used therapeutic proteins, adjusted for the altered activity or serum half-life of the relevant composition. The vectors or pharmaceutical formulations of this invention can supplement treatment conditions by any known conventional therapy, including antibody administration, vaccine administration, administration of cytotoxic agents, natural amino acid polypeptides, nucleic acids, nucleotide analogues, biologic response modifiers, and the like.

For administration, formulations of the present invention are administered at a rate determined by the LD-50 or ED-50 of the relevant formulation, and/or observation of any side-effects of the unnatural amino acid polypeptides at various concentrations, including but not limited to, as applied to the mass and overall health of the patient. Administration can be accomplished via single or divided doses.

If a patient undergoing infusion of a formulation develops fevers, chills, or muscle aches, he/she receives the appropriate dose of aspirin, ibuprofen, acetaminophen or other pain/fever controlling drug. Patients who experience reactions to the infusion such as fever, muscle aches, and chills are premedicated 30 minutes prior to the future infusions with either aspirin, acetaminophen, or, including but not limited to, diphenhydramine. Meperidine is used for more severe chills and muscle aches that do not quickly respond to antipyretics and antihistamines. Cell infusion is slowed or discontinued depending upon the severity of the reaction.

Human IL-2 polypeptides of the invention can be administered directly to a mammalian subject. Administration is by any of the routes normally used for introducing IL-2 polypeptide to a subject. The IL-2 polypeptide compositions according to embodiments of the present invention include those suitable for oral, rectal, topical, inhalation (including but not limited to, via an aerosol), buccal (including but not limited to, sub-lingual), vaginal, parenteral (including but not limited to, subcutaneous, intramuscular, intradermal, intraarticular, intrapleural, intraperitoneal, inracerebral, intraarterial, or intravenous), topical (i.e., both skin and mucosal surfaces, including airway surfaces), pulmonary, intraocular, intranasal, and transdermal administration, although the most suitable route in any given case will depend on the nature and severity of the condition being treated. Administration can be either local or systemic. The formulations of compounds can be presented in unit-dose or multi-dose sealed containers, such as ampoules and vials. IL-2 polypeptides of the invention can be prepared in a mixture in a unit dosage injectable form (including but not limited to, solution, suspension, or emulsion) with a pharmaceutically acceptable carrier. IL-2 polypeptides of the invention can also be administered by continuous infusion (using, including but not limited to, minipumps such as osmotic pumps), single bolus or slow-release depot formulations.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. Solutions and suspensions can be prepared from sterile powders, granules, and tablets of the kind previously described.

Freeze-drying is a commonly employed technique for presenting proteins which serves to remove water from the protein preparation of interest. Freeze-drying, or lyophilization, is a process by which the material to be dried is first frozen and then the ice or frozen solvent is removed by sublimation in a vacuum environment. An excipient may be included in pre-lyophilized formulations to enhance stability during the freeze-drying process and/or to improve stability of the lyophilized product upon storage. Pikal, M. Biopharm. 3(9)26-30 (1990) and Arakawa et al. Pharm. Res. 8(3):285-291 (1991).

The spray drying of pharmaceuticals is also known to those of ordinary skill in the art. For example, see Broadhead, J. et al., "The Spray Drying of Pharmaceuticals," in Drug Dev. Ind. Pharm, 18 (11 & 12), 1169-1206 (1992). In addition to small molecule pharmaceuticals, a variety of biological materials have been spray dried and these include: enzymes, sera, plasma, micro-organisms and yeasts. Spray drying is a useful technique because it can convert a liquid pharmaceutical preparation into a fine, dustless or agglomerated powder in a one-step process. The basic technique comprises the following four steps: a) atomization of the feed solution into a spray; b) spray-air contact; c) drying of the spray; and d) separation of the dried product from the drying air. U.S. Pat. Nos. 6,235,710 and 6,001,800, which are incorporated by reference herein, describe the preparation of recombinant erythropoietin by spray drying.

The pharmaceutical compositions and formulations of the invention may comprise a pharmaceutically acceptable carrier, excipient, or stabilizer. Pharmaceutically acceptable carriers are determined in part by the particular composition being administered, as well as by the particular method used to administer the composition. Accordingly, there is a wide variety of suitable formulations of pharmaceutical compositions (including optional pharmaceutically acceptable carriers, excipients, or stabilizers) of the present invention (see, e.g., *Remington's Pharmaceutical Sciences,* $17^{th}$ ed. 1985)).

Suitable carriers include but are not limited to, buffers containing succinate, phosphate, borate, HEPES, citrate, histidine, imidazole, acetate, bicarbonate, and other organic acids; antioxidants including but not limited to, ascorbic acid; low molecular weight polypeptides including but not limited to those less than about 10 residues; proteins, including but not limited to, serum albumin, gelatin, or immunoglobulins; hydrophilic polymers including but not limited to, polyvinylpyrrolidone; amino acids including but not limited to, glycine, glutamine, asparagine, arginine, histidine or histidine derivatives, methionine, glutamate, or lysine; monosaccharides, disaccharides, and other carbohydrates, including but not limited to, trehalose, sucrose, glucose, mannose, or dextrins; chelating agents including but not limited to, EDTA and edentate disodium; divalent metal ions including but not limited to, zinc, cobalt, or copper; sugar alcohols including but not limited to, mannitol or sorbitol; salt-forming counter ions including but not limited to, sodium and sodium chloride; fillers such as microcrystalline cellulose, lactose, corn and other starches; binding agents; sweeteners and other flavoring agents; coloring agents; and/or nonionic surfactants including but not limited to Tween™ (including but not limited to, Tween 80 (polysorbate 80) and Tween 20 (polysorbate 20), Pluronics™ and other pluronic acids, including but not limited to, pluronic acid F68 (poloxamer 188), or PEG. Suitable surfactants include for example but are not limited to polyethers based upon poly(ethylene oxide)-poly(propylene oxide)-poly(ethylene oxide), i.e., (PEO-PPO-PEO), or poly(propylene oxide)-poly(ethylene oxide)-poly(propylene oxide), i.e., (PPO-PEO-PPO), or a combination thereof. PEO-PPO-PEO and PPO-PEO-PPO are commercially available under the trade names Pluronicsm, R-Pluronicsm, Tetronicsm and R-Tetronicsm (BASF Wyandotte Corp., Wyandotte, Mich.) and are further described in U.S. Pat. No. 4,820,352 incorporated herein in its entirety by reference. Other ethylene/polypropylene block polymers may be suitable surfactants. A surfactant or a combination of surfactants may be used to stabilize PEGylated IL-2 against one or more stresses including but not limited to stress that results from agitation. Some of the above may be referred to as "bulking agents." Some may also be referred to as "tonicity modifiers." Antimicrobial preservatives may also be applied for product stability and antimicrobial effectiveness; suitable preservatives include but are not limited to, benzyl alcohol, benzalkonium chloride, metacresol, methyl/propyl parabene, cresol, and phenol, or a combination thereof. U.S. Pat. No. 7,144,574, which is incorporated by reference herein, describe additional materials that may be suitable in pharmaceutical compositions and formulations of the invention and other delivery preparations.

IL-2 polypeptides of the invention, including those linked to water-soluble polymers such as PEG can also be administered by or as part of sustained-release systems. Sustained-release compositions include, including but not limited to, semi-permeable polymer matrices in the form of shaped articles, including but not limited to, films, or microcapsules. Sustained-release matrices include from biocompatible materials such as poly(2-hydroxyethyl methacrylate) (Langer et al., *J Biomed. Mater. Res.,* 15: 267-277 (1981); Langer, *Chem. Tech.,* 12: 98-105 (1982), ethylene vinyl acetate (Langer et al., supra) or poly-D-(−)-3-hydroxybutyric acid (EP 133,988), polylactides (polylactic acid) (U.S. Pat. No. 3,773,919; EP 58,481), polyglycolide (polymer of glycolic acid), polylactide co-glycolide (copolymers of lactic acid and glycolic acid) polyanhydrides, copolymers of L-glutamic acid and gamma-ethyl-L-glutamate (Sidman et al., *Biopolymers,* 22, 547-556 (1983), poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Sustained-release compositions also include a liposomally entrapped compound. Liposomes containing the compound are prepared by methods known per se: DE 3,218,121; Eppstein et al., *Proc. Natl. Acad. Sci. U.S.A.,* 82: 3688-3692 (1985); Hwang et al., *Proc. Natl. Acad. Sci. U.S.A.,* 77: 4030-4034 (1980); EP 52,322; EP 36,676; U.S. Pat. No. 4,619,794; EP 143,949; U.S. Pat. No. 5,021,234; Japanese Pat. Appln. 83-118008; U.S. Pat. Nos. 4,485,045 and 4,544,545; and EP 102,324. All references and patents cited are incorporated by reference herein.

Liposomally entrapped IL-2 polypeptides can be prepared by methods described in, e.g., DE 3,218,121; Eppstein et al., *Proc. Nail. Acad. Sci. U.S.A.,* 82: 3688-3692 (1985); Hwang et al., *Proc. Natl. Acad. Sci. U.S.A.,* 77: 4030-4034 (1980); EP 52,322; EP 36,676; U.S. Pat. No. 4,619,794; EP 143,949; U.S. Pat. No. 5,021,234; Japanese Pat. Appln. 83-118008; U.S. Pat. Nos. 4,485,045 and 4,544,545; and EP 102,324. Composition and size of liposomes are well known or able to be readily determined empirically by one of ordinary skill in the art. Some examples of liposomes as described in, e.g., Park J W, et al., *Proc. Natl. Acad. Sci. USA* 92:1327-1331 (1995); Lasic D and Papahadjopoulos D (eds): MEDICAL APPLICATIONS OF LIPOSOMES (1998); Drummond D C, et al., Liposomal drug delivery systems for cancer therapy, in Teicher B (ed): CANCER DRUG DISCOVERY AND DEVELOPMENT (2002); Park J W, et al., *Clin. Cancer Res.* 8:1172-1181 (2002); Nielsen U B, et al., *Biochim. Biophys. Acta* 1591(1-3):109-118 (2002); Mamot C, et al., *Cancer Res.* 63: 3154-3161 (2003). All references and patents cited are incorporated by reference herein.

The dose administered to a patient in the context of the present invention should be sufficient to cause a beneficial response in the subject over time. Generally, the total pharmaceutically effective amount of the IL-2 polypeptide of the present invention administered parenterally per dose is in the range of about 0.01 μg/kg/day to about 100 μg/kg, or about 0.05 mg/kg to about 1 mg/kg, of patient body weight, although this is subject to therapeutic discretion. In specific aspects of this embodiment, the conjugate can be administered at a dose in a range of greater than 4 μ/kg per day to about 20 μg/kg per day. In yet other aspects, the conjugate can be administered at a dose in a range of greater than 4 μg/kg per day to about 9 μg/kg per day. In yet other aspects, the conjugate can be administered at a dose in a range of about 4 μg/kg per day to about 12.5 μg/kg per day. In a specific aspect, the conjugate can be administered at or below a dose that is the maximum dose tolerated without undue toxicity. Further, the conjugate can be administered at least two times a week or the conjugate can be administered at least three times a week, at least four times a week, at least five times a week, at least six times a week, or seven times a week. In a specific aspect, where the conjugate is administered more than once, the conjugate can be administered at a dose of greater than 4 μg/kg per day each time. In particular, the conjugate can be administered over a period of two weeks or greater. In certain aspects, the growth of interleukin-2 receptor expressing cells can be inhibited by at least 50%, at least 65%, at least 75%, at least 80%, at least 85%, at least 90%, at least 95% or by at least 99% as compared to a reference sample, i.e., a sample of cells not contacted with a conjugate of the invention. In a specific aspect of this embodiment, the conjugate can be administered at a dose of about 5.3 μg/kg per day, or at a dose of about 7.1 μg/kg per day, or at a dose of about 9.4 μg/kg per day, or at a dose of about 12.5 μg/kg per day. The frequency of dosing is also subject to therapeutic discretion and may be more frequent or less frequent than the commercially available IL-2 polypeptide products approved for use in humans. Generally, an IL-2 polypeptide, PEGylated IL-2 polypeptide, conjugated IL-2 polypeptide, or PEGylated conjugated IL-2 polypeptide of the invention can be administered by any of the routes of administration described above.

XV. Therapeutic Uses of IL-2 Polypeptides of the Invention

The IL-2 polypeptides of the invention are useful for treating a wide range of disorders. The invention also includes a method of treating a mammal that is at risk for, is having, and/or has had a cancer responsive to IL-2, CD8+ T-cell stimulation, and/or IL-2 formulations. Administration of IL-2 polypeptides may result in a short term effect, i e. an immediate beneficial effect on several clinical parameters observed and this may 12 or 24 hours from administration, and, on the other hand, may also result in a long term effect, a beneficial slowing of progression of tumor growth, reduction in tumor size, and/or increased circulating CD8+ T cell levels and the IL-2 polypeptides of the present invention may be administered by any means known to those skilled in the art, and may beneficially be administered via infusion, e.g. by arterial, intraperitoneal or intravenous injection and/ or infusion in a dosage which is sufficient to obtain the desired pharmacological effect.

The IL-2 polypeptide dosage may range from 10-200 mg, or 40-80 mg IL-2 polypeptide per kg body weight per treatment. For example, the dosage of IL-2 polypeptide which is administered may be about 20-100 mg IL-2 polypeptide per kg body weight given as a bolus injection and/or as an infusion for a clinically necessary period of time, e.g. for a period ranging from a few minutes to several hours, e.g. up to 24 hours. If necessary, the IL-2 polypeptide administration may be repeated one or several times. The administration of IL-2 polypeptide may be combined with the administration of other pharmaceutical agents such as chemotherapeutic agents. Furthermore, the present invention relates to a method for prophylaxis and/or treatment of cancer comprising administering a subject in need thereof an effective amount of IL-2 polypeptide.

Average quantities of the IL-2 may vary and in particular should be based upon the recommendations and prescription of a qualified physician. The exact amount of IL-2 is a matter of preference subject to such factors as the exact type of condition being treated, the condition of the patient being treated, as well as the other ingredients in the composition. The invention also provides for administration of a therapeutically effective amount of another active agent. The amount to be given may be readily determined by one of ordinary skill in the art based upon therapy with IL-2.

EXAMPLES

The following examples are offered to illustrate, but not to limit the claimed invention.

Example 1—Determination of Residue Positions in IL-2 to be Mutated into Amber Stop Codon to Incorporate Unnatural Amino Acids IL-2 has been used in treating several cancers such as renal cell carcinoma and metastatic melanoma. The commercial available IL-2 Aldesleukin® is a recombinant protein that is nonglycosylated and has a removed alanine-1 and a replaced residue cysteine-125 by serine-125 (Whittington et al., Drugs, 46(3): pp: 446-514 (1993)). Although IL-2 is the earliest FDA approved cytokine in cancer treatment, it has been shown that IL-2 exhibited severe side effects when used in high-dose. This greatly limited its application on potential patients. The underlying mechanism of the severe side effects has been attributed to the binding of IL-2 to one of its receptors, IL-2Rα. In general, IL-2 not only can form a heterotrimeric complex with its receptors including IL-2Rα (or CD25), IL-2Rβ (or CD122) and IL-2Rγ (or CD132) when all of three receptors are present in the tissue, but also can form heterodimeric complex with IL-2Rβ and IL-2Rγ. In clinical settings, when high dose of IL-2 is used, IL-2 starts to bind IL-2αβγ, which is a major receptor form in $T_{reg}$ cells. The suppressive effect of $T_{reg}$ cells causes undesired effects of IL-2 application in cancer immunotherapy. To mitigate the side effects of IL-2, many approaches have been employed previously. One of the major breakthroughs is the invention from Nektar that uses 6 PEGylated lysines to mask the IL2Rα binding region on IL-2 surface (Charych et al., Clin Cancer Res, 22(3): pp: 680-90 (2016)). PEGylated IL-2 not only has an extended half-life, but also showed dramatically reduced side effects. However, the results from activity studies showed that the effective form of PEGylated IL-2 in this heterogeneous 6-PEGylated IL-2 mixture is the single PEGylated form only. Therefore, more effective PEGylated IL-2 with a homogeneous product is needed.

In the current application, the incorporated unnatural amino acids provide unique conjugation sites to be used in IL-2 PEGylation. The resulting PEGylated IL-2 muteins have homogeneous product rather than previously heterogeneous 6-PEGylated IL-2 from Nektar.

The sites to be used in generating IL-2 muteins can be chosen by analyzing the existing crystal structure of IL-2 and its heterotrimeric receptors. Specifically, the structure of IL-2Rα and its interface with IL-2 has been investigated in detail (FIG. 1). The interface has been divided into two regions comprising of a hydrophobic center and a polarized region. The hydrophobic center is formed between IL-2Rα residues Leu-2$^α$, Met-25$^α$, Leu-42$^α$, and Tyr-43$^α$ and IL-2 residues Phe-42$^{IL-2}$, Phe-44$^{IL-2}$, Tyr-45$^{IL-2}$, Pro-65$^{IL-2}$, and Leu-72$^{IL-2}$. The polarized region is formed between IL-2Rα and IL-2 five ionic pairs including Lys-38$^α$/Glu-61$^{IL-2}$, Arg-36$^α$/Glu-62$^{IL-2}$, Glu-1$^α$/Lys-35$^{IL-2}$, Asp-6$^α$/Arg-38$^{IL-2}$, and Glu-29$^α$/Lys-43$^{IL-2}$. Additionally, electrostatic mapping suggested that some other residues might play a role in mediating the interaction between IL-2Rα and IL-2. These residues are Thr-37$^{IL-2}$, Thre-41$^{IL-2}$, Lys-64$^{IL-2}$, Glu-68$^{IL-2}$, and Tyr-107$^{IL-2}$. Therefore, the sites that can be used are Phe-42$^{IL-2}$, Phe-44$^{IL-2}$, Tyr-45$^{IL-2}$, Pro-65$^{IL-2}$, Leu-72$^{IL-2}$, Glu-61$^{IL-2}$, Glu-62$^{IL-2}$, Lys-35$^{IL-2}$, Arg-38$^{IL-2}$, Lys-43$^{IL-2}$, Thr-37$^{IL-2}$, Thr-3$^{IL-2}$, Lys-64$^{IL-2}$, Glu-68$^{IL-2}$, and Tyr-107$^{IL-2}$. A list of protein sequences used to produce muteins with unnatural amino acid is listed in Table 2 below.

TABLE 2

IL-2 protein sequences with potential sites to be used in PEGylation

| SEQ ID. NO | Residue Position | Protein Sequences with incorporated Unnatural Amino Acid |
|---|---|---|
| 9 | F42 | APTSSSTKKTQLQLEHLLLDLQMILNGINNYKNPKLTRMLT*UKFY MPKKATELKHLQCLEEELKPLEEVLNLAQSKNFHLRPRDLISNINVI VLELKGSETTFMCEYADETATIVEFLNRWITFCQSIISTLT |
| 10 | F44 | APTSSSTKKTQLQLEHLLLDLQMILNGINNYKNPKLTRMLTFK*UY MPKKATELKHLQCLEEELKPLEEVLNLAQSKNFHLRPRDLISNINVI VLELKGSETTFMCEYADETATIVEFLNRWITFCQSIISTLT |
| 11 | Y45 | APTSSSTKKTQLQLEHLLLDLQMILNGINNYKNPKLTRMLTFKF*U MPKKATELKHLQCLEEELKPLEEVLNLAQSKNFHLRPRDLISNINVI VLELKGSETTFMCEYADETATIVEFLNRWITFCQSIISTLT |
| 12 | P65 | APTSSSTKKTQLQLEHLLLDLQMILNGINNYKNPKLTRMLTFKFYM PKKATELKHLQCLEEELK*ULEEVLNLAQSKNFHLRPRDLISNINVI VLELKGSETTFMCEYADETATIVEFLNRWITFCQSIISTLT |
| 13 | L72 | APTSSSTKKTQLQLEHLLLDLQMILNGINNYKNPKLTRMLTFKFYM PKKATELKHLQCLEEELKPLEEVLN*UAQSKNFHLRPRDLISNINVI VLELKGSETTFMCEYADETATIVEFLNRWITFCQSIISTLT |
| 14 | E61 | APTSSSTKKTQLQLEHLLLDLQMILNGINNYKNPKLTRMLTFKFYM PKKATELKHLQCLE*UELKPLEEVLNLAQSKNFHLRPRDLISNINVI VLELKGSETTFMCEYADETATIVEFLNRWITFCQSIISTLT |
| 15 | E62 | APTSSSTKKTQLQLEHLLLDLQMILNGINNYKNPKLTRMLTFKFYM PKKATELKHLQCLEE*ULKPLEUVLNLAQSKNFHLRPRDLISNINVI VLELKGSETTFMCEYADETATIVEFLNRWITFCQSIISTLT |
| 16 | K35 | APTSSSTKKTQLQLEHLLLDLQMILNGINNYKNP*ULTRMLTFKFY MPKKATELKHLQCLEEELKPLEEVLNLAQSKNFHLRPRDLISNINVI VLELKGSETTFMCEYADETATIVEFLNRWITFCQSIISTLT |
| 17 | R38 | APTSSSTKKTQLQLEHLLLDLQMILNGINNYKNPKLT*UMLTFKFY MPKKATELKHLQCLEEELKPLEEVLNLAQSKNFHLRPRDLISNINVI VLELKGSETTFMCEYADETATIVEFLNRWITFCQSIISTLT |
| 18 | K43 | APTSSSTKKTQLQLEHLLLDLQMILNGINNYKNPKLTRMLTF*UFY MPKKATELKHLQCLEEELKPLEEVLNLAQSKNFHLRPRDLISNINVI VLELKGSETTFMCEYADETATIVEFLNRWITFCQSIISTLT |
| 19 | T37 | APTSSSTKKTQLQLEHLLLDLQMILNGINNYKNPKL*URMLTFKFY MPKKATELKHLQCLEEELKPLEEVLNLAQSKNFHLRPRDLISNINVI VLELKGSETTFMCEYADETATIVEFLNRWITFCQSIISTLT |
| 20 | T3 | AP*USSSTKKTQLQLEHLLLDLQMILNGINNYKNPKLTRMLTFKFY MPKKATELKHLQCLEEELKPLEEVLNLAQSKNFHLRPRDLISNINVI VLELKGSETTFMCEYADETATIVEFLNRWITFCQSIISTLT |
| 21 | K64 | APTSSSTKKTQLQLEHLLLDLQMILNGINNYKNPKLTRMLTFKFYM PKKATELKHLQCLEEEL*UPLEEVLNLAQSKNFHLRPRDLISNINVI VLELKGSETTFMCEYADETATIVEFLNRWITFCQSIISTLT |
| 22 | E68 | APTSSSTKKTQLQLEHLLLDLQMILNGINNYKNPKLTRMLTFKFYM PKKATELKHLQCLEEELKPLE*UVLNLAQSKNFHLRPRDLISNINVI VLELKGSETTFMCEYADETATIVEFLNRWITFCQSIISTLT |
| 23 | Y107 | APTSSSTKKTQLQLEHLLLDLQMILNGINNYKNPKLTRMLTFKFYM PKKATELKHLQCLEEELKPLEEVLNLAQSKNFHLRPRDLISNINVIV LELKGSETTFMCE*UADETATIVEFLNRWITFCQSIISTLT |

*U: unnatural amino acid

Example 2: Human IL-2 Expression System

This section describes expression methods used for IL-2 polypeptides comprising a non-natural amino acid. Host cells are transformed with constructs for orthogonal tRNA, orthogonal aminoacyl tRNA synthetase, and a polynucleotide encoding IL-2 polypeptide as in SEQ ID NOs: 4, 6, or 8, or a polynucleotide encoding the amino acid sequences shown in SEQ ID NOs: 1, 2, 3, 5, 7, and 9 through 23, comprising a selector codon.

Figure 2:
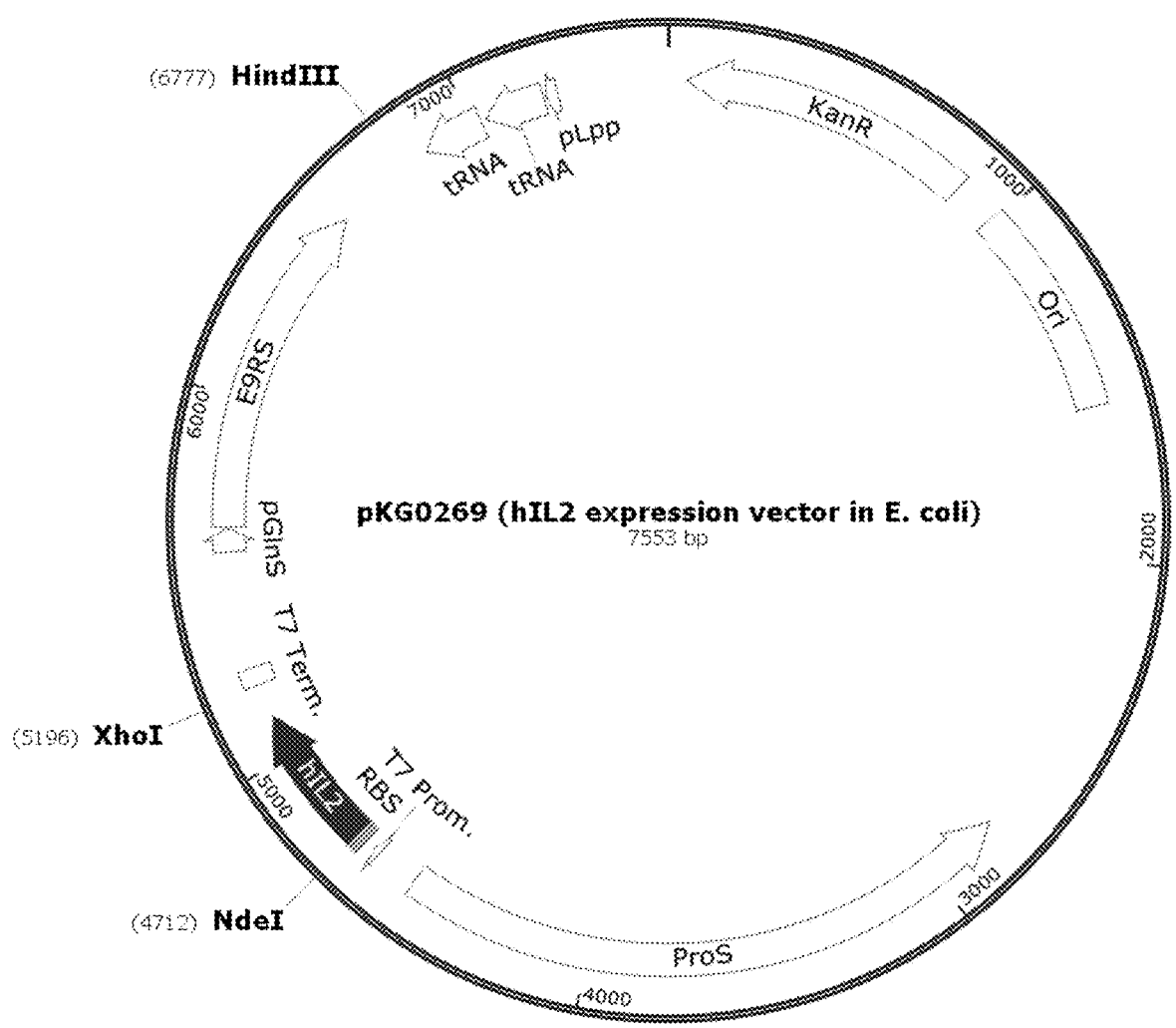
FIG. 2 shows a plasmid map of the expression vector for expression of IL-2 in E. coli.

E. coli expression vector construction and sequence verification: This example details the cloning and expression of human IL-2 (hIL-2) including a non-naturally encoded amino acid in E. coli. All human IL-2 expression plasmids were constructed either by recombination-based cloning method using Gibson Assembly kit (New England Biolabs (NEB), Ipswich, MA) or by using QuikChange mutagenesis kit (Agilent Technologies, Santa Clara, CA) in E. coli NEB5α cloning strain (New England Biolabs, MA) as described below. The E. coli expression plasmid is shown in FIG. 2.

Gibson Assembly: The primers for amplifying various gene of interests (GOIs) containing Donor fragments had about 18-24 base pair (bp) overlap sequence at their 5'-termini with the Acceptor vector sequences for homologous recombination and were synthesized at Integrated DNA Technologies (IDT) (San Diego, CA). The PCR fragments were amplified using high fidelity DNA polymerase mix, Pfu Ultra II Hotstart PCR Master Mix (Cat. No: 600852, Agilent Technologies). The PCR products were digested with Dpn1 restriction enzyme (NEB #R0176L) for 2 hours at 37° C. to remove plasmid background followed by column purification using Qiagen PCR column purification kit (Qiagen, Valencia, CA; #28104) and quantitated by Nanodrop (ThermoFisher, Carlsbad, CA). The Acceptor vectors were linearized by digesting with unique restriction enzymes (NEB, MA) within the vector for 3 to 5 hours at supplier recommended temperatures, PCR column purified and quantitated. The Donor inserts and appropriately prepared Acceptor vectors were mixed at a 3:1 molar ratio, incubated at 50° C. for 15 min, using Gibson Assembly kit (NEB #E2611S), and then used for transformation into E. coli NEB5α strain (NEB #2987).

The recombinants were recovered by plating Gibson Assembly mix on to LB agar plates containing appropriate antibiotics. The next day, 4 to 6 well-isolated single colonies were inoculated into 5 mL LB+50 µg/mL kanamycin sulfate (Sigma, St Louis, MO; cat #K0254) media and grown overnight at 37° C. The recombinant plasmids were isolated using Qiagen plasmid DNA mini-prep kit (Qiagen #27104) and verified by DNA sequencing (Eton Biosciences, San Diego, CA). The complete GOI region plus 100 bp upstream and 100 bp downstream sequences were verified by using gene-specific sequencing primers.

QuickChange Mutagenesis (QCM): All Amber variants containing TAG stop codon were created by using QuickChange Lightning site directed mutagenesis kit (Agilent Technologies #201519). All QCM oligonucleotides were designed using QuickChange Web Portal (Agilent Technologies), and ordered from IDT (San Diego, CA). The QCM PCR mix contained 5 µl of 10× buffer, 2.5 µl of dNTP Mix, 1 µl (100 ng) of plasmid template, 1 µl of oligo mix (10 uM concentration each), 1 µl of QuickChange Lightning enzyme, 2.5 µl of Quick solution and 37 µl of distilled water (DW). The DNA was amplified using the PCR program recommended by the kit for 18 cycles only.

After completion of the PCR reaction, the mix was digested with DpnI enzyme that came with the kit (Agilent Technologies) for 2-3 hour at 37° C., and ran on a gel to check the presence of amplified PCR product. Thereafter, 2.5 to 5 µl of PCR product was transformed into E. coli NEB5α strain. The recombinant plasmids from 4 to 6 colonies were then isolated and sequence verified as described in Gibson Assembly section above.

Expression strain (AXID) construction and verification: To prepare AXID production strains, chemically competent E. coli W3110B60 host cells were transformed with sequence-verified plasmid DNA (50 ng), the recombinant cells were selected on 2×YT+1% glucose agar plates containing 50 µg/mL kanamycin sulfate (Sigma, cat #K0254), and incubated overnight at 37° C. A single colony from the fresh transformation plate was then propagated thrice on 2×YT+1% glucose agar plates containing 50 µg/mL kanamycin sulfate by sequential triple-streaking and incubating overnight at 37° C. Finally, a single colony from the third-streaked plate was inoculated into 20 mL Super Broth (Fisher-Optigrow™, #BP1432-10B1) containing 50 µg/mL kanamycin sulfate (Sigma, cat #K0254) and incubated overnight at 37° C. and 250 rpm. The overnight grown culture was then diluted with glycerol to a final glycerol concentration of 20% (w/v) (KIC, Ref #67790-GL99UK). This cell suspension was then dispensed into 1 mL aliquots into several cryovials and frozen at −80° C. as AXID production strain vials.

After the generation of glycerol vials of the AXID production strains as described above, they were further validated by DNA sequencing and phenotypic characterization of antibiotic resistance markers. To confirm that the AXID production strain vial had the correct plasmid in the production host, the plasmid was sequence verified. Twenty mL LB containing 50 µg/mL kanamycin sulfate was inoculated with a stab from a glycerol vial of the AXID clone and grown at 37° C., 250 rpm overnight. The plasmid DNA was isolated using Qiagen Miniprep Kit (#27104) and the presence of intact GOI ORF in the isolated plasmid was confirmed by DNA sequencing (Eton Biosciences, CA).

To further verify the strain genotype of the AXID production strains, cells from the same vial were streaked onto four separate plates of LB: LB containing 50 ug/mL Kanamycin sulfate, LB containing 15 ug/mL Tetracycline, LB containing 34 ug/mL Chloramphenicol and LB containing 75 ug/mL Trimethoprim. They were then checked for positive growth on all of these plates, as expected with the strain genotype of W3110B60 production host strain.

Expression system: The amino acid and E. coli-codon optimized DNA sequences encoding hIL-2 are shown in Tables 1 and 2. An introduced translation system that comprises an orthogonal tRNA (O-tRNA) and an orthogonal aminoacyl tRNA synthetase (O—RS) is used to express hIL-2 containing a non-naturally encoded amino acid (see plasmid map pKG0269; FIG. 2). The O—RS preferentially aminoacylates the O-tRNA with a non-naturally encoded amino acid. In turn the translation system inserts the non-naturally encoded amino acid into IL-2 or IL-2 variants, in response to an encoded selector codon. Suitable O—RS and O-tRNA sequences are described in WO2006/068802 entitled "Compositions of Aminoacyl-tRNA Synthetase and Uses Thereof" and WO2007/021297 entitled "Compositions of tRNA and Uses Thereof", which are incorporated by reference in their entirety herein.

The transformation of E. coli with plasmids containing the modified IL-2 variant polynucleotide sequence and the orthogonal aminoacyl tRNA synthetase/tRNA pair (specific for the desired non-naturally encoded amino acid) allows the site-specific incorporation of non-naturally encoded amino acid into the IL-2 polypeptide. Expression of IL-2 variant polypeptides is under the control of the T7 promoter and induced by the addition of arabinose in the media (see plasmid map pKG0269; FIG. 2).

Suppression with para-acetyl-phenylalanine (pAF): Plasmids for the expression IL-2 polypeptides are transformed into W3110B60 E. coli cells. Para-acetyl-phenylalanine (pAF) is added to the cells, and protein expression is induced by the addition of arabinose. SDS-PAGE analysis of the expression of IL-2 polypeptide is performed, the IL-2 polypeptides are observed. Lanes are run for comparison between the original wild type IL-2 polypeptide; and for the pAF substituted IL-2 polypeptides, an IL-2 with, for example, a para-acetylphenylalanine substitution made at a particular amino acid residue. Expression of the T7 polymerase is under control of an arabinose-inducible T7 bacteriophage promoter. Para-acetyl-phenylalanine (pAF) is added to the cells, and protein expression is induced by the addition of arabinose (0.2% final). Cultures are incubated for few hours (3-5 hours) at 37° C.

Additional constructs to increase hIL-2 expression in E. coli: To increase the production of hIL-2 in E. coli, the following expression parameters could be further optimized in addition to DNA sequence optimization based on E. coli codon usage reported herein: Testing different promoters besides T7 bacteriophage promoter such as arabinose B (araB), pTrc and bacteriophage T5 promoters; Stabilization of hIL-2 mRNA; Screening of different E. coli host strains besides the standard W3110B60 strain; Production process parameters optimization such as temperature, culture media, inducer concentration etc.; Transcriptional and translational control elements optimization such as start and stop codons, ribosome binding site (RBS), transcriptional terminators etc; Plasmid copy number and plasmid stability optimization; Translational initiation region (TIR) optimization.

Figure 3A:
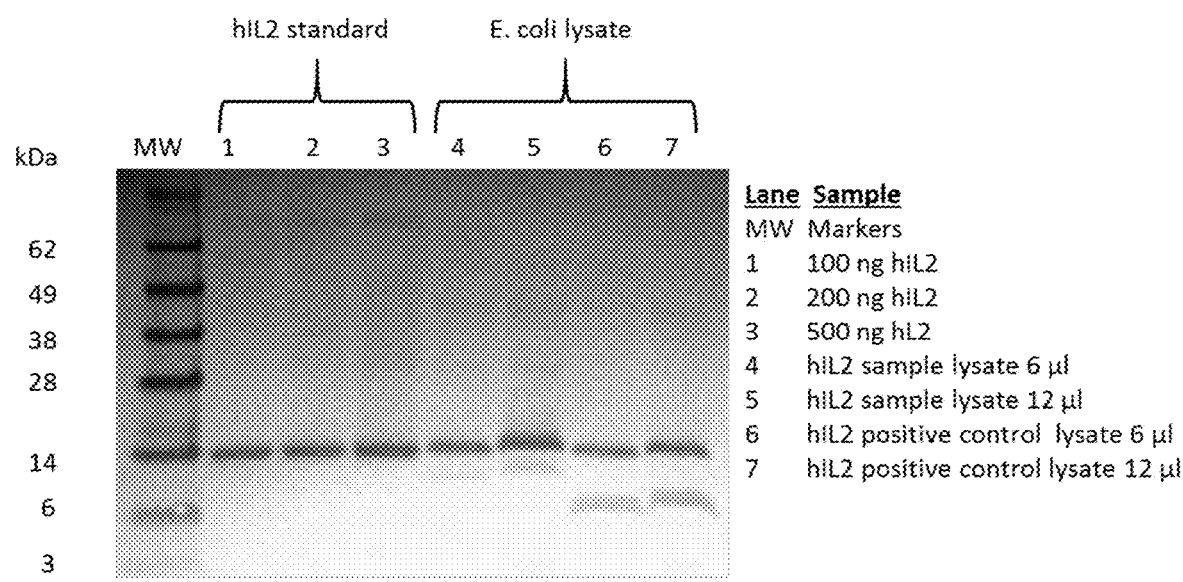
FIG. 3A shows a Western blot analysis of expression of the IL-2 protein in E. coli.

Example 3—this Example Details E. Co/i Shake Flask Expression Testing and High Cell Density Fermentation Shake-flask expression testing: The AXID production strain as described above was used to test for hIL-2 expression in shake flask experiments. Briefly, an inoculum from the AXID glycerol vial was put into a 5 mL of Super Broth (Fisher-Optigrow™, #BP1432-10B1) media containing with 50 µg/mL of kanamycin sulfate (Sigma, MO) and grown overnight at 37° C. with shaking. The overnight culture was diluted 1:100 in Super Broth (Fisher-Optigrow™, #BP1432-10B1) media containing 50 µg/mL of kanamycin sulfate (Sigma, MO) and grown at 37° C. with shaking. When the culture density reached an OD600 of 0.6-0.8, it was induced with 0.2% arabinose and pAF added followed by harvesting after several hours (usually 3 to 5 hours) of production. An aliquot from the harvested cells was taken and analyzed by SDS-PAGE. Optimal expression of hIL-2 was standardized by varying temperature, duration of induction and inducer concentration. Immunoblot of crude extracts with standard monoclonal antibodies against hIL-2 further confirmed the expression of hIL-2, (FIG. 3A) according to the following Western assay used to analyze the hIL2 expression: The harvested cell pellets were normalized to OD600 of 5 and dissolved into the calculated amount of B-PER solution (ThermoFisher) with lysozyme (100 µg/ml) and DNase 1 (1 U/ml). The pellets were mixed by vortexing 2-5 minutes at high speed and by incubating the mixture at 37° C., 250 rpm. The samples were mixed with the sample buffer (4×) and sample reducing agent (10×), provided by the manufacturer, by adjusting the final concentration to 1×. Total of 20 µl of samples were loaded on a pre-cast polyacrylamide gel (ThermoFisher) along with the hIL2 standard (R&D Systems, Minneapolis, MN) and the electrophoresis separation carried out in 1×MES buffer (ThermoFisher). The protein samples were transferred onto a Nitrocellulose membrane using iBlot apparatus and gel transfer stacks. hIL2 was captured by goat anti-human IL-2 antigen (R&D Systems) and detected by HRP conjugated anti-goat IgG secondary antibody (R&D Systems) with opti 4CN colorimetric substrate (Bio-Rad, Hercules, CA).

High cell density fermentations: The fermentation process for production of hIL-2 consists of two stages: (i) inoculum preparation and (ii) fermentor production. The inoculum is started from a single glycerol vial, thawed, diluted 1:1000 (v/v) into 50 mL of defined seed medium in a 250 mL baffled Erlenmeyer flask, and incubated at 37° C. and 250 rpm. Prior to use, the fermentor is cleaned and autoclaved. A specified amount of basal medium is added to the fermentor and steam sterilized. Specified amounts of kanamycin sulfate solution, feed medium and P2000 antifoam are added to the basal medium prior to inoculation. All solutions added to the fermentor after autoclaving are either 0.2 µm filtered or autoclaved prior to aseptic addition.

The fermentor is batched with 4 L of chemically defined medium that utilizes glycerol as a carbon source. The seed culture is added to the fermentor to an initial OD600 nm of 0.05. Dissolved oxygen is maintained at 30% air saturation using agitation from 480 to 1200 rpm and oxygen enrichment with a head pressure of 6 psig and air flow of 5 slpm. The temperature and pH are controlled at 37° C. and 7.0, respectively. When the culture reaches an OD600 nm of 35±5, feeding commences at a rate of 0.25 mL/L/min. Consequently, L-Ala-pAcF, (also referred to as L-Ala-pAF), dipeptide is added at 0.4 g/L. Fifteen minutes after the addition of dipeptide, the culture is induced with L-arabinose at a final concentration of 2 g/L. The culture is harvested at 6 h post induction.

Figure 3B:
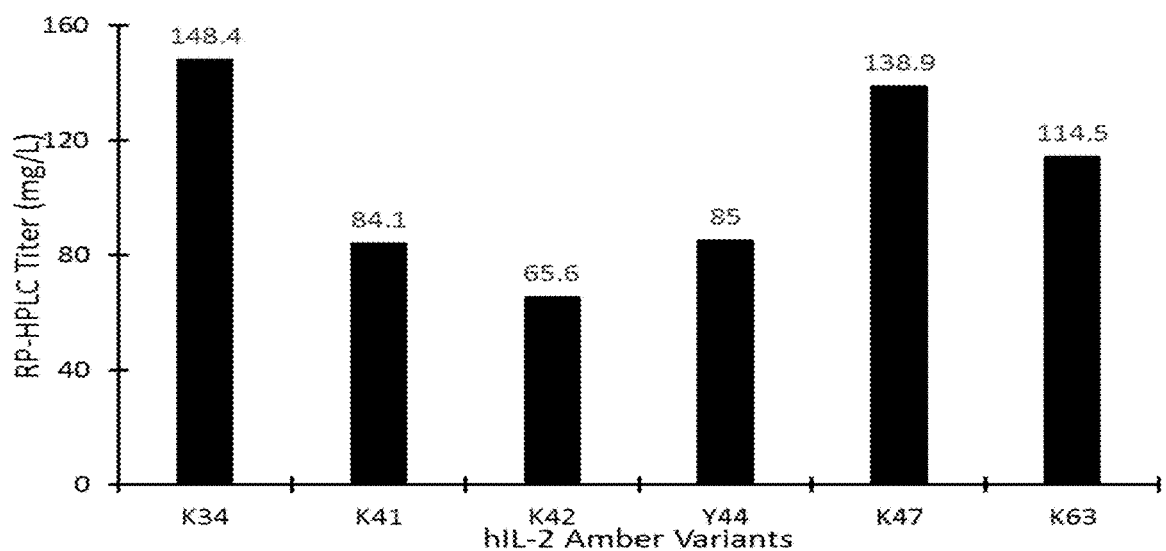
FIG. 3B shows titer of IL-2 variants in E. coli.

Reverse Phase-HPLC titer analysis: 1.0 mL of E. coli fermentation samples (cell paste) were first dried and weighed to determine the mass for sample prep. Lysonase Bioprocessing Reagent (EMD Millipore #71230) and Benzonase Nuclease Reagent (EMD Millipore #70664) were each diluted 1:500 in BugBuster Protein Extraction Reagent (EMD Millipore #70584) and used for chemical lysis of the cell paste. 1.0 mL of the Bugbuster-Lysonase-Benzonase mixture was added to 1.0 mL of dried cell paste and the resulting mixture was vortexed vigorously. The mixture was then placed on an Eppendorf Thermomixer R shaker for 20 minutes at 22° C. with shaking at 1000 rpm. After incubation, the cellular lysate was centrifuged at 16,050 ref for 5 minutes to pellet the cellular debris. A 200 µL aliquot of the cellular lysate supernatant was then filtered through a 0.22 m PVDF centrifugal filter (EMD Millipore #UFC30GVNB) at 16,050 rcf for 1 minute. The filtered product was then analyzed by reverse-phase chromatography to determine the amount of hIL2 present in the fermentation samples. A 4.6×150 mm Zorbax 300SB-C3 (Agilent #863973-909) reverse phase column packed with 3.5 µm particles was used to separate hIL2 from the host cell protein contaminants. Mobile Phase A was used to bind hIL2 contained 0.1% trifluoroacetic in water. Mobile Phase B containing 0.1% trifluoroacetic acid in acetonitrile was used to elute hIL2 from the column. The amount of hIL2 in the sample was determined by comparing the observed area count from a fixed injection volume against the line equation obtained from a standard curve generated using purified hIL2. Several of the IL-2 amber variants tested, as exemplified in FIG. 3B, showed high titer expression ranging from about 65 to 150 mg/L, in high cell density *E. coli* fermentation.

Example 4—this Example Details Inclusion Body Preparation, Refolding, Purification and PEGylation Inclusion body preparation and solubilization: The cell pastes harvested from high cell density fermentation are re-suspended by mixing to a final 10% solid in 4° C. inclusion body (IB) Buffer I (50 mM Tris pH 8.0; 100 mM NaCl; 1 mM EDTA; 1% Triton X-100; 4° C.). The cells are lysed by passing the re-suspended material through a micro-fluidizer a total of two times. The samples are then centrifuged (14,000 g; 15 minutes; 4° C.), and the supernatants are decanted. The inclusion body pellets are washed by re-suspending in an additional volume of IB buffer 1 (50 mM Tris pH 8.0; 100 mM NaCl; 1 mM EDTA; 1% Triton X-100; 4° C.), and the re-suspended materials are passed through the micro-fluidizer a total of two times. The samples are then centrifuged (14,000 g; 15 minutes; 4° C.), and the supernatants are decanted. The inclusion body pellets are each re-suspended in one volume of buffer 11 (50 mM Tris pH 8.0; 100 mM NaCl; 1 mM EDTA; 4° C.). The samples are centrifuged (14,000 g; 15 minutes; 4° C.), and the supernatants are decanted. The inclusion body pellets are re-suspended in ½ volume of buffer II (50 mM Tris pH 8.0; 100 mM NaCl; 1 mM EDTA; 4° C.). The inclusion bodies are then aliquoted into appropriate containers. The samples are centrifuged (14,000 g; 15 minutes; 4° C.), and the supernatants were decanted. The inclusion bodies were solubilized or stored at −80° C. until further use.

Inclusion bodies are solubilized to a final concentration between 10-15 mg/mL in solubilization buffer (20 mM Tris, pH 8.0; 8M Guanidine; 10 mM—ME). The solubilized inclusion bodies are then incubated at room temperature under constant mixing for 1 hour or until fully solubilized. The samples are then centrifuged (10,000 g; 20 minutes; 4° C.) to remove any un-solubilized material. The protein concentration of each sample is then adjusted by dilution with additional solubilization buffer if the protein concentration was high.

Refolding and purification: Refolding is performed by diluting the samples to a final protein concentration of 0.5 mg/mL in 20 mM Tris, pH 8.0; 60% Sucrose; 4° C. Refolding is allowed for 5 days at 4° C. Refolded material is diluted 1:1 with Milli-Q H$_2$O. Material is filtered through a 0.22 μm PES filter and loaded over a Blue Sepharose FF column (GE Healthcare) equilibrated in 20 mM Tris, pH 8.0; 0.15 M NaCl (buffer A). In up flow, the column is washed with 5 column volumes 30% buffer B (20 mM Tris, pH 8.0; 2 M NaCl; 50% Ethylene Glycol). IL-2 polypeptides are eluted by washing the column with 10 column volumes of 100% buffer B.

PEGylation and post-PEGylation purification: The IL-2 pool is taken and diluted 10× with Milli-Q water. The pH of each sample is adjusted to 4.0 with 50% glacial acetic acid. The samples are concentrated down to ~1.0 mg/mL. 1:12 molar excess activated PEG (hydroxylamine PEG) is added to each sample. The samples are then incubated at 27° C. for 48-72 hours. Samples are taken and diluted 8-10 fold with water (<8 m/S) and loaded over a SP HP column (GE Healthcare) equilibrated in Buffer A (50 mM NaAc, pH 6.0; 50 mM NaCl; 0.05% Zwittergent 3-14). The IL-2 polypeptides are eluted with 5 column volumes of buffer B (50 mM NaAc, pH 6.0; 500 mM NaCl; 0.05% Zwittergent 3-14). Fractions of IL-2 are pooled and run over a Superdex 200 sizing column equilibrated in IL-2 storage buffer (20 mM NaAc, pH 5.0; 150 mM NaCl; 0.05% Zwittergent 3-14). The PEGylated material is collected and stored at 4° C.

Example 5—this Example Details IL-2 Purification from *E. coli* and Mammalian Expression Systems. This Example Also Discloses PEGylation, Site Specific Conjugation, and PEG-IL-2 Purification Process Preparation from *E. coli* Inclusion body prep: IL-2 inclusion bodies were isolated through a series of wash steps. Frozen cell paste was re-suspended in wash buffer I (50 mM Tris, pH 8.0; 1% triton X-100; 1M urea, 5 mM EDTA, 1 mM PMSF) to a concentration of 10% (W/V) and homogenized at 4° C. followed by centrifuged (15,000 g, 30 minutes, 4° C.). The supernatant was discarded, and the inclusion body pellet was re-suspended in wash buffer 11 (50 mM Tris, pH 8.0; 1% triton X-100; 1M urea, 5 mM EDTA). Re-suspended inclusion bodies were centrifuged at 15,000 g for 30 minutes at 4° C. The supernatant was discarded, and the inclusion body pellet was re-suspended in wash buffer III (50 mM Tris, pH 8.0; sodium deoxycholate, 5 mM EDTA). Re-suspended inclusion bodies were centrifuged at 15,000 g for 30 minutes at 4° C. The supernatant was discarded, and the inclusion body pellet was re-suspended in water followed by centrifugation at 15,000 g for 30 minutes at 4° C. Washed inclusion bodies were stored at −80° C. until further use.

Refold: IL-2 inclusion bodies were solubilized by resuspension in water and adjusting the pH of the mixture to pH 12.2. Insoluble material was removed by centrifugation (12,000 g, 15 minutes). Solubilized IL-2 was refolded by adjusting the pH down to pH 8.8±0.2. Proper disulfide bond formation was facilitated by the addition of 50 μM cystine to the refold reaction. The refold reaction was allowed to sit at room temperature for 16-22 hours. Host cell contaminants were precipitated by adjusting the refold reaction to pH 6.8 with hydrochloric acid. The precipitate was removed by centrifugation (12,000 g, 15 minutes) and the clarified supernatant was adjusted to pH 7.8 with sodium hydroxide and 0.22 μm filtered.

Column Purification: The refolded IL-2 was loaded over a Capto Adhere Impres (GE Healthcare) column equilibrated in buffer A (20 mM sodium phosphate, pH 7.8). After loading, the column was washed with buffer A (20 mM sodium phosphate, pH 7.8) and IL-2 was eluted from the column using a linear pH gradient to 100% buffer B (20 mM sodium phosphate, 20 mM citric acid, pH 4.0) over 20 column volumes. Fractions containing IL-2 were collected, pH was adjusted to 4.0 with 10% acetic acid, and then buffer exchanged into 20 mM sodium acetate, 2.5% trehalose, pH 4.0. IL-2 was concentrated to 1-10 mg/mL, 0.22 μM filtered, and stored at −80° C.

Purification of IL-2 from Eukaryotic Expression System: Cell culture media containing His tagged IL-2 was pH adjusted to 7.8 with sodium hydroxide and loaded over a Ni Excel column (GE Healthcare) equilibrated in 20 mM sodium phosphate, pH 7.8. After loading, the column was washed with buffer A (20 mM sodium phosphate, pH 7.8) followed by wash buffer B (20 mM sodium phosphate, 1.0M sodium chloride, 30 mM imidazole, pH 7.8) to remove host cell contaminants. IL-2 was eluted from the column with elution buffer (10 mM sodium phosphate, 300 mM imidazole, pH 7.8) and fraction containing IL-2 were pooled. The IL-2 pooled material was loaded over a Capto Adhere Impres (GE Healthcare) column equilibrated in buffer A (20 mM sodium phosphate, pH 7.8). After loading, the column was washed with buffer A (20 mM sodium phosphate, pH 7.8) and IL-2 was eluted from the column using a linear pH gradient to 100% buffer B (20 mM sodium phosphate, 20 mM citric acid, pH 4.0) over 20 column volumes. Fractions containing IL-2 were collected, pH was adjusted to 4.0 with 10% acetic acid, and buffer exchanged into 20 mM sodium acetate, 2.5% trehalose, pH 4.0. IL-2 was concentrated to 1-10 mg/mL, 0.22 µM filtered, and stored at −80° C. until further use.

Site Specific Conjugation and PEG-IL-2 Purification: IL-2 variants containing non-natural amino acid (nnAA), para-acetyl phenylalanine were buffer exchanged into conjugation buffer (20 mM sodium acetate, pH 4.0) and concentrated to 1-10 mg/mL. A final of 100 mM acetic hydrazide was added to the reactions followed by a 10 molar excess of aminooxy functionalized PEG. The conjugation reactions were incubated for 18-20 hours at 25-30° C. Following conjugation, the PEGylated IL-2 was diluted 1:10 with 20 mM sodium acetate, pH 5.0 and loaded over a Capto SP Impres column. After loading, the column was washed with buffer A (20 mM sodium acetate, pH 5.0) and PEGylated IL-2 was eluted from the column using a linear gradient to 100% buffer B (20 mM sodium acetate, 1.0M sodium chloride, pH 5.0) over 20 column volumes. Fractions containing PEGylated IL-2 were collected and buffer exchanged into 10 mM sodium phosphate, 100 mM sodium chloride, 2.5% trehalose, pH 7.0. IL-2 was concentrated to 1-2 mg/mL, 0.22 µM filtered, and stored at ~80° C. until further use.

Figure 4A:
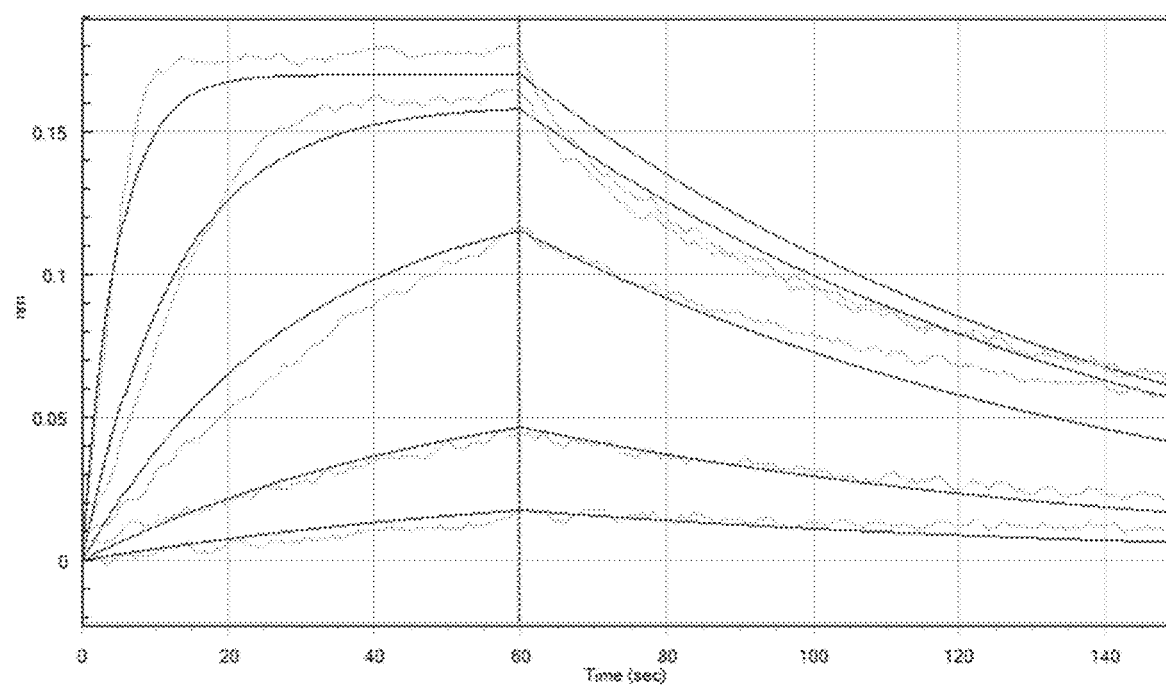
FIG. 4A shows binding kinetic sensorgram and model fitting lines and calculated measurements for IL-2 wild type to CD25.

IL-2/CD-25 Binding Assay by Bio-Layer Interferometery: IL-2/CD25 multi-concentration binding kinetic experiments were performed on an Octet RED96 (PALL/ForteBio) instrument at 30° C. Anti-human Fc capture biosensors (PALL/ForteBio, cat #18-5063) were loaded with purified CD25-Fc fusion protein in 1×HBS-P+ Buffer (GE Healthcare, cat #BR-1008-27). Immobilization levels between 0.8 nm and 1.0 nm were reached. The loaded biosensors were washed with 1×HBS-P+ Buffer to remove any unbound protein before measuring association and dissociation kinetics. For association phase monitoring, IL-2 analyte samples were diluted with 1×HBS-P+ Buffer and transferred to solid-black 96 well plates (Greiner Bio-One, cat #655209). IL-2 samples were allowed to bind to CD25-Fc loaded biosensors for 60 seconds. The dissociation phase was recorded in wells of a solid black 96-well plate containing 1×HBS-P+ Buffer for 90 seconds. Data were referenced using a parallel buffer blank subtraction, and the baseline was aligned to the y-axis and smoothed by a Savitzky-Golay filter in the Octet data analysis software version 10.0 (PALL/ForteBio). The processed kinetic sensorgrams were globally fitted using the Langmuir model describing a 1:1 binding stoichiometry, (FIG. 4A).

Example 6—this Example Details Cloning and Expression of an IL-2 Including a Non-Naturally Encoded Amino Acid in Mammalian System. This Example Also Describes Methods to Assess the Biological Activity of Modified IL-2

Preparation of IL-2 variants in mammalian cells. Natural human IL-2 is a glycosylated protein that has O-linked glycosylation on Thr-3 (Conradt et al., Eur J Biochem, 153(2): pp: 255-61 (1985)). Although it has been shown that nonglycosylated IL-2 has similar activities to glycosylated IL-2, glycosylated human IL-2 was shown to have better activity in terms of clonal out-growth and long-term propagation of activated human T cells. There are also some reports suggesting that natural IL-2 has higher specific activities. It is also suggested that, expression of IL 2 in mammalian cells has advantages over their expression in E. coli (Kim et al., J Microbiol Biotechnol, 14(4), 810-815 (2004)). In the present invention, wild type IL-2 and its various muteins designed above, Tables 1 and 2 respectively, can be produced in CHO cells (as described in the Examples herein.

To produce IL-2 muteins that contain unnatural amino acid at desired position, each mutein is produced in either a stable pool or stable cell line that is derived from transfected platform cell lines that contain an engineered orthogonal tRNA/tRNA synthetase pair (Tian et al., Proc Natl Acad Sci USA, 111(5): pp: 1766-71 (2014)) and PCT/2018US/035764: each incorporated herein by reference in its entirety). Briefly, CHOK1 cells were engineered to be platform cell line(s) stably expressing proprietary orthogonal tRNA synthetase(O—RS) and its cognate amber suppressing tRNA(O-tRNA) for efficient incorporation of a non-natural amino acid, for example pAF, into therapeutic proteins such as IL-2 for example, in CHO cells. The platform cell line was then pre-adapted to suspension growth for rapid progression into bioreactors. The platform cell line has been well characterized and evolved with improved non-natural amino acid incorporation efficiency and clone selection efficiency. The platform cell line is used as parental cells to produce non-natural amino acid incorporated therapeutic proteins by fast and efficient transient expression with titer greater than 100 mg/L for early-stage research use. Transient transfection and stable pool generation are conducted to evaluate the expression of candidate molecules and provide material for functional assay to identify the lead molecule. Production cell lines are generated to produce non-natural amino acid incorporated IL-2 proteins by transfecting amber nonsense codon containing the gene of interest in GS expression system into the platform cell line. Stable cell line development strategy is implemented to obtain production cell line with 5-10 PCD in 3-4 months and 20-30 PCD in 6 months using the platform cell line as parental cells.

Figure 4B:
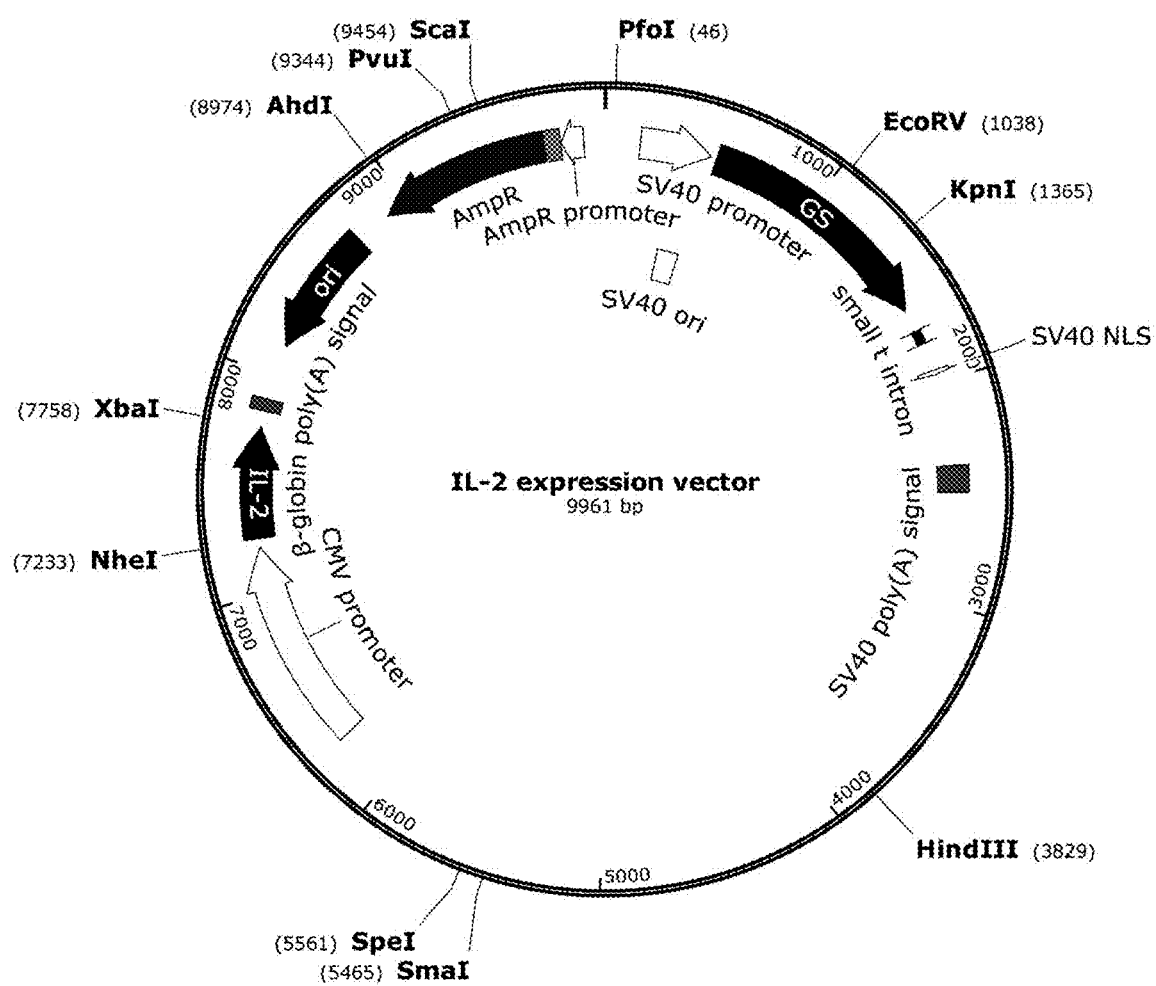
FIG. 4B shows a plasmid map of the expression vector for expression of IL-2 in mammalian cells.

In the present invention, human IL-2 cDNA (NM_000586.3) with its natural signal peptide sequences was synthetized and cloned into a mammalian expression vector containing GS selection marker (FIG. 4B). As shown in Table 1, the cloned wild type human IL-2 cDNA keeps its original DNA sequences of each amino acid without any mutations. In contrast, during the generation of IL-2 variants, (Table 2), each of the 15 muteins has a unique position that was mutated into an Amber stop codon (TAG), which can be suppressed and expressed in engineered cells to produce nnAA containing proteins.

Figure 5:
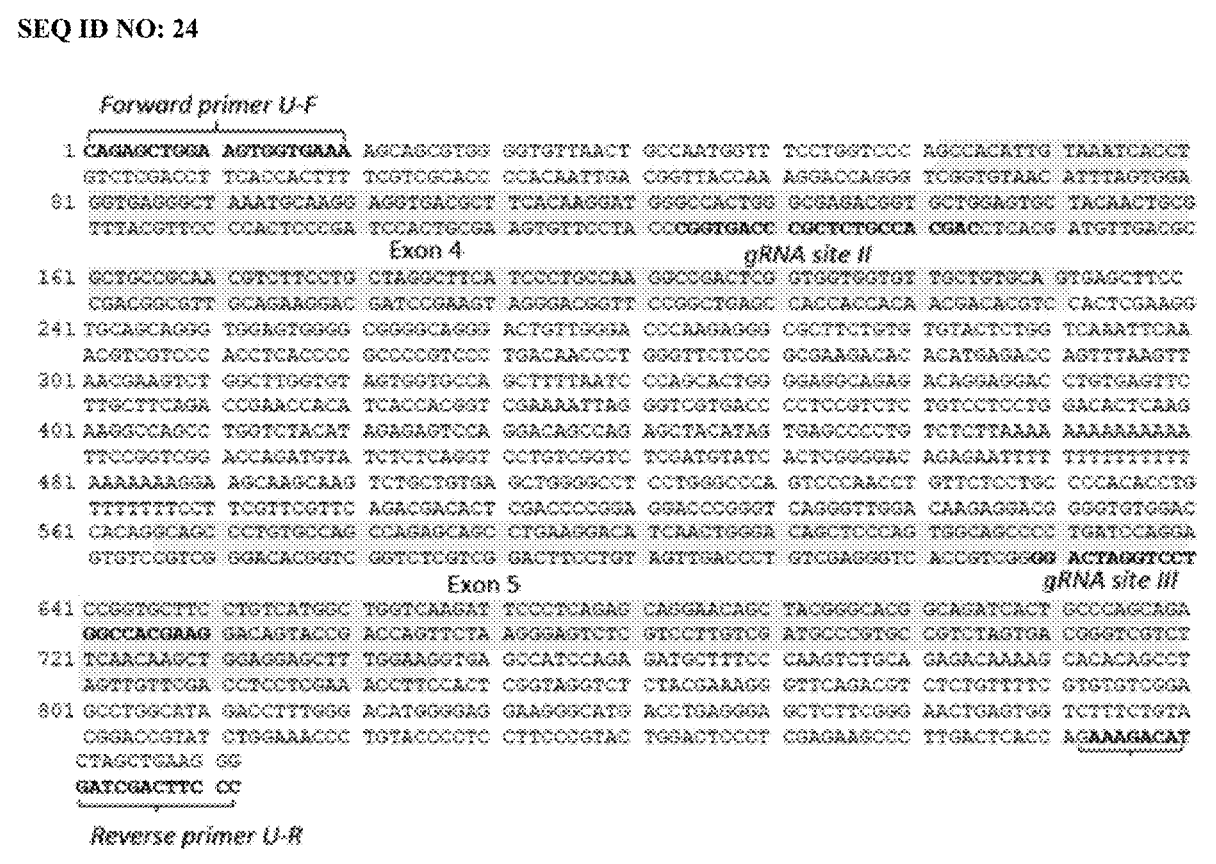
Figure 6:
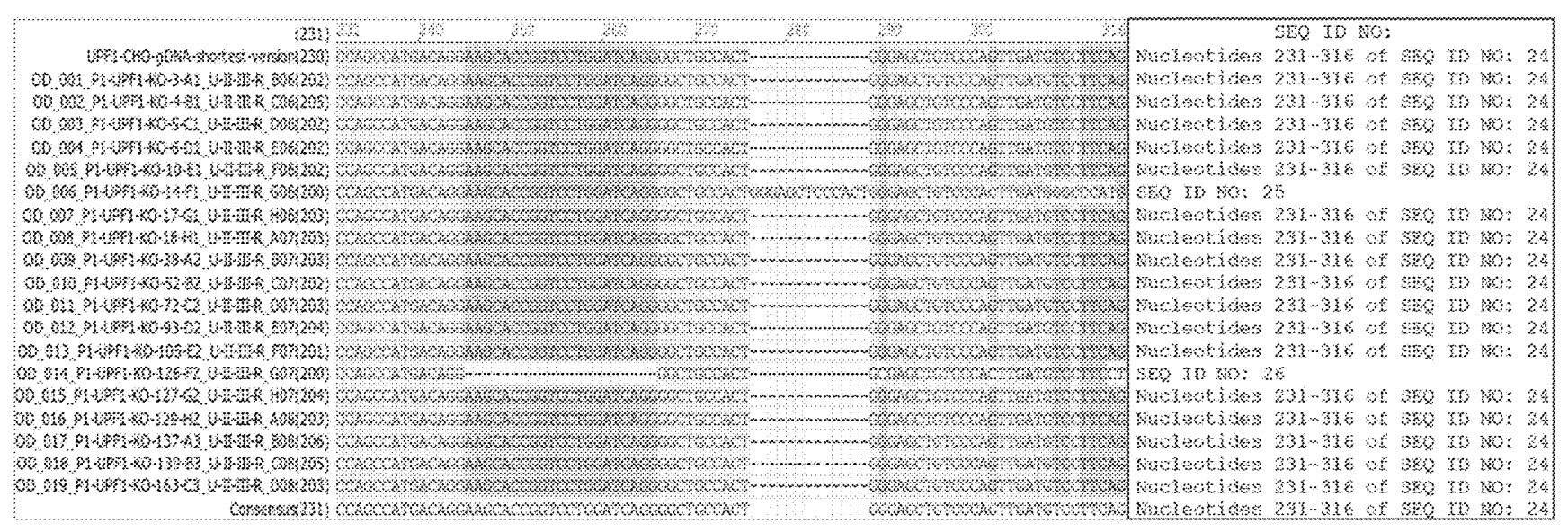

Establishment of engineered CHO cells to be used for IL-2 variants expression. Engineered CHO cells were derived from gene knockout of previously established proprietary platform cells (PCT/2018US/035764, incorporated herein by reference in its entirety). Briefly, a web-based target finding tool, CRISPy, was used to rapidly identify gRNA target sequences preferably in the early exons with zero off-target in the CHO-K1 cells. The gRNAs were cloned into mammalian expression vector pGNCV co-expressing with CHO codon-optimized version of Cas9. A production cell line was transfected with protein expression vector to generate a pool of cells followed by cloning to identify single cell isolates with gene knockout. The indel (insert/deletion) frequency from composite results of multiple projects was 30-90% and 50-80% for the pool of cells and single cell isolates, respectively. CRISPR was used to knockout the targeted gene in CHO cells. Specifically, to increase the mRNA stability of IL-2, the UPF1 gene was knocked out using CRISPR technology. The gRNAs used in knockout are shown in FIG. 5. After screening 192 clones, two UPF1-KO cell lines were obtained and verified by sequencing to have UPF1 knockout (FIG. 6). The obtained UPF1-KO cell lines were then used to transiently express IL-2 variants.

Figure 7A:
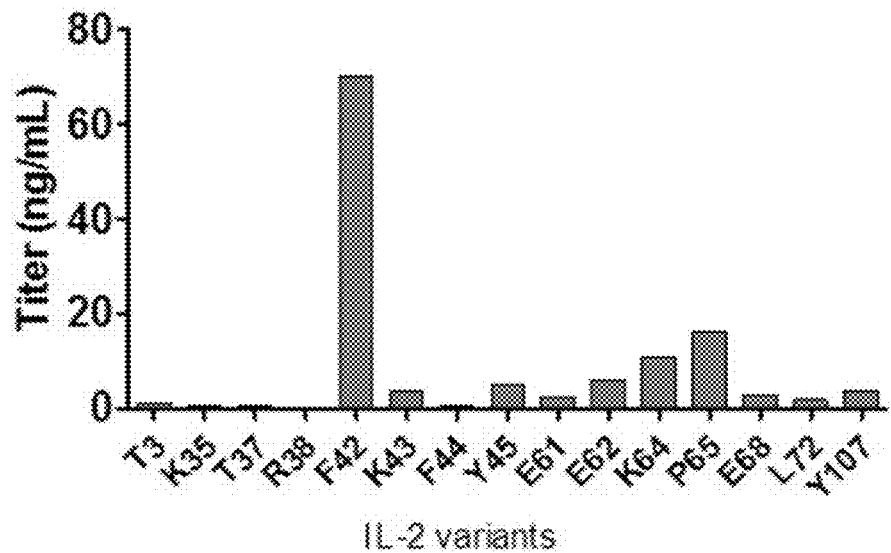
FIG. 7A shows transient expression of various IL-2 variants in mammalian cells.
Figure 7B:
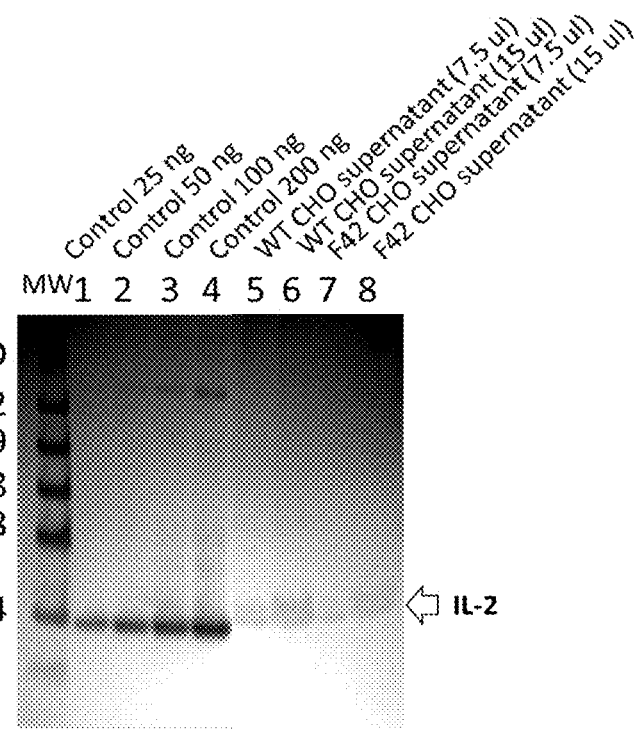
FIG. 7B shows Western blot analysis of wild-type IL-2 and IL-2 variants produced in mammalian cells.

Transient expression of IL-2 in engineered CHO cells. IL-2 variants were transiently expressed in UPF1-KO cell lines obtained as disclosed in the above Example. Transfection was done with electroporation using Amaxa kit for suspension cells (Lonza). 6 ug of plasmid prepared as disclosed in the above Example, was transfected into $2 \times 10^6$ engineered CHO cells. After transfection, cells were incubated at 37° C. for 4 days before the analysis of titer by ELISA using a commercial kit from Invitrogen (Carlsbad, CA). As shown in FIGS. 7A and 7B, variant F42 exhibit the highest expression level among 15 variants during transient expression.

Figure 8:
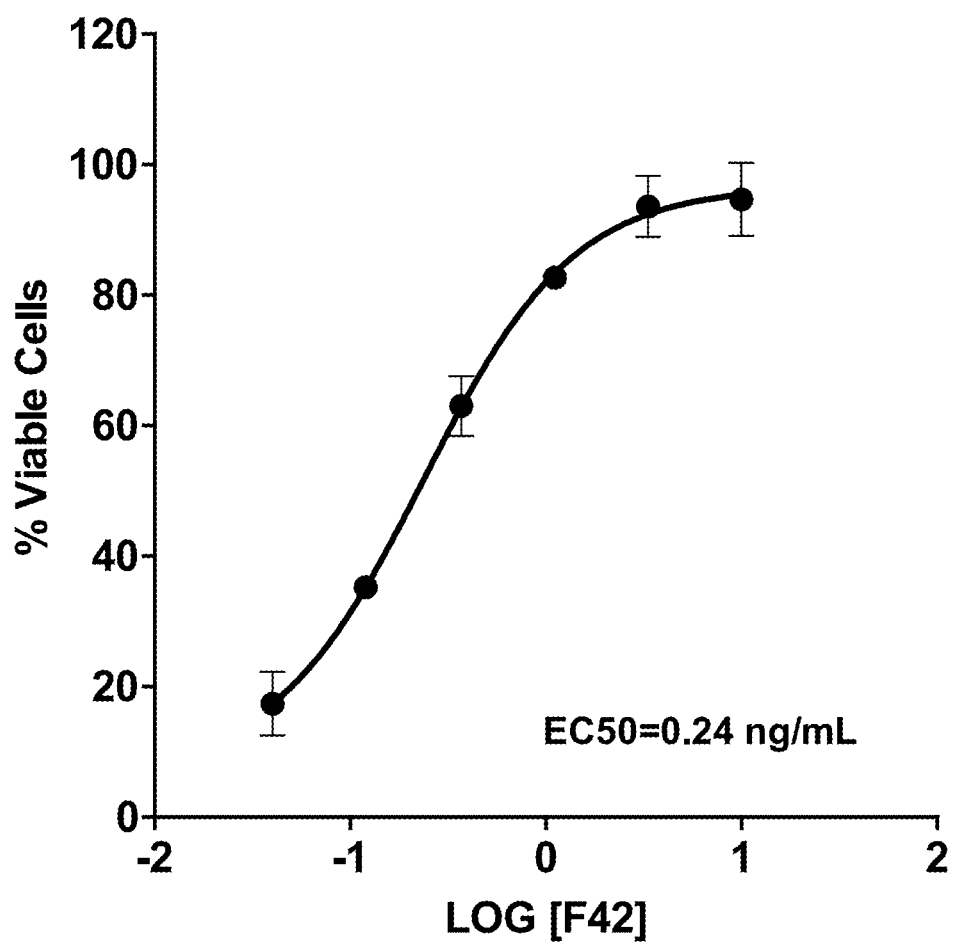
FIG. 8 shows CTLL-2 expansion assay of F42 variant of IL-2.
Figure 16:
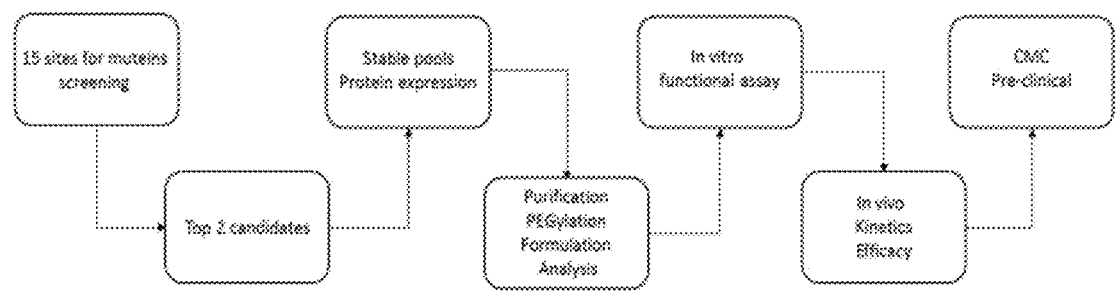
FIG. 16 show a general procedure in efficacy study of PEGylated IL-2 muteins with unnatural amino acids.

T cell expansion test of IL-2 variants in CTLL-2 cells. CTLL-2 cell expansion assay was performed using transiently expressed F42 variant supernatant from transfected engineered CHO cells. During the cell proliferation assay, wild type IL-2 was used as a control of 100% proliferation (shown in FIG. 8). Variant F42 was prepared into serial dilutions in the assay, 10 ng/mL, 3.33 ng/mL, 1.11 ng/mL, 0.37 ng/mL, 0.12 ng/mL, and 0.04 ng/mL. Cell proliferation was performed using Cell Titer Glo (Promega, WI). Luminescent signal was read on TECAN genios pro. As shown in FIG. 8, F42 showed an $EC_{50}$ around 0.24 ng/mL while retaining 95% of the function compared to its wild type control. A general procedure for studying the IL-2 variants of the present invention is shown in FIG. 16.

Example 7—Screening of IL-2 Variants by CTLL-2 Cell Expansion

Figure 9:
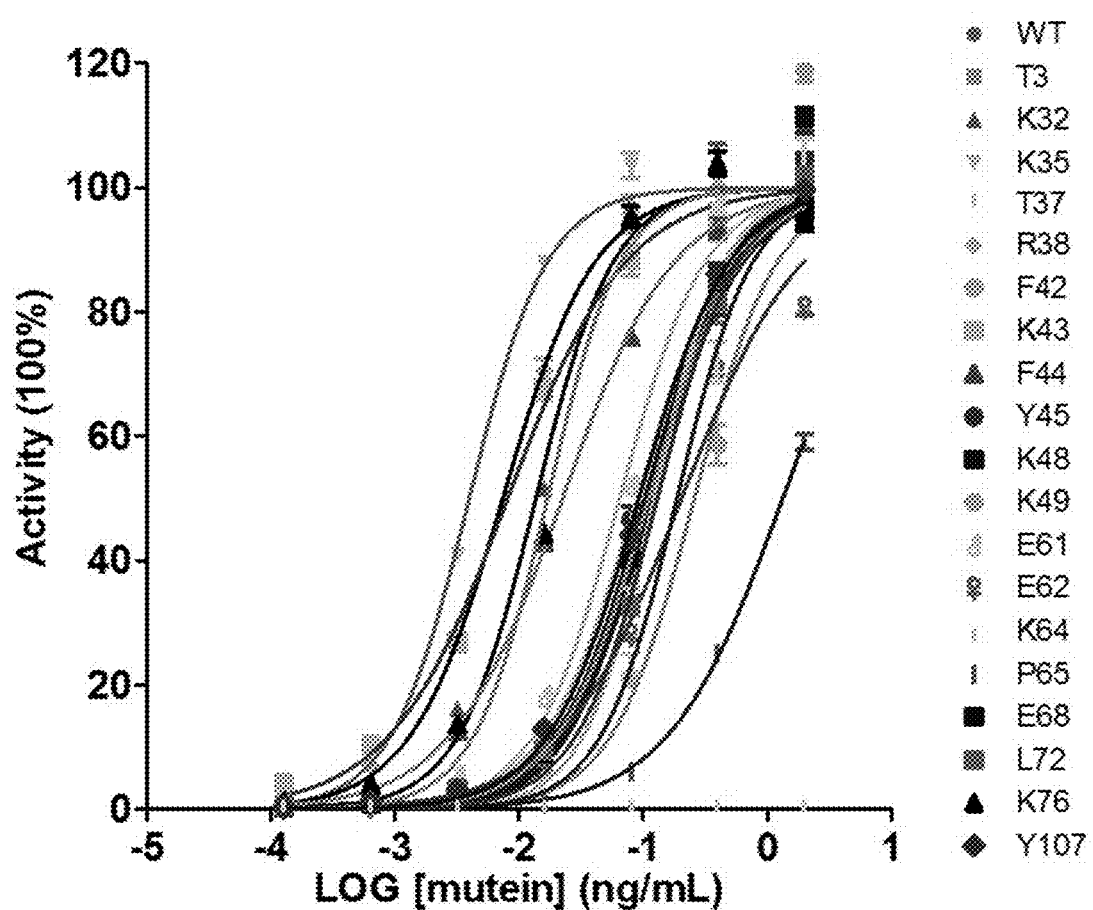
FIG. 9 shows screening of IL-2 variants by CTLL-2 proliferation assay.

Utilizing a CTLL-2 cell expansion assay as disclosed in the Examples, 20 different IL-2 variants including 16 originally selected sites (wild type included) and 4 additional sites (K32, K48, K49, K76) known in the art were screened (Charych, D., et al., PLoS One, 12(7): p. e0179431, 2017). As shown in FIG. 9 and Table 3, most variants retained their activities after mutagenesis. Due to the nature of CTLL-2 cells having residual expression of IL-2Rα, variants with mutagenesis having the least binding to CTLL2 cells still exhibited some inherent binding to IL-2Rα, although it was minimal. For example, it was observed that the P65 IL-2 variant, which exhibited the least binding to IL-2Rα, showed some inherent biased binding to IL-2Rα. Identified variants were further analyzed for their binding capabilities after PEGylation.

TABLE 3

Activity of IL-2 variants using CTLL2 proliferation assay

| IL-2 variants | EC50 (nM) |
|---|---|
| WT | 1.96 |
| T3 | 1.86 |
| K32 | 0.27 |
| K35 | 2.39 |
| T37 | 1.64 |
| R38 | 1.67 |

TABLE 3-continued

Activity of IL-2 variants using CTLL2 proliferation assay

| IL-2 variants | EC50 (nM) |
|---|---|
| F42 | 8.70 |
| K43 | 0.17 |
| F44 | 0.37 |
| Y45 | 1.87 |
| K48 | 2.87 |
| K49 | 3.93 |
| E61 | 1.17 |
| E62 | 1.98 |
| K64 | 4.09 |
| P65 | 13.90 |
| E68 | 1.73 |
| L72 | 2.45 |
| K76 | 0.29 |
| Y107 | 1.60 |

Example 8—Analysis of Selected Variants with In Vitro Binding Assay

Figure 10A:
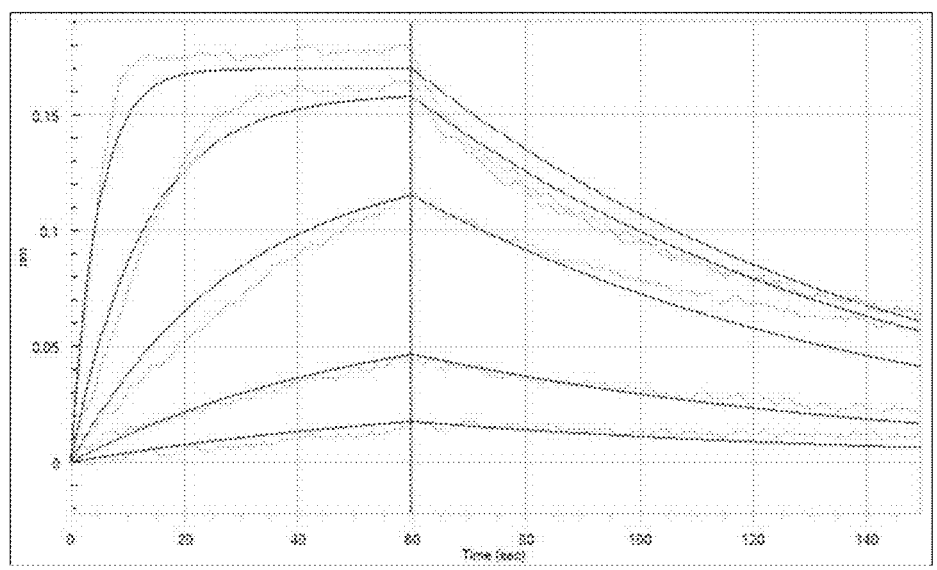
FIG. 10A shows binding kinetic sensorgram for IL-2 wild type and F42 variant.
Figure 10A:
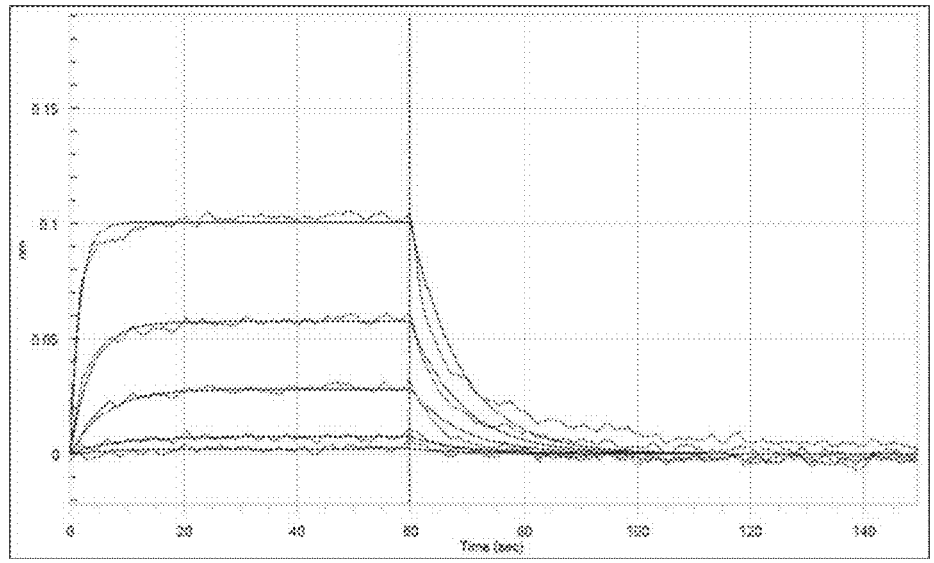
Figure 10B:
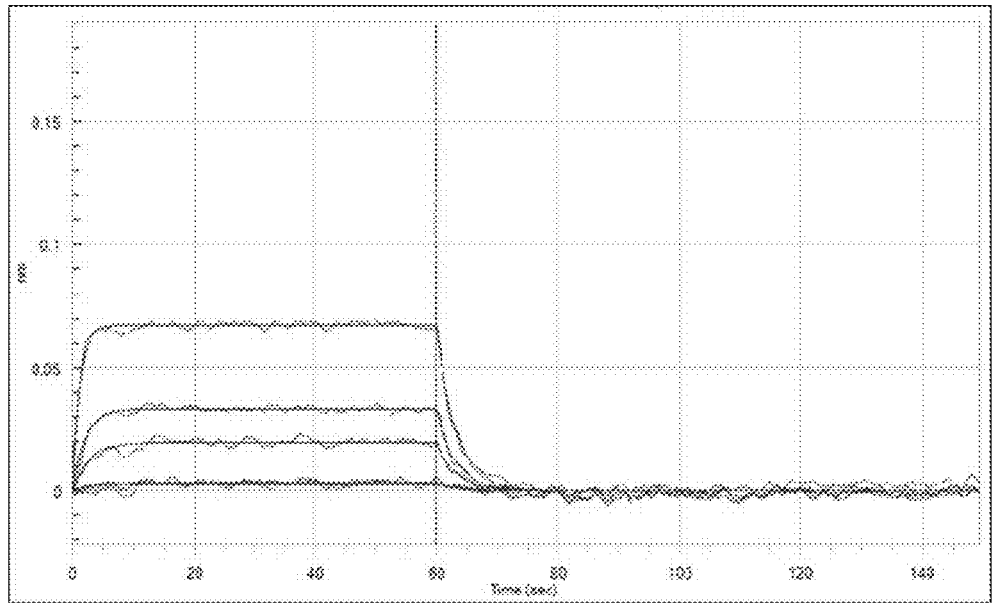
FIG. 10B shows binding kinetic sensorgram for K35 and Y45 variants.
Figure 10B:
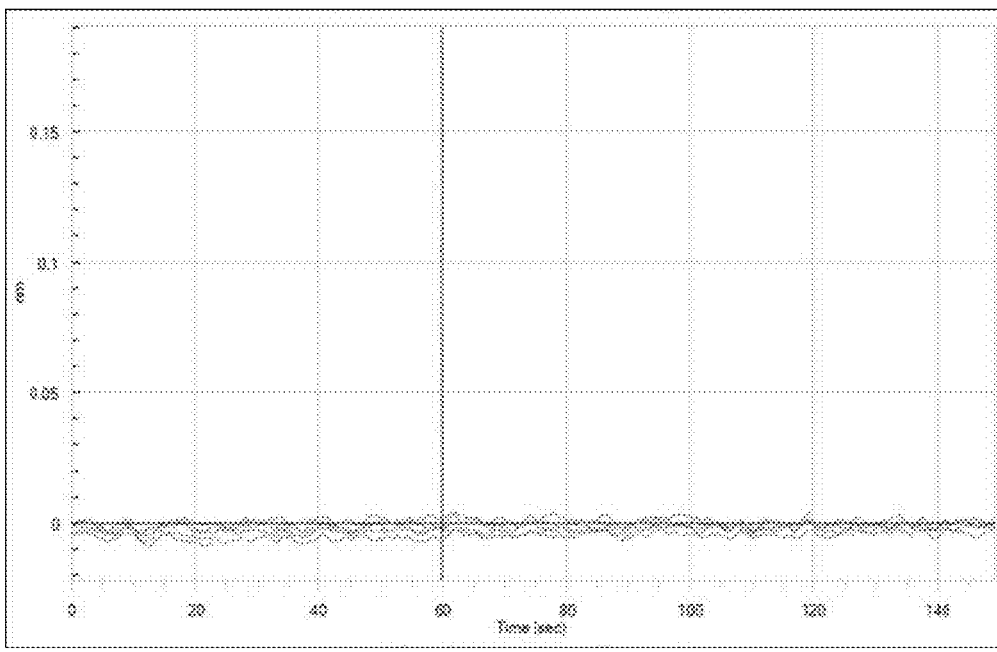
Figure 10C:
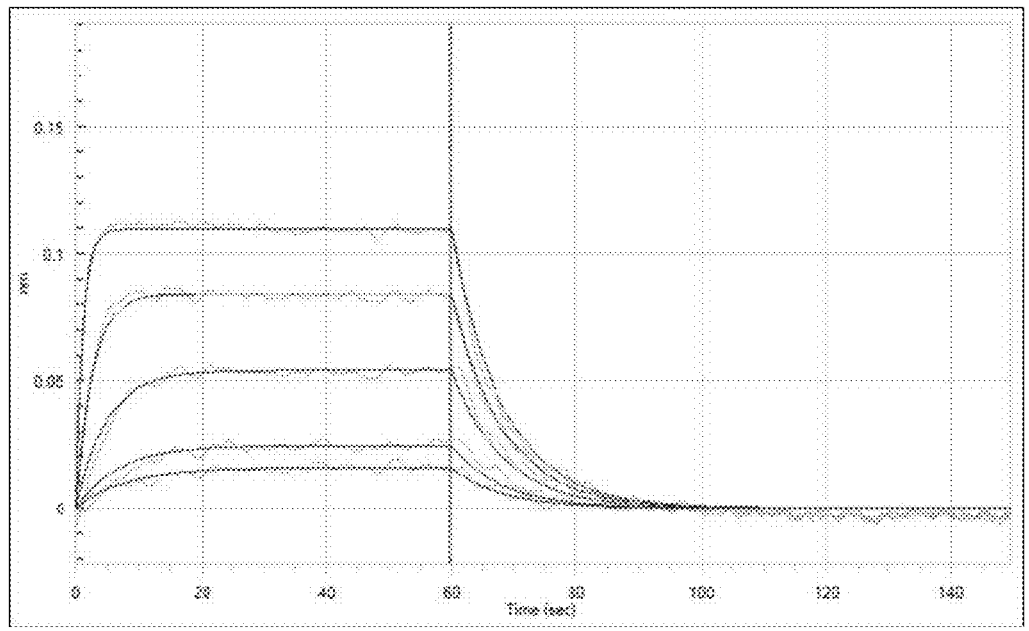
FIG. 10C shows binding kinetic sensorgram for T37 and P65 variants.
Figure 10C:
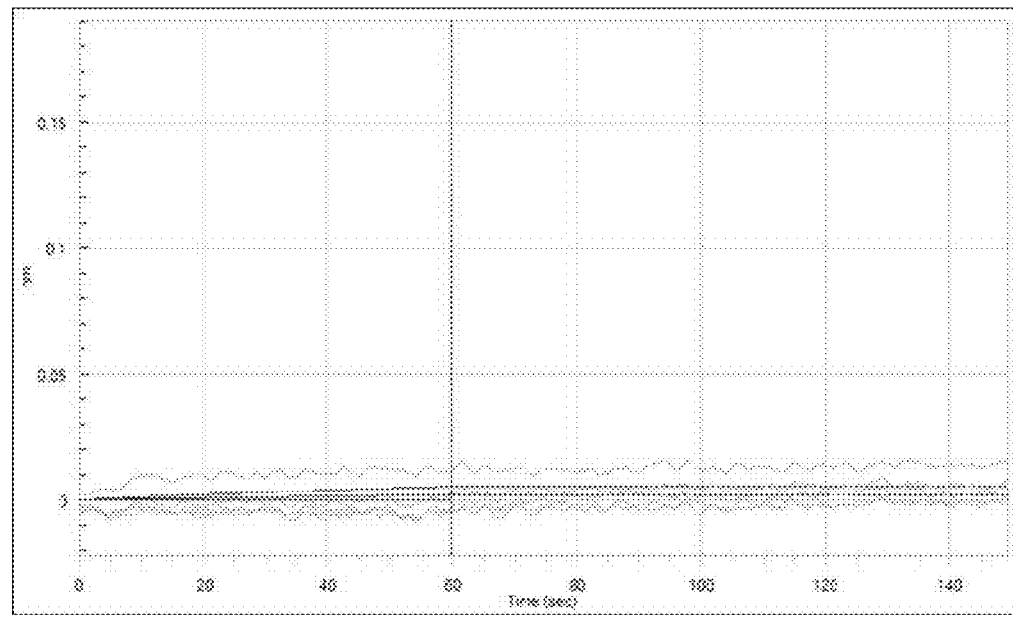

An analysis of selected variants P65, Y45, E61, F42, K35, K49 and T37 was conducted using an in vitro binding assay, Bio-Layer Interferometery assay, as described in the above Examples. Each of the variants were conjugated with 20K PEG at their specific sites respectively. PEGylated variants were then analyzed by BLI (Bio-Layer Interferometry) assay described elsewhere in the Examples. As shown in FIGS. 10A-10C, PEGylated variants were tested on Octet for their binding to IL-2Rα. Wild type IL-2 was used as a positive control in assays. After PEGylation, most variants showed dramatically reduced binding to IL-2Rα of between 92.9% and 99.9%. Among the tested PEGylated variants, P65 and Y45 showed over 99% of blocked activity, Table 4.

TABLE 4

In vitro binding activity of IL-2 variants

| IL-2 variants | Steady State Kd (nM) | Binding to IL-2Rα blockade |
|---|---|---|
| IL-2 WT | 11 | 0% |
| P65-PEG20K | 32000 | 99.9% |
| Y45-PEG20K | 1900 | 99.4% |
| E61-EPG20K | 1400 | 99.0% |
| F42-PEG20K | 1100 | 99.0% |
| K35-PEG20K | 840 | 98.7% |
| K49-PEG20K | 180 | 93.8% |
| T37-PEG20K | 155 | 92.9% |

Example 9—Analysis of Selected Variants with PathHunter Dimerization Assay

Figure 11:
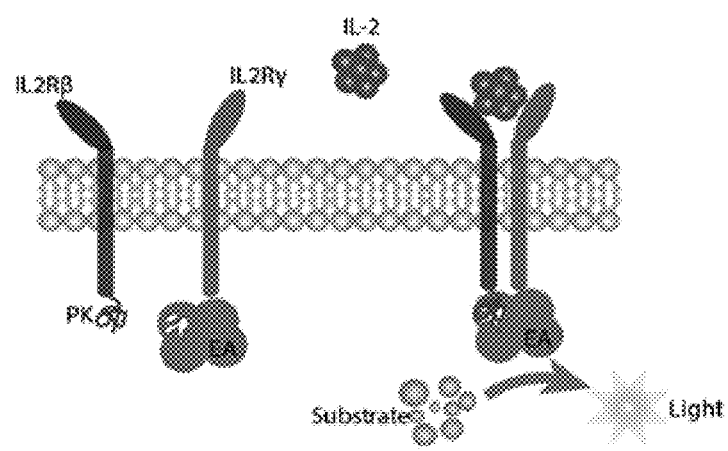
FIG. 11 shows an illustration of IL-2 receptor dimerization assay.
Figure 11:
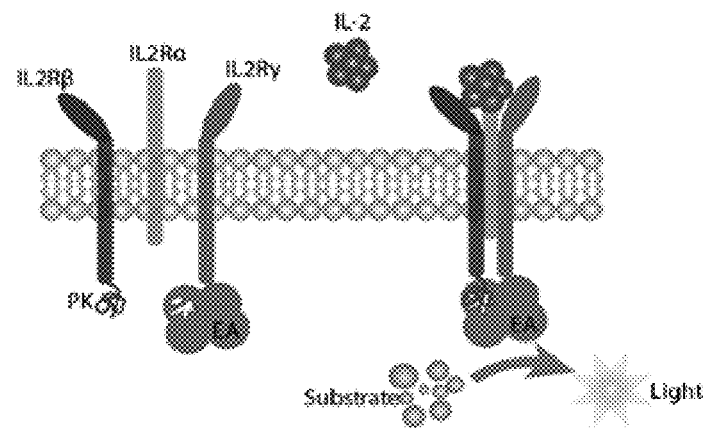

To find the best site for conjugation of PEG, a PathHunter Dimerization Assay developed by DiscoverX (Fremont, CA) was employed. In general, the assay system uses exogenously expressed IL-2 receptors that have been engineered to have complementary binding domains of an enzyme to give rise to a chemiluminescent signal once previously separated receptors are activated after dimerization by added IL-2 molecules, (FIG. 11). Two cell lines were generated in U2OS cells. One cell line expressed three receptors, IL-2Rα, IL-2Rβ and IL-2Rγ. The other cell line expressed IL-2Rβ and IL-2Rγ. A ratio of binding $EC_{50}$ values ($EC_{50}$-βγ/$EC_{50}$-αβγ) of each variant is used to estimate their relative retained binding capability. As shown in Table 5, the best possible variant has a value of 1, meaning that 100% of their βγ binding ability is retained while α binding is 100% blocked. As noted, variant Y45-BR4, (variant Y45 with a 20K 4-branched PEG conjugated), and P65-PEG20K, (variant P65 with a 20K-linear PEG conjugated), showed the lowest values, indicating that these two PEGylated variants would be best candidates for further evaluation.

TABLE 5

Binding activity of IL-2 variants using dimerization assay-Expt. 1

| Compound | βγ EC50 (nM) | αβγ EC50 (nM) | βγ/αβγ Ratio |
|---|---|---|---|
| Best possible | 0.41 | 0.41 | 1 |
| Y45-BR4 | 5.69 | 1.18 | 5 |
| P65-PEG20K | 7.40 | 1.51 | 5 |
| Y45-BR2 | 6.10 | 0.46 | 13 |
| IL-2 WT | 0.41 | 0.02 | 25 |
| E61-PEG20K | 3.78 | 0.02 | 168 |
| Y45-PEG20K | 5.50 | 0.03 | 206 |

As shown in Table 6, in an additional experiment conducted, variant P65-BR4, (variant P65 with a 20K 4-branched PEG conjugated), and P65-BR2, (variant P65 with a 20K 2-branched PEG conjugated) were also selected as candidates for further evaluation in addition to variants Y45-BR4 and P65-PEG20K.

TABLE 6

Improved binding activity of IL-2 variants using dimerization assay-Expt. 2

| Compound | βγ EC50 (nM) | αβγ EC50 (nM) | βγ/αβγ Ratio |
|---|---|---|---|
| Best possible | 0.41 | 0.41 | 1 |
| P65-BR4 | 8.50 | 4.86 | 1.75 |
| P65-BR2 | 13.06 | 4.80 | 2.96 |
| Y45-BR4 | 3.67 | 0.84 | 4.31 |
| P65-PEG20K | 5.21 | 1.10 | 5.06 |
| Y45-BR2 | 3.39 | 0.40 | 8.34 |
| IL-2 WT | 0.41 | 0.03 | 16.67 |
| Y45-PEG20K | 2.34 | 0.04 | 30.87 |

Example 10—Ex Vivo pSTAT5 Assay of IL-2 Variants

Figure 12:
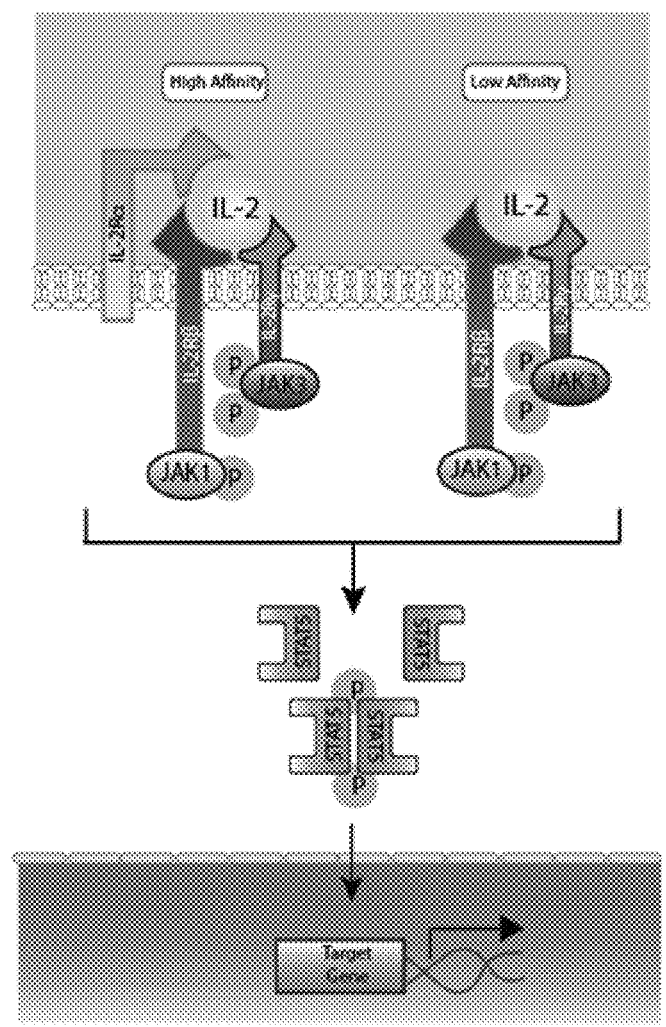
FIG. 12 shows an illustration of ex-vivo pSTAT5 assay.

To further evaluate the in vitro function of PEGylated variants, an ex vivo assay using PBMCs was employed. As shown in FIG. 12, binding of IL-2 to its receptors triggered increased phosphorylation of STAT5 (pSTAT5). Therefore, detecting pSTAT5 levels should be an index to the binding of IL-2 variants to endogenous IL-2 receptors. Human whole PBMCs was treated with selected PEGylated variants such as Y45-BR2, (variant Y45 with a 20K 2-branched PEG conjugated), Y45-BR4, (variant Y45 with a 20K 4-branched PEG conjugated), and P65-PEG20K, (variant P65 with a linear 20K PEG), following by separation into two populations, CD8+ T cells and CD4+ Treg cells. As shown in Table 7, all three variants exhibited much improved activity regarding their retained βγ binding ability and blocked α binding activity. These results were further supported by variants tested in an additional pSTAT5 assay as shown in Table 8. The results from this pSTAT5 assay, (Table 8), showed that multiple variants had dramatically improved activity in terms of their reduced ability to bind to Treg cells and relatively maintained binding to CD8+ cells. The calculated ratio of CD8+/Treg is used in Table 8 to indicate the ranking of variants so that the PathHunter assay results can be directly compared to pSTAT5 assay results by a similar ranking system.

TABLE 7

Binding activity of IL-2 variants using an ex vivo assay-Expt. 1

| Compound | EC50-CD8 (nM) | EC50-Treg (nM) | βγ-retaining activity (%) | βγ/αβγ-retaining activity (%) | Ratio (βγ/αβγ) |
|---|---|---|---|---|---|
| IL-2 WT | 0.1346 | 0.00034 | 100 | 100 | 1.00 |
| Y45-BR2 | 1.065 | 0.4504 | 12.64 | 0.1 | 169.87 |
| Y45-BR4 | 2.714 | 1.337 | 4.96 | 0.03 | 197.88 |
| P65-PEG20K | 9.204 | 4.179 | 1.46 | 0.01 | 182.38 |

TABLE 8

Improved binding activity of IL-2 variants using an ex vivo assay-Expt. 2

| Compound | EC50-CD8 (nM) | EC50-Treg (nM) | Ratio (CD8/Treg) |
|---|---|---|---|
| IL-2 WT | 0.03377 | 0.0002857 | 118.2 |
| Y45-BR2 | 4.604 | 36.003 | 0.13 |
| Y45-PEG20K | 3.367 | 5.377 | 0.61 |
| P65-BR2 | 41.467 | 111.644 | 0.37 |
| Y45-BR4 | 7.462 | 3.398 | 2.20 |
| P65-PEG20K | 10.643 | 4.514 | 2.36 |
| P65-BR4 | 23.961 | 4.351 | 5.51 |

Example 11—Clonal Outgrowth and Long-Term Propagation of CTLL-2 Cells in the Presence of Glycosylated IL-2 Produced in CHO Mammalian Cells Versus Non-Glycosylated IL-2 Produced in *E. coli*

It has been reported that native human IL-2 is a glycosylated protein that has O-linked glycosylation on Thr-3 (Conradt et al., Eur J Biochem 153(2): 255-261 (1985)). In comparison to nonglycosylated IL-2, the function of this glycosylation is related to higher solubility at physiological pH, slower clearance in vivo and less immunogenicity in cancer therapy (Robb et al., Proc Natl Acad Sci USA 81(20): 6486-6490 (1984); Goodson et al., Biotechnology (NY) 8(4): 343-346 (1990)). More importantly, it has been shown that glycosylated IL-2 is superior to nonglycosylated IL-2 in promoting clonal out-growth and long-term propagation of alloactivated human T cells (Pawelec et al., Immunobiology 174(1): 67-75 (1987)), suggesting glycosylated IL-2 is a better choice in therapeutic applications.

Figure 13:
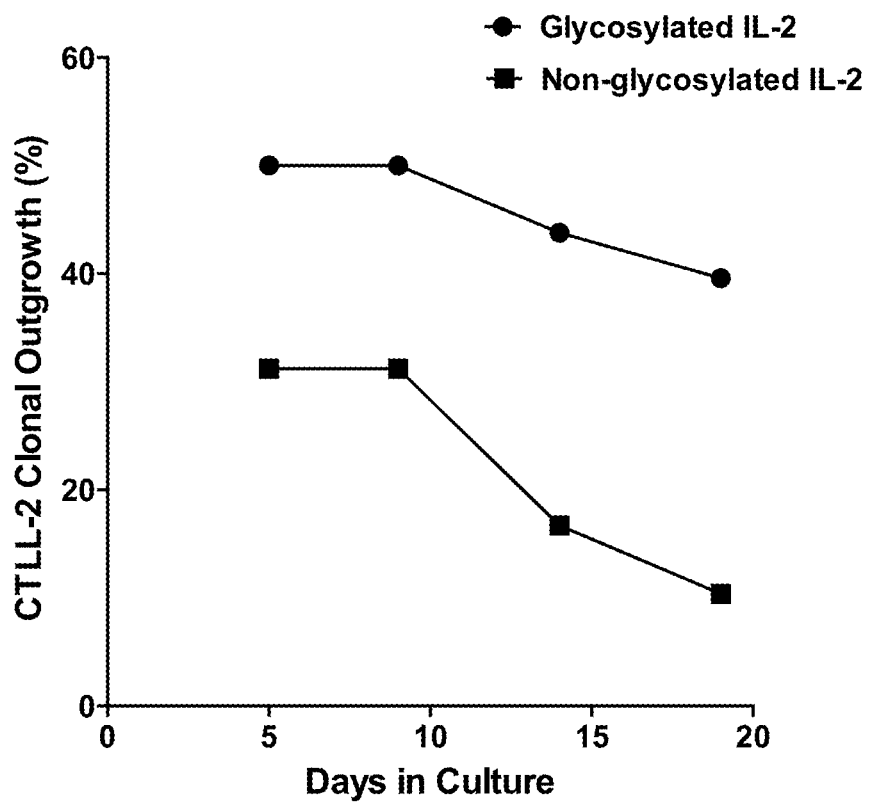
FIG. 13 shows outgrowth and long-term propagation of CTLL-2 cells in the presence of glycosylated or non-glycosylated IL-2.

To further analyze the biological function of glycosylated IL-2 and non-glycosylated IL-2, an experiment analyzing clonal outgrowth rate and long-term propagation frequency of CTLL-2 cells was performed (FIG. 13). Single CTLL-2 cells were deposited into 96-well plates with a precoated feeder layer of γ-irradiated CF1-MEF (Mouse Embryonic Fibroblast) cells (Thermo Fisher, Waltham, MA, CAT #A34180). During 19 days of growth with a single treatment of various concentrations, (0.005 nM, 0.05 nM, 0.5 nM and 5 nM), of wild type IL-2 produced from CHO cells or *E. coli*, the percentage of the grown colony numbers and percentage of survived colonies at the end of 19-day incubation were counted and analyzed. As shown in FIG. 13, (using 0.5 nM treatment as an example), glycosylated IL-2 showed superior activity in promoting clonal outgrowth than non-glycosylated IL-2. On average, the ability of glycosylated IL-2 to promote the clonal outgrowth is 2-fold higher than non-glycosylated IL-2 in the presence of 0.5 nM IL-2 concentration, which is the optimal cell culture condition for CTLL-2 cells growth. After long-term incubation (~19 days), the colony survival rate from the glycosylated IL-2 treatment was 4-fold higher than the non-glycosylated IL-2 treatment. The data clearly demonstrate that glycosylated IL-2 has superior activity in promoting clonal outgrowth and long-term propagation of IL-2 responding cells, and further supports its promising therapeutic applications.

Example 12—Titer Improvement for IL-2 Expression in New Stable Host CHO Cell Lines Many approaches have been attempted in the field to increase the expression of wild type IL-2 and its variants in CHO cells, (see, for example, Kim et al., J Microbiol Biotechnol, 14(4), 810-815 (2004)). However, increasing expression of non-natural amino acid-containing proteins in the industry has been challenged by the relative low yield in mammalian cells. To address this problem in the present invention, proprietary technology in eukaryotic cell lines for improving the production of protein titer as disclosed in PCT/2018US/035764, (incorporated herein by reference in its entirety), is utilized to generate stable pool cells of IL-2 and its variants, and is being used to generated stable IL-2 cell lines.

Briefly, five different generations of platform cell lines expressing Bax/Bak knockout were found to dramatically improved the protein expressions of IL-2 and increase production of IL-2 protein to about 40% over the parental cell line. In addition to the inhibition of apoptosis in these cells via Bax/Bak knockout, a UPF1 knockout was found to further improve the expression of IL-2.

Figure 14:
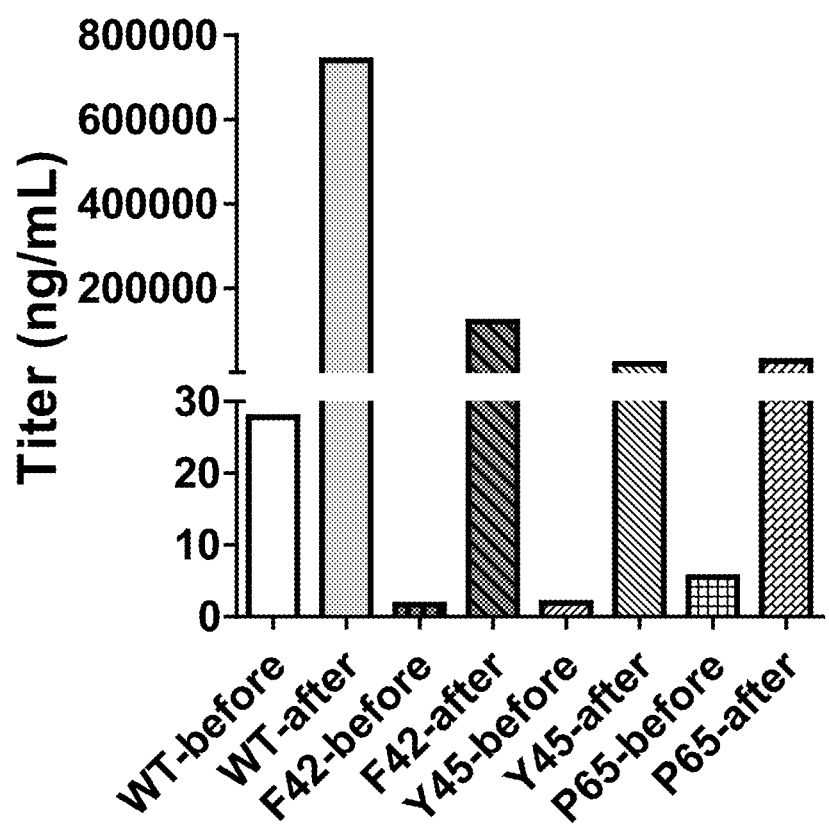
FIG. 14 shows a comparison of titer before and after the generation of stable pools of corresponding wild type IL-2 or its selected variants.

Both wild type IL-2 and its variants (F42, Y45 and P65) have been tested by generating stable pools of them. As shown in FIG. 13, stable pools of three IL-2 variants F42, Y45 and P65, including wild type IL-2, have tremendously increased expression levels, compared to that in the art (see, for example, Kim et. al., J Microbiol Biotechnol., 14(4), 810-815, (2004)), up to about 740 mg/L for wild type; and up to 120 mg/L for F42 variant, (shown in FIG. 14), after generation of stable pools of each. The data shows that IL-2 protein production or yield can be improved or increased, by the generation of a new CHO cell line having a non-natural amino acid efficiently incorporated. It also suggests that the expression levels and functionality are site specifically relevant.

Example 13—IL-2 Variant F42-R38A Showed Complete Blockade of IL-2R Alpha Binding As disclosed herein, the non-naturally encoded amino acid substitution(s) will be combined with other additions, substitutions or deletions within the IL-2 to affect other biological traits of the IL-2 polypeptide including but not limited to, increase the stability (including but not limited to, resistance to proteolytic degradation) of the IL-2 or increase affinity of the IL-2 for its receptor; increase the pharmaceutical stability of the IL-2; enhance the activity of the IL-2 for tumor inhibition and/or tumor reduction; increase the solubility (including but not limited to, when expressed in *E. coli* or other host cells) of the IL-2 or variants; increase the IL-2 solubility following expression in *E coli* or other recombinant host cells; increasing the polypeptide solubility following expression in *E. coli* or other recombinant host cells; that modulates affinity for the IL-2 receptor, binding proteins, or associated ligand, modulates signal transduction after binding to the IL-2 receptor, modulates circulating half-life, modulates release or bio-availability, facilitates purification, or improves or alters a particular route of administration; increases the affinity of the IL-2 variant for its receptor; increases the affinity of the IL-2 variant to IL-2-Rbeta and/or IL-2-Rgamma.

Figure 15A:
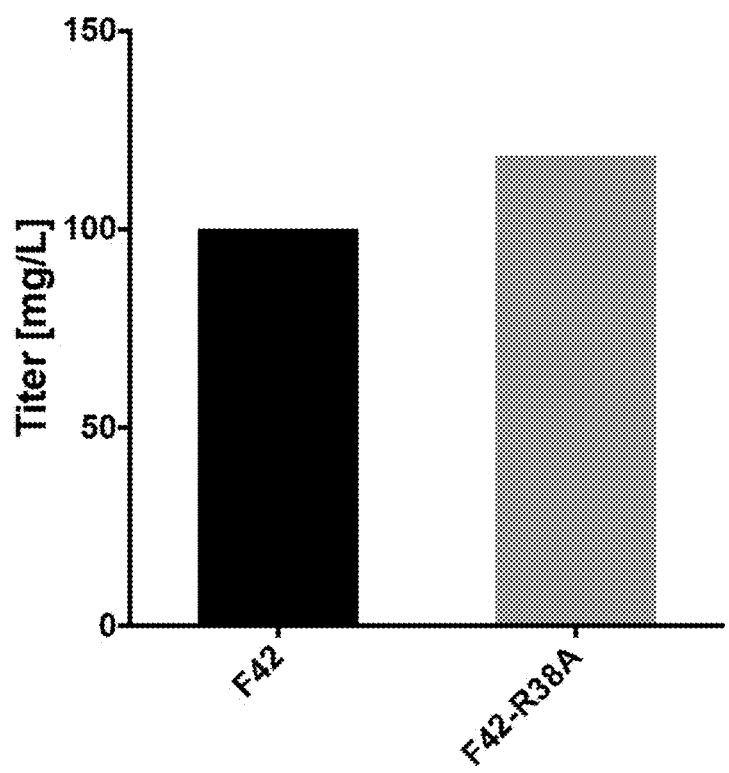
FIG. 15A shows titer in mammalian cells expressing F42-R38A variant.
Figure 15B:
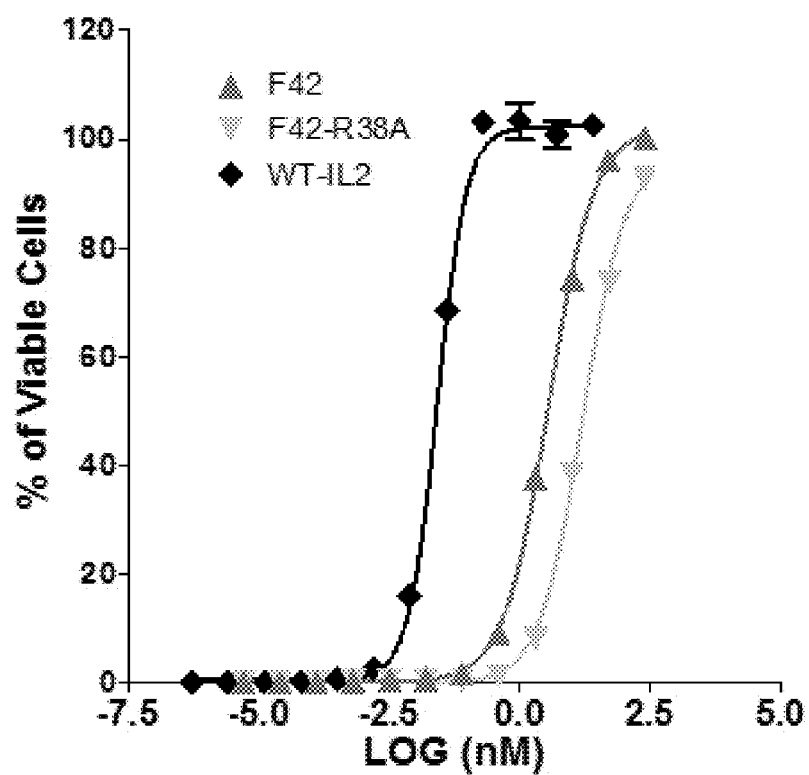
FIG. 15B shows CTLL-2 binding assay of F42-R38A variants.

Therefore, to improve the function of variant F42, a new variant with an additional mutation, R38A, was prepared in CHO cells. As shown in FIG. 15A, the titer increased to 118 mg/L with the combination of a non-natural amino acid and a natural amino acid substitution in the IL-2 variant F42 in a stable pool during the generation of a stable cell line. The protein expression level of variant F42 was not only maintained, but also showed a 20% increase in the presence of the R38A mutation. To test the function of PEGylated F42-R38A variant, a CTLL-2 cell binding assay was performed. As shown in Table 9, the F42-R38A 20K 2-branched PEG (variant F42-$R_{38}$-BR2) conjugate showed an $EC_{50}$ of 15.9 nM in Contrast to the $EC_{50}$ of F42, showing 3.6 nM, with the binding blockade efficiency more than 4-fold increased (FIG. 15B). Based on the $EC_{50}$ of wild type IL-2 of 0.025 nM, the binding blockade efficiency is over 99.9%. This variant showed great potential for its therapeutic applications in terms of its high protein expression levels and its efficiency at blocking binding to IL-2Ralpha.

TABLE 9

| CTLL-2 binding assay of PEGylated F42-R38A variant | | | |
|---|---|---|---|
| | WT-IL2 | F42-PEG20K-BR2 | F42-R38A-PEG20K-BR2 |
| EC50 | 0.025 nM | 3.6 nM | 15.9 nM |

Figure 15C:
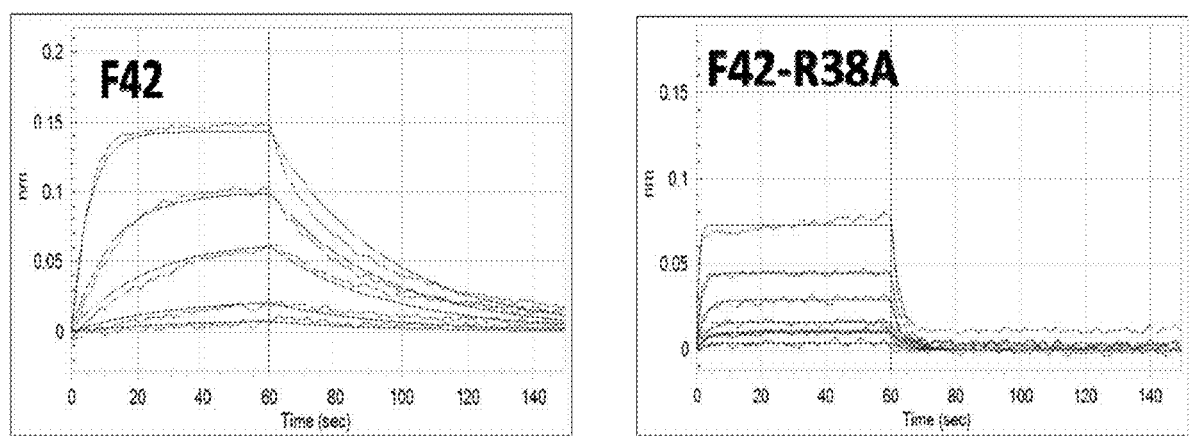
FIG. 15C shows binding kinetic sensorgrams for F42-R38A variants.
Figure 15C:
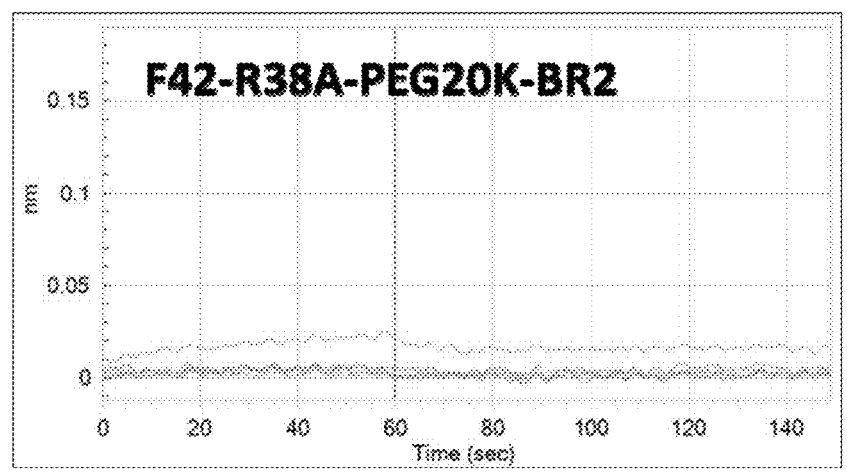

Binding kinetics of F42pAF variant, R38A-F42pAF variant (comprising a non-natural amino acid and a point mutation), and F42-R38A-PEG20K-BR2 were evaluated by BLI to determine effects of the R38A mutation on binding to IL-2Ralpha. FIG. 15C shows the binding sensorgrams for the three constructs and the associated binding constants (KD) are shown in Table 10. As seen in Table 10, IL-2-F42pAF has an IL-2Ralpha binding KD of 20 nM. With the added R38A mutation, IL-2-F42-R38ApAF has an IL-2Ralpha binding KD of 233 nM, which corresponds to a 12 fold reduction in IL-2Ralpha binding. Upon conjugation of IL-2-R38A-F42pAF with a 20K 2-branch PEG molecule, IL-2Ralpha binding was prevented. The results clearly demonstrated that additional mutation effectively blocked the binding of F42-R38A to its receptor IL-2Rα.

TABLE 10

| Binding of IL-2 PEGylated variants with natural and non-natural amino acid subsitutions | | |
|---|---|---|
| F42pAF | F42-PEG20K-BR2 | F42-R38A-PEG20K-BR2 |
| $K_D$ 20 nM | 233 nM | No binding |

It is understood that the examples and embodiments described herein are for illustrative purposes only and that various modifications or changes in light thereof will be suggested to those of ordinary skill in the art and are to be included within the spirit and purview of this application and scope of the appended claims. All publications, patents, patent applications, and/or other documents cited in this application are incorporated by reference in their entirety for all purposes to the same extent as if each individual publication, patent, patent application, and/or other document were individually indicated to be incorporated by reference for all purposes.

The present invention is further described by the following numbered embodiments.

1. An IL-2 polypeptide comprising one or more non-naturally encoded amino acids, wherein said IL-2 polypeptide has reduced interaction with its receptor subunit compared to wild-type IL-2.

2. The IL-2 of embodiment 1, wherein the IL-2 polypeptide is 90% homologous to SEQ ID NO: 2 or SEQ ID NO: 3.

3. The IL-2 of embodiment 1, wherein the IL-2 polypeptide is at least 95% homologous to SEQ ID NO: 2.

4. The IL-2 of embodiment 1, wherein the IL-2 polypeptide is at least 98% homologous to SEQ ID NO: 2.

5. The IL-2 of embodiment 1, wherein the IL-2 polypeptide is at least 99% homologous to SEQ ID NO: 2.

6. The IL-2 of embodiment 1, wherein the IL-2 is conjugated to one or more water-soluble polymers.

7. The IL-2 of embodiment 6, wherein at least one of the water-soluble polymers is linked to at least one of the non-naturally encoded amino acids.

8. The IL-2 of embodiment 7, wherein the water-soluble polymer is PEG.

9. The IL-2 of embodiment 8, wherein the PEG has a molecular weight between 10 and 50.

10. The IL-2 of embodiment 1, wherein the non-naturally encoded amino acid is substituted at a position selected from the group consisting of residues before position 1 (i.e. at the N-terminus), 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, or added to the carboxyl terminus of the protein, and any combination thereof, and any combination thereof.

11. The IL-2 of embodiment 10, wherein the IL-2 comprises one or more amino acid substitution, addition or deletion that modulates affinity of the IL-2 polypeptide for its IL2Rα receptor subunit compared to wild-type IL-2.

12. The IL-2 of embodiment 10, wherein the IL-2 comprises one or more amino acid substitution, addition or deletion that increases the stability or solubility of the IL-2.

13. The IL-2 of embodiment 10, wherein the IL-2 comprises one or more amino acid substitution, addition or deletion that increases the expression of the IL-2 polypeptide in a recombinant host cell or synthesized in vitro.

14. The IL-2 of embodiment 10, wherein non-naturally encoded amino acid is substituted at a position selected from the group consisting of residues 3, 35, 37, 38, 41, 42, 43, 44, 45, 61, 62, 64, 65, 68, 72, and 107, and any combination thereof.

15. The IL-2 of embodiment 10, wherein the non-naturally encoded amino acid is reactive toward a linker, polymer, or biologically active molecule that is otherwise unreactive toward any of the 20 common amino acids in the polypeptide.

16. The IL-2 of embodiment 10, wherein the non-naturally encoded amino acid comprises a carbonyl group, an aminooxy group, a hydrazine group, a hydrazide group, a semicarbazide group, an azide group, or an alkyne group.

17. The IL-2 of embodiment 16, wherein the non-naturally encoded amino acid comprises a carbonyl group.

18. The IL-2 of embodiment 10, wherein the IL-2 is linked to a biologically active molecule, a cytotoxic agent, a water-soluble polymer, or an immunostimulatory agent.

19. The IL-2 of embodiment 18, wherein the conjugated IL-2 is attached to one or more water-soluble polymers.

20. The IL-2 of embodiment 18, wherein the biologically active molecule, cytotoxic agent, or immunostimulatory agent is linked to the IL-2 by a linker.

21. The IL-2 of embodiment 18, wherein the biologically active molecule, cytotoxic agent, or immunostimulatory agent is linked to the IL-2 by a cleavable or non-cleavable linker.

22. The IL-2 of embodiment 18, wherein the biologically active molecule, cytotoxic agent, or immunostimulatory agent is conjugated directly to one or more of the non-naturally encoded amino acids in the IL-2.

23. The IL-2 of embodiment 10, wherein the non-naturally encoded amino acid has the structure:

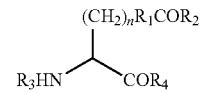

wherein n is 0-10; $R_1$ is an alkyl, aryl, substituted alkyl, or substituted aryl; $R_2$ is H, an alkyl, aryl, substituted alkyl, and substituted aryl; and $R_3$ is H, an amino acid, a polypeptide, or an amino terminus modification group, and $R_4$ is H, an amino acid, a polypeptide, or a carboxy terminus modification group.

24. The IL-2 of embodiment 23, wherein the non-naturally encoded amino acid comprises an aminooxy group.

25. The IL-2 of embodiment 23, wherein the non-naturally encoded amino acid comprises a hydrazide group.

26. The IL-2 of embodiment 23, wherein the non-naturally encoded amino acid comprises a hydrazine group.

27. The IL-2 of embodiment 23, wherein the non-naturally encoded amino acid residue comprises a semicarbazide group.

28. The IL-2 polypeptide of embodiment 23, wherein the non-naturally encoded amino acid residue comprises an azide group.

29. The IL-2 of embodiment 1, wherein the non-naturally encoded amino acid has the structure:

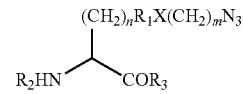

wherein n is 0-10; $R_1$ is an alkyl, aryl, substituted alkyl, substituted aryl or not present; X is O, N, S or not present; m is 0-10; $R_2$ is H, an amino acid, a polypeptide, or an amino terminus modification group, and $R_3$ is H, an amino acid, a polypeptide, or a carboxy terminus modification group.

30. The IL-2 of embodiment 29, wherein the non-naturally encoded amino acid comprises an alkyne group.

31. The IL-2 of embodiment 1, wherein the non-naturally encoded amino acid has the structure:

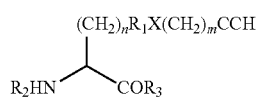

wherein n is 0-10; $R_1$ is an alkyl, aryl, substituted alkyl, or substituted aryl; X is O, N, S or not present; m is 0-10, $R_2$ is H, an amino acid, a polypeptide, or an amino terminus modification group, and $R_3$ is H, an amino acid, a polypeptide, or a carboxy terminus modification group.

32. The IL-2 of embodiment 7, wherein the water-soluble polymer has a molecular weight of between about 0.1 kDa and about 100 kDa.

33. The IL-2 polypeptide of embodiment 32, wherein the water-soluble polymer has a molecular weight of between about 0.1 kDa and about 50 kDa.

34. The IL-2 of embodiment 16, wherein the aminooxy, hydrazine, hydrazide or semicarbazide group is linked to the water-soluble polymer through an amide linkage.

35. The IL-2 of embodiment 19, which is made by reacting a water-soluble polymer comprising a carbonyl group with a polypeptide comprising a non-naturally encoded amino acid that comprises an aminooxy, a hydrazine, a hydrazide or a semicarbazide group.

36. The IL-2 of embodiment 1, wherein the IL-2 is glycosylated.

37. The IL-2 of embodiment 1, wherein the IL-2 polypeptide further comprises a linker, polymer, or biologically active molecule linked to the polypeptide via the non-naturally encoded amino acid.

38. The IL-2 of embodiment 37, wherein the IL-2 polypeptide wherein the linker, polymer, or biologically active molecule linked to the polypeptide via a saccharide moiety.

39. A method of making the IL-2 of embodiment 1, the method comprising contacting an isolated IL-2 polypeptide comprising a non-naturally encoded amino acid with a linker, polymer, or biologically active molecule comprising a moiety that reacts with the non-naturally encoded amino acid.

40. The method of embodiment 39, wherein the polymer comprises a moiety selected from a group consisting of a water-soluble polymer and poly(ethylene glycol).

41. The method of embodiment 39, wherein the non-naturally encoded amino acid comprises a carbonyl group, an aminooxy group, a hydrazide group, a hydrazine group, a semicarbazide group, an azide group, or an alkyne group.

42. The method of embodiment 39, wherein the non-naturally encoded amino acid comprises a carbonyl moiety and the linker, polymer, or biologically active molecule comprises an aminooxy, a hydrazine, a hydrazide or a semicarbazide moiety.

43. The method of embodiment 39, wherein the aminooxy, hydrazine, hydrazide or semicarbazide moiety is linked to the linker, polymer, or biologically active molecule through an amide linkage.

44. The method of embodiment 39, wherein the non-naturally encoded amino acid comprises an alkyne moiety and the linker, polymer, or biologically active molecule comprises an azide moiety.

45. The method of embodiment 39, wherein the non-naturally encoded amino acid comprises an azide moiety and the linker, polymer, or biologically active molecule comprises an alkyne moiety.

46. The IL-2 polypeptide of embodiment 7, wherein the water-soluble polymer is a poly(ethylene glycol) moiety.

47. The IL-2 polypeptide of embodiment 46, wherein the poly(ethylene glycol) moiety is a branched or multiarmed polymer.

48. A composition comprising the IL-2 of embodiment 10 and a pharmaceutically acceptable carrier.

49. The composition of embodiment 48, wherein the non-naturally encoded amino acid is linked to a water-soluble polymer.

50. A method of treating a patient having a disorder modulated by IL-2 comprising administering to the patient a therapeutically-effective amount of the composition of embodiment 42.

51. A composition comprising the IL-2 of embodiment 10 conjugated to a biologically active molecule with a pharmaceutically acceptable carrier.

52. A composition comprising the IL-2 of embodiment 10 further comprising a linker and a conjugate with a pharmaceutically acceptable carrier.

53. A method of making an IL-2 comprising a non-naturally encoded amino acid, the method comprising, culturing cells comprising a polynucleotide or polynucleotides encoding an IL-2 polypeptide comprising a selector codon, an orthogonal RNA synthetase and an orthogonal tRNA under conditions to permit expression of the IL-2 polypeptide comprising a non-naturally encoded amino acid; and purifying said polypeptide.

54. A method of modulating serum half-life or circulation time of an IL-2 polypeptide, the method comprising substituting one or more non-naturally encoded amino acids for any one or more naturally occurring amino acids in said polypeptide.

55. An IL-2 polypeptide comprising one or more amino acid substitution, addition or deletion that increases the expression of the IL-2 polypeptide in a recombinant host cell.

56. An IL-2 polypeptide comprising at least one linker, polymer, or biologically active molecule, wherein said linker, polymer, or biologically active molecule is attached to the polypeptide through a functional group of a non-naturally encoded amino acid ribosomally incorporated into the polypeptide.

57. An IL-2 polypeptide comprising a linker, polymer or biologically active molecule that is attached to one or more non-naturally encoded amino acids wherein said non-naturally encoded amino acid is ribosomally incorporated into the polypeptide at pre-selected sites.

58. A method for reducing the number of tumor cells in a human diagnosed with cancer, comprising administering to a human in need of such reduction a pharmaceutical composition comprising a PEG-IL-2 of embodiment 56.

59. The method of embodiment 58, wherein the conjugate is administered at a dose of about 0.1 µ/kg to about 50 µ/kg.

What is claimed is:

1. An IL-2 polypeptide conjugate, comprising:
   an IL-2 polypeptide having the amino acid sequence of SEQ ID NO: 2 comprising one non-natural amino acid incorporated into position 45, wherein the non-natural amino acid is para-acetyl-phenylalanine;
   wherein the IL-2 polypeptide is conjugated to one water-soluble polymer through the non-natural amino acid via a non-cleavable linker; and
   wherein said IL-2 polypeptide conjugate has reduced interaction with IL-2 receptor alpha compared to wild-type IL-2.

2. The IL-2 polypeptide conjugate of claim 1, wherein the one water-soluble polymer is a poly(ethylene glycol) (PEG) moiety.

3. The IL-2 polypeptide conjugate of claim 2, wherein the PEG moiety has a molecular weight of between about 0.1 kDa and about 100 kDa.

4. The IL-2 polypeptide conjugate of claim 1, wherein the IL-2 polypeptide is glycosylated.

5. The IL-2 polypeptide conjugate of claim 2, wherein the PEG moiety has a molecular weight of between about 0.1 kDa and about 50 kDa.

6. The IL-2 polypeptide conjugate of claim 2, wherein the PEG moiety has a molecular weight of between about 10,000 Da and about 40,000 Da.

7. The IL-2 polypeptide conjugate of claim 2, wherein the PEG moiety is linear.

8. A composition comprising an IL-2 polypeptide conjugate of claim 1 and a pharmaceutically acceptable carrier.

9. A method of treating a patient having a disease, condition or disorder modulated by IL-2, the method comprising administering to the patient a therapeutically-effective amount of the composition of claim 8.

10. The method of claim 9, wherein the disease, condition or disorder is cancer.

11. The IL-2 polypeptide conjugate of claim 1, wherein the non-cleavable linker is an oxime linkage.

12. The IL-2 polypeptide conjugate of claim 11, wherein the one water-soluble polymer is a poly(ethylene glycol) (PEG) moiety having a molecular weight of about 30,000 Da.

13. The IL-2 polypeptide conjugate of claim 12, wherein the PEG moiety is linear.

14. The IL-2 polypeptide conjugate of claim 4, wherein the IL-2 polypeptide is produced in mammalian cells.

15. The IL-2 polypeptide conjugate of claim 14, wherein the mammalian cells are Chinese hamster ovary (CHO) cells.

16. The composition of claim 8, wherein the IL-2 polypeptide is glycosylated.

* * * * *